United States Patent
Apuya et al.

(10) Patent No.: US 9,441,233 B2
(45) Date of Patent: Sep. 13, 2016

(54) TRANSGENIC PLANTS HAVING INCREASED BIOMASS

(75) Inventors: Nestor Apuya, Culver City, CA (US); Vijay Sharma, Wildwood, MO (US); Chuan-Yin Wu, Newbury Park, CA (US)

(73) Assignee: Ceres, Inc., Thousand Oaks, CA (US)

( * ) Notice: Subject to any disclaimer, the term of this patent is extended or adjusted under 35 U.S.C. 154(b) by 595 days.

(21) Appl. No.: 13/696,506

(22) PCT Filed: May 5, 2011

(86) PCT No.: PCT/US2011/035345
§ 371 (c)(1),
(2), (4) Date: Jan. 28, 2013

(87) PCT Pub. No.: WO2011/140329
PCT Pub. Date: Nov. 10, 2011

(65) Prior Publication Data
US 2013/0125263 A1    May 16, 2013

Related U.S. Application Data

(60) Provisional application No. 61/331,984, filed on May 6, 2010, provisional application No. 61/378,477, filed on Aug. 31, 2010.

(51) Int. Cl.
| C12N 15/82 | (2006.01) |
| C07K 14/415 | (2006.01) |
| C12N 9/10 | (2006.01) |
| C12Q 1/68 | (2006.01) |

(52) U.S. Cl.
CPC ......... *C12N 15/8242* (2013.01); *C07K 14/415* (2013.01); *C12N 9/1048* (2013.01); *C12N 15/8261* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| 4,987,071 A | 1/1991 | Cech et al. |
| 5,034,323 A | 7/1991 | Jorgensen et al. |
| 5,204,253 A | 4/1993 | Sanford et al. |
| 5,231,020 A | 7/1993 | Jorgensen et al. |
| 5,254,678 A | 10/1993 | Haseloff et al. |
| 5,538,880 A | 7/1996 | Lundquist et al. |
| 5,766,847 A | 6/1998 | Jackle et al. |
| 5,878,215 A | 3/1999 | Kling et al. |
| 6,013,863 A | 1/2000 | Lundquist et al. |
| 6,326,527 B1 | 12/2001 | Kirihara et al. |
| 6,329,571 B1 | 12/2001 | Hiei |
| 6,423,885 B1 | 7/2002 | Waterhouse et al. |
| PP13,008 P2 | 9/2002 | Walsh |
| 6,452,067 B1 | 9/2002 | Bedbrook et al. |
| 6,573,099 B2 | 6/2003 | Graham |
| PP14,743 P2 | 5/2004 | Speichert et al. |
| 6,753,139 B1 | 6/2004 | Baulcombe et al. |
| 6,777,588 B2 | 8/2004 | Waterhouse et al. |
| PP15,193 P2 | 9/2004 | Smith et al. |
| 6,906,244 B2 | 6/2005 | Fischer et al. |
| PP16,176 P3 | 1/2006 | Cosner et al. |
| PP18,161 P2 | 10/2007 | Probst |
| 7,396,979 B2 | 7/2008 | Alexandrov et al. |
| 2003/0175783 A1 | 9/2003 | Waterhouse et al. |
| 2003/0175965 A1 | 9/2003 | Lowe et al. |
| 2003/0180945 A1 | 9/2003 | Wang et al. |
| 2004/0123343 A1 | 6/2004 | La Rosa et al. |
| 2004/0214330 A1 | 10/2004 | Waterhouse et al. |
| 2005/0011105 A1 | 1/2005 | Cameron et al. |
| 2005/0023639 A1 | 2/2005 | Yeh et al. |
| 2005/0032221 A1 | 2/2005 | Chang et al. |
| 2005/0034308 A1 | 2/2005 | Palmowski |
| 2005/0034343 A1 | 2/2005 | Weisbart |
| 2005/0223422 A1 | 10/2005 | Cook et al. |
| 2005/0246785 A1 | 11/2005 | Cook |
| 2006/0015970 A1 | 1/2006 | Pannell et al. |
| 2006/0021083 A1 | 1/2006 | Cook et al. |
| 2006/0038236 A1 | 2/2006 | Yamamoto |
| 2006/0040572 A1 | 2/2006 | Mizuguchi |
| 2006/0041952 A1 | 2/2006 | Cook |
| 2006/0090216 A1 | 4/2006 | Apuya |
| 2006/0107345 A1* | 5/2006 | Alexandrov et al. ......... 800/278 |
| 2006/0112445 A1 | 5/2006 | Dang |
| 2006/0260004 A1 | 11/2006 | Fang |
| 2006/0265777 A1 | 11/2006 | Apuya |
| 2006/0265788 A1 | 11/2006 | Rommens |

(Continued)

FOREIGN PATENT DOCUMENTS

| EP | 0 534 858 | 4/2000 |
| WO | WO 97/01952 | 1/1997 |

(Continued)

OTHER PUBLICATIONS

Jain et al., 2006, Funct. Integr. Genomics 6: 47-59.*
Liscum and Reed, 2002, Plant Molecular Biology 49: 387-400.*
GenBank sequence with Accession No. NM_201661.1, published May 22, 2008.*
Yi et al., 2005, Plant Physiology 138: 2087-2096.*
U.S. Appl. No. 60/637,140, filed Dec. 16, 2004, Feldmann.
U.S. Appl. No. 60/612,891, filed Sep. 23, 2004, Kwok.
U.S. Appl. No. 60/583,691, filed Jun 30, 2004, Alexandrov et al.
U.S. Appl. No. 60/583,609, filed Jun. 30, 2004, Alexandrov.
U.S. Appl. No. 60/558,869, filed Apr. 1, 2004, Cook et al.
U.S. Appl. No. 60/544,771, filed Feb. 13, 2004, Cook et al.
U.S. Appl. No. 60/518,075, filed Nov. 6, 2003, Pennell et al.
U.S. Appl. No. 60/505,689, filed Sep. 23, 2003, Cook et al.

(Continued)

*Primary Examiner* — David T Fox
*Assistant Examiner* — Bratislav Stankovic
(74) *Attorney, Agent, or Firm* — Fish & Richardson P.C.

(57) ABSTRACT

Methods and materials for modulating biomass levels in plants are disclosed. For example, nucleic acids encoding biomass-modulating polypeptides are disclosed as well as methods for using such nucleic acids to transform plant cells. Also disclosed are plants having increased biomass levels and plant products produced from plants having increased biomass levels.

9 Claims, 144 Drawing Sheets

(56) References Cited

U.S. PATENT DOCUMENTS

| | | | |
|---|---|---|---|
| 2007/0006335 | A1 | 1/2007 | Cook et al. |
| 2007/0006337 | A1 | 1/2007 | Cook |
| 2007/0042387 | A1 | 2/2007 | Pennell |
| 2007/0056058 | A1 | 3/2007 | Olivier et al. |
| 2007/0062762 | A1 | 3/2007 | Ach |
| 2008/0072340 | A1 | 3/2008 | Troukhan et al. |
| 2009/0094717 | A1 | 4/2009 | Troukhan et al. |
| 2010/0146663 | A1 | 6/2010 | Schneeberger et al. |
| 2011/0167514 | A1 | 7/2011 | Brover et al. |
| 2011/0179529 | A1 | 7/2011 | Kwok et al. |

FOREIGN PATENT DOCUMENTS

| | | | |
|---|---|---|---|
| WO | WO 98/36083 | | 8/1998 |
| WO | WO 98/53083 | | 11/1998 |
| WO | WO 99/32619 | | 7/1999 |
| WO | WO 02/46449 | | 6/2002 |
| WO | WO 2007/120989 | | 10/2007 |
| WO | WO 2007/127501 | | 11/2007 |
| WO | WO 2008/069878 | | 6/2008 |
| WO | WO 2010/034681 | * | 4/2010 |
| WO | WO 2011/044254 | | 4/2011 |

OTHER PUBLICATIONS

Aasland et al., "The SANT domain: a putative DNA-binding domain in the SWI-SNF and ADA complexes, the transcriptional co-repressor N-CoR and TFIIIB," Trends Biochem Sci. Mar. 1996;21(3):87-8.

Abler and Scandalios, "Isolation and characterization of a genomic sequence encoding the maize Cat3 catalase gene," Plant Molecular Biology, 1993, 22:1031-1038.

Akashi et al., "Gene Discovery by Ribozyme and siRNA Libraries," Nature Reviews Mol. Cell Biology, May 2005, 6:413-422.

Alberto et al., "The three-dimensional structure of invertase (beta-fructosidase) fromThermotoga maritime reveals a bimodular arrangement and an evolutionary relationship between retaining and inverting glycosidases," J Biol Chem., Feb. 2004, 79(18):18903-10.

Alonso-Blanco et al. "Arabidopsis Protocols," Methods in Molecular Biology, 1998, 82:137-146.

Anantharaman and Aravind, "The Gold domain, a novel protein module involved in Golgi function and secretion," Genome Biol. 2002; 3(5):1-7, Epub Apr. 24, 2002.

Annunen et al., "Cloning of the Human Prolyl 4-Hydroxylase a Subunit Isoform a(II) and Characterization of the Type II Enzyme Tetramer," J Biol Chem, Jul. 1997, 272:17342-17348.

Aravind and Koonin, "The DNA-repair protein AlkB, EGL-9, and leprecan define new families of 2-oxoglutarate- and iron-dependent dioxygenases," Genome Biol., Feb. 2001, 2:RESEARCH0007.

Baerson et al., "Developmental regulation of an acyl carrier protein gene promoter in vegetative and reproductive tissues," Plant Mol. Biol., 1993, 22(2):255-267.

Barral et al., "A Major Allergen from Pollen Defines a Novel Family of Plant Proteins and Shows Intra- and Interspecie Cross-Reactivity," The Journal of Immunology, 2004, 172:3644-3651.

Bateman et al., "Pfam 3.1: 1313 multiple alignments and profile HMMs match the majority of proteins," Nucl. Acids Res., 1999, 27:260-262.

Bechtold, N. et al., "In planta Agrobacterium mediated gene transfer by infiltration of adult Arabidopsis thaliana plants," C.R. Acad. Sci. Paris, 1993, 316:1194-1199.

Borden and Freemont, "The Ring finger domain: a recent example of a sequence-structure family," Curr Opin Struct Biol, Jun. 1996, 6:395-401.

Braga et al., "Expression of the CrylAb Protein in Genetically Modified Sugarcane for the Control of Diatraea saccharalis (Lepidoptera: Crambidae)," Journal of New Seeds, 2003, 5:209-221.

Burr et al., "Gene Mapping with Recombinant Inbreds in Maize," Genetics, 1998, 118: 519-526.

Burr et al., "Mapping Genes with Recombinant Inbreds," The Maize Handbook, 1994, pp. 249-254.

Bustos et al., "Regulation of B-Glucuronidase Expression in Transgenic Tobacco Plants by an A/T-Rich, cis-Acting Sequence Found Upstream of a French Bean B-Phaseolin Gene," The Plant Cell, 1989, 1(9):839-853.

Cerdan et al., "A 146 bp fragment of the tobacco Lhcbl*2 promoter confers very-low-fluence and high-irradiance responses of phytochrome to a minimal CaMV 35S promoter," Plant Mol. Biol., 1997, 33:245-255.

Chen et al., "Functional analysis of regulatory elements in a plant embryo-specific gene," Proc. Natl. Acad. Sci. USA, 1986, 83:8560-8564.

Chenna et al., "Multiple sequence alignment with the Clustal series of programs," Nucleic Acids Res., 2003, 31(13):3497-500.

Conceicao, "A cotyledon regulatory region is responsible for the different spatial expression patterns of Arabidopsis 2S albumin genes," The Plant Journal, 1994, 5:493-505.

Conkling et al., "Isolation of Transcriptionally Regulated Root-Specific Genes from Tobacco," Plant Physiol., 1990, 93:1203-1211.

Dai et al., "RF2b, a rice bZIP transcription activator, interacts with RF2a and is involved in symptom development of rice tungro disease," Proc. Natl. Acad. Sci. USA, 2004, 101(2):687-692.

de Feyter and Gaudron, "Expressing Ribozymes in Plants," Methods in Molecular Biology, 74(43).

DeBant et al., "The multidomain protein Trio binds the LAR transmembrane tyrosine phosphatase, contains a protein kinase domain, and has separate rac-specific and rho-specific guanine nucleotide exchange factor domains," Proc Natl Acad Sci U S A., May 1996, 93(11):5466-71.

Dieffenbach and Dveksler, eds., "PCR Primer: A Laboratory Manual," Cold Spring Harbor Laboratory Press, 1995.

Do et al., "ProbCons: Probabilistic consistency-based multiple sequence alignment," Genome Res., 2005, 15(2):330-40.

Durbin et al., Biological Sequence Analysis: Probabilistic Models of Proteins and Nucleic Acids, Cambridge University Press, Cambridge, UK (1998).

Fejes et al., "A 268 bp upstream sequence mediates the circadian clock-regulated transcription of the wheat Cab-1 gene in transgenic plants," Plant Mol. Biol., 1990, 15:921-932.

Fromm et al., An Octopine Synthase Enhancer Element Directs Tissue-Specific Expression and Binds ASF-1, a Factor from Tobacco Nuclear Extracts, The Plant Cell, 1989, 1:977-984.

Gardiner et al., "Development of a Core RFLP Map in Maize Using an Immortalized F2 Population," Genetics Society of America, 1993, 134: 917-930.

GenBank No. AF096096, 1999, 2 pages.
GenBank No. AF129516, 1999, 2 pages.
GenBank No. L05934, 1993, 3 pages.
GenBank No. U93215, 2002, 42 pages.

Green et al., "Binding site requirements for pea nuclear protein factor GT-1 correlate with sequences required for light-dependent transcriptional activation of the rbcS-3A gene," The EMBO J., 1988, 7:4035-4044.

Helaakoski et al., "Cloning, baculovirus expression, and characterization of a second mouse prolyl 4-hydroxylase a-subunit isoform: Formation of an a2B2 tetramer with the protein disulfide-isomerase/B subunit," Proc Natl Acad Sci USA, May 1995, 92:4427-4431.

Henrissat and Davies, "Glycoside Hydrolases and Glycosyltransferases. Families, Modules, and Implications for Genomics," Plant Physiol., Dec. 2000, 124:1515-1519.

Henrissat et al., "A census of carbohydrate-active enzymes in the genome of Arabidopsis thaliana," Plant Mol Biol., 2001, 47:55-72.

Hong et al., "Promoter sequences from two different Brassica napus tapetal oleosin-like genes direct tapetal expression of B-glucuronidase in transgenic Brassica plants," Plant Mol. Biol., 1997, 34(3):549-555.

Hurst., "Transcription factors 1: bZIP proteins," Protein Profile, 1995, 2(2):101-68.

Hwang et al., "Aleurone- and embryo-specific expression of the B-glucuronidase gene controlled by the barley Chi26 and Ltpl promoters in transgenic rice," Plant Cell Rep, 2001, 20:647-654.

(56) References Cited

OTHER PUBLICATIONS

Hyrup et al., "Peptide Nucleic Acids (PNA): Synthesis, Properties and Potential Applications," Bioorganic & Medicinal Chemistry, 1996, 4(1):5-23.
Jordano et al., "A Sunflower Helianthinin Gene Upstream Sequence Ensemble Contains an Enhancer and Sites of Nuclear Protein Interaction," The Plant Cell, 1989, 1:855-866.
Kasuga et al., "Improving plant drought, salt, and freezing tolerance by gene transfer of a single stress-inducible transcription factor," Nature Biotechnology, 1999, 17: 287-291.
Keller and Baumgartner, "Vascular-Specific Expression of the Bean GRP 1.8 Gene is Negatively Regulated," The Plant Cell, 1991, 3(10):1051-1061.
Kulaeva and Prokoptseva, "Recent advances in the study of mechanisms of action of phytohormones," Biochemistry (Mosc), Mar. 2004, 69(3):233-47.
Lam et al., "Site-specific mutations alter in vitro factor binding and change promoter expression pattern in transgenic plants," Proc. Natl. Acad. Sci. USA, 1989, 86:7890-7894.
Li et al., "Small dsRNAs induce transcriptional activation in human cells," Proc Natl Acad Sci USA, 2006, 103(46):17337-42.
Lloyd et al., "Targeted mutagenesis using zinc-finger nucleases in Arabidopsis," Proc. Natl. Acad. Sci. USA, Feb. 2005, 102:2232-2237.
Luan et al., A Rice cab Gene Promoter Contains Separate cis-Acting Elements That Regulate Expression in Dicot and Monocot Plants, The Plant Cell, Aug. 1992, 4:971-981.
Lubberstedt et al., "Promoters from Genes for Plastid Proteins Possess Regions with Different Sensitivities toward Red and Blue Light," Plant Physiol., 1994, 104:997-1006.
Marini et al., "A Family of Ammonium Transporters in *Saccharomyces cerevisiae*," Mol Cell Biol, Aug. 1997, 17:4282-4293.
Marini et al., "The Rh (rhesus) blood group polypeptides are related to NH4+ transporters," Trends Biochem Sci, Dec. 1997, 22:460-461.
Matsuoka et al., "Tissue-specific light-regulated expression directed by the promoter of a C4 gene, maize pyruvate, orthophosphate dikinase, in a C3 plant, rice," Proc. Natl. Acad. Sci. USA, Oct. 1993, 90:9586-9590.
Matzke and Birchler, "RNAi-Mediated Pathways in the Nucleus," Nature Reviews Genetics, Jan. 2005, 6:24-35.
McCallum et al., "Targeted screening for induced mutations," Nature Biotechnology, Apr. 2000, 18: 455-457.
Medberry et al., "The Commelina Yellow Mottle Virus Promoter Is a Strong Promoter in Vascular and Reproductive Tissues," The Plant Cell, Feb. 1992, 4(2):185-192.
Meier et al., "Elicitor-Inducible and Constitutive in Vivo DNA Footprints Indicate Novel cis-Acting Elements in the Promoter of a Parsley Gene Encoding Pathogenesis-Related Protein 1," The Plant Cell, Mar. 1991, 3:309-316.
Mittal, "Improving the Efficiency of RNA Interference in Mammals," Nature Reviews Genetics, May 2004, 5:355-365.
Nature.Com, "Nature Reviews RNA interference collection," Oct. 2005, [retrieved on Apr. 12, 2012]. Retrieved from Internet: URL http://www.nature.com/focus/rnai/index.html. 2 pages.
Paulsen and Skurray, "The POT family of transport proteins," Trends Biochem Sci, 1994, 19:404-404.
Pellegrini et al., "Structure of serum response factor core bound to DNA," Nature, 1995, 376:490-8.
Perriman et al., "Effective ribozyme delivery in plant cells," Proc. Natl. Acad. Sci. USA, Jun. 1995, 92(13):6175-6179.
Raetz and Whitfield, "Lipopolysaccharide Endotoxins," Annu Rev Biochem., 2002, 71:635-700.
Rhoads and Friedberg, "Sequence motifs for calmodulin recognition," FASEB J., 1997, 11(5):331-40.
Riggs et al., "Cotyledon Nuclear Proteins Bind to DNA Fragments Harboring Regulatory Elements of Phytohemagglutinin Genes," The Plant Cell, Jun. 1989, 1(6):609-621.
Rivera et al., "Genomic evidence for two functionally distinct gene classes," Proc. Natl. Acad. Sci. USA, May 1998, 95:6239-6244.
Roach et al., "Crystal structure of isopenicillin N synthase is the first from a new structural family of enzymes," Nature, 1995, 375:700-704.
Roudier et al., "COBRA, an Arabidopsis Extracellular Glycosyl-Phosphatidyl Inositol-Anchored Protein, Specifically Controls Highly Anisotropic Expansion through Its Involvement in Cellulose Microfibril Orientation," The Plant Cell, Jun. 2005, 17(6):1749-63.
Sheridan et al., "The macl Gene: Controlling the Commitment to the Meiotic Pathway in Maize," Genetics, 1996, 142:1009-1020.
Shibuya et al., "RNA-directed DNA methylation induces transcriptional activation in plants," Proc Natl Acad Sci USA, Feb. 2009,106(5):1660-1665.
Shimofurutani et al., "Functional analyses of the Dof domain, a zinc finger DNA-binding domain, in a pumpkin DNA-binding protein AOBP," FEBS Letters, 1998, 430:251-256.
Slocombe et al., "Temporal and Tissue-Specific Regulation of a Brassica napus Stearoyl-Acyl Carrier Protein Desaturase Gene," Plant Physiol., 1994, 104(4):167-176.
Sonnhammer et al., "Pfam: A Comprehensive Database of Protein Domain Families Based on Seed Alignments," Proteins, 1997, 28:405-420.
Sonnhammer et al., "Pfam: multiple sequence alignments and HMM-profiles of protein domains," Nucl. Acids Res., 1998, 26:320-322.
Stemple, "TILLING—a high-throughput harvest for functional genomics," Nat Rev Genet, Feb. 2004, 5(2):145-50.
Strayer et al., "Cloning of the Arabidopsis Clock Gene TOC1, an Autoregulatory Response Regulator Homolog," Science, 2000, 289:768-771.
Summerton and Weller, "Morpholino Antisense Oligomers: Design, Preparation, and Properties," Antisense Nucleic Acid Drug Dev., 1997, 7:187-195.
Tovkach et al., "A toolbox and procedural notes for characterizing novel zinc finger nucleases for genome editing in plant cells," The Plant Journal, 2009, 57:747-757.
Townsend et al., "High-frequency modification of plant genes using engineered zinc-finger nucleases," Nature, May 2009, 459:442-445.
Truernit et al., "The promoter of the Arabidopsis thaliana SUC2 sucrose-H+ symporter gene directs expression of B-glucuronidase to the phloem: Evidence for phloem loading and unloading by SUC2," Planta, 1995, 196:564-570.
Refseth et al., "Hybridization capture of microsatellites directly from genomic DNA," Electrophoresis, 1997, 18: 1519-1523.
Urao et al, "Molecular cloning and characterization of a gene that encodes a MYC-related protein in Arabidopsis," Plant Mol. Biol., 1996, 32:571-57.
Weigel et al., "Activation Tagging in Arabidopsis," Plant Physiology, Apr. 2000, 122:1003-1013.
Yamamoto et al., "The Promoter of a Pine Photosynthetic Gene Allows Expression of a B-Glucuronidase Reporter Gene in Transgenic Rice Plants in a Light-Independent but Tissue-Specific Manner," Plant Cell Physiol., 1994, 35:773-778.
Yan et al., "New Construct Approaches for Efficient Gene Silencing in Plants," Plant Physiol., Aug. 2006, 141:1508-1518.
Zhang et al., "DNA Sequences That Activate Isocitrate Lyase Gene Expression during Late Embryogenesis and during Postgerminative Growth," Plant Physiology, 1996, 110:1069-1079.
Zhang et al., "From Laboratory to Field. Using Information from Arabidopsis to Engineer Salt, Cold, and Drought Tolerance in Crops," Plant Physiol., Jun. 2004, 135:612-621.
Zheng et al., "SPK1 Is an Essential S-Phase-Specific Gene of *Saccharomyces cerevisiae* That Encodes a Nuclear Serine/Threonine/Tyrosine Kinase," Mol. Cell Biol., Sep. 1993, 13:5829-5842.

* cited by examiner

| | | |
|---|---|---|
| SEQ_ID_NO_253 | T | 485 |
| SEQ_ID_NO_255 | S | 484 |
| SEQ_ID_NO_257 | R | 482 |
| SEQ_ID_NO_258 | . | 476 |
| SEQ_ID_NO_260 | D K | 480 |
| SEQ_ID_NO_261 | H | 483 |
| SEQ_ID_NO_262 | A | 485 |
| SEQ_ID_NO_264 | E | 483 |
| SEQ_ID_NO_265 | Y | 481 |
| SEQ_ID_NO_267 | K | 485 |
| SEQ_ID_NO_268 | D | 479 |
| SEQ_ID_NO_269 | K | 483 |
| SEQ_ID_NO_270 | | 491 |

| SEQ_ID_NO_1541 | ADHSRSQGFR | FDTQAQALLA | NAPLSY | 308 |
| SEQ_ID_NO_1542 | ADHSRSQGFK | YDTQAQALLA | NAPAGY | 309 |
| SEQ_ID_NO_1544 | ADHSRSQGFK | YDTQAQALLA | NAPAGY | 310 |
| SEQ_ID_NO_1545 | ADHSRSQGFK | YETESQALLA | NATSY | 307 |
| SEQ_ID_NO_1547 | ADHSRNQGFK | YETQSQALLT | DATTY | 314 |
| SEQ_ID_NO_1548 | ADDSKADGFR | YEKEAQEVLA | SF----PN | 304 |
| SEQ_ID_NO_1550 | ADDSKANGFS | YEKQSQDLLV | T----AN | 308 |
| SEQ_ID_NO_1552 | ADDSKAQGFR | YEKQSQALLA | I----PH | 301 |
| SEQ_ID_NO_1553 | ADMSKANGFK | YELESQDLLA | -----S | 280 |
| SEQ_ID_NO_1555 | ADDSKADGFL | YEKQFQEIL | -----D | 301 |

| SEQ_ID | | | | | | | | | |
|---|---|---|---|---|---|---|---|---|---|
| SEQ_ID_NO_663 | PFLNDVKPRV | LLVTGSSPKP | CENPVGDHYL | LKSIKNKIDY | CRVHGI EIFY | 180 |
| SEQ_ID_NO_665 | PFLNDIKPRV | LLVTGSSPKP | CENPVGDHYL | LKSIKNKMDY | CRVHGI EVFY | 180 |
| SEQ_ID_NO_667 | PFLNDIKPRV | LLVTGSAPKP | CENPVGDHYL | LKSIKNKMDY | CRVHGI EVFY | 181 |
| SEQ_ID_NO_668 | PFVNDVKPRV | LLVTGSSPKP | CENPVGDHYL | LKSIKNKIDY | CRLHGLEIFY | 181 |
| SEQ_ID_NO_669 | NFIGPNKPRV | LLVTGSSPKP | CENPVGDHYL | LKSIKNKIDY | CRLHGI EIFY | 192 |
| SEQ_ID_NO_670 | NFIGPNKPRV | LLVTGSSPKP | CENPVGDHYL | LKSIKNKIDY | CRLHGI EIFY | 185 |
| SEQ_ID_NO_672 | NFIGANKPRV | LLVTGSSPKP | CENPVGDHYL | LKSIKNKIDY | CRLHGI EIFY | 192 |
| SEQ_ID_NO_674 | NFIGPNKPRV | LLVTGSSPKP | CENPVGDHYL | LKSIKNKIDY | CRLHGI EIFY | 192 |
| SEQ_ID_NO_675 | NFVAPNKPRV | LLVTGSSPKP | CENPVGDHYL | LKSIKNKIDY | CRLHGI EIFY | 193 |

| SEQ_ID | | | | | | | | | |
|---|---|---|---|---|---|---|---|---|---|
| SEQ_ID_NO_663 | NMALLDAEMA | GFWAKLPLIR | ALLLAHPEVE | FLVWMDSDAM | FTDMAFELPW | 230 |
| SEQ_ID_NO_665 | NMALLDAEMA | GFWAKLPLLR | ALLLAHPEFE | FIVWMDSDAM | FTDMAFELPW | 230 |
| SEQ_ID_NO_667 | NMALLDAEMA | GFWAKLPLMR | ALLLAHPEVE | FLVWMDSDAM | FTDMAFELPW | 231 |
| SEQ_ID_NO_668 | NMALLDAEMA | GFWAKLPLIR | ALLLAHPEVE | FLVWMDSDAM | FSDMAFELPW | 231 |
| SEQ_ID_NO_669 | NMALLDAEMA | GFWAKLPLIR | ALLLAHPEIE | FLVWMDSDAM | FTDMAFELPW | 242 |
| SEQ_ID_NO_670 | NMALLDAEMA | GFWAKLPLIR | KLLLSHPEVE | FLVWMDSDAM | FTDMAFEVPW | 235 |
| SEQ_ID_NO_672 | NMALLDAEMA | GFWAKLPLIR | KLLISHPEVE | FLVWMDSDAM | FTDMAFELPW | 242 |
| SEQ_ID_NO_674 | NMALLDAEMA | GFWAKLPLIR | KLLLSHPEVE | FLVWMDSDAM | FTDMAFEVPW | 242 |
| SEQ_ID_NO_675 | NFALLDAEMS | GFWAKLPLIR | KLLLSHPEVE | FLVWMDSDAM | FTDMAFELPW | 243 |

| SEQ_ID | | | | | | | | | |
|---|---|---|---|---|---|---|---|---|---|
| SEQ_ID_NO_663 | ERYGPYNLVM | HGWDEMVYDD | KNWGLNTGS | FLLRNCQWSL | DMLDTWAPMG | 280 |
| SEQ_ID_NO_665 | ERYGPYNLIM | HGWDEMVYDD | KNWGLNTGS | FLLRNCQWSL | DMLDTWAPMG | 280 |
| SEQ_ID_NO_667 | ERYGPYNLIM | HGWDEMVYDD | KNWGLNTGS | FLLRNCQWSL | DMLDTWAPMG | 281 |
| SEQ_ID_NO_668 | ERYGPYNLVM | HGWDEMVYDD | KNWGLNTGS | FLLRNCQWSL | DELDTWAPMG | 281 |
| SEQ_ID_NO_669 | ERYKDYNLVM | HGWNEMVYDQ | KNWGLNTGS | FLLRNQWAL | DLDTWAPMG | 292 |
| SEQ_ID_NO_670 | ERYKDSNFVM | HGWNEMVYDQ | KNWGLNTGS | FLLRNCQWSL | DILDAWAPMG | 285 |
| SEQ_ID_NO_672 | ERYKDSNFVM | HGWNEMVYDQ | KNWGLNTGS | FLLRNGQWSL | DILDAWAPMG | 292 |
| SEQ_ID_NO_674 | ERYKDSNFVM | HGWNEMVYDQ | KNWGLNTGS | FLLRNCQWSL | DLLDAWSPMG | 292 |
| SEQ_ID_NO_675 | ERYKDHNFVM | HGWNEMVYDQ | RNWGLNTGS | FLLRNCQWSL | DILDTWAPMG | 293 |

FIG. 7C

| SEQ ID NO | Sequence | Position |
|---|---|---|
| SEQ_ID_NO_663 | PKGPVRIEAG KVLTKSLKDR PVFEADDQSA MVYILATQRE KWGDKVYYLEN | 330 |
| SEQ_ID_NO_665 | PKGPVRIEAG KVLTKSLKDR PVFEADDQSA MVYILATQRE KWGDKVYYLEN | 330 |
| SEQ_ID_NO_667 | PKGPVRIEAG KVLTKSLKDR PVFEADDQSA MVYILATQRE KWGDKVYYLEN | 331 |
| SEQ_ID_NO_668 | PKGPVRIEAG KVLTKYLKDR PVFEADDQSA MVYILATQRE KWGDKVYYLEN | 331 |
| SEQ_ID_NO_669 | PKGKIREEAG KVLTRELKDR PVFEADDQSA MVYILATERE AMGNKVYYLES | 342 |
| SEQ_ID_NO_670 | RTEAG KILTRELKDR PVFEADDQSA MVYLLATQRD TWGGKVYYLES | 335 |
| SEQ_ID_NO_672 | PKGKIREEAG KVLTRELKNR PVFEADDQSA MVYLLATQRE KWGDKVYYLEN | 342 |
| SEQ_ID_NO_674 | PKGKIRDEAG KVLTRELKDR PVFEADDQSA MVYLLATQRD KWGDKVYYLEN | 342 |
| SEQ_ID_NO_675 | PKGKIRDEAG ELLTRELKDR PVFEADDQSA MVYILTTQRE KWAGKVYLES | 343 |

| SEQ ID NO | Sequence | Position |
|---|---|---|
| SEQ_ID_NO_663 | GYYLHGYWGI LVDRYEEMLE NYKPGLGDHR WPLVTHFVGC KPCGKFGDYP | 380 |
| SEQ_ID_NO_665 | GYYLHGYWGI LVDRYEEMLE NYKPGLGDHR WPLVTHFVGC KPCGKFGDYP | 380 |
| SEQ_ID_NO_667 | GYYLHGYWGI LVDRYEEMLE NYKPGLGDHR WPLVTHFVGC KPCGKFGDYP | 381 |
| SEQ_ID_NO_668 | GYYLHGYWGI LVDRYEEMLE NYHPGLGDHR WPLVTHFVGC KPCGKFGDYP | 381 |
| SEQ_ID_NO_669 | AYYLHGYWGI LVDRYEEMIE NYHPGLGDHR WPLVTHFVGC KPCGKFGDYP | 392 |
| SEQ_ID_NO_670 | SYYLHGYWGI LVDRYEEMIE NYHPGLGDHR WPLVTHFVGC KPCGKFGDYP | 385 |
| SEQ_ID_NO_672 | AYYLHGYWGI LVDRYEEMIE NYHPGLGDHR WPLVTHFVGC KPCGKFGDYS | 392 |
| SEQ_ID_NO_674 | AYYLHGYWGI LVDRYEEMIE NYHPGLGDHR WPLVTHFVGC KPCGKFGDYS | 392 |
| SEQ_ID_NO_675 | AYYLHGYWGI LVDRYEEMIE NYHPGLGDHR WPLVTHFVGC KPCGKFGDYS | 393 |

| SEQ ID NO | Sequence | Position |
|---|---|---|
| SEQ_ID_NO_663 | VERCLKQMDR AFNFGDNQIL QMYGFTHKSL ASRRVKRIRN ETSNPLEMKD | 430 |
| SEQ_ID_NO_665 | VERCLKNMDR AFNFGDNQIL QMYGFTHKSL ASRRVKRIRN ETSNPLETKD | 430 |
| SEQ_ID_NO_667 | VERCLKNMDR AFNFGDNQIL QMYGFTHKSL ASRRVKRIRN ETSNPLETKD | 431 |
| SEQ_ID_NO_668 | VERCLKQMER AFNFGDNQIL QIYGFTHKSL GSRKVKRIRN ETSNPLDVKD | 431 |
| SEQ_ID_NO_669 | VERCLKQMDR AFNFGDNQIL QIYGFTHKSL ASRKVKRVRN DTNNPLEMKD | 442 |
| SEQ_ID_NO_670 | VERCLKQMER AFNFGDNQVL QIYGFTHKSL GSRRVKRTRN ETSNPLEVKD | 435 |
| SEQ_ID_NO_672 | VERCLKQMDR AFNFGDNQIL QIYGFTHKSL ASRKVKRVRN ETGNPLEAKD | 442 |
| SEQ_ID_NO_674 | VERCLKQMDR AHNFADNQIL QIYGFTHKSL ASRKVKRVRN ETGNPLEAKD | 442 |
| SEQ_ID_NO_675 | VERCLKQMDR AFNFGDNQIL QMYGFTHKSL ASRKVKRTRN ETSNPLEVQD | 443 |

| | | | | |
|---|---|---|---|---|
| SEQ_ID_NO_663 | ELGLLHPAFK | AVKT- - | ST | 446 |
| SEQ_ID_NO_665 | ELGLLHPAFK | AVKT- - | ST | 446 |
| SEQ_ID_NO_667 | ELGLLHPAFK | AVKT- - | ST | 447 |
| SEQ_ID_NO_668 | ELGLLHPAFK | AMKTT- | ST | 448 |
| SEQ_ID_NO_669 | ELGLLHPAFK | AVKVQT | NQV | 461 |
| SEQ_ID_NO_670 | ELGLLHPAFK | AVKVS- | SS | 452 |
| SEQ_ID_NO_672 | ELGLLHPAFK | AVKVS- | SS | 459 |
| SEQ_ID_NO_674 | ELGLLHPAFK | AVKVS- | AS | 459 |
| SEQ_ID_NO_675 | ELGLLHPAFK | AVKVS- | AS | 460 |

| | | | |
|---|---|---|---|
| SEQ_ID_NO_1366 | VNRTLQEAKS | SSNTCRQ | 425 |
| SEQ_ID_NO_1368 | VNRTLEEAKS | GSNSCRR | 421 |
| SEQ_ID_NO_1370 | VNRTLEEAKS | SSNSCRR | 421 |
| SEQ_ID_NO_1371 | NRALEGGEF | GSKSCRR | 406 |
| SEQ_ID_NO_1372 | VTNLLEGSNS | QSNQC-K | 409 |
| SEQ_ID_NO_1374 | KNLLDEWNS | QMNQC-K | 398 |
| SEQ_ID_NO_1375 | TNELDDLNS | QSNQC-K | 395 |
| SEQ_ID_NO_1377 | SSLLSNEKF | RPRQC-V | 421 |
| SEQ_ID_NO_1378 | VTSLLSEEKF | HPRQC-K | 425 |

| | | | |
|---|---|---|---|
| SEQ_ID_NO_928 | SAL F L L A L L | L A P | 445 |
| SEQ_ID_NO_930 | -AASAF L L A L | L V A | 446 |
| SEQ_ID_NO_932 | -AASAF L L L L | L V A | 450 |
| SEQ_ID_NO_933 | -AASAI L V V L | L V A | 441 |
| SEQ_ID_NO_935 | ST C L V L L L L | L A A | 449 |
| SEQ_ID_NO_936 | -AAS L L L L L L | S M G | 453 |
| SEQ_ID_NO_937 | L A L L L L L M I | S I W | 440 |
| SEQ_ID_NO_938 | AAP L L L M L L | Y T I W | 462 |
| SEQ_ID_NO_940 | L F T I L L L L F | S I W | 431 |
| SEQ_ID_NO_941 | V F I T M L V M | A L W | 463 |
| SEQ_ID_NO_943 | AFM L L F F L | A V W | 431 |
| SEQ_ID_NO_944 | F I SSV I F L L | V T V W | 460 |

| SEQ_ID_NO | | | | | | |
|---|---|---|---|---|---|---|
| SEQ_ID_NO_1215 | LSRVYPSIAV | GKDAHLYVFN | NGEADIKVSH | LTAWEMKKPL | MNGAEVTDG | 586 |
| SEQ_ID_NO_1217 | LSRVYPSIAI | GKEAHLYVFN | NGDVDVKVSS | LTAWEMKKPL | MN------- | 579 |
| SEQ_ID_NO_1218 | LSRVYPSIAV | GKDAHLYVFN | NGEVDVTVSG | LTAWEMKKPL | MN------- | 588 |
| SEQ_ID_NO_1219 | LSRVYPSIAV | GQNAHLYVFN | NGEADIKVSH | LTAWEMKKPL | MN------- | 574 |
| SEQ_ID_NO_1220 | LSRVYPSMAI | GDKAHLYVFN | NGEADIKISH | LKAWEMKKPL | MN------- | 575 |
| SEQ_ID_NO_1221 | LSRVYPSMAL | GKDAHLYVFN | NGETDIKVSK | LTAWEMKRPL | MN------- | 581 |
| SEQ_ID_NO_1223 | LSRVYPSMAL | GKDNARLHVFN | NGVTDIKVSV | LTAWEMKKPA | MN------- | 579 |
| SEQ_ID_NO_1224 | LSRVYPTLAL | GKNARLHVFN | NGKVDIKVSE | LKAWEIRRPL | LMN------ | 566 |
| SEQ_ID_NO_1225 | LSRVYPSLAV | YENAHLYVFN | NGSADVKVSE | LDAWSMKKPL | MN------- | 584 |
| SEQ_ID_NO_1226 | SSRVYPTLAV | EEKAHLFVFN | NGSETITVEN | LDAWSMKMPV | R-------- | 590 |
| SEQ_ID_NO_1227 | TSRVYPTLAV | SKKAHLYAFN | NGSETVTVES | LNAWTMHRPQ | MNVP----- | 581 |
| SEQ_ID_NO_1228 | TSRVYPTLAI | NDEAHLFAFN | NGTEAVTIKK | LDAWSMGKAK | MN------- | 572 |
| SEQ_ID_NO_1230 | TSRVYPTLAI | FDKAHLFAFN | NGTEPVTIES | LNAWSMADAK | IQ------- | 582 |
| SEQ_ID_NO_1231 | TSRVYPTLAI | GEKAHLFVFN | NGTEAITIET | LNAVSMADAK | L-------- | 579 |
| SEQ_ID_NO_1233 | TSRVYPTKAV | | NGSQPVTVES | LNAVMQKPL | KMNQ----- | 587 |

| SEQ_ID_NO | | | |
|---|---|---|---|
| SEQ_ID_NO_1215 | NDVWEMKKLL | VMNGA | 601 |
| SEQ_ID_NO_1217 | | GA | 581 |
| SEQ_ID_NO_1218 | | GA | 590 |
| SEQ_ID_NO_1219 | | GA | 576 |
| SEQ_ID_NO_1220 | | GA | 577 |
| SEQ_ID_NO_1221 | | GA | 583 |
| SEQ_ID_NO_1223 | | GA | 581 |
| SEQ_ID_NO_1224 | | GA | 568 |
| SEQ_ID_NO_1225 | | GS | 586 |
| SEQ_ID_NO_1226 | | MN | 592 |
| SEQ_ID_NO_1227 | | VKS | 584 |
| SEQ_ID_NO_1228 | | Y | 572 |
| SEQ_ID_NO_1230 | | H | 583 |
| SEQ_ID_NO_1231 | | | 580 |
| SEQ_ID_NO_1233 | | GAK | 590 |

| | | | | | | |
|---|---|---|---|---|---|---|
| SEQ_ID_NO_580 | GVSAKDWPSV | AKKGKVDMME | LELKKLEETI | KNIHEEMFYL | REREEEMQDL | 189 |
| SEQ_ID_NO_582 | GVSAKDYPSV | AKKGKVDMME | LELKKLEETI | KNIHEEMFYL | REREEEMQDL | 189 |
| SEQ_ID_NO_584 | GVSAKDYPSV | AKKGKVDMME | LELKKLEETI | RNIHEEMFYL | REREEEMQDL | 189 |
| SEQ_ID_NO_585 | GVAAKDWSNV | AKKGQVDMME | LELKKLEETI | KSIHEEMFYL | REREEQMQNI | 190 |
| SEQ_ID_NO_587 | GVTAKDWSNV | AKKGKVDVME | MELKKLEDTI | TSIQEEMNYL | REREEDMQDL | 188 |
| SEQ_ID_NO_589 | GVAAKDWSNV | AKKGQVDMME | MELKKMYDTV | TSIHEEMFYL | REREEEMQEL | 176 |
| SEQ_ID_NO_591 | GVAAKDWSNV | AKKGQVEVME | LELKKLQDTV | TSIHEEMFYL | REREEEMQEL | 181 |
| SEQ_ID_NO_592 | GVAAKDWSKV | AKKGQVEVME | LELRKLEETV | NSIHEEMFYL | REREEEMQNL | 170 |
| SEQ_ID_NO_594 | GVQSKSMSSV | AKKSQVEVME | FDVKRLYDTV | TSIHDEMYL | REREEEMQEL | 174 |
| SEQ_ID_NO_595 | GVEAKDWTKI | AKRDKIDGME | LELRKLEEYM | LFLHDEMFYL | RAREEEMQDL | 188 |
| SEQ_ID_NO_596 | GVAAKDWYKI | AKKDQIDVME | SELQRLYDTV | KIFFERKKLL | RGREEEMQDL | 172 |
| SEQ_ID_NO_580 | NRRTNSRMAW | LGFLSLGICL | SVAGLQLWHL | KTFFERKKLL | | 229 |
| SEQ_ID_NO_582 | NRRTNSRMAW | LGFLSLGICL | SVAGLQLWHL | KTFFERKKLL | | 229 |
| SEQ_ID_NO_584 | NRRTNSRMAW | LGFLSLGICL | SVAGLQLWHL | KTFFERKKLL | | 229 |
| SEQ_ID_NO_585 | NKQTNSRMAW | SFLSLGICL | SVAGLQLWHL | KTFFQKKKLI | | 230 |
| SEQ_ID_NO_587 | NRQTNSRMGW | SFLSIIVCL | SVAGLQVWHL | KTFFERKKLI | | 228 |
| SEQ_ID_NO_589 | NTSTNVKMAW | SLLSLFVCL | SVAGMQLWHL | KTFFERKKLL | | 216 |
| SEQ_ID_NO_591 | NRTTNSRMFW | SFLSLFVCL | SVAGMQLWHL | KTFFERKKLL | | 221 |
| SEQ_ID_NO_592 | NRATNSKMAT | SFLSLLVCL | SVAGMQFVHL | KTFFERKKVI | | 210 |
| SEQ_ID_NO_594 | NASTNSKMAW | FGLMSFLVCL | SVAAGMQLWHL | KSFFEKKKVI | | 214 |
| SEQ_ID_NO_595 | NREITDRRMFT | EFCSIICL | SVAGMQLWHL | KIFFERKKLL | | 228 |
| SEQ_ID_NO_596 | | | | | | 212 |

| | | | | | | | |
|---|---|---|---|---|---|---|---|
| SEQ_ID_NO_154 | MPFTPGPYSG | VSTLALVARA | SAFGVGVVYG | SIKLSILKAT | - -K- -PL | KKEEE | 46 |
| SEQ_ID_NO_156 | MPFTPGPYSG | VSTLALVARA | SAFSVGVVYG | SIKLSILKAT | - -K- -PL | KKEEE | 46 |
| SEQ_ID_NO_158 | MPFTPGPYSG | VSTLALVARA | SMFGFGVVYG | SIKLSILKAT | - -K- -PL | KKEEE | 46 |
| SEQ_ID_NO_159 | MPFTPGPYSG | VSTLALVARV | SALGVGVVYG | AVKLSILKAT | - -K- -PL | PNKKEA | 47 |
| SEQ_ID_NO_161 | MPFTPGPYSG | KSTLALVARA | SAVGVGVVYG | SVKLGLKMT | - -K- -PL | KKEEA | 46 |
| SEQ_ID_NO_163 | MAL-PGPYSG | VSTLAEVARA | SAFAFGVVYG | SVKLSYLQVK | AKF- -H- | KKEEE | 47 |
| SEQ_ID_NO_165 | MTLPPGPYSG | ASALALVARA | SAFSFGLVYG | SVKLKILKMK | ANS- -H- | KKAE | 48 |
| SEQ_ID_NO_167 | MAIPPGLYSG | TSSLALVARA | SAFSVGLLYG | SMKLKVLKMT | - -KKP- | HKVE | 47 |
| SEQ_ID_NO_168 | MAPPPGPYSG | TSTLALVARV | SAFSAGLVYG | SIKLKYLKSK | AKS-Q- | KKAE | 48 |

| | | |
|---|---|---|
| SEQ_ID_NO_154 | AHAHH | 51 |
| SEQ_ID_NO_156 | AHAHH | 51 |
| SEQ_ID_NO_158 | AHAHH | 51 |
| SEQ_ID_NO_159 | ANAHH | 52 |
| SEQ_ID_NO_161 | AAAHH | 51 |
| SEQ_ID_NO_163 | AKGHH | 52 |
| SEQ_ID_NO_165 | AKAHH | 53 |
| SEQ_ID_NO_167 | ATAHH | 52 |
| SEQ_ID_NO_168 | AKSHH | 53 |

| | | | | |
|---|---|---|---|---|
| SEQ_ID_NO_187 | QEI TAASPEF | VSSVRDLSLS | C RLD | 286 |
| SEQ_ID_NO_188 | - - - SVAGESR | - - - - - - - - - - | VLPAI | 217 |
| SEQ_ID_NO_190 | - - - SAAAEER | - - - - - - - - - - | - SSGE | 163 |
| SEQ_ID_NO_192 | - - - - - - - - - - | - - - - - - - - - - | - - - - - | 151 |

| SEQ_ID_NO | | | | | | |
|---|---|---|---|---|---|---|
| SEQ_ID_NO_1592 | | | | MYCSDPPHPL | HLVASDKQQK | DHKLIILSWKK | ::MDPNTPAD | 8 |
| SEQ_ID_NO_1580 | | | | | | | PTMDSDPLGV | 40 |
| SEQ_ID_NO_2622 | | | | | | | ::MDSDQHGV | 8 |
| SEQ_ID_NO_1585 | | | | | | | ::MDSNSSEY | 8 |
| SEQ_ID_NO_2621 | | | | | | | ::MESNTSRF | 8 |
| SEQ_ID_NO_2623 | | | | | | | ::MDSNASGF | 8 |

| SEQ_ID_NO_1592 | FFKGSS | KFHT | --KKG | GGVI DLGLSL | RTI QHETYLP | 46 |
| SEQ_ID_NO_1580 | FPNLSP | KYHP | YYSQT--TEF | GGVI DLGLSL | RTI QHELYHS | 77 |
| SEQ_ID_NO_2622 | FPSLSP | KYHP | YYPQN--TEC | GGVI DLGLSL | RTI QHELYHT | 45 |
| SEQ_ID_NO_1585 | LLNHAT | TLPS | VYQTNNKEN | GNFI DLGLSL | RALQPEAYYP | 48 |
| SEQ_ID_NO_2621 | LLN-SS | TLHS | VFYQE--KQD | DGII DLGLSL | GTVRHEAYHS | 45 |
| SEQ_ID_NO_2623 | LLN-PP | ALHS | TYYQP--RED | DGII DLGLSL | RTLKPEAYHP | 45 |

| SEQ_ID_NO_1592 | PARMI GLDGY | GELIDWSQPS | YNSI TQLKSE | DTGHQRLAQG | 86 |
| SEQ_ID_NO_1580 | SGQR- | | | | 81 |
| SEQ_ID_NO_2622 | SGQK- | | | | 49 |
| SEQ_ID_NO_1585 | STHG------GY | DELIDWQHLH | PQLSKNSRSE | YPTNFN--NY | 82 |
| SEQ_ID_NO_2621 | SIANL-----YD | EELMDWPHSN | LNLKNSRTMH | SRSVHQ--NF | 79 |
| SEQ_ID_NO_2623 | SGHR- | | | | 49 |

| SEQ_ID_NO_1592 | YYNNEGLESR | GKYAYVKVNL | DGLVVGRKVC | LVDQGAYATL | 125 |
| SEQ_ID_NO_1580 | YCSNEGY--R | RKWGYVKVTM | DGLVVGRKVC | VLDHGSYSTL | 119 |
| SEQ_ID_NO_2622 | YCSNEGY--R | RNMGYVKVTM | DGFVVGRKVC | MLDHGYSTL | 87 |
| SEQ_ID_NO_1585 | DDESEGI QSK | ERWEYVKVNM | DGVIVGRKIC | LLEHSSYSSL | 122 |
| SEQ_ID_NO_2621 | DEEIEGVQSN | ERWAYVKVNM | DGVTIGRKIC | VLDHGGYSSL | 119 |
| SEQ_ID_NO_2623 | MPLAEGVQSK | DRWAYVKVNM | DGVIVGRKIC | MLDHGGYSSL | 89 |

| SEQ_ID_NO_1592 | ALQLNDMFGM | QTVSGLRLFQ | TESEFSLVYR | DREGIWRNVG | 165 |
| --- | --- | --- | --- | --- | --- |
| SEQ_ID_NO_1580 | AHQLEDMFGM | QSVSGLRLFQ | MESEFCLVYR | DEEGLWRNAG | 159 |
| SEQ_ID_NO_2622 | AHQLEDMFGM | QSVSGLRLFQ | MESEFCLVYR | DEEGIWRNVG | 127 |
| SEQ_ID_NO_1585 | ATQLEDMFGK | QNMDGLRLFQ | DGSEFSLFYK | DRNDQWRIVG | 162 |
| SEQ_ID_NO_2621 | ALQLEDMFGS | QSVSGLRLFQ | SGSEYSLFYK | DRQDNWRPVG | 159 |
| SEQ_ID_NO_2623 | ALQLEDMFGR | QSASGLRLFQ | AGSEFCLFYK | DREENWRITVG | 129 |

| SEQ_ID_NO_1592 | DVPWKEFVES | VDRMRIARRN | DALLPF---- | ---- | 191 |
| --- | --- | --- | --- | --- | --- |
| SEQ_ID_NO_1580 | DVPWNEFIES | VERLRITRRN | DAVLPF---- | ---- | 185 |
| SEQ_ID_NO_2622 | DVPWNEFIET | VERLRITRRN | DVLLPF---- | ---- | 153 |
| SEQ_ID_NO_1585 | DVPWNEFADR | VKRLRIMRKD | EAFFPN---- | ---T | 188 |
| SEQ_ID_NO_2621 | DVPWNEFIEC | VKRLRIARKN | SGIVSYSSRC | ---S | 190 |
| SEQ_ID_NO_2623 | DVPWKEFVES | VKRLRIARKS | EPLLPYSPAF | | 160 |

| | | | | | | |
|---|---|---|---|---|---|---|
| SEQ_ID_NO_851 | : : : : : : : : SKVEK TPEKE KE : : : : : : : : : : : : : : : : : : : : : : : : : : : : : : : : | | | | | 145 |
| SEQ_ID_NO_853 | ENVKP TPNPT : : : : : : : : : : : : : : : : : : : : : : : : : : : : : : : : : : : : : : : : : : | | | | | 209 |
| SEQ_ID_NO_854 | : : : : : : : : : : : : : : : : : : : : : : : : : : : : : : : : : : : : : : : : : : : : : : : : : | | | | | 174 |
| SEQ_ID_NO_856 | : : : : : : : : : : : : : : : : : : : : : : : : : : : : : : : : : : : : : : : : : : : : : : : : : | | | | | 78 |
| SEQ_ID_NO_857 | AKIEA EPEAK KEETVLEVVE KIATSTEEDG AKTVEAI QES IVSVTVTDGE | | | | | 242 |

| | | | | | | |
|---|---|---|---|---|---|---|
| SEQ_ID_NO_851 | : : : : : : : : : : | : : : : : : : : : : | : : : : : : : : : : | TPEEVKI WG | PLLEDDRSD | VVLLKFLRAR | 174 |
| SEQ_ID_NO_853 | QE | VAKEE QKVAS | SSPEEVPI | PLLKDDRSD | VVLLKFLRAR | | 251 |
| SEQ_ID_NO_854 | ES | LLKHE | PLQEDVSI WG | PLLKDERSD | MILLKFLRAR | | 212 |
| SEQ_ID_NO_856 | : : : : : : : : : : | : : : : : : : : : : | EEVSI WG | VPLF KDDRTD | VILLKFLRAR | | 105 |
| SEQ_ID_NO_857 | QPVTETVGEA | VAVAE MEVTP | TTPEEVEI WG | PLLIA DERSD | VILLKFLRAR | | 292 |

| | | | | | | |
|---|---|---|---|---|---|---|
| SEQ_ID_NO_851 | EFKVKDSFAM | LKNTI KWRKE | FKI DELVEED | LMDDLDKVVF | MHGHDREGHP | | 224 |
| SEQ_ID_NO_853 | DFKVRDAFVM | IKNTI QWRRD | FKI DELVDED | LGDDLEKVVF | MHGYDREGHP | | 301 |
| SEQ_ID_NO_854 | EFKVKEAFAM | LKNTI FMRKE | FGI DALVDDD | LGEHLEKVVF | MHGFDRDGHP | | 262 |
| SEQ_ID_NO_856 | ELKVKDALVM | FQNTL RWRKD | DALLDED | LGDHLEKVVF | MHGHGREGHP | | 155 |
| SEQ_ID_NO_857 | DFKVKEAYTM | KQTVI WRKE | FGI EALLQED | LGTDMDKVVF | TDGYDKEGHP | | 342 |

| | | | | | | |
|---|---|---|---|---|---|---|
| SEQ_ID_NO_851 | VCYNVYGEFQ | NKELYNKTFS | DEEEKRKHFLR | TRI QFLERSI | RKLDFSS- GG | | 273 |
| SEQ_ID_NO_853 | VCYNVYGEFQ | NKELYQKTFS | DEEEKRLKFLR | WRI QFLERSI | RKLDFSPI GG | | 350 |
| SEQ_ID_NO_854 | VCYNVVGEFQ | NKELYQKTFS | DEEEKRMKFLR | WRI QFLERSI | RKLDFTPI GG | | 311 |
| SEQ_ID_NO_856 | VCYNVYGEFQ | NKDLYHIKAFS | SQDNRNKFLR | WRI QLLERSI | RHLDFTPSSG | | 205 |
| SEQ_ID_NO_857 | VYYNVF GEFE | NKELYQNTFS | DDEEKRTKFI R | WRI QSLEKSI | RKLDFTPI SG | | 391 |

| | | | | | | |
|---|---|---|---|---|---|---|
| SEQ_ID_NO_851 | VSTI FQVNDM | KNSPGL GKKE | LRSATKQAVE | LLQDNYPEFV | FKQAFI NVPW | | 323 |
| SEQ_ID_NO_853 | ISTI FQVNDL | KNSPGPGKRE | RLATKQALQ | SLQDNYPEFV | AKQVFI NVPW | | 400 |
| SEQ_ID_NO_854 | VNTI FQVNDL | KNSPGPGKME | LRQATKQALQ | LLQDNYPEFV | AKQVFI NVPW | | 361 |
| SEQ_ID_NO_856 | : : : : : : : : : : | KNSPGPGKAE | RLATKQALQ | LLQDNYPEFV | RHLDFTPSSG | | 255 |
| SEQ_ID_NO_857 | ISTI MQVNDL | KNSPGL GKKE | LRQATNKALQ | LLQDNYPEFV | AKQVFI NVPW | | 441 |

FIG. 24B

| | | | | | | |
|---|---|---|---|---|---|---|
| SEQ_ID_NO_851 | WYL VFYTVI G | PFMT PRSKSK | L VFAGPSRSA | ETL FKYI SPE | QVPVQYGGLS | 373 |
| SEQ_ID_NO_853 | WYLAFYTVMS | PFMTQRTKSK | FVFAGPSNSA | ETLFKYI SPE | QVPI QYGGLC | 450 |
| SEQ_ID_NO_854 | WYLAFYTMI N | PFLTQRTKSK | FVFAS PAKSA | KTLFKYI SPE | QVPI QYGGLS | 411 |
| SEQ_ID_NO_856 | WYLAFYTMI S | PFLTS RTKSK | FVFAGPSKSP | DTLFKYI FPE | QVPVQYGGLS | 305 |
| SEQ_ID_NO_857 | WYLAFS RFLS | AF LTQRTKSK | FVFAGPSKSA | DTLFKYI APE | QVPVQYGGLS | 491 |
| | | | | | | |
| SEQ_ID_NO_851 | VDP CDCNPDF | SL EDSASEI T | VKPQ TKQTVE | I I YEKC LV | WEI RV L GWEV | 423 |
| SEQ_ID_NO_853 | VDFCDCNPEF | TI ADPATDI T | VKPATKQTVE | I I YEKCI LV | RVV GWEV | 500 |
| SEQ_ID_NO_854 | VDYCDCNPDF | GI ADPVTEI T | VKPSTKQTVE | LVSEQCVI V | WEVRVVGWEV | 461 |
| SEQ_ID_NO_856 | VDFCDCNPDF | TMSDPVTEI P | I KPTI TKQTVE | A YEKCI I V | WEL RVVGWEV | 355 |
| SEQ_ID_NO_857 | RI E - - GEQEF | I T ADPATEVT | NRKVAPA DE T | FPL SEK S TLV | WEVRV DMSM | 538 |
| | | | | | | |
| SEQ_ID_NO_851 | SYK AEFVPEE | KDAYTVVI QK | PRKMR PSDEP | VLTHSFKVNE | LGKVLLTVDN | 473 |
| SEQ_ID_NO_853 | SYS AEFMPEA | KDAYTI I I TK | PTKMSPTDEP | VVSNSFKVGE | LGKI LLTVDN | 550 |
| SEQ_ID_NO_854 | AYG AEFI PDA | EDE YTVVVQK | ATKMSPTDDP | VM C NSFKI KE | LGKi VI TI DN | 511 |
| SEQ_ID_NO_856 | SYN AEFI PDA | KDAYTVI I QK | A TKMSPTDEP | VVSNSFKVE | LGKL LLTI DN | 405 |
| SEQ_ID_NO_857 | NYG AEFVPS A | EDGYTVI I QK | NRKVAPA DE T | I SNTFKI GE | P GKVI LTI DN | 588 |
| | | | | | | |
| SEQ_ID_NO_851 | PTSKKKKLVY | RFN VKP | | | | 489 |
| SEQ_ID_NO_853 | PTSKKKKLLY | RFKI NP | | | | 566 |
| SEQ_ID_NO_854 | PTSKKKKLLY | RFKTPECHI E | VQFNI QSAED | YTTHSNRVYA | TRLASLHSSG | 561 |
| SEQ_ID_NO_856 | PTL KKRLLY | RFKI KP | | | | 421 |
| SEQ_ID_NO_857 | Q S SKKKKLLY | RS KT P | | | | 604 |
| | | | | | | |
| SEQ_ID_NO_851 | | | | | | 490 |
| SEQ_ID_NO_853 | | | | L FSD | | 569 |
| SEQ_ID_NO_854 | DI SKI RRRLT | AGGDRDLTYS | HSGPRI ACW E | | | 591 |
| SEQ_ID_NO_856 | | | | YSD | | 424 |
| SEQ_ID_NO_857 | | | | I SE | | 607 |

|  |  |  |  |  |  |
|---|---|---|---|---|---|
| SEQ_ID_NO_1016 | G-EERMCS- | KSMEEDRGYN | KGEDIPIYAEV | SL------SKS | KSCKALDMRL | 277 |
| SEQ_ID_NO_1018 | GGEEKLCF--- | KSMEED---NR | G-EDMSYTQV | SG------GKS | KSCKALDMRL | 255 |
| SEQ_ID_NO_1020 | A-EERPCSYM | KSLVEEREYA | L-EECSSMSI | SEPGF---NEE | KACRVLNMNI | 258 |
| SEQ_ID_NO_1021 | T-EERPCL--- | LVDERDYR | L-EECSSMGI | SEPGF---NEE | KACRVLNMNI | 250 |
| SEQ_ID_NO_1023 | P-EERSCSYM | KSLVDEREYL | L-EECSSMGI | SEHEF---NRE | KSCRVLNMNL | 225 |
| SEQ_ID_NO_1024 | S-EDRPCSYM | KSLVDERDYQ | D-EECSSIGA | PETEFNHDNN | KPCRVLNMNP | 258 |

|  |  |  |
|---|---|---|
| SEQ_ID_NO_1016 | CL----EK | 280 |
| SEQ_ID_NO_1018 | CL----ER | 258 |
| SEQ_ID_NO_1020 | KGDGSGV | 265 |
| SEQ_ID_NO_1021 | KGEEPGD | 257 |
| SEQ_ID_NO_1023 | ------- | 225 |
| SEQ_ID_NO_1024 | KAADSGG | 265 |

| | | | | | |
|---|---|---|---|---|---|
| SEQ_ID_NO_2150 | AVS- | C--- | --- | DI W- | --- | P | 277 |
| SEQ_ID_NO_2152 | AAS- | C--- | --- | NI W- | --- | S | 339 |
| SEQ_ID_NO_2154 | AVS- | S--- | IT- | SMW- | --- | P | 313 |
| SEQ_ID_NO_2155 | AMS- | CL-- | MT- | TMW- | --- | P | 303 |
| SEQ_ID_NO_2157 | VTS- | CGGA | GV | DVWPWD- | --- | | 359 |
| SEQ_ID_NO_2159 | VTS- | CGGP | GV | DVWPWD- | HSN | GGLSK | 320 |
| SEQ_ID_NO_2160 | VTS- | CGGP | GV | DVWPWDH | HSN | GGLSK | 331 |
| SEQ_ID_NO_2161 | ---- | GGGE | VG | DAMGWDN | NHSN | GGLSK | 298 |
| SEQ_ID_NO_2163 | MQHG | GGA | DAV | DVWGWDS | SSN | GAMSK | 311 |

FIG. 29E

| SEQ_ID_NO | | | | | | |
|---|---|---|---|---|---|---|
| SEQ_ID_NO_2196 | MSG----AITCS | AADLATLLG | PNATA----AA | DYICGQLGTV | 34 |
| SEQ_ID_NO_2197 | MSG----AITCS | AADLATLLG | PNATA----AA | DYICGQLGTV | 34 |
| SEQ_ID_NO_2199 | MAA----SMTCS | AGDLAQLLG | SNVTNSTGAA | DFICSQFNTA | 36 |
| SEQ_ID_NO_2200 | MAA---LPECS | AANLAQLG | PNATDAAAVA | GFICDQFIAV | 37 |
| SEQ_ID_NO_2201 | MARATSLSCS | ADLLAGFLLG | PNATNASSAAA | SLICSQLEAI | 39 |
| SEQ_ID_NO_2202 | MAS---LNCS | AEQLAQLLG | PNGTA----AA | SFICDRFSAV | 33 |
| SEQ_ID_NO_2204 | MAF------- | ANLAPLLG | PNITT--AVAAA | SYICNQFSGM | 33 |
| SEQ_ID_NO_2206 | MT-------- | VDILAPFLG | VNGTG----AA | DYICSKL--- | 26 |
| SEQ_ID_NO_2207 | MAS---TLGCS | AITDLVPHLTG | VN-NATAVA | DFICGRLDAV | 36 |
| SEQ_ID_NO_2208 | MS-----TC- | AADLAPLLG | PAAAN----AT | DYLCG----- | 25 |
| SEQ_ID_NO_2210 | MS-----TC- | AADLAPLLG | PAAAN----AT | DYLCG----- | 25 |
| SEQ_ID_NO_2211 | MA-----TC- | AADLGPLLG | PVAAN----AT | DYLCN----- | 25 |
| SEQ_ID_NO_2212 | MSA----TC- | AADSLAPLLG | AAAAN----AT | DYLCN----- | 26 |
| SEQ_ID_NO_2214 | MA-----TC- | AASLAPLLG | AAAAN----AT | DYLCN----- | 25 |

| SEQ_ID_NO | | | | | | |
|---|---|---|---|---|---|---|
| SEQ_ID_NO_2196 | NNKFTDAAFA | IDNTYLLFSA | YLVFAMQLGF | AMLCAGSVRA | 74 |
| SEQ_ID_NO_2197 | NNKFTDAAFA | IDNTYLLFSA | YLVFAMQLGF | AMLCAGSVRA | 74 |
| SEQ_ID_NO_2199 | ADNFSATQYA | VDNTYLLFSA | YLVFSMQLGF | AMLCAGSVRA | 76 |
| SEQ_ID_NO_2200 | GQRFSDTAFA | VDSTYLLFSA | YLVFSMQLGF | AMLCAGSVRA | 77 |
| SEQ_ID_NO_2201 | NNKFTDTAYA | VDSTYLLFSA | YLVFAMQLGF | AMLCAGSVRA | 79 |
| SEQ_ID_NO_2202 | SNNFTDTNYA | VDNTYLLFSA | YLVFSMQLGF | AMLCAGSVRA | 73 |
| SEQ_ID_NO_2204 | SDRFVDTGYA | IDSTYLLFSA | YLVFAMQLGF | AMLCAGSVRA | 73 |
| SEQ_ID_NO_2206 | ---FSDASYA | VDNTYLLFSA | YLVFAMQLGF | AMLCAGSVRA | 63 |
| SEQ_ID_NO_2207 | SITKLSDTTYA | VDATYLLFSA | YLVFSMQLGF | AMLCAGSVRA | 76 |
| SEQ_ID_NO_2208 | ----QFADTASA | VDATYLLFSA | YLVFAMQLGF | AMLCAGSVRA | 63 |
| SEQ_ID_NO_2210 | ----QFADTASA | VDATYLLFSA | YLVFAMQLGF | AMLCAGSVRA | 63 |
| SEQ_ID_NO_2211 | ----RFADTTSA | VDSTYLLFSA | YLVFAMQLGF | AMLCAGSVRA | 63 |
| SEQ_ID_NO_2212 | ----READTTSA | VDSTYLLFSA | YLVFAMQIGF | AMLCAGSVRA | 64 |
| SEQ_ID_NO_2214 | ----READTISA | VDSTYLLFSA | YLVFAMQIGF | AMLCAGSVRA | 63 |

| SEQ_ID_NO | | | | | | | |
|---|---|---|---|---|---|---|---|
| SEQ_ID_NO_2196 | KNTMNI | MLTN | VLDAAAGGLF | YYLFGYAFAF | GG- - - | SSEGFI | | 112 |
| SEQ_ID_NO_2197 | KNTMNI | MLTN | VLDAAAGGEF | YYLFGFAFAF | GG- - - | SSEGFI | | 112 |
| SEQ_ID_NO_2199 | KNTMNI | MLTN | VLDAAAGGLF | YYLFGFAFAF | GT- - - | PSNGFI | | 114 |
| SEQ_ID_NO_2200 | KNTMNI | MLTN | VLDAAAGGLF | YYLFGFAFAF | GI - - - L | PSNGFI | | 115 |
| SEQ_ID_NO_2201 | KNTMNI | KLTN | VLDAATGGLF | YYLFGFAFAF | GA - - - | PSNGFI | | 117 |
| SEQ_ID_NO_2202 | KNTMNI | MLTN | VLDAAAGGLF | YYLFGFAFAF | GT- - - | PSNGFI | | 111 |
| SEQ_ID_NO_2204 | KNTMNI | MLTN | VLDAATGGLF | YYLFGFAFAW | GS- - - | PSNGFI | | 111 |
| SEQ_ID_NO_2206 | KNTMNI | MLTN | VLDAAAGGLS | YYLFGFAFAF | GS- - - | PSNGFI | | 101 |
| SEQ_ID_NO_2207 | KNTMNI | MLTN | VLDAAAGALF | YYLFGFAFAF | GSRSNAF | | | 116 |
| SEQ_ID_NO_2208 | KNTMNI | MLTN | VLDAAAGALF | YYLFGFAFAF | GT- - - | PSNGFI | | 101 |
| SEQ_ID_NO_2210 | KNTMNI | MLTN | VLDAAAGALF | YYLFGFAFAF | GT- - - | PSNGFI | | 101 |
| SEQ_ID_NO_2211 | KNTMNI | MLTN | VLDAAAGALF | YYLFGFAFAF | GT- - - | PSNGFI | | 101 |
| SEQ_ID_NO_2212 | KNTMNI | MLTN | VLDAAAGALF | YYLFGFAFAF | GT- - - | PSNGFI | | 102 |
| SEQ_ID_NO_2214 | KNTMNI | MLTN | VLDAAAGALF | YYLFGFAFAY | GT- - - | PSNGFI | | 101 |

| SEQ_ID_NO | | | | | | | |
|---|---|---|---|---|---|---|---|
| SEQ_ID_NO_2196 | GRHNFAL | RDF | PTPTADYSFF | LYQWAFAIAA | AGI | TSGSI | AE | 152 |
| SEQ_ID_NO_2197 | GRHNFAL | RDF | PTPTADYSFF | LYQWAFAIAA | AGI | TSGSI | AE | 152 |
| SEQ_ID_NO_2199 | GKHNFGL | KNF | PSSSFDYSYF | LYQWAFAIAA | AGI | TSGSI | AE | 154 |
| SEQ_ID_NO_2200 | GRHFFGL | KDV | PTVAFDYSYF | LYQWAFAIAA | AGI | TSGSI | AE | 155 |
| SEQ_ID_NO_2201 | GRHNFAL | KSF | PTSNFDYSNF | LYQWAFAIAA | AGI | TSGSI | AE | 157 |
| SEQ_ID_NO_2202 | GKHFFAL | KSI | PTKTFDYSNF | LYQWAFAIAA | AGI | TSGSI | AE | 151 |
| SEQ_ID_NO_2204 | GRHFFGL | KEI | PSNSFDYSNF | LYQWAFAIAA | AGI | TSGSI | AE | 151 |
| SEQ_ID_NO_2206 | GRHNFAL | ESI | PSSEDYSNF | LYQWAFAIAA | AGI | TSGSI | AE | 141 |
| SEQ_ID_NO_2207 | GHYSFAL | TGV | PSAHDYSFF | LYQWAFAIAA | AGI | TSGSI | AE | 156 |
| SEQ_ID_NO_2208 | GKQFFGL | KHL | PRTGFDYFFF | LYQWAFAIAA | AGI | TSGSI | AE | 141 |
| SEQ_ID_NO_2210 | GKQFFGL | QHL | PKITGFDYFFF | LYQWAFAIAA | AGI | TSGSI | AE | 141 |
| SEQ_ID_NO_2211 | GKQFFGL | KHM | PQTGFDYSFF | LFQWAFAIAA | AGI | TSGSI | AE | 141 |
| SEQ_ID_NO_2212 | GKHFFGL | KDM | PQTGFDYSFF | FQWAFAVAA | AGI | TSGSI | AE | 142 |
| SEQ_ID_NO_2214 | GKQFFGL | KRL | PQVGFDYDFF | FQWAFAIAA | AGI | TSGSI | AE | 141 |

| SEQ_ID_NO_2196 | - - - - - - - - - - - - - - - - - - - - - - - - - - - - - - | 496 |
|---|---|---|
| SEQ_ID_NO_2197 | - - - - - - - - - - - - - - - - - - - - - - - - - - - - - - | 517 |
| SEQ_ID_NO_2199 | EFLPSAAAAA ACDAIYIVGT GKGVI FRQPV LEELTLVLNA | 603 |
| SEQ_ID_NO_2200 | - - - - - - - - - - - - - - - - - - - - - - - - - - - - - - | 500 |
| SEQ_ID_NO_2201 | - - - - - - - - - - - - - - - - - - - - - - - - - - - - - - | 500 |
| SEQ_ID_NO_2202 | - - - - - - - - - - - - - - - - - - - - - - - - - - - - - - | 500 |
| SEQ_ID_NO_2204 | - - - - - - - - - - - - - - - - - - - - - - - - - - - - - - | 488 |
| SEQ_ID_NO_2206 | - - - - - - - - - - - - - - - - - - - - - - - - - - - - - - | 471 |
| SEQ_ID_NO_2207 | - - - - - - - - - - - - - - - - - - - - - - - - - - - - - - | 511 |
| SEQ_ID_NO_2208 | - - - - - - - - - - - - - - - - - - - - - - - - - - - - - - | 496 |
| SEQ_ID_NO_2210 | - - - - - - - - - - - - - - - - - - - - - - - - - - - - - - | 494 |
| SEQ_ID_NO_2211 | - - - - - - - - - - - - - - - - - - - - - - - - - - - - - - | 530 |
| SEQ_ID_NO_2212 | - - - - - - - - - - - - - - - - - - - - - - - - - - - - - - | 492 |
| SEQ_ID_NO_2214 | - - - - - - - - - - - - - - - - - - - - - - - - - - - - - - | 487 |

| SEQ_ID_NO_2196 | - - - - - - - - - - - - - - - - - - - - - - - - - - - - - - | 496 |
|---|---|---|
| SEQ_ID_NO_2197 | - - - - - - - - - - - - - - - - - - - - - - - - - - - - - - | 517 |
| SEQ_ID_NO_2199 | QCRGYPCGKP KKGCQSNLNF RLESKARAKG PVFCGKEKSK | 643 |
| SEQ_ID_NO_2200 | - - - - - - - - - - - - - - - - - - - - - - - - - - - - - - | 500 |
| SEQ_ID_NO_2201 | - - - - - - - - - - - - - - - - - - - - - - - - - - - - - - | 500 |
| SEQ_ID_NO_2202 | - - - - - - - - - - - - - - - - - - - - - - - - - - - - - - | 500 |
| SEQ_ID_NO_2204 | - - - - - - - - - - - - - - - - - - - - - - - - - - - - - - | 488 |
| SEQ_ID_NO_2206 | - - - - - - - - - - - - - - - - - - - - - - - - - - - - - - | 471 |
| SEQ_ID_NO_2207 | - - - - - - - - - - - - - - - - - - - - - - - - - - - - - - | 511 |
| SEQ_ID_NO_2208 | - - - - - - - - - - - - - - - - - - - - - - - - - - - - - - | 496 |
| SEQ_ID_NO_2210 | - - - - - - - - - - - - - - - - - - - - - - - - - - - - - - | 494 |
| SEQ_ID_NO_2211 | - - - - - - - - - - - - - - - - - - - - - - - - - - - - - - | 530 |
| SEQ_ID_NO_2212 | - - - - - - - - - - - - - - - - - - - - - - - - - - - - - - | 492 |
| SEQ_ID_NO_2214 | - - - - - - - - - - - - - - - - - - - - - - - - - - - - - - | 487 |

FIG. 30I

| SEQ_ID_NO_2196 | --- | --- | --- | --- | --- | 496 |
|---|---|---|---|---|---|---|
| SEQ_ID_NO_2197 | RGL NRYFPW | I I AKYRRCYA | GVAVPQLDWT | PEPPVDLLIL | - - - | 517 |
| SEQ_ID_NO_2199 | --- | --- | --- | --- | --- | 683 |
| SEQ_ID_NO_2200 | --- | --- | --- | --- | --- | 500 |
| SEQ_ID_NO_2201 | --- | --- | --- | --- | --- | 500 |
| SEQ_ID_NO_2202 | --- | --- | --- | --- | --- | 500 |
| SEQ_ID_NO_2204 | --- | --- | --- | --- | --- | 488 |
| SEQ_ID_NO_2206 | --- | --- | --- | --- | --- | 471 |
| SEQ_ID_NO_2207 | --- | --- | --- | --- | --- | 511 |
| SEQ_ID_NO_2208 | --- | --- | --- | --- | --- | 496 |
| SEQ_ID_NO_2210 | --- | --- | --- | --- | --- | 494 |
| SEQ_ID_NO_2211 | --- | --- | --- | --- | --- | 530 |
| SEQ_ID_NO_2212 | --- | --- | --- | --- | --- | 492 |
| SEQ_ID_NO_2214 | --- | --- | --- | --- | --- | 487 |

| SEQ_ID_NO_2196 | --- | --- | --- | --- | --- | 496 |
|---|---|---|---|---|---|---|
| SEQ_ID_NO_2197 | --- | --- | --- | --- | --- | 517 |
| SEQ_ID_NO_2199 | FGLDKGVI VY | I CDSRGVRDL | NETDFYELPV | VMKALMI QPD | --- | 723 |
| SEQ_ID_NO_2200 | --- | --- | --- | --- | --- | 500 |
| SEQ_ID_NO_2201 | --- | --- | --- | --- | --- | 500 |
| SEQ_ID_NO_2202 | --- | --- | --- | --- | --- | 500 |
| SEQ_ID_NO_2204 | --- | --- | --- | --- | --- | 488 |
| SEQ_ID_NO_2206 | --- | --- | --- | --- | --- | 471 |
| SEQ_ID_NO_2207 | --- | --- | --- | --- | --- | 511 |
| SEQ_ID_NO_2208 | --- | --- | --- | --- | --- | 496 |
| SEQ_ID_NO_2210 | --- | --- | --- | --- | --- | 494 |
| SEQ_ID_NO_2211 | --- | --- | --- | --- | --- | 530 |
| SEQ_ID_NO_2212 | --- | --- | --- | --- | --- | 492 |
| SEQ_ID_NO_2214 | --- | --- | --- | --- | --- | 487 |

FIG. 30J

| | | | | | | |
|---|---|---|---|---|---|---|
| SEQ_ID_NO_2196 | - - - - - - - | - - - - - - - | - - - - - - - | - - - - - - - | - - - - - - - | 496 |
| SEQ_ID_NO_2197 | - - - - - - - | - - - - - - - | - - - - - - - | - - - - - - - | - - - - - - - | 517 |
| SEQ_ID_NO_2199 | VFSVCDQASA | NFFILTICSP | VVNKGTASAS | EILAGALKDN | - - - - - - - | 763 |
| SEQ_ID_NO_2200 | - - - - - - - | - - - - - - - | - - - - - - - | - - - - - - - | - - - - - - - | 500 |
| SEQ_ID_NO_2201 | - - - - - - - | - - - - - - - | - - - - - - - | - - - - - - - | - - - - - - - | 500 |
| SEQ_ID_NO_2202 | - - - - - - - | - - - - - - - | - - - - - - - | - - - - - - - | - - - - - - - | 500 |
| SEQ_ID_NO_2204 | - - - - - - - | - - - - - - - | - - - - - - - | - - - - - - - | - - - - - - - | 488 |
| SEQ_ID_NO_2206 | - - - - - - - | - - - - - - - | - - - - - - - | - - - - - - - | - - - - - - - | 471 |
| SEQ_ID_NO_2207 | - - - - - - - | - - - - - - - | - - - - - - - | - - - - - - - | - - - - - - - | 511 |
| SEQ_ID_NO_2208 | - - - - - - - | - - - - - - - | - - - - - - - | - - - - - - - | - - - - - - - | 496 |
| SEQ_ID_NO_2210 | - - - - - - - | - - - - - - - | - - - - - - - | - - - - - - - | - - - - - - - | 494 |
| SEQ_ID_NO_2211 | - - - - - - - | - - - - - - - | - - - - - - - | - - - - - - - | - - - - - - - | 530 |
| SEQ_ID_NO_2212 | - - - - - - - | - - - - - - - | - - - - - - - | - - - - - - - | - - - - - - - | 492 |
| SEQ_ID_NO_2214 | - - - - - - - | - - - - - - - | - - - - - - - | - - - - - - - | - - - - - - - | 487 |

| | | | | | | |
|---|---|---|---|---|---|---|
| SEQ_ID_NO_2196 | - - - - - - - | - - - - - - - | - - - - - - - | - - - - - - - | - - - - - - - | 496 |
| SEQ_ID_NO_2197 | - - - - - - - | - - - - - - - | - - - - - - - | - - - - - - - | - - - - - - - | 517 |
| SEQ_ID_NO_2199 | KRAVLYGEPT | FWKGKIQSVF | QLSDGSGLAV | TVARYETPAH | - - - - - - - | 803 |
| SEQ_ID_NO_2200 | - - - - - - - | - - - - - - - | - - - - - - - | - - - - - - - | - - - - - - - | 500 |
| SEQ_ID_NO_2201 | - - - - - - - | - - - - - - - | - - - - - - - | - - - - - - - | - - - - - - - | 500 |
| SEQ_ID_NO_2202 | - - - - - - - | - - - - - - - | - - - - - - - | - - - - - - - | - - - - - - - | 500 |
| SEQ_ID_NO_2204 | - - - - - - - | - - - - - - - | - - - - - - - | - - - - - - - | - - - - - - - | 488 |
| SEQ_ID_NO_2206 | - - - - - - - | - - - - - - - | - - - - - - - | - - - - - - - | - - - - - - - | 471 |
| SEQ_ID_NO_2207 | - - - - - - - | - - - - - - - | - - - - - - - | - - - - - - - | - - - - - - - | 511 |
| SEQ_ID_NO_2208 | - - - - - - - | - - - - - - - | - - - - - - - | - - - - - - - | - - - - - - - | 496 |
| SEQ_ID_NO_2210 | - - - - - - - | - - - - - - - | - - - - - - - | - - - - - - - | - - - - - - - | 494 |
| SEQ_ID_NO_2211 | - - - - - - - | - - - - - - - | - - - - - - - | - - - - - - - | - - - - - - - | 530 |
| SEQ_ID_NO_2212 | - - - - - - - | - - - - - - - | - - - - - - - | - - - - - - - | - - - - - - - | 492 |
| SEQ_ID_NO_2214 | - - - - - - - | - - - - - - - | - - - - - - - | - - - - - - - | - - - - - - - | 487 |

| SEQ_ID_NO_2493 | NPSMLNLQAN | PNQFIWPDD | EKPISI-N- | VL | ELDVPLIDLQ | 67 |
|---|---|---|---|---|---|---|
| SEQ_ID_NO_2494 | DASLLRHQLN | LPKQFIWPDD | EKPCM-N- | VP | ELVVPLIDLR | 70 |
| SEQ_ID_NO_2495 | DASVLKHQTQ | LPKQFIWPDD | EKPCV-N- | AP | ELQVPLIDLG | 67 |
| SEQ_ID_NO_2496 | DASFLKNQLN | LPKRFIWPDD | EKPCM-N- | VP | ELDVPLIDFK | 68 |
| SEQ_ID_NO_2497 | DASFLKNQLN | LPKQFIWPDE | EKPCM-N- | VP | ELDVPLIDLR | 68 |
| SEQ_ID_NO_2498 | DASVLRHQTN | LPQQFIWPDE | EKPRA-N- | AP | ELQVPLIDFK | 67 |
| SEQ_ID_NO_2499 | DAQVLRHQTN | LPQQFIWPDH | EKPNI-N- | VP | ELVVPLVDLG | 72 |
| SEQ_ID_NO_2500 | DASLLRYEHN | LPKQFIWPDE | EKPNL-N- | AP | ELEVPLIDLG | 70 |
| SEQ_ID_NO_2501 | DASVLQHEGN | LPQQFIWPDA | EKPNTQK | PP | ELPVPLIDLG | 65 |
| SEQ_ID_NO_2502 | DASQMKREYN | LPTQFIWPDD | EKPRA-V- | SK | ELSMPLIDLG | 65 |
| SEQ_ID_NO_2503 | DASVLRHQSN | LPKQFIWPDH | EKPGD-KI | AR | ELVVPLVDLG | 67 |
| SEQ_ID_NO_2504 | DSLILQHETN | LPQQFIWPDH | EKPNLQK- | AT | ELAMPLVDLR | 64 |
| SEQ_ID_NO_2505 | DSLLLQHETN | LPEQFIWPDD | EKPNSQK- | TK | QLHVPLIDLR | 57 |
| SEQ_ID_NO_2506 | DASHMKRESN | LPTQFIWPDD | EKPCAFL- | AK | ELEVPVIDME | 61 |
| SEQ_ID_NO_2507 | DSKILRNQAS | LPKEFIWPDD | EKPDH-E- | VQ | ECPVPVIDLA | 62 |
| SEQ_ID_NO_2508 | DSSVLRHETN | LPTEFVWPEH | EKPGSIYA- | AA | ELEVPVIDME | 62 |
| SEQ_ID_NO_2509 | DAAVLSGRAD | LPSQFIWPEG | ESPITP- | AP | ELHVPLIDIG | 45 |
| SEQ_ID_NO_2510 | | | DAAE | | | |

FIG. 31B

| | | | | | |
|---|---|---|---|---|---|
| SEQ_ID_NO_2493 | NLLSLDPSST | LDASRLISEA | CKKHGFFLVV | NHGISEELIS | 106 |
| SEQ_ID_NO_2494 | GFLSGDPVAT | MEAARMVGEA | CQKHGFFLVV | NHGIDANLIS | 110 |
| SEQ_ID_NO_2495 | GFLSGDDPVAA | KEASRLVGEA | CRKHGFFLVV | NHGVDSSLIA | 107 |
| SEQ_ID_NO_2496 | NFLSGDPFAA | MEASKTIGEA | CEKHGFFLVV | NHGIDTKLIE | 108 |
| SEQ_ID_NO_2497 | NFLSGDPFAA | MEASKTIGEA | CEKHGFFLVV | NHGIDTKLIE | 108 |
| SEQ_ID_NO_2498 | GFLSGDPITAA | NEASSLVGKA | CQKHGFFLVV | NHGVDDKLIA | 107 |
| SEQ_ID_NO_2499 | DFLSGNPVAA | VEASRLVGEA | CQKHGFFLVV | NHGVDKTLIS | 112 |
| SEQ_ID_NO_2500 | GFLSGDPVAA | METSKLVSEA | CRKHGFFLVT | NHGIDSRLIA | 110 |
| SEQ_ID_NO_2501 | GFLSGDPVAA | KKASNLVGEA | CQKHGFFLVV | NHGVDENLIS | 105 |
| SEQ_ID_NO_2502 | GFLSGHSCST | QQASRLVGEA | CRNHGFFLVV | NHGVNANLIS | 105 |
| SEQ_ID_NO_2503 | GFLSGDPVAA | MEATRLVREA | CQKHGFFLVV | NHGVDDKLIY | 107 |
| SEQ_ID_NO_2504 | GFLSGDPAAA | KEASLVVGDA | CKKHGFFLVT | NHGVDASLIA | 104 |
| SEQ_ID_NO_2505 | GFLSGRPSSA | KEASVVVGEA | CKKHGFFLVK | NHGVDASLIV | 97 |
| SEQ_ID_NO_2506 | GFLSGRASSA | QQASELVGEA | CRGHGFFLVV | NHGVDANLIS | 101 |
| SEQ_ID_NO_2507 | GFCREETKST | NNASKLVNEA | FMKHGFFLVK | NHGVEAELIK | 102 |
| SEQ_ID_NO_2508 | AFRSGDPAAV | AETLKLVNEA | CKKHGFFLVV | NHGVDPDRIS | 102 |
| SEQ_ID_NO_2509 | GMLSGDPRAT | AEVTRLVGEA | CERHGFFQVV | NHGIDAELLA | 85 |

FIG. 31C

| | | | | | |
|---|---|---|---|---|---|
| SEQ_ID_NO_2493 | DAHEYTSRFF | DMPLSEKQRV | LRKSGESVGY | ASSFTGRFST | 146 |
| SEQ_ID_NO_2494 | HAHSYMDDFF | EVPLTQKQRA | QRKTGEHCGY | ASSFTGRFSS | 150 |
| SEQ_ID_NO_2495 | DAHRYMDHFF | ELPLNEKQRA | RRKLGEHCGY | ASSFTGRFSS | 147 |
| SEQ_ID_NO_2496 | HAHSYMNDFF | EVPLSQKQRC | QRKTGEHCGY | ASSFTGRFSS | 148 |
| SEQ_ID_NO_2497 | HAHSYMNDFF | EVPLSQKQRC | QRKVGEHCGY | ASSFTGRFSF | 148 |
| SEQ_ID_NO_2498 | HAHQYIDYF | ELPMSAKQRA | QRKTGESCGY | ASSFTGRFSS | 147 |
| SEQ_ID_NO_2499 | HAHNYMDTFF | ELPLSEKQRA | QRKIGESCGY | ASSFTGRFSS | 152 |
| SEQ_ID_NO_2500 | HAHRFMDDFF | ELPLSQKQRA | QRKAGEHCGY | ASSFTSRFSS | 150 |
| SEQ_ID_NO_2501 | DAHQYMDLFF | DLPLSEKQRA | QRKLEEHCGY | ASSFTGRFSS | 145 |
| SEQ_ID_NO_2502 | NAHRYMDMF | GLPLAKKQRA | QRKLGEHCGY | ASSFTGRFSS | 145 |
| SEQ_ID_NO_2503 | KAHQYMDSF | ELPLSDKQRV | QRKIGESCGY | ASSFTGRFSS | 147 |
| SEQ_ID_NO_2504 | DAHRYMDLFF | ELPFDKQRV | QRKIGEHCGY | ASSFTGRFTS | 144 |
| SEQ_ID_NO_2505 | NAHRYMDTFF | ELPLLEKQKA | QRKLGESCGY | ASSFTGRFSS | 137 |
| SEQ_ID_NO_2506 | HTHKYMREFF | ELPLVEKQRV | QRKLGEHCGY | ASSFTRRFSC | 141 |
| SEQ_ID_NO_2507 | DALRHMDRFF | DLPLSSKEKA | LRKVGEHCGY | ASSFTGRFSA | 142 |
| SEQ_ID_NO_2508 | DAHRCVDAFF | TMPLPEKQRA | LRRPGESCGY | ASSFIGRFAS | 125 |

| SEQ ID | | | | | | |
|---|---|---|---|---|---|---|
| SEQ_ID_NO_2493 | KLPWKETLSF | RFCDDM- | R | SKSVQDYFCD | ALGHGFQPFG | 184 |
| SEQ_ID_NO_2494 | KLPWKETLSF | QFSAEEK | S | STIVKDYLCN | TLGQEFEQFG | 188 |
| SEQ_ID_NO_2495 | KLPWKETLSF | RYSAEKI | S L S | NNIVEDYLLN | TMGDEFKQFG | 186 |
| SEQ_ID_NO_2496 | NLPWKETLSF | QFSDEKI | N | SNIVKDYLSN | TLGEDFQQFG | 186 |
| SEQ_ID_NO_2497 | NLPWKETLSF | QFSDEKI | P | SHIVQDYLSN | TLGEDFQQFG | 186 |
| SEQ_ID_NO_2498 | KLPWKETLSF | RSSAQP | S | SNIVQDYLCN | TMGEDFKPFG | 185 |
| SEQ_ID_NO_2499 | KLPWKETLSF | RYTAEKI | D | SKHIEEYFHN | RMGEDFAEFG | 190 |
| SEQ_ID_NO_2500 | KLPWKETLSF | QFSADKI | N | QNLVKDYLCE | KVGHEFEQFG | 188 |
| SEQ_ID_NO_2501 | KLPWKETLSF | QYSADEI | S | SDIVKDYFKD | KMGEEFIRLG | 183 |
| SEQ_ID_NO_2502 | KLPWKETLSF | RYSAEEI | N | SHLVEEYFQN | TMGESFSHLG | 183 |
| SEQ_ID_NO_2503 | KLPWKETLSF | SYSAEKI | D | SNAVQEYFLN | KMGEDFSEFG | 185 |
| SEQ_ID_NO_2504 | KLPWKETLSF | QFSGEKI | S | ANGVKDYFEN | TLGKEFIRLG | 182 |
| SEQ_ID_NO_2505 | KLPWKETLSF | QFSGEKI | K | SKIVEEYFEK | TMGKEFARLG | 175 |
| SEQ_ID_NO_2506 | KLPWKETLSF | RYSAKKI | S | SHIVEEYFQS | TLGESFNHLG | 179 |
| SEQ_ID_NO_2507 | KLPWKETLSF | PYSPEEAN | E | TKVVEEYFNS | KMTKDFAHMG | 181 |
| SEQ_ID_NO_2508 | KLPWKETLSF | RYSAQKI | C | SHIVEEYFQE | SLGQEFAHLG | 180 |
| SEQ_ID_NO_2509 | KLPWKETLSF | RSCPS-- | D | PALVMDYIVA | TLGEDHRRLG | 161 |
| SEQ_ID_NO_2510 | | | | | | |

FIG. 31F

| SEQ ID NO | Sequence | Position |
|---|---|---|
| SEQ_ID_NO_2493 | KVYQEYCEAM SSLSLKI MEL LGLSLGV KRD YFREFFEEND | 224 |
| SEQ_ID_NO_2494 | RVYQDYCDAM SNLSLGI MEL LGMSLGV GKA CFREFFEEND | 228 |
| SEQ_ID_NO_2495 | RVYQEYCESM SRLSLGI MEL LAI SLGV GRA HFKEFFEEND | 226 |
| SEQ_ID_NO_2496 | EVYQEYCEAM SKLSLGI MEL LGMSLGV GKE CFRDFFEENK | 226 |
| SEQ_ID_NO_2497 | EVYQEYCEAM SKLSLGI MEL LGMSLGV GKE CFRDFFEENE | 226 |
| SEQ_ID_NO_2498 | SVYQDYCDAM STLSLGI MEL LGMSLGV SQG HYREFFEEND | 225 |
| SEQ_ID_NO_2499 | MVYQEYCEAM STLSLVI MEL LGMSLGV SRE HFREFFDEND | 230 |
| SEQ_ID_NO_2500 | NVYQDYCNAM SNLSLGI MEL LGMSLGV GRT CFREFFDKNN | 228 |
| SEQ_ID_NO_2501 | NVYQEYCNAM NRLSLGI MEL LGMSLGV GRE HFKEFFQEND | 223 |
| SEQ_ID_NO_2502 | QVYQEYCEAM STLSLVI MEL LGMSLGI GGA HFREFFEENE | 223 |
| SEQ_ID_NO_2503 | KVYQEYCEAM STLSLGI MEL LGMSLGV HRA HFKEFFEEND | 225 |
| SEQ_ID_NO_2504 | KVYQEYCEAM SRLSLGI MEL LGMSLGV EQS HFKEFFEEND | 222 |
| SEQ_ID_NO_2505 | NVYQEYCNAM SRLSLGI MEL LGMSLGV EKS HFKEFFKEND | 215 |
| SEQ_ID_NO_2506 | KLYQEYCEAM NTLSLGI MEL LGLSLGV GRQ YFRDYFQEND | 219 |
| SEQ_ID_NO_2507 | LVYQKYSNEM SKLALEI MEV LGMGLGV NRK HFSDFQEND | 221 |
| SEQ_ID_NO_2508 | EVYARYCSEM SRLSLEI MEV LGESLGV GRA HYRRFFEGND | 220 |
| SEQ_ID_NO_2509 | | 201 |

| | | | | | | |
|---|---|---|---|---|---|---|
| SEQ_ID_NO_2493 | SIMRLNYYPP | CLKPDLTLGT | GPHCDPTSLT | LHQDH-VNG | 263 |
| SEQ_ID_NO_2494 | SIMRLNYYPP | CQKPDLTLGT | GPHCDPTSLT | LHQDQ-VGG | 267 |
| SEQ_ID_NO_2495 | SIMRLNYYPP | CQKPELTLGT | GPHCDPTSLT | LHQDQ-VGG | 265 |
| SEQ_ID_NO_2496 | SIMRLNYYPP | CQKPDLTLGT | GPHCDPTSLT | LHQDQ-VGG | 265 |
| SEQ_ID_NO_2497 | SIMRLNYYPP | CQKPDLTLGT | GPHCDPTSLT | LHQDQ-VGG | 265 |
| SEQ_ID_NO_2498 | SIMRLNYYPP | CQKPDLTLGT | GPHCDPTSLT | LHQDK-VGG | 264 |
| SEQ_ID_NO_2500 | SIMRLNYYPP | CQKPDLTLGT | GPHCDPTSLT | LHQDN-VGG | 269 |
| SEQ_ID_NO_2501 | SIMRLNYYPP | CQKPDLTLGT | GPHCDPTSLT | LHQDQ-VGG | 267 |
| SEQ_ID_NO_2502 | SIMRLNYYPP | CQKPDLTLGT | GPHCDPTSLT | LHQDS-VGG | 262 |
| SEQ_ID_NO_2503 | SIMRLNYYPR | CQKPDLTLGT | GPHCDPTSLT | LHQDQ-VGG | 262 |
| SEQ_ID_NO_2504 | SIMRLNYYPP | CLKPDLTLGT | GPHCDPTSLT | LHQDS|-VGG | 264 |
| SEQ_ID_NO_2505 | SIMRLNYYPP | CQKPDLQTLGT | GPHCDPTSLT | LHQD|T- | 261 |
| SEQ_ID_NO_2506 | SVMRLNYYPP | CQEPELALGT | GPHCDPTSLT | LHQDC--VGG | 254 |
| SEQ_ID_NO_2507 | SVMRLNY|CPP | CQKPELALGT | GPHCDPTSLT | LHQDH-VGG | 258 |
| SEQ_ID_NO_2508 | SIMRLNYYPP | CQKPELTLGT | GPHCDPTSLT | LHQDH-VNG | 260 |
| SEQ_ID_NO_2509 | | CQRP|ME|TLGT | GPHCDPTSLT | LHQDN|S-VGG | 260 |
| SEQ_ID_NO_2510 | SIMRLNYYPP | | GPHCDPTSLT | LHQDN-VGG | 240 |

FIG. 31G

| SEQ ID | Sequence | | | | Length |
|---|---|---|---|---|---|
| SEQ_ID_NO_2493 | LQVFVENQWR | SIRPNPKAFV | VNIGDTFMAL | SNDRYKSCLH | 303 |
| SEQ_ID_NO_2494 | LQVFVDNEWH | SINPNFNAFV | VNIGDTFMAL | SNGRYKSCLH | 307 |
| SEQ_ID_NO_2495 | LQVFVDNEWH | SISPNFEAFV | VNIGDTFMAL | SNGRYKSCLH | 305 |
| SEQ_ID_NO_2496 | LQVFVDNEWH | SIRPNFNAFV | VNIGDTFMAL | SNGRYKSCLH | 305 |
| SEQ_ID_NO_2497 | LQVFVDNEWH | SIRPNFNAFV | VNIGDTFMAL | SNGRYKSCLH | 305 |
| SEQ_ID_NO_2498 | LQVFVDNEWH | SITPNFNAFV | VNIGDTFMAL | SNGRYKSCLH | 305 |
| SEQ_ID_NO_2499 | LQVFVDNEWH | SISPNFDAFV | VNIGDTFMAL | SNGIYKSCLH | 304 |
| SEQ_ID_NO_2500 | LQVFVDNEWH | SITPNFNAFV | VNIGDTFMAL | SNGRYKSCLH | 309 |
| SEQ_ID_NO_2501 | LQVYVDNEWH | SIAPNSQAFV | VNIGDTFMAL | SNGRYKSCLH | 307 |
| SEQ_ID_NO_2502 | EVFVDNEWR | SVSPNFNAFV | VNIGDTFMAL | SNGRYKSCLH | 302 |
| SEQ_ID_NO_2503 | LQVFVDDKWW | SISPNFDAFV | VNIGDTFMAL | SNGRYKSCLH | 302 |
| SEQ_ID_NO_2504 | LEVFIDNEWR | SIAPNSNAFV | VNIGDTFMAL | SNGRYKSCLH | 304 |
| SEQ_ID_NO_2505 | LEVFIDNEWR | SIAPNLNTFV | VNIGDTFMAL | SNGRYKSCLH | 301 |
| SEQ_ID_NO_2506 | LQVFVDDEWR | SISPNFNAFV | VNIGDTFMAL | SNGQYRSCLH | 294 |
| SEQ_ID_NO_2507 | LQVFVDGEWR | FIYPRFDTFV | VNIGDTFMAL | SNGKYKSCLH | 298 |
| SEQ_ID_NO_2508 | LQVCVDNEWR | SVSPSPNAFV | VNIGDTFMAL | SNGIYKSCLH | 300 |
| SEQ_ID_NO_2509 | LQVHTEGRMR | SIRPRADAFV | VNIGDTFMAL | SNGRYKSCLH | 300 |
| SEQ_ID_NO_2510 | | | | | 280 |

FIG. 31H

| | | | | | | |
|---|---|---|---|---|---|---|
| SEQ_ID_NO_2493 | RAVVNSESER | KSLAFFLCPK | KDRVVTPPPRE | LLDS- | ITSRR | 342 |
| SEQ_ID_NO_2494 | RAVVNSKTTR | KSLAFFLCPK | GDKVVSPPPSE | LVDD- | LTPRL | 346 |
| SEQ_ID_NO_2495 | RAVVNSQTTR | KSLAFFLCPK | NDKVVSPPPSE | LVDTY | SSPRI | 345 |
| SEQ_ID_NO_2496 | RAVVNNKTTR | KSLAFFLCPK | GDKVVSPPPSE | LVND- | LTPRI | 344 |
| SEQ_ID_NO_2497 | RAVVNNKTTR | KSLAFFLCPK | GDKVVSPPPSE | LVND- | LTPRI | 344 |
| SEQ_ID_NO_2498 | RAVVNSKTPR | KSLAFFLCPK | NDKMVTPPPSE | LVDS- | LCPRV | 343 |
| SEQ_ID_NO_2500 | RAVVNSQTPR | KSLAFFLCPG | DDKVVTPPPSE | LVDT- | CNPRI | 348 |
| SEQ_ID_NO_2501 | RAVVNSQTTR | KSLAFFLCPK | KDKVVSPPPEK | LVDH- | VSPRI | 346 |
| SEQ_ID_NO_2502 | RAVVNSKTPR | KSLAFFLCPE | KDKVVVSPPNE | LVDQ- | KNPRI | 341 |
| SEQ_ID_NO_2503 | RAVVNRIHR | KSLAFFLCPK | KDKVVRPPTE | LVDT- | NNPRI | 341 |
| SEQ_ID_NO_2504 | RAVVNNKIHR | KSLAFFLCPK | KDKVVSPPPDE | LVDE- | NSPRI | 343 |
| SEQ_ID_NO_2505 | RAVVNSKTPR | KSLAFFLCPN | KDKVVSPPNE | LVDT- | KNPRI | 340 |
| SEQ_ID_NO_2506 | RAVVNSKTPR | KSLAFFLCPK | KDKVVSPPPDE | LVDE- | NNPRI | 333 |
| SEQ_ID_NO_2507 | RAVVNDTSPR | KSLAFFLCPH | EDLVCPPPNE | LVDS- | SSPRV | 337 |
| SEQ_ID_NO_2508 | RAVVNSTLTR | KSMAFFLCPH | EDKVVTPPPE | LVNE- | THPRL | 339 |
| SEQ_ID_NO_2509 | RAVVNSKVPR | KSLAFFLCPE | MDKVVAPPIGT | LVDA- | ANPRA | 319 |

FIG. 31I

| SEQ_ID | Sequence | | | | End |
|---|---|---|---|---|---|
| SEQ_ID_NO_2493 | YPDFTWSMFL | EFTQKHYRAD | MNTLQAFSDW | LTKP------ | 376 |
| SEQ_ID_NO_2494 | YPDFTWPMLL | EFTQKHYRAD | MKTLEAFTNW | LQQKR----- | 381 |
| SEQ_ID_NO_2495 | YPDFTWPMLL | EFTQKHYRAD | MKTLEAFTNW | LQQKKQ---- | 381 |
| SEQ_ID_NO_2496 | YPDFTWPMLL | EFTQKHYRAD | MRTLEAFTKW | LQQKQ----- | 379 |
| SEQ_ID_NO_2497 | YPDFTWPMLL | EFTQKHYRAD | MRTLEAFTKW | LQQKQ----- | 379 |
| SEQ_ID_NO_2498 | YPDFTWPMLL | EFTQKHYRAD | VKTLEVFSNW | LQQKN----- | 378 |
| SEQ_ID_NO_2499 | YPDFTWPMLL | EFTQKHYRAD | MKTLEVFTNW | LHQQS----- | 383 |
| SEQ_ID_NO_2500 | YPDFTWPMLL | EFTQKHYRAD | MNTLEQFANW | VQRNK----- | 381 |
| SEQ_ID_NO_2501 | YPDFTWSTFL | EFTQKHYRAD | MNTLKAFSNW | VQQETS---- | 377 |
| SEQ_ID_NO_2502 | YPDFTWPTLL | EFTQKHYRAD | MNTLQTFSNW | LKQKTA---- | 377 |
| SEQ_ID_NO_2503 | YPDFTWSNLL | EFTQKHYRAD | MKTLEVFSSW | LQQKTA---- | 379 |
| SEQ_ID_NO_2504 | YPDFTWSTFL | EFTQKHYRAD | MNTLQAFSNW | LQQKN----- | 375 |
| SEQ_ID_NO_2505 | YPDFTWPTLL | EFTQKHYRAD | MNTLQAFTNW | QQKN------ | 368 |
| SEQ_ID_NO_2506 | YPDFTWPIFL | EFTQKHYRAD | MNTLQTFSNW | HDQHNT---- | 374 |
| SEQ_ID_NO_2507 | YPDFTWPIFL | EFTQKHYRAD | TDTLLNFSRW | VRERNQVQS- | 379 |
| SEQ_ID_NO_2508 | YPDFKMPTLL | EFTQKHYRSD | TDTLLSFSAM | LQQNQTP--- | 376 |
| SEQ_ID_NO_2509 | YPDFTWRSLL | DFTQKHYRAD | MKTLEVFSSW | VQQQGQ---- | 357 |
| SEQ_ID_NO_2510 | YPDFTWRSLL | DFTQKHYRAD | MKTLEVFSSW | VQQQGQ---- | 357 |

| SEQ_ID_NO | | | | | | |
|---|---|---|---|---|---|---|
| SEQ_ID_NO_2271 | MDSTS- | G | GAT- | -A-P | GPNSG- | EPCP | SAATAG | SSSA | 30 |
| SEQ_ID_NO_2273 | MDSAS- | G | EAP- | P-PP | QPTSVE | APPP | SGSSA | PATSA | 32 |
| SEQ_ID_NO_2274 | MDSAS- | G | GGA- | -A- | DPSS- | GEGP | SA- | - | 20 |
| SEQ_ID_NO_2276 | MDSAS- | G | GSD- | -N- | SIK- | EAIP | ATASALL | SAA | 27 |
| SEQ_ID_NO_2278 | MEPGPDAPAG | G | GGGGGTSIS | | EPAEA- | GPSP | SSSSAAAAS | | 39 |
| SEQ_ID_NO_2280 | MEPGPDAPRG | G | EGA- | -S- | APE- | ESGP | SSSSV | AVEKA | 31 |
| SEQ_ID_NO_2281 | MEPSP- | G | APR- | -A- | GAAE- | QPGP | SSSASAP- | | 26 |
| SEQ_ID_NO_2283 | MESAD- | S | GRS- | | DPVK- | GDDP | G- | | 18 |

| SEQ_ID_NO | | | | | | |
|---|---|---|---|---|---|---|
| SEQ_ID_NO_2271 | S- | | | | QPQQQPE | | 38 |
| SEQ_ID_NO_2273 | | | | | PAPTQP | | 38 |
| SEQ_ID_NO_2274 | | | | | GAA | | 27 |
| SEQ_ID_NO_2276 | S- | Q | -G- | -GGG- | GGGSE | | 37 |
| SEQ_ID_NO_2278 | S- | SSRQQ | OG- | -G- | AQAQPQPQH | | 75 |
| SEQ_ID_NO_2280 | EEPQAQAQ | AEQEAQQQQG | AQQREQPAVR | EHLQPQPLSQ | | 61 |
| SEQ_ID_NO_2281 | APAASSN- | PPEGGGQQV | ALQ- | QEAQPQPLAQ | | 57 |
| SEQ_ID_NO_2283 | | EEEGRHQSQ | AQQQV- | PSF | | 21 |

| SEQ_ID_NO | | | | | |
|---|---|---|---|---|---|
| SEQ_ID_NO_2271 | GSSPPAPPSR | YESQKRRDWN | TFLQYI KNHK | PPLTLARCSG | 78 |
| SEQ_ID_NO_2273 | EGSSPAPPSR | YESQKRRDWN | TFLQYL QNHR | PPLTLARCSG | 78 |
| SEQ_ID_NO_2274 | EGSSPAPPSR | YESQKRRDWN | TFLQYL KNHK | PPLTLARCSG | 67 |
| SEQ_ID_NO_2276 | SSPSPAPPSR | YESQKRRDWN | TFLQYL NHK | PPLTLARCSG | 77 |
| SEQ_ID_NO_2278 | QQQPPAGLSR | YESQKRRDWN | TFLQYL RNHK | PPLTLARCSG | 115 |
| SEQ_ID_NO_2280 | QDPVRAGLSR | YESQKRRDWN | TFLQYL RNHK | PPLTLARCSG | 101 |
| SEQ_ID_NO_2281 | QAPAAAGLSR | YESQKRRDWN | TFLQYL RNHK | PPLILPRCSG | 97 |
| SEQ_ID_NO_2283 | VSSPPATPSR | YESQKRRDWN | TFLQYL KNHK | PPLALSRCSG | 61 |

FIG. 32A

| SEQ_ID_NO_2271 | AHVIEFLKYL | DQFGKTKVHI | TGCPYFGHPN | PPAPCSCPLK | 118 |
| --- | --- | --- | --- | --- | --- |
| SEQ_ID_NO_2273 | AHVIEFLKYL | DQFGKTKVHV | TGCPYFGHPN | PPAPCTCPLK | 118 |
| SEQ_ID_NO_2274 | AHVIEFLKYL | DQFGKTKVHI | SGCPYFGHPN | PPAPCACPLK | 107 |
| SEQ_ID_NO_2276 | AHVIEFLRYL | DQFGKTKVHI | DCPYFGHVN  | PPAPCTCPLR | 117 |
| SEQ_ID_NO_2278 | AHVIEFLKYL | DQFGKTKVHA | EGCAYFGQPN | PPAPCACPLR | 155 |
| SEQ_ID_NO_2280 | AHVIEFLKYL | DQFGKTKVHA | DGCAYFGQPN | PPAPCACPLR | 141 |
| SEQ_ID_NO_2281 | AHVIEFLKYL | DQFGKTKVHA | DGCAYFGEPN | PPAPCACPLR | 137 |
| SEQ_ID_NO_2283 | AHVIEFLKYL | DQFGKTKVHV | AACPYFGHQQ | PPSPCSCPLK | 101 |

| SEQ_ID_NO_2271 | QAWGSLDALI | GRLRAAYEEN | GGLPESNPFG | ARAVRIYLRE | 158 |
| --- | --- | --- | --- | --- | --- |
| SEQ_ID_NO_2273 | QAWGSLDALI | GRLRAAYEEN | GGRPESNPFG | ARAVRIYLRE | 158 |
| SEQ_ID_NO_2274 | QAWGSLDALI | GRLRAAYEEN | GGRPESNPFG | ARAVRITCLRE | 147 |
| SEQ_ID_NO_2276 | QAWGSLDALI | GRLRAAYEEN | GGRPESNPFG | ARAVRIYLRE | 157 |
| SEQ_ID_NO_2278 | QAWGSLDALI | GRLRAAYEES | GGRPESNPFA | AKAVRIYLRD | 195 |
| SEQ_ID_NO_2280 | QAWGSLDALI | GRLRAAYEES | GGRPESNPFA | ARAVRIYLRE | 181 |
| SEQ_ID_NO_2281 | QAWGSLDALI | GRLRAAYEES | GGRPESNPFA | ARAVRIYLRE | 177 |
| SEQ_ID_NO_2283 | QAWGSLDALI | GRLRAAYEEN | GGRPDSNPFA | ARAVRIYLRE | 141 |

| SEQ_ID_NO_2271 | VREGQAKARG | PYEKKKRK   | RPI-NVAVSVA | ----SVI---  | 189 |
| --- | --- | --- | --- | --- | --- |
| SEQ_ID_NO_2273 | VREGQAKARG | PYEKKKRK   | RT--TMTVSAV | ----SIS---  | 188 |
| SEQ_ID_NO_2274 | VREGQAKARG | PYEKKKRK   | RPI-TVTATAV | ----VAAT    | 179 |
| SEQ_ID_NO_2276 | VREGQAKARG | PYEKKKRK   | RPI-TVTTTAV | ----GVI---  | 187 |
| SEQ_ID_NO_2278 | VREAQAKARG | PYEKKKRK   | RG--SAAAPV  | --APPI---   | 226 |
| SEQ_ID_NO_2280 | VREAQAKARG | PYEKKKE-RK | RG--STSAPAA | --APPI---   | 211 |
| SEQ_ID_NO_2281 | VREAQAKARG | PYEKKKRK   | RG--AAAAAA  | PPVVAPPI--- | 212 |
| SEQ_ID_NO_2283 | VRESQAKARG | PYEKKKRK   | RPP-TVTTVRV | ----DVI---  | 172 |

| SEQ_ID_NO_1741 | | | | | | 257 |
|---|---|---|---|---|---|---|
| SEQ_ID_NO_1743 | CFDI | DFCR-S | KLSAF- | TY-P | SQSVSHSVST | SSIEYGVVPD | 257 |
| SEQ_ID_NO_1745 | CFDI | DFCR-S | KLISF-SY | P-Q | SQSLSHSVSS | SSLDVGVVPD | 269 |
| SEQ_ID_NO_1747 | CFDVDFCR-S | KFPTF-SY | P | TKSQSHSVSS | SSLEVGVVPD | 249 |
| SEQ_ID_NO_1748 | CFDVDFCR-S | KLSSF-NY | | SNSLSQSVSS | SSLDVGVVPD | 261 |
| SEQ_ID_NO_1749 | HFEIDFTQ-S | HIKSY-NT | | --PSLISVSS | SSLDVGIVPD | 267 |
| SEQ_ID_NO_1750 | SFEIDFSAAS | KPYVY-GF-H | AQCLSQSVSS | SSMDVSVVPD | 248 |
| SEQ_ID_NO_1751 | SFELDFSAGS | KPFVY-GYHH | ARCLSQSVSS | SSMDISVVPD | 246 |
| SEQ_ID_NO_1752 | TYELDFTIG-S | KPYMY-NF-T | SQSISQSVSS | SSLDVGVVPD | 260 |
| SEQ_ID_NO_1753 | CFDITEK | -ATY-SYTT | TTSLSHSVSS | SSLDVGVVPD | 286 |
| SEQ_ID_NO_1754 | LFGMEC-E-T | KLSEY-NY- | NTSISHSVSV | SSLDVGVVPE | 260 |
| | DINNDFST-S | KPFTY-NY- | NHSVSS | PSLEVGVVPD | 220 |

| SEQ_ID_NO_1741 | GNT- | NNSVNR | S-TI | TYTDPSMPI | TLSSTTGGDH | 278 |
|---|---|---|---|---|---|---|
| SEQ_ID_NO_1743 | GNS- | MSDISY | P-FGRSM--N | DPSA-PIWAA | SGSTINQAAA | 304 |
| SEQ_ID_NO_1745 | GNS- | VSDISY | T-FGRTM--G | DSSG-LVMV | TANNQAPPQA | 284 |
| SEQ_ID_NO_1747 | GNT- | VSDMSY | S-FGRNS--N | NSNS-SIDL- | SGNSVGQGAT | 295 |
| SEQ_ID_NO_1748 | GSS- | ISEISY | P-YIRTM--S | AA | SF-NSANHQE | 300 |
| SEQ_ID_NO_1749 | GNT- | MTDVCD | B-YTKSM-AA | | VESTHQAV | 275 |
| SEQ_ID_NO_1750 | GNA- | VT | | AAAG- | VETSQPAV | 261 |
| SEQ_ID_NO_1751 | HSA- | MTDVSN | T-FVMNS--S | EL | TGTDTEAVPN | 290 |
| SEQ_ID_NO_1752 | A--T- | LSDMSR | PI-LNRGV--F | G--- | ANPGVNVGI | 313 |
| SEQ_ID_NO_1753 | S--T- | MSDMSV | S-HSRPP--K | | FSSTPMQVPT | 290 |
| SEQ_ID_NO_1754 | GNV- | MSEMSY | CGYGR | TIDL- | -----TEIAV | 238 |

| | | |
|---|---|---|
| SEQ_ID_NO_1741 | HAQYGVVPTF -- | 355 |
| SEQ_ID_NO_1743 | DTHYGVVPSF -- | 384 |
| SEQ_ID_NO_1745 | DNQYGIVPSF -- | 368 |
| SEQ_ID_NO_1747 | DTPYGVVPSF LT | 374 |
| SEQ_ID_NO_1748 | ESRYGVVPSF -- | 386 |
| SEQ_ID_NO_1749 | LCRYGVVPSF -- | 343 |
| SEQ_ID_NO_1750 | MCRYGVVPSF -- | 329 |
| SEQ_ID_NO_1751 | DASYGVVPSF -- | 360 |
| SEQ_ID_NO_1752 | ELSYGLVPSF -- | 384 |
| SEQ_ID_NO_1753 | DGGYGIVPSF -- | 362 |
| SEQ_ID_NO_1754 | YDGYGVVPSC -- | 312 |

FIG. 33G

| SEQ_ID_NO_1980 | MSITFLLRIL | -LP------LLI | IAMTLPRRSE | AESEQWCIAD | 34 |
|---|---|---|---|---|---|
| SEQ_ID_NO_1982 | MPILVKRTM | -LA------LLL | LSIAPRKSD | GELEQWCIAD | 33 |
| SEQ_ID_NO_1984 | MATEMLKLV | -LP------LLF | LEMPPKTAY | AEFEQWCVAD | 34 |
| SEQ_ID_NO_1985 | MPIALLRIV | -LG------LLL | LVSTGTKSA | GEFEQWCIAD | 33 |
| SEQ_ID_NO_1986 | MATTTATILLW | PLPLLLVLMI | FVSAANLTE | GAVAQWCIAD | 39 |

| SEQ_ID_NO_1980 | EQTPDDELQA | ALDWACGKGG | ADCSKMQEN | QPCFLPNTIR | 74 |
|---|---|---|---|---|---|
| SEQ_ID_NO_1982 | EQTPDDELQL | ALDWACGKGG | ADCSKIQ-VN | QPCYLPNTVR | 72 |
| SEQ_ID_NO_1984 | EQTIESELQA | ALDWACGKGG | ADCSKIQ-VN | QPCYLPNTLK | 73 |
| SEQ_ID_NO_1985 | EQTPDDELQA | GIDWACGEGG | ADCSKIQ-VN | KPCYLPNTVR | 72 |
| SEQ_ID_NO_1986 | PQAPDDMLQS | ALDWVCGYGG | ADCSKTQ-PN | QECFLPDNLA | 78 |

| SEQ_ID_NO_1980 | DHASFAFNSY | YQIYKNKGGS | CYFKGAAMIT | ELDPSHGS- | 112 |
|---|---|---|---|---|---|
| SEQ_ID_NO_1982 | DHASYAFNNY | FQKFKHKGGS | CYFKGAAILT | ELDPSHSS- | 110 |
| SEQ_ID_NO_1984 | DHASYAFNSY | YQKFKHSGGS | CYFRGAAILT | EVDPSHGS- | 111 |
| SEQ_ID_NO_1985 | DHASYAFNSY | YQKFKNKGGT | CYFNGAAMIT | ELDPLTFGMA | 112 |
| SEQ_ID_NO_1986 | SHASTAFNSY | MQKTKHQGAS | CYEDSAALVT | ESDPSHDG- | 116 |

| SEQ_ID_NO_1980 | -------- | -------- | -------- | -CQY-EYN | 118 |
|---|---|---|---|---|---|
| SEQ_ID_NO_1982 | -------- | -------- | -------- | -CQY-EFH | 116 |
| SEQ_ID_NO_1984 | -------- | -------- | -------- | -CHY-EFJ | 117 |
| SEQ_ID_NO_1985 | KSHTADQIIE | SDLDQSHQRW | HHSHLTWYFF | CKYSMFVQAT | 152 |
| SEQ_ID_NO_1986 | -------- | -------- | -------- | -CEY-DEV | 122 |

| SEQ_ID_NO_1980 | P | 119 |
|---|---|---|
| SEQ_ID_NO_1982 | P | 117 |
| SEQ_ID_NO_1984 | P | 118 |
| SEQ_ID_NO_1985 | P | 153 |
| SEQ_ID_NO_1986 | A | 123 |

FIG. 34

| SEQ_ID_NO_1812 | M-VFVKSTKS | NAYFKRYQVK | FRRRRDGKTD | YRARIRLINQ | 39 |
|---|---|---|---|---|---|
| SEQ_ID_NO_1814 | M-VFVKPSKS | NAYFKRYQVK | FRRRRDGKTD | YRARIRLINQ | 39 |
| SEQ_ID_NO_1815 | M-AFAKAQKS | RAYFKRYQVK | FKRRRAGKTD | YRARIRLINQ | 39 |
| SEQ_ID_NO_1817 | M-VYVKAQKS | KAYFKRYQVK | FKRRREGKTD | YRARIRLINQ | 39 |
| SEQ_ID_NO_1819 | ML-AFVKAQKT | KAYFKRFQVP | YKRRRAGKTD | YRARIRLINQ | 39 |
| SEQ_ID_NO_1821 | MGGFVKTHKT | NAYFKRFQVK | FKRRREGKTD | YRARIRLINQ | 40 |
| SEQ_ID_NO_1822 | MJAFAKAQKT | KAYSKRFQVK | FKRRRAGKTD | YRARIRLINQ | 39 |
| SEQ_ID_NO_1824 | MGGFVKTQKT | SAYSKRFQVK | FKRRRAGKTD | YRARIRLINQ | 40 |
| SEQ_ID_NO_1826 | M-VFVKNQKT | RAYSKRFQVK | FKRRRQGKTD | YRARIRLTNQ | 39 |
| SEQ_ID_NO_1827 | MLAFI-KVQKT | RAYFKRFQVK | FKRRREGKTD | YRARINRLINQ | 39 |
| SEQ_ID_NO_1828 | MGGFVKTQKT | NAYYKRFQVK | FKRRRQGKTD | YRARIRLTNQ | 40 |
| SEQ_ID_NO_1829 | M-VFVKAQKT | RAYFKRFQVK | FKRRREGKID | YRARIRLLNQ | 39 |

| SEQ_ID_NO_1812 | DKNKYNTPKY | RFVVRFTNKD | VAQIVSASI | AGDIVKASAY | 79 |
|---|---|---|---|---|---|
| SEQ_ID_NO_1814 | DKNKYNTPKY | RFVVRFTNKD | VAQIYSASI | AGDIVKASAY | 79 |
| SEQ_ID_NO_1815 | DKNKYNTPKY | RFVVRFSNKD | LAQIASASI | AGDIVLAAAY | 79 |
| SEQ_ID_NO_1817 | DKNKYNTPKY | RFVVRFSNKD | I-SASI | AGDIVLAAAY | 79 |
| SEQ_ID_NO_1819 | DKNKYNTPKY | RFVVRFSNKD | VAQIVSSANI | AGDMVLASAY | 79 |
| SEQ_ID_NO_1821 | DKNKYNTPKY | RFVVRETNKD | TAQI-SASI | AGDMVLASAY | 80 |
| SEQ_ID_NO_1822 | DKNKYNTPKY | RFVVRTSNKD | TAQIVSASI | AGDLVLASAY | 79 |
| SEQ_ID_NO_1824 | DKNKYNTPKY | RFVVRFTNKD | TAQIVSASI | AGDMVLAAAY | 80 |
| SEQ_ID_NO_1826 | DKNKYNTPKY | RFVVRFTNKD | VAQIVYATI | AGDIVMAAAY | 79 |
| SEQ_ID_NO_1827 | DKNKYNTPKY | RFVVRFTNRD | I-AQIVSASI | AGDIVMAAAY | 79 |
| SEQ_ID_NO_1828 | DKNKYNTPKY | RFVVRFSNKD | ITAQIVYATI | AGDMILASAY | 80 |
| SEQ_ID_NO_1829 | DKNKYNTPKY | RLVVRFSNKD | VVAQILYATL | AGDVVMAAAY | 79 |

FIG. 35A

| | | | | | |
|---|---|---|---|---|---|
| SEQ_ID_NO_1812 | AHELPQYGLT | VGLTNYAAAY | CTGLLLARRV | LKMLEMDDEY | 119 |
| SEQ_ID_NO_1814 | AHELPQYGLT | VGLTNYAAAY | CTGLLLARRV | LKMLEMDDEY | 119 |
| SEQ_ID_NO_1815 | AHELPRYGLE | AGLTNYAAAY | CTGLLLARRV | LKMLEMDDEY | 119 |
| SEQ_ID_NO_1817 | AHELPRYGLE | VGLTNYAAAY | CTGLLLARRV | LKTLEMDDEY | 119 |
| SEQ_ID_NO_1819 | SHELPRYGLE | VGLTNYAAAY | CTGLLLGRRV | LKIRGLDKEY | 119 |
| SEQ_ID_NO_1821 | SHELPQYGLE | VGLTNYAAAY | CTGLLLARRV | LKMLEMDAEY | 120 |
| SEQ_ID_NO_1822 | SHELPRYGLE | VGLTNYAAAY | CTGLLLARRV | LKMLEMDAEY | 119 |
| SEQ_ID_NO_1824 | SHELPRYGLE | VGLTNYAAAY | CTGLLLARRV | LKLRDLDQEY | 120 |
| SEQ_ID_NO_1826 | ASELPHFGLK | VGLTNYAAAY | CTGLLLARRV | LKQRDLDQEY | 119 |
| SEQ_ID_NO_1827 | SHELPRYGLE | VGLTNYAAAY | CTGLLLARRV | LKKLEMDEEY | 119 |
| SEQ_ID_NO_1828 | SHELPRYGLE | VGLTNYAAAY | CTGLLLARRV | LKLRGLDQEY | 120 |
| SEQ_ID_NO_1829 | SRELPRYGLE | VGLTNYAAAY | CTGLLLARRV | LKQLEMDEEY | 119 |

| | | | | | |
|---|---|---|---|---|---|
| SEQ_ID_NO_1812 | EGNVEATGED | FSVEPTDSRR | PFRALLDVGL | RTTTGNRVF | 159 |
| SEQ_ID_NO_1814 | EGNLEATGED | FSVEPTESRR | PFRALLDVGL | RTTTGNRVF | 159 |
| SEQ_ID_NO_1815 | EGNVEATGED | FSVEPADSRR | PFRALLDVGL | RTTTGNRVF | 159 |
| SEQ_ID_NO_1817 | EGNVEATGED | FSVEPAESRR | PFRALLDVGL | RTTTGNRVF | 159 |
| SEQ_ID_NO_1819 | QGNVEATGED | FSVEPTDTRR | PFRALLDVGL | RTTTGNRVF | 159 |
| SEQ_ID_NO_1821 | EGNVEATGED | FSVEPADERR | PFRALLDVGL | RTTTGNRVF | 160 |
| SEQ_ID_NO_1822 | EGNVEATGED | YSVEPADTRR | PFRALLDVGL | RTTTGNRVF | 159 |
| SEQ_ID_NO_1824 | EGNVEATGED | FSVEPADERR | PFRALLDVGL | RTTTGNRVF | 160 |
| SEQ_ID_NO_1826 | EGNVEAIGED | FSVEPADERR | PFRALLDVGL | RTTTGNRVF | 159 |
| SEQ_ID_NO_1827 | QGNLDVNGED | YSVEPAESRR | PFRALLDVGL | RTTTGNRVF | 159 |
| SEQ_ID_NO_1828 | EGNLEASGED | YMVEPADERR | PFRALLDVGL | VRTTTGNRVF | 160 |
| SEQ_ID_NO_1829 | VGNEEASGED | YSVEPNDARR | PFRALLDVGL | VRTTTGNRVF | 159 |

FIG. 35B

| SEQ_ID_NO_1812 | GALKGALDGG | LDI PHSDKRF | AGFHKENKQL | DAEI HRNYI Y | 199 |
| --- | --- | --- | --- | --- | --- |
| SEQ_ID_NO_1814 | GALKGALDGG | LDI PHSDKRF | AGFNKENKQL | DAEI HRNYI Y | 199 |
| SEQ_ID_NO_1815 | GALKGALDGG | LDI PHSDKRF | AGFAKDNKQL | DAEVHRKYI Y | 199 |
| SEQ_ID_NO_1817 | GALKGALDGG | LDI PHSDKRF | AGFDKEKKEL | DAEVHRKYVF | 199 |
| SEQ_ID_NO_1819 | GALKGALDAG | LDI PHSDKRF | AGFSKDNKQL | DAEVHSKYI Y | 199 |
| SEQ_ID_NO_1821 | GALKGALDGG | LDI PHSDKRF | AGFKKDDKQL | DADTHRRYI F | 200 |
| SEQ_ID_NO_1822 | GALKGALDGG | LDI PHSEKRF | AGYAKNGQQL | DVEVHRKYI Y | 199 |
| SEQ_ID_NO_1824 | GALKGALDGG | LDI PHSDKRF | AGFKKDEKQL | DAEI HRKYI Y | 200 |
| SEQ_ID_NO_1826 | GALKGALDGG | LDI PHSDKRF | AGFKKDEKQL | DAEVHRKFI Y | 199 |
| SEQ_ID_NO_1827 | GALKGALDGG | LDI PHSEKRF | AGYSKDSKQL | DSDI HRKYI Y | 199 |
| SEQ_ID_NO_1828 | GALKGALDGG | LDI PHSDKRF | AGFKKDEKQL | DADLHRKYI Y | 200 |
| SEQ_ID_NO_1829 | GALKGALDGG | LDI PHSDKRF | AGYNKESKSL | DADLHRKYI L | 199 |

| SEQ_ID_NO_1812 | GGHVSNYMKL | LGEDEPEKLQ | THFSAYI KKG | VEAESI EELY | 239 |
| --- | --- | --- | --- | --- | --- |
| SEQ_ID_NO_1814 | GGHVSNYMKM | LNEDEPEKFQ | THFSQYLKKG | VDAESMEELY | 239 |
| SEQ_ID_NO_1815 | GGHVAAYMRT | LMEDEPEKYQ | SHFSEYLKRG | DADGMEALY | 239 |
| SEQ_ID_NO_1817 | GGHVAAYMKL | LAEDEPEKYQ | HFSEYI KRG | EADGI EALY | 239 |
| SEQ_ID_NO_1819 | GGHVAAYMRT | LMEDEPEKYQ | HFSEYI KKG | EADNI ESLY | 239 |
| SEQ_ID_NO_1821 | GGHVADYMKN | LAEEEPEKYQ | AHFSDYI KKG | VEAEEI EALY | 240 |
| SEQ_ID_NO_1822 | GGHVAAYMRT | LMEDEPEKYQ | SHFSEYI KKG | EADELEGLY | 239 |
| SEQ_ID_NO_1824 | GGHVAEYMRT | LAEEEPEKYQ | SHFSDYI KKG | EADDMEALY | 240 |
| SEQ_ID_NO_1826 | GGHVADYMKS | LADEEPEKYQ | SHFSEYI KKG | EADNLEEMY | 239 |
| SEQ_ID_NO_1827 | GGHVTAYMNT | LMEDEPEKYQ | THFSLYI KAG | DADGMEALY | 239 |
| SEQ_ID_NO_1828 | GGHVADYMRS | MAEEEPEKFQ | AHFSEYLKKG | LEPENLEELY | 240 |
| SEQ_ID_NO_1829 | GGHVAAYMKT | LREDEPEKYQ | SQFSEYHKKG | LEPENLEELY | 239 |

FIG. 35C

| | | | | | |
|---|---|---|---|---|---|
| SEQ_ID_NO_1812 | KKVHAAI RAD | PNPXKTVKPA | PKQHKRYNLK | KLTYEERKNK | 279 |
| SEQ_ID_NO_1814 | KKVHAAI RAD | PNPKKTEKPA | PKTHNRYNLK | KLTYEERKNK | 279 |
| SEQ_ID_NO_1815 | KKVHAAI RAD | PTAKKSEKQP | PKEHKRYNLK | KLTYEERKAK | 279 |
| SEQ_ID_NO_1817 | KKVHAAI RAD | PTLKKSDKQT | PKQHKRFNLK | KLTYEERKNK | 279 |
| SEQ_ID_NO_1819 | KNVHAAI RAD | PTAKKTEKEP | PKEHKRYNLK | KLTYEERKAK | 280 |
| SEQ_ID_NO_1821 | KKVHAAI RAD | PSVVKSTKQP | PKAHKRYNLK | KLTYDERKAR | 279 |
| SEQ_ID_NO_1822 | KKVHAAI RAN | PLAKKSDKPQ | PKEHKRYNPK | KLTYEQRKAS | 280 |
| SEQ_ID_NO_1824 | KKVHAAI RAD | PTMAKSTKQP | PKTHKRYNPK | KLTYEQRKAS | 279 |
| SEQ_ID_NO_1826 | KKVHAAI RAD | PKKSGKQP | PKTHKRYNLK | KLTYEQRKAS | 279 |
| SEQ_ID_NO_1827 | KKVHAAI RAD | PTMAKSTKKE | PAIHKRYNLK | KLTYEERKAK | 279 |
| SEQ_ID_NO_1828 | KKVHAAI RAD | PTIKMSEKHV | PKIVQKHYLTR | KLTYEERKNK | 280 |
| SEQ_ID_NO_1829 | KKVHAAI RAD | | | | 279 |

| | | | | |
|---|---|---|---|---|
| SEQ_ID_NO_1812 | LI ERVR- | AAGDDDD- | -H | 286 |
| SEQ_ID_NO_1814 | LI ERVKALNG | AAL--- | EDEE | 302 |
| SEQ_ID_NO_1815 | LVERLNALNS | AAD-N- | DEDDE | 297 |
| SEQ_ID_NO_1817 | LI SRVAALNS | AAGL-D- | SEEED | 298 |
| SEQ_ID_NO_1819 | LI ERLHTLNA | SGGADD-L | DEDDE | 298 |
| SEQ_ID_NO_1821 | LI ERLNQLNS | AADGDDDD | DEDDE | 302 |
| SEQ_ID_NO_1822 | LVERLNALNS | SGGADDDD | DEDDE | 302 |
| SEQ_ID_NO_1824 | LI ERLNALNS | SAGADV-D | EDDDD | 303 |
| SEQ_ID_NO_1826 | LVERLNALNS | AGGNDDDD- | DEDDE | 301 |
| SEQ_ID_NO_1827 | LI ERLNALNA | SAGADF-DDE | EEDDD | 302 |
| SEQ_ID_NO_1828 | LVERLNALNS | GA------D- | EEDDE | 304 |
| SEQ_ID_NO_1829 | LARLNALNA | | EEDDE | 297 |

| SEQ_ID_NO_2124 | DRSAMYRVGC | LFYAIYFIVS | FPMFFRMDEK | STDEWDLSRV | 236 |
| --- | --- | --- | --- | --- | --- |
| SEQ_ID_NO_2126 | DRASMYKVGS | LFYAIYFEVS | FPMFLRIDEK | PGDLWELPRV | 243 |
| SEQ_ID_NO_2128 | DRDSMYKVGS | LFYAIYFIVS | FPMFLRIDEK | PGDKWDLPRV | 236 |
| SEQ_ID_NO_2129 | DRASMYKVGS | LFYAIYFIVS | FPMFLRIDEK | PGNTWDLPRV | 238 |
| SEQ_ID_NO_2131 | DRDIMYKVGS | LFYAIYFIVS | FPMFSRIDEK | DFEKWSLSRV | 248 |
| SEQ_ID_NO_2133 | DRDIMYKVGS | LFYAIYFIVS | FPMFSRIDEK | DFEKWDLSRV | 251 |
| SEQ_ID_NO_2135 | DRDIMYKVGS | LFYAIYFIVS | FPMFSRIDEK | A-EKWDLPRV | 248 |
| SEQ_ID_NO_2136 | DRDIMYKVGS | LFYAIYFIVS | FPMFSRIDEN | E-EKWNLSRV | 277 |

| SEQ_ID_NO_2124 | AVDALGAAML | VTIILDLWRL | FLGPIVPLPE | GQNCLQSGLP | 276 |
| --- | --- | --- | --- | --- | --- |
| SEQ_ID_NO_2126 | AVDSLGAAML | VTIILDLWRI | FLGPIVPLPV | TKQCLQQGLP | 283 |
| SEQ_ID_NO_2128 | DRDSMYKVGS | VTIILDLWRI | FLGPIVPIAD | TKQCPQVGLP | 276 |
| SEQ_ID_NO_2129 | AVDSLGAAML | VTIILDLWRI | FLGPIVLIPE | SNQCHQPGLP | 278 |
| SEQ_ID_NO_2131 | AVDALGAAML | VTIILDLWRI | FLGPIVPVPE | SRQCGQPGLA | 288 |
| SEQ_ID_NO_2133 | AVDALGAAML | VTIILDLWRI | FLGPIVPIPE | SRRCGQPGLA | 291 |
| SEQ_ID_NO_2135 | AVDALGAAML | VTIILDLWRI | FLGPIVPIPE | SRRCAQPGLA | 288 |
| SEQ_ID_NO_2136 | AVDALGAAML | VTIILDLWRI | FLGPIVPIPE | SRRCGQPGLA | 317 |

| SEQ_ID_NO_2124 | WFS----N | 280 |
| --- | --- | --- |
| SEQ_ID_NO_2126 | WFPGHATQT | 292 |
| SEQ_ID_NO_2128 | WFTGHANLK | 285 |
| SEQ_ID_NO_2129 | WFPGHGPKA | 287 |
| SEQ_ID_NO_2131 | WFQAQNGST | 297 |
| SEQ_ID_NO_2133 | WFHAQL--N | 297 |
| SEQ_ID_NO_2135 | WFHAQNESV | 297 |
| SEQ_ID_NO_2136 | WFQVQKESV | 326 |

| SEQ ID NO | | | | | | | |
|---|---|---|---|---|---|---|---|
| SEQ_ID_NO_2035 | TAI RGAI I LA | KLSVVPVRRG | YWGNKI GKPH | TVPCKVTGKC | 181 |
| SEQ_ID_NO_2037 | TAI RGGI I LA | KLSVI PVRRG | YWGNKI GKPH | TVPCKVTGKC | 181 |
| SEQ_ID_NO_2039 | TAI RGAI I LA | KLSVI PVRRG | YWGNKI GKPH | TVPCKVTGKC | 173 |
| SEQ_ID_NO_2041 | TAI RGAI I LA | KLSVVPVRRG | YWGNKI GKPH | TVPCKVTGKC | 167 |
| SEQ_ID_NO_2043 | TAI RGAI I LA | KLSVI PVRRG | YWGNKI GQPH | TVPCKVTGKC | 176 |
| SEQ_ID_NO_2045 | TAI RGAI I LA | KLSVVPVRRG | YWGNKI GKPH | TVPCKVTGKC | 176 |
| SEQ_ID_NO_2047 | TAI RGAI I LA | KLSVI PVRRG | YWGNKI GQPH | TVPCKVTGKC | 176 |
| SEQ_ID_NO_2048 | TAI RGAI I LA | KLSVVPVRRG | YWGNKI GKPH | TVPCKVTGKC | 171 |
| SEQ_ID_NO_2049 | TAI RGAI I LA | KLSVI PVRRG | YWGNKI GLPH | TVPCKVTGKC | 174 |
| SEQ_ID_NO_2051 | TAI RGAI I LA | KLSVI PVRRG | YWGNKI GKPH | TVPCKVTGKC | 175 |
| SEQ_ID_NO_2052 | TAI RGAI I LA | KMSVVPVRRG | YWGNKI GKVH | TVPCKVTGKC | 177 |
| SEQ_ID_NO_2053 | TAI RGAI I QA | KLSVI PVRRG | YWGNKI GKPH | TVPVKVTGKC | 177 |
| SEQ_ID_NO_2054 | HSLQGSMI LA | KLNVVPVRRG | YWGSKLGAPH | TVPTKVI GKC | 174 |
| SEQ_ID_NO_2055 | | | | TI PTKVHGKC | 176 |

| SEQ ID NO | | | | | | | |
|---|---|---|---|---|---|---|---|
| SEQ_ID_NO_2035 | GSVTVRMVPA | PRGSGI VAAR | VPKKVLQFAG | DDVFTSSRG | 221 |
| SEQ_ID_NO_2037 | GSVTVRMVPA | PRGAGI VAAR | VPKKVLQFAG | DDVFTSSRG | 221 |
| SEQ_ID_NO_2039 | GSVTVRMVPA | PRGSGI VAAR | VPKKVLQFAG | DDVFTSSRG | 213 |
| SEQ_ID_NO_2041 | GSVTVRMVPA | PRGAGI VAAR | VPKKVLQFAG | EDVFTSSRG | 207 |
| SEQ_ID_NO_2043 | GSVTVRMVPA | PRGSGI VAAR | VPKKVLQFAG | EDVFTSSRG | 216 |
| SEQ_ID_NO_2045 | GSVTVRMVPA | PRGSGI VAAR | VPKKVLQFAG | DDVFTSSRG | 216 |
| SEQ_ID_NO_2047 | GSVTVRMVPA | PRGAGI VAAR | VPKKVLQFAG | EDVFTSSRG | 216 |
| SEQ_ID_NO_2048 | GSVTVRMVPA | PRGSGI VAAH | VPKKVLQFAG | EDVFTSSRG | 211 |
| SEQ_ID_NO_2049 | GSVTVRMVPA | PRGAGI VAAR | VPKKVLQFAG | DDVFTSSRG | 214 |
| SEQ_ID_NO_2051 | GSVTVRMVPA | PRGSGI VAAR | VPKKVLQFAG | EDVFTSSRG | 215 |
| SEQ_ID_NO_2052 | GSVTVRLVPA | PRGAGI VAAR | VPKKVLQFAG | EDVFTSSRG | 217 |
| SEQ_ID_NO_2053 | GSVTVRMVPA | PRGAGI VAAR | TPKKVLMAG | EDCYTSSRG | 217 |
| SEQ_ID_NO_2054 | GSVI RLTPA | PRGAGI VAAR | VPKKVLQFAG | EDVFTSSRG | 214 |
| SEQ_ID_NO_2055 | GSVMVRLI PA | PRGAGI VASG | MKKVLAMAG | LHDVYTCSRG | 216 |

| | | | | | | |
|---|---|---|---|---|---|---|
| SEQ_ID_NO_2425 | P----- | -HLDL- | ----- ELN- | ----- | ----- | ----- | 552 |
| SEQ_ID_NO_2426 | ----- | --HDL- | RANSV | NCGV | FCVRVRDKPT | WRKAVSLTIR | 615 |
| SEQ_ID_NO_2428 | KGYGDDH- | ELH- | ----- | ----- | ----- | 630 |
| SEQ_ID_NO_2430 | PDYHHHQPG | TANTI | ----- | ----- | ----- | 593 |
| SEQ_ID_NO_2431 | ----- | ----- | ----- | ----- | ----- | 583 |
| SEQ_ID_NO_2433 | ----- | ----- | ----- | ----- | ----- | 591 |

| | | |
|---|---|---|
| SEQ_ID_NO_2425 | ---NEQ | 555 |
| SEQ_ID_NO_2426 | --QLKH | 619 |
| SEQ_ID_NO_2428 | HQRCGND | 637 |
| SEQ_ID_NO_2430 | ---DMKY | 597 |
| SEQ_ID_NO_2431 | ---ASKV | 587 |
| SEQ_ID_NO_2433 | ----SN | 593 |

FIG. 38E

TRANSGENIC PLANTS HAVING INCREASED BIOMASS

CROSS-REFERENCE TO RELATED APPLICATIONS

This Application is a National Stage application under 35 U.S.C. 371 of International Application No. PCT/US2011/035345, having an International Filing Date of May 5, 2011, which claims priority under 35 U.S.C. 119(e) to U.S. Provisional Application No. 61/331,984, filed May 6, 2010, and to U.S. Provisional Application No. 61/378,477, filed Aug. 31, 2010, which are incorporated herein by reference in their entirety.

STATEMENT AS TO FEDERALLY SPONSORED RESEARCH

This invention was made in part with government support under Grant No. CALW-2009-00426 awarded by the National Institute of Food and Agriculture. The government has certain rights in the invention.

TECHNICAL FIELD

This document relates to methods and materials involved in modulating biomass levels in plants. For example, this document provides plants having increased biomass levels as well as materials and methods for making plants and plant products having increased biomass levels.

INCORPORATION-BY-REFERENCE OF SEQUENCE LISTING

The material in the accompanying sequence listing is hereby incorporated by reference into this application. The accompanying file, named 60645683.txt was created on Apr. 25, 2011, and is 7.97 MB. The file can be accessed using Microsoft Word on a computer that uses Windows OS.

BACKGROUND

The present invention relates to methods of increasing biomass in plants and plants generated thereby. Plants having increased and/or improved biomass are useful for agriculture, horticulture, biomass to energy conversion, paper production, plant product production, and other industries. In particular, there is a need for increases in biomass for dedicated energy crops such as *Panicum virgatum* L. (switchgrass), *Miscanthus×gigantus* (miscanthus), *Sorghum* sp., and *Saccharum* sp. (sugar cane). Throughout human history, access to plant biomass for both food and fuel has been essential to maintaining and increasing population levels. Scientists are continually striving to improve biomass in agricultural crops. The large amount of research related to increasing plant biomass, particularly for dedicated energy crops, indicates the level of importance placed on providing sustainable sources of energy for the population. The urgency of developing sustainable and stable sources of plant biomass for energy is underscored by current events, such as rising oil prices. The amount of biomass produced by plants is a quantitative trait affected by a number of biochemical pathways. There is a need for molecular genetic approaches to more rapidly produce plants having increased biomass. There is also a need to produce plant species that grow more efficiently and produce more biomass in various geographic and/or climatic environments. It would be desirable for such approaches to be applicable to multiple plant species (Zhang et al., *Plant Physiol.* 135: 615-621 (2004)). Despite some progress in molecular genetic approaches, there is also a need to identify specific genes and/or sequences that can be used to effectively increase biomass in plants.

SUMMARY

This document provides methods and materials related to plants having modulated levels of biomass. For example, this document provides transgenic plants and plant cells having increased levels of biomass, nucleic acids used to generate transgenic plants and plant cells having increased levels of biomass, methods for making plants having increased levels of biomass, and methods for making plant cells that can be used to generate plants having increased levels of biomass. Such plants and plant cells can be grown to produce, for example, plants having increased height, increased tiller number, or increased dry weight. Plants having increased biomass levels may be useful to produce biomass for food and feed, which may benefit both humans and animals. Plants having increased biomass levels may be useful in converting such biomass to a liquid fuel (e.g., ethanol), or other chemicals, or may be useful as a thermochemical fuel.

This document features a method of producing a plant. The method includes growing a plant cell comprising an exogenous nucleic acid, the exogenous nucleic acid comprising a regulatory region operably linked to a nucleotide sequence encoding a polypeptide, wherein the HMM bit score of the amino acid sequence of the polypeptide is greater than about 65, wherein the HMM is based on the amino acid sequences depicted in one of FIGS. 1-38, and wherein the plant has a difference in the level of biomass as compared to the corresponding level of a control plant that does not comprise the nucleic acid. For example, the plant can have an increased level of biomass relative to the control plant.

This document also features a method of producing a plant. The method includes growing a plant cell comprising an exogenous nucleic acid, the exogenous nucleic acid comprising a regulatory region operably linked to a nucleotide sequence encoding a polypeptide having 80 percent or greater sequence identity to an amino acid sequence selected from the group consisting of SEQ ID NOs: 2, 4, 6-9, 11, 13-15, 17, 18, 20-27, 29, 31-33, 35, 36, 38-51, 53, 54, 56-61, 63-67, 69, 70, 72-76, 78, 80-83, 85, 86, 88-91, 93-97, 99-103, 105, 107, 109, 110, 112, 113, 115, 117, 119-152, 154, 156, 158, 159, 161, 163, 165, 167, 168, 170, 172, 174, 176, 178, 180-185, 187, 188, 190, 192-194, 196, 198, 200, 202, 203, 205, 207-211, 213-251, 253, 255, 257, 258, 260-262, 264, 265, 267-272, 274-279, 281-283, 285, 287-292, 294, 295-297, 299, 301, 303-305, 307, 309, 310, 312, 314, 316-318, 320, 321, 323, 325, 327-329, 331, 332, 334, 335, 337-339, 341, 342, 344, 345, 347, 349, 351, 353, 355, 357, 359, 361-366, 368, 370, 372, 373, 375-378, 380, 382-387, 389, 391, 393, 395, 396, 398-404, 406-414, 416, 418, 420, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497-502, 504, 506, 508, 509, 511-517, 519, 521, 522, 524-527, 529, 530, 532, 533, 535, 536, 537, 539, 541, 543, 545, 546, 548, 550, 552-555, 557, 558, 560, 562, 564, 566, 568, 570-578, 580, 582, 584, 585, 587, 589, 591, 592, 594-596, 598, 600, 601, 603, 604, 606-608, 610, 611, 613, 615, 617, 619, 621, 623, 625, 626, 628-632, 634, 636, 638, 640, 642, 643, 645, 647, 649, 651, 653, 655, 657, 659, 661, 663, 665, 667-670, 672, 674, 675, 677, 679-682, 684, 685, 687, 689-692, 694-698, 700-704, 706, 707, 709-718, 720, 722, 724, 726-728, 730, 731, 733-739, 741, 743, 745, 746, 748, 750, 752, 754, 756, 758, 760-764, 766, 768, 770, 772, 774, 776, 778, 780, 782, 784, 785, 787, 789, 791, 793-795, 797, 799, 801, 803, 805, 806, 808, 810, 812, 814, 816, 818-820, 822-824, 826, 828, 830, 832, 834, 836, 838-840, 842, 843, 845-847, 849, 851, 853, 854, 856-858, 860, 862, 863, 865, 866, 868, 870-873, 875-878, 880-882, 884-886, 888, 890, 892, 893, 895, 897, 899, 900, 902, 903, 905, 907, 909, 911, 912, 913, 915, 917, 919, 921, 923, 925, 926, 928, 930, 932, 933, 935, 936-938, 940, 941, 943-945, 947, 949, 950, 952-955, 957-961, 963, 965-969, 971, 972, 974, 975, 977, 978, 980, 982, 984, 986, 988, 990, 992, 994, 996, 998, 1000-1014, 1016, 1018, 1020, 1021, 1023, 1024, 1026, 1027, 1029, 1030, 1032, 1033, 1035, 1037, 1038, 1040, 1042, 1043, 1045, 1047, 1049, 1051, 1053, 1055, 1057, 1059, 1061-1063, 1065, 1067, 1069, 1070, 1072, 1073, 1075, 1076, 1078-1080, 1082, 1083, 1085, 1087, 1089, 1091, 1093, 1095, 1096, 1098, 1100, 1101, 1103, 1105, 1106, 1108, 1110, 1112, 1114-1116, 1118, 1120-1123, 1125, 1127-1131, 1133, 1134, 1136, 1137, 1139-1145, 1147-1156, 1158-1161, 1163, 1165-1178, 1180-1188, 1190, 1191, 1193-1202, 1204, 1205-1207, 1209-1213, 1215, 1217-1221, 1223-1228, 1230, 1231, 1233-1241, 1243, 1245, 1247, 1249-1252, 1254, 1255, 1257-1259, 1261, 1263, 1264, 1266-1272, 1274-1276, 1278, 1280, 1282-1286, 1288, 1289, 1291-1331, 1333-1337, 1339, 1341, 1343, 1345, 1347-1350, 1352, 1354, 1356, 1358, 1360, 1362, 1364, 1366, 1368, 1370-1372, 1374, 1375, 1377-1379, 1381, 1383, 1384, 1386, 1388-1390, 1392-1397, 1399, 1400, 1402, 1403, 1405, 1407-1410, 1412-1418, 1420, 1422, 1424, 1426, 1428, 1430, 1432-1436, 1438, 1440, 1442-1444, 1446, 1447, 1449, 1450, 1452-1454, 1456, 1457, 1459, 1460, 1462, 1463, 1465-1468, 1470, 1471, 1473, 1475, 1477-1483, 1485, 1487, 1489, 1491-1493, 1495, 1496, 1498, 1499, 1501, 1503, 1504, 1506, 1508, 1510, 1511, 1513, 1514, 1516-1521, 1523, 1524, 1526, 1528-1532, 1534, 1536-1539, 1541, 1542, 1544, 1545, 1547, 1548, 1550, 1552, 1553, 1555-1559, 1561, 1563-1565, 1567, 1568, 1570, 1571, 1573, 1575, 1576, 1578, 1580, 1582, 1583, 1585, 1587, 1589, 1590, 1592, 1593, 1595, 1597, 1599, 1600, 1602-1606, 1608-1613, 1615, 1616, 1618-1626, 1628, 1629, 1631, 1633, 1634, 1636, 1637, 1639-1643, 1645, 1646-1739, 1741, 1743, 1745, 1747-1756, 1758, 1760, 1762-1764, 1766, 1767, 1769, 1770, 1772-1774, 1776, 1778-1783, 1785-1792, 1794, 1796, 1798, 1799, 1801, 1802, 1804, 1806, 1808-1810, 1812, 1814, 1815, 1817, 1819, 1821, 1822, 1824, 1826-1830, 1832, 1834, 1835, 1837, 1839-1841, 1843, 1844, 1846, 1847, 1849, 1851, 1852, 1854, 1856, 1858, 1860-1863, 1865-1953, 1955-1958, 1960, 1962, 1964, 1966-1968, 1970, 1972-1976, 1978, 1980, 1982, 1984-1986, 1988, 1990, 1991, 1993, 1995, 1997, 1999, 2001, 2003, 2005, 2007, 2009, 2011, 2013, 2015, 2017, 2019, 2021, 2023-2027, 2029, 2031, 2033, 2035, 2037, 2039, 2041, 2043, 2045, 2047-2049, 2051-2057, 2059, 2061, 2063, 2065, 2067, 2069, 2071, 2073, 2075, 2077, 2079, 2080, 2082, 2084, 2086, 2088, 2090, 2092, 2093, 2095, 2097, 2098, 2100-2122, 2124, 2126, 2128, 2129, 2131, 2133, 2135-2137, 2139, 2141, 2142, 2144-2148, 2150, 2152, 2154, 2155, 2157, 2159-2161, 2163, 2165, 2166, 2168, 2170, 2172-2175, 2177, 2179, 2181, 2183, 2184, 2186, 2188, 2189, 2191-2194, 2196, 2197, 2199-2202, 2204, 2206-2208, 2210-2212, 2214, 2215, 2217-2220, 2222, 2224-2226, 2228, 2230-2232, 2234-2242, 2244-2254, 2256-2269, 2271, 2273, 2274, 2276, 2278, 2280, 2281, 2283, 2285, 2286, 2288, 2290, 2292, 2294, 2296, 2297, 2299, 2301, 2303, 2305, 2307, 2309, 2311, 2313, 2314, 2316-2318, 2320, 2322, 2324, 2326, 2327, 2329, 2331, 2333, 2335, 2337, 2339, 2341, 2342, 2344, 2345, 2347-2349, 2351, 2353, 2355, 2357, 2359, 2361, 2363, 2365, 2367-2369, 2371, 2373, 2375, 2377, 2379, 2381, 2383, 2385, 2386, 2388, 2390, 2391, 2393, 2395, 2397, 2399, 2400, 2402, 2404, 2405, 2407, 2409, 2411, 2413, 2415, 2417, 2419, 2421, 2423, 2425, 2426, 2428, 2430, 2431, 2433, 2435, 2437, 2438-2440, 2442, 2444, 2445, 2447, 2449, 2451, 2453, 2455, 2457, 2459, 2461, 2463-2468, 2470, 2472, 2474, 2476, 2478, 2479, 2481, 2482, 2484, 2485, 2487-2491, 2493-2498, 2500-2510, 2512-2515, 2517-2531, 2533-2536, 2538-2542, 2544-2548, 2550, 2551, 2553, 2555-2558, 2560, 2562, 2564, 2566-2573, 2575-2579, 2581, 2583-2585, 2587-2602, 2604-2611, 2613, 2615, 2617, and 2619-2623. A plant produced from the plant cell has a difference in the level of biomass as compared to the corresponding level of a control plant that does not include the nucleic acid. For example, the plant can have an increased level of biomass relative to the control plant.

This document also features a method of producing a plant. The method includes growing a plant cell comprising an exogenous nucleic acid, the exogenous nucleic acid comprising a regulatory region operably linked to a nucleotide sequence having 80 percent or greater sequence identity to a nucleotide sequence selected from the group consisting of SEQ ID NO: 1, 3, 5, 10, 12, 16, 19, 28, 30, 34, 37, 52, 55, 62, 68, 71, 77, 79, 84, 87, 92, 98, 104, 106, 108, 111, 114, 116, 118, 153, 155, 157, 160, 162, 164, 166, 169, 171, 173, 175, 177, 179, 186, 189, 191, 195, 197, 199, 201, 204, 206, 212, 252, 254, 256, 259, 263, 266, 273, 280, 284, 286, 293, 298, 300, 302, 306, 308, 311, 313, 315, 319, 322, 324, 326, 330, 333, 336, 340, 343, 346, 348, 350, 352, 354, 356, 358, 360, 367, 369, 371, 374, 379, 381, 388, 390, 392, 394, 397, 405, 415, 417, 419, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 503, 505, 507, 510, 518, 520, 523, 528, 531, 534, 538, 540, 542, 544, 547, 549, 551, 556, 559, 561, 563, 565, 567, 569, 579, 581, 583, 586, 588, 590, 593, 597, 599, 602, 605, 609, 612, 614, 616, 618, 620, 622, 624, 627, 633, 635, 637, 639, 641, 644, 646, 648, 650, 652, 654, 656, 658, 660, 662, 664, 666, 671, 673, 676, 678, 683, 686, 688, 693, 699, 705, 708, 719, 721, 723, 725, 729, 732, 740, 742, 744, 747, 749, 751, 753, 755, 757, 759, 765, 767, 769, 771, 773, 775, 777, 779, 781, 783, 786, 788, 790, 792, 796, 798, 800, 802, 804, 807, 809, 811, 813, 815, 817, 821, 825, 827, 829, 831, 833, 835, 837, 841, 844, 848, 850, 852, 855, 859, 861, 864, 867, 869, 874, 879, 883, 887, 889, 891, 894, 896, 898, 901, 904, 906, 908, 910, 914, 916, 918, 920, 922, 924, 927, 929, 931, 934, 939, 942, 946, 948, 951, 956, 962, 964, 970, 973, 976, 979, 981, 983, 985, 987, 989, 991, 993, 995, 997, 999, 1015, 1017, 1019, 1022, 1025, 1028, 1031, 1034, 1036, 1039, 1041, 1044, 1046, 1048, 1050, 1052, 1054, 1056, 1058, 1060, 1064, 1066, 1068, 1071, 1074, 1077, 1081, 1084, 1086, 1088, 1090, 1092, 1094, 1097, 1099, 1102, 1104, 1107, 1109, 1111, 1113, 1117, 1119, 1124, 1126, 1132, 1135, 1138, 1146, 1157, 1162, 1164, 1179, 1189, 1192, 1203, 1208, 1214, 1216, 1222, 1229, 1232, 1242, 1244, 1246, 1248, 1253, 1256, 1260, 1262, 1265, 1273, 1277, 1279, 1281, 1287, 1290, 1332, 1338, 1340, 1342, 1344, 1346, 1351, 1353, 1355, 1357, 1359, 1361, 1363, 1365, 1367, 1369, 1373, 1376, 1380, 1382, 1385, 1387, 1391, 1398, 1401, 1404, 1406, 1411, 1419, 1421, 1423, 1425, 1427, 1429, 1431, 1437, 1439, 1441, 1445, 1448, 1451, 1455, 1458, 1461, 1464, 1469, 1472, 1474, 1476, 1484, 1486, 1488, 1490, 1494, 1497, 1500, 1502, 1505, 1507, 1509, 1512, 1515, 1522, 1525, 1527, 1533, 1535, 1540, 1543, 1546, 1549, 1551, 1554, 1560, 1562, 1566, 1569, 1572, 1574, 1577, 1579, 1581, 1584, 1586, 1588, 1591, 1594, 1596, 1598, 1601, 1607, 1614, 1617, 1627, 1630, 1632, 1635, 1638, 1644, 1740, 1742, 1744, 1746, 1757, 1759, 1761, 1765, 1768, 1771, 1775, 1777, 1784, 1793, 1795, 1797, 1800, 1803, 1805, 1807, 1811, 1813, 1816, 1818, 1820, 1823, 1825, 1831, 1833, 1836, 1838, 1842, 1845, 1848, 1850, 1853, 1855, 1857, 1859, 1864, 1954, 1959, 1961, 1963, 1965, 1969, 1971, 1977, 1979, 1981, 1983, 1987, 1989, 1992, 1994, 1996, 1998, 2000, 2002, 2004, 2006, 2008, 2010, 2012, 2014, 2016, 2018, 2020, 2022, 2028, 2030, 2032, 2034, 2036, 2038, 2040, 2042, 2044, 2046, 2050, 2058, 2060, 2062, 2064, 2066, 2068, 2070, 2072, 2074, 2076, 2078, 2081, 2083, 2085, 2087, 2089, 2091, 2094, 2096, 2099, 2123, 2125, 2127, 2130, 2132, 2134, 2138, 2140, 2143, 2149, 2151, 2153, 2156, 2158, 2162, 2164, 2167, 2169, 2171, 2176, 2178, 2180, 2182, 2185, 2187, 2190, 2195, 2198, 2203, 2205, 2209, 2213, 2216, 2221, 2223, 2227, 2229, 2233, 2243, 2255, 2270, 2272, 2275, 2277, 2279, 2282, 2284, 2287, 2289, 2291, 2293, 2295, 2298, 2300, 2302, 2304, 2306, 2308, 2310, 2312, 2315, 2319, 2321, 2323, 2325, 2328, 2330, 2332, 2334, 2336, 2338, 2340, 2343, 2346, 2350, 2352, 2354, 2356, 2358, 2360, 2362, 2364, 2366, 2370, 2372, 2374, 2376, 2378, 2380, 2382, 2384, 2387, 2389, 2392, 2394, 2396, 2398, 2401, 2403, 2406, 2408, 2410, 2412, 2414, 2416, 2418, 2420, 2422, 2424, 2427, 2429, 2432, 2434, 2436, 2441, 2443, 2446, 2448, 2450, 2452, 2454, 2456, 2458, 2460, 2462, 2469, 2471, 2473, 2475, 2477, 2480, 2483, 2486, 2492, 2499, 2511, 2516, 2532, 2537, 2543, 2549, 2552, 2554, 2559, 2561, 2563, 2565, 2574, 2580, 2582, 2586, 2603, 2612, 2614, 2616, and 2618, or a fragment thereof. A plant produced from the plant cell has a difference in the level of biomass as compared to the corresponding level of a control plant that does not include the nucleic acid. For example, the plant can have an increased level of biomass relative to the control plant.

This document also features a method of producing a plant. The method includes growing a plant cell comprising an exogenous nucleic acid, the exogenous nucleic acid effective for downregulating an endogenous nucleic acid in the plant cell, wherein the endogenous nucleic acid encodes a polypeptide and wherein the HMM bit score of the amino acid sequence of the polypeptide is greater than about 65, the HMM based on the amino acid sequences depicted in one of FIGS. 1-38.

In another aspect, this document features a method of modulating the level of biomass in a plant. The method includes introducing into a plant cell an exogenous nucleic acid, the exogenous nucleic acid including a regulatory region operably linked to a nucleotide sequence encoding a polypeptide, wherein the HMM bit score of the amino acid sequence of the polypeptide is greater than about 65, the HMM based on the amino acid sequences depicted in one of FIGS. 1-38, and wherein a plant produced from the plant cell has a difference in the level of biomass as compared to the corresponding level of a control plant that does not include the exogenous nucleic acid. For example, the plant can have an increased level of biomass relative to the control plant.

This document also features a method of modulating the level of biomass in a plant. The method includes introducing into a plant cell an exogenous nucleic acid, the exogenous nucleic acid comprising a regulatory region operably linked to a nucleotide sequence encoding a polypeptide having 80 percent or greater sequence identity to an amino acid sequence selected from the group consisting of SEQ ID NOs: 2, 4, 6-9, 11, 13-15, 17, 18, 20-27, 29, 31-33, 35, 36, 38-51, 53, 54, 56-61, 63-67, 69, 70, 72-76, 78, 80-83, 85, 86, 88-91, 93-97, 99-103, 105, 107, 109, 110, 112, 113, 115, 117, 119-152, 154, 156, 158, 159, 161, 163, 165, 167, 168, 170, 172, 174, 176, 178, 180-185, 187, 188, 190, 192-194, 196, 198, 200, 202, 203, 205, 207-211, 213-251, 253, 255, 257, 258, 260-262, 264, 265, 267-272, 274-279, 281-283, 285, 287-292, 294, 295-297, 299, 301, 303-305, 307, 309, 310, 312, 314, 316-318, 320, 321, 323, 325, 327-329, 331, 332, 334, 335, 337-339, 341, 342, 344, 345, 347, 349, 351, 353, 355, 357, 359, 361-366, 368, 370, 372, 373, 375-378, 380, 382-387, 389, 391, 393, 395, 396, 398-404, 406-414, 416, 418, 420, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497-502, 504, 506, 508, 509, 511-517, 519, 521, 522, 524-527, 529, 530, 532, 533, 535, 536, 537, 539, 541, 543, 545, 546, 548, 550, 552-555, 557, 558, 560, 562, 564, 566, 568, 570-578, 580, 582, 584, 585, 587, 589, 591, 592, 594-596, 598, 600, 601, 603, 604, 606-608, 610, 611, 613, 615, 617, 619, 621, 623, 625, 626, 628-632, 634, 636, 638, 640, 642, 643, 645, 647, 649, 651, 653, 655, 657, 659, 661, 663, 665, 667-670, 672, 674, 675, 677, 679-682, 684, 685, 687, 689-692, 694-698, 700-704, 706, 707, 709-718, 720, 722, 724, 726-728, 730, 731, 733-739, 741, 743, 745, 746, 748, 750, 752, 754, 756, 758, 760-764, 766, 768, 770, 772, 774, 776, 778, 780, 782, 784, 785, 787, 789, 791, 793-795, 797, 799, 801, 803, 805, 806, 808, 810, 812, 814, 816, 818-820, 822-824, 826, 828, 830, 832, 834, 836, 838-840, 842, 843, 845-847, 849, 851, 853, 854, 856-858, 860, 862, 863, 865, 866, 868, 870-873, 875-878, 880-882, 884-886, 888, 890, 892, 893, 895, 897, 899, 900, 902, 903, 905, 907, 909, 911, 912, 913, 915, 917, 919, 921, 923, 925, 926, 928, 930, 932, 933, 935, 936-938, 940, 941, 943-945, 947, 949, 950, 952-955, 957-961, 963, 965-969, 971, 972, 974, 975, 977, 978, 980, 982, 984, 986, 988, 990, 992, 994, 996, 998, 1000-1014, 1016, 1018, 1020, 1021, 1023, 1024, 1026, 1027, 1029, 1030, 1032, 1033, 1035, 1037, 1038, 1040, 1042, 1043, 1045, 1047, 1049, 1051, 1053, 1055, 1057, 1059, 1061-1063, 1065, 1067, 1069, 1070, 1072, 1073, 1075, 1076, 1078-1080, 1082, 1083, 1085, 1087, 1089, 1091, 1093, 1095, 1096, 1098, 1100, 1101, 1103, 1105, 1106, 1108, 1110, 1112, 1114-1116, 1118, 1120-1123, 1125, 1127-1131, 1133, 1134, 1136, 1137, 1139-1145, 1147-1156, 1158-1161, 1163, 1165-1178, 1180-1188, 1190, 1191, 1193-1202, 1204, 1205-1207, 1209-1213, 1215, 1217-1221, 1223-1228, 1230, 1231, 1233-1241, 1243, 1245, 1247, 1249-1252, 1254, 1255, 1257-1259, 1261, 1263, 1264, 1266-1272, 1274-1276, 1278, 1280, 1282-1286, 1288, 1289, 1291-1331, 1333-1337, 1339, 1341, 1343, 1345, 1347-1350, 1352, 1354, 1356, 1358, 1360, 1362, 1364, 1366, 1368, 1370-1372, 1374, 1375, 1377-1379, 1381, 1383, 1384, 1386, 1388-1390, 1392-1397, 1399, 1400, 1402, 1403, 1405, 1407-1410, 1412-1418, 1420, 1422, 1424, 1426, 1428, 1430, 1432-1436, 1438, 1440, 1442-1444, 1446, 1447, 1449, 1450, 1452-1454, 1456, 1457, 1459, 1460, 1462, 1463, 1465-1468, 1470, 1471, 1473, 1475, 1477-1483, 1485, 1487, 1489, 1491-1493, 1495, 1496, 1498, 1499, 1501, 1503, 1504, 1506, 1508, 1510, 1511, 1513, 1514, 1516-1521, 1523, 1524, 1526, 1528-1532, 1534, 1536-1539, 1541, 1542, 1544, 1545, 1547, 1548, 1550, 1552, 1553, 1555-1559, 1561, 1563-1565, 1567, 1568, 1570, 1571, 1573, 1575, 1576, 1578, 1580, 1582, 1583, 1585, 1587, 1589, 1590, 1592, 1593, 1595, 1597, 1599, 1600, 1602-1606, 1608-1613, 1615, 1616, 1618-1626, 1628, 1629, 1631, 1633, 1634, 1636, 1637, 1639-1643, 1645, 1646-1739, 1741, 1743, 1745, 1747-1756, 1758, 1760, 1762-1764, 1766, 1767, 1769, 1770, 1772-1774, 1776, 1778-1783, 1785-1792, 1794, 1796, 1798, 1799, 1801, 1802, 1804, 1806, 1808-1810, 1812, 1814, 1815, 1817, 1819, 1821, 1822, 1824, 1826-1830, 1832, 1834, 1835, 1837, 1839-1841, 1843, 1844, 1846, 1847, 1849, 1851, 1852, 1854, 1856, 1858, 1860-1863, 1865-1953, 1955-1958, 1960, 1962, 1964, 1966-1968, 1970, 1972-1976, 1978, 1980, 1982, 1984-1986, 1988, 1990, 1991, 1993, 1995, 1997, 1999, 2001, 2003, 2005, 2007, 2009, 2011, 2013, 2015, 2017, 2019, 2021, 2023-2027, 2029, 2031, 2033, 2035, 2037, 2039, 2041, 2043, 2045, 2047-2049, 2051-2057, 2059, 2061, 2063, 2065, 2067, 2069, 2071, 2073, 2075, 2077, 2079, 2080, 2082, 2084, 2086, 2088, 2090, 2092, 2093, 2095, 2097, 2098, 2100-2122, 2124, 2126, 2128, 2129, 2131, 2133, 2135-2137, 2139, 2141, 2142, 2144-2148, 2150, 2152, 2154, 2155, 2157, 2159-2161, 2163, 2165, 2166, 2168, 2170, 2172-2175, 2177, 2179, 2181, 2183, 2184, 2186, 2188, 2189, 2191-2194, 2196, 2197, 2199-2202, 2204, 2206-2208, 2210-2212, 2214, 2215, 2217-2220, 2222, 2224-2226, 2228, 2230-2232, 2234-2242, 2244-2254, 2256-2269, 2271, 2273, 2274, 2276, 2278, 2280, 2281, 2283, 2285, 2286, 2288, 2290, 2292, 2294, 2296, 2297, 2299, 2301, 2303, 2305, 2307, 2309, 2311, 2313, 2314, 2316-2318, 2320, 2322, 2324, 2326, 2327, 2329, 2331, 2333, 2335, 2337, 2339, 2341, 2342, 2344, 2345, 2347-2349, 2351, 2353, 2355, 2357, 2359, 2361, 2363, 2365, 2367-2369, 2371, 2373, 2375, 2377, 2379, 2381, 2383, 2385, 2386, 2388, 2390, 2391, 2393, 2395, 2397, 2399, 2400, 2402, 2404, 2405, 2407, 2409, 2411, 2413, 2415, 2417, 2419, 2421, 2423, 2425, 2426, 2428, 2430, 2431, 2433, 2435, 2437, 2438-2440, 2442, 2444, 2445, 2447, 2449, 2451, 2453, 2455, 2457, 2459, 2461, 2463-2468, 2470, 2472, 2474, 2476, 2478, 2479, 2481, 2482, 2484, 2485, 2487-2491, 2493-2498, 2500-2510, 2512-2515, 2517-2531, 2533-2536, 2538-2542, 2544-2548, 2550, 2551, 2553, 2555-2558, 2560, 2562, 2564, 2566-2573, 2575-2579, 2581, 2583-2585, 2587-2602, 2604-2611, 2613, 2615, 2617, and 2619-2623. A plant produced from the plant cell has a difference in the level of biomass as compared to the corresponding level of a control plant that does not include the nucleic acid. For example, the plant can have an increased level of biomass relative to the control plant.

In the methods described herein, a polypeptide can include an O-methyltransferase domain having 60 percent or greater sequence identity to the O-methyltransferase domain of residues 92 to 139 of SEQ ID NO: 1333 and a dimerization domain having 60 percent or greater sequence identity to the dimerization domain of residues 31 to 83 of SEQ ID NO: 1333.

In the methods described herein, a polypeptide can include a glycosyl transferase family 8 domain having 60 percent or greater sequence identity to the glycosyl transferase family 8 domain of residues 314 to 525 of SEQ ID NO: 1489.

In the methods described herein, a polypeptide can include a raffinose synthase domain having 60 percent or greater sequence identity to the raffinose synthase domain of residues 2 to 727 of SEQ ID NO: 504.

In the methods described herein, a polypeptide can include an LpxC domain having 60 percent or greater sequence identity to the LpxC domain of residues 24 to 315 of SEQ ID NO: 198.

In the methods described herein, a polypeptide can include an UDPGT domain having 60 percent or greater sequence identity to the UDPGT domain of residues 11 to 480 of SEQ ID NO: 253.

In the methods described herein, a polypeptide can include a glycosyl hydrolases family 18 domain having 60 percent or greater sequence identity to the glycosyl hydrolases family 18 domain of residues 36 to 287 of SEQ ID NO: 1541.

In the methods described herein, a polypeptide can include a Glyco_transf_34 domain having 60 percent or greater sequence identity to the Glyco_transf_34 domain of residues 136 to 380 of SEQ ID NO: 663.

In the methods described herein, a polypeptide can include a branch domain having 60 percent or greater sequence identity to the branch domain of residues 77 to 303 of SEQ ID NO: 1366.

In the methods described herein, a polypeptide can include a COBRA domain having 60 percent or greater sequence identity to the COBRA domain of residues 51 to 215 of SEQ ID NO: 928.

In the methods described herein, a polypeptide can include a Glyco_transf_34 N terminal domain having 60 percent or greater sequence identity to the Glyco_transf_34 N terminal domain of residues 57 to 374 of SEQ ID NO: 1215 and a Glyco_transf_34 C terminal domain having 60 percent or greater sequence identity to the Glyco_transf_34 C terminal domain of residues 415 to 533 of SEQ ID NO: 1215.

In the methods described herein, a polypeptide can include an Alpha-L-AF_C domain having 60 percent or greater sequence identity to the Alpha-L-AF_C domain of residues 454 to 639 of SEQ ID NO: 4 and a CBM_4_9 domain having 60 percent or greater sequence identity to the CBM_4_9 domain of residues 71 to 229 of SEQ ID NO: 4.

In the methods described herein, a polypeptide can include a EMP24_GP25L domain having 60 percent or greater sequence identity to the EMP24_GP25L domain of residues 36 to 224 of SEQ ID NO: 580.

In the methods described herein, a polypeptide can include a Methyltransf_3 domain having 60 percent or greater sequence identity to the Methyltransf_3 domain of residues 34 to 246 of SEQ ID NO: 53.

In the methods described herein, a polypeptide can include a SRF-TF domain having 60 percent or greater sequence identity to the SRF-TF domain of residues 11 to 61 of SEQ ID NO: 1112 and a K box domain having 60 percent or greater sequence identity to the K box domain of residues 79 to 179 of SEQ ID NO: 1112.

In the methods described herein, a polypeptide can include a zf-C3HC4 domain having 60 percent or greater sequence identity to the zf-C3HC4 domain of residues 95 to 136 of SEQ ID NO: 634 or residues 132 to 173 of SEQ ID NO:187.

In the methods described herein, a polypeptide comprises an epimerase domain having 60 percent or greater sequence identity to the epimerase domain of residues 5 to 244 of SEQ ID NO: 368.

In the methods described herein, a polypeptide can include an UDPGP domain having 60 percent or greater sequence identity to the UDPGP domain of residues 31 to 442 of SEQ ID NO: 1599.

In the methods described herein, a polypeptide can include an IQ domain having 60 percent or greater sequence identity to the IQ domain of residues 115 to 135 of SEQ ID NO: 1065.

In the methods described herein, a polypeptide can include an AUX_IAA domain having 60 percent or greater sequence identity to the AUX_IAA domain of residues 10 to 184 of SEQ ID NO: 1580 or residues 32 to 190 of SEQ ID NO:1592.

In the methods described herein, a polypeptide can include a CRAL_TRIO domain having 60 percent or greater sequence identity to the CRAL_TRIO domain of residues 212 to 391 of SEQ ID NO: 851 and CRAL_TRIO_N domain having 60 percent or greater sequence identity to the CRAL_TRIO_N domain of residues 114 to 200 of SEQ ID NO:851.

In some embodiments, a polypeptide is selected from the group consisting of SEQ ID NOs: 2, 4, 6-9, 11, 13-15, 17, 18, 20-27, 29, 31-33, 35, 36, 38-51, 53, 54, 56-61, 63-67, 69, 70, 72-76, 78, 80-83, 85, 86, 88-91, 93-97, 99-103, 105, 107, 109, 110, 112, 113, 115, 117, 119-152, 154, 156, 158, 159, 161, 163, 165, 167, 168, 170, 172, 174, 176, 178, 180-185, 187, 188, 190, 192-194, 196, 198, 200, 202, 203, 205, 207-211, 213-251, 253, 255, 257, 258, 260-262, 264, 265, 267-272, 274-279, 281-283, 285, 287-292, 294, 295-297, 299, 301, 303-305, 307, 309, 310, 312, 314, 316-318, 320, 321, 323, 325, 327-329, 331, 332, 334, 335, 337-339, 341, 342, 344, 345, 347, 349, 351, 353, 355, 357, 359, 361-366, 368, 370, 372, 373, 375-378, 380, 382-387, 389, 391, 393, 395, 396, 398-404, 406-414, 416, 418, 420, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497-502, 504, 506, 508, 509, 511-517, 519, 521, 522, 524-527, 529, 530, 532, 533, 535, 536, 537, 539, 541, 543, 545, 546, 548, 550, 552-555, 557, 558, 560, 562, 564, 566, 568, 570-578, 580, 582, 584, 585, 587, 589, 591, 592, 594-596, 598, 600, 601, 603, 604, 606-608, 610, 611, 613, 615, 617, 619, 621, 623, 625, 626, 628-632, 634, 636, 638, 640, 642, 643, 645, 647, 649, 651, 653, 655, 657, 659, 661, 663, 665, 667-670, 672, 674, 675, 677, 679-682, 684, 685, 687, 689-692, 694-698, 700-704, 706, 707, 709-718, 720, 722, 724, 726-728, 730, 731, 733-739, 741, 743, 745, 746, 748, 750, 752, 754, 756, 758, 760-764, 766, 768, 770, 772, 774, 776, 778, 780, 782, 784, 785, 787, 789, 791, 793-795, 797, 799, 801, 803, 805, 806, 808, 810, 812, 814, 816, 818-820, 822-824, 826, 828, 830, 832, 834, 836, 838-840, 842, 843, 845-847, 849, 851, 853, 854, 856-858, 860, 862, 863, 865, 866, 868, 870-873, 875-878, 880-882, 884-886, 888, 890, 892, 893, 895, 897, 899, 900, 902, 903, 905, 907, 909, 911, 912, 913, 915, 917, 919, 921, 923, 925, 926, 928, 930, 932, 933, 935, 936-938, 940, 941, 943-945, 947, 949, 950, 952-955, 957-961, 963, 965-969, 971, 972, 974, 975, 977, 978, 980, 982, 984, 986, 988, 990, 992, 994, 996, 998, 1000-1014, 1016, 1018, 1020, 1021, 1023, 1024, 1026, 1027, 1029, 1030, 1032, 1033, 1035, 1037, 1038, 1040, 1042, 1043, 1045, 1047, 1049, 1051, 1053, 1055, 1057, 1059, 1061-1063, 1065, 1067, 1069, 1070, 1072, 1073, 1075, 1076, 1078-1080, 1082, 1083, 1085, 1087, 1089, 1091, 1093, 1095, 1096, 1098, 1100, 1101, 1103, 1105, 1106, 1108, 1110, 1112, 1114-1116, 1118, 1120-1123, 1125, 1127-1131, 1133, 1134, 1136, 1137, 1139-1145, 1147-1156, 1158-1161, 1163, 1165-1178, 1180-1188, 1190, 1191, 1193-1202, 1204, 1205-1207, 1209-1213, 1215, 1217-1221, 1223-1228, 1230, 1231, 1233-1241, 1243, 1245, 1247, 1249-1252, 1254, 1255, 1257-1259, 1261, 1263, 1264, 1266-1272, 1274-1276, 1278, 1280, 1282-1286, 1288, 1289, 1291-1331, 1333-1337, 1339, 1341, 1343, 1345, 1347-1350, 1352, 1354, 1356, 1358, 1360, 1362, 1364, 1366, 1368, 1370-1372, 1374, 1375, 1377-1379, 1381, 1383, 1384, 1386, 1388-1390, 1392-1397, 1399, 1400, 1402, 1403, 1405, 1407-1410, 1412-1418, 1420, 1422, 1424, 1426, 1428, 1430, 1432-1436, 1438, 1440, 1442-1444, 1446, 1447, 1449, 1450, 1452-1454, 1456, 1457, 1459, 1460, 1462, 1463, 1465-1468, 1470, 1471, 1473, 1475, 1477-1483, 1485, 1487, 1489, 1491-1493, 1495, 1496, 1498, 1499, 1501, 1503, 1504, 1506, 1508, 1510, 1511, 1513, 1514, 1516-1521, 1523, 1524, 1526, 1528-1532, 1534, 1536-1539, 1541, 1542, 1544, 1545, 1547, 1548, 1550, 1552, 1553, 1555-1559, 1561, 1563-1565, 1567, 1568, 1570, 1571, 1573, 1575, 1576, 1578, 1580, 1582, 1583, 1585, 1587, 1589, 1590, 1592, 1593, 1595, 1597, 1599, 1600, 1602-1606, 1608-1613, 1615, 1616, 1618-1626, 1628, 1629, 1631, 1633, 1634, 1636, 1637, 1639-1643, 1645, 1646-1739, 1741, 1743, 1745, 1747-1756, 1758, 1760, 1762-1764, 1766, 1767, 1769, 1770, 1772-1774, 1776, 1778-1783, 1785-1792, 1794, 1796, 1798, 1799, 1801, 1802, 1804, 1806, 1808-1810, 1812, 1814, 1815, 1817, 1819, 1821, 1822, 1824, 1826-1830, 1832, 1834, 1835, 1837, 1839-1841, 1843, 1844, 1846, 1847, 1849, 1851, 1852, 1854, 1856, 1858, 1860-1863, 1865-1953, 1955-1958, 1960, 1962, 1964, 1966-1968, 1970, 1972-1976, 1978, 1980, 1982, 1984-1986, 1988, 1990, 1991, 1993, 1995, 1997, 1999, 2001, 2003, 2005, 2007, 2009, 2011, 2013, 2015, 2017, 2019, 2021, 2023-2027, 2029, 2031, 2033, 2035, 2037, 2039, 2041, 2043, 2045, 2047-2049, 2051-2057, 2059, 2061, 2063, 2065, 2067, 2069, 2071, 2073, 2075, 2077, 2079, 2080, 2082, 2084, 2086, 2088, 2090, 2092, 2093, 2095, 2097, 2098, 2100-2122, 2124, 2126, 2128, 2129, 2131, 2133, 2135-2137, 2139, 2141, 2142, 2144-2148, 2150, 2152, 2154, 2155, 2157, 2159-2161, 2163, 2165, 2166, 2168, 2170, 2172-2175, 2177, 2179, 2181, 2183, 2184, 2186, 2188, 2189, 2191-2194, 2196, 2197, 2199-2202, 2204, 2206-2208, 2210-2212, 2214, 2215, 2217-2220, 2222, 2224-2226, 2228, 2230-2232, 2234-2242, 2244-2254, 2256-2269, 2271, 2273, 2274, 2276, 2278, 2280, 2281, 2283, 2285, 2286, 2288, 2290, 2292, 2294, 2296, 2297, 2299, 2301, 2303, 2305, 2307, 2309, 2311, 2313, 2314, 2316-2318, 2320, 2322, 2324, 2326, 2327, 2329, 2331, 2333, 2335, 2337, 2339, 2341, 2342, 2344, 2345, 2347-2349, 2351, 2353, 2355, 2357, 2359, 2361, 2363, 2365, 2367-2369, 2371, 2373, 2375, 2377, 2379, 2381, 2383, 2385, 2386, 2388, 2390, 2391, 2393, 2395, 2397, 2399, 2400, 2402, 2404, 2405, 2407, 2409, 2411, 2413, 2415, 2417, 2419, 2421, 2423, 2425, 2426, 2428, 2430, 2431, 2433, 2435, 2437, 2438-2440, 2442, 2444, 2445, 2447, 2449, 2451, 2453, 2455, 2457, 2459, 2461, 2463-2468, 2470, 2472, 2474, 2476, 2478, 2479, 2481, 2482, 2484, 2485, 2487-2491, 2493-2498, 2500-2510, 2512-2515, 2517-2531, 2533-2536, 2538-2542, 2544-2548, 2550, 2551, 2553, 2555-2558, 2560, 2562, 2564, 2566-2573, 2575-2579, 2581, 2583-2585, 2587-2602, 2604-2611, 2613, 2615, 2617, and 2619-2623.

This document also features a method of modulating the level of biomass in a plant. The method includes introducing into a plant cell an exogenous nucleic acid, the exogenous nucleic acid comprising a regulatory region operably linked to a nucleotide sequence having 80 percent or greater sequence identity to a nucleotide sequence selected from the group consisting of SEQ ID NO: 1, 3, 5, 10, 12, 16, 19, 28, 30, 34, 37, 52, 55, 62, 68, 71, 77, 79, 84, 87, 92, 98, 104, 106, 108, 111, 114, 116, 118, 153, 155, 157, 160, 162, 164, 166, 169, 171, 173, 175, 177, 179, 186, 189, 191, 195, 197, 199, 201, 204, 206, 212, 252, 254, 256, 259, 263, 266, 273, 280, 284, 286, 293, 298, 300, 302, 306, 308, 311, 313, 315, 319, 322, 324, 326, 330, 333, 336, 340, 343, 346, 348, 350, 352, 354, 356, 358, 360, 367, 369, 371, 374, 379, 381, 388, 390, 392, 394, 397, 405, 415, 417, 419, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 503, 505, 507, 510, 518, 520, 523, 528, 531, 534, 538, 540, 542, 544, 547, 549, 551, 556, 559, 561, 563, 565, 567, 569, 579, 581, 583, 586, 588, 590, 593, 597, 599, 602, 605, 609, 612, 614, 616, 618, 620, 622, 624, 627, 633, 635, 637, 639, 641, 644, 646, 648, 650, 652, 654, 656, 658, 660, 662, 664, 666, 671, 673, 676, 678, 683, 686, 688, 693, 699, 705, 708, 719, 721, 723, 725, 729, 732, 740, 742, 744, 747, 749, 751, 753, 755, 757, 759, 765, 767, 769, 771, 773, 775, 777, 779, 781, 783, 786, 788, 790, 792, 796, 798, 800, 802, 804, 807, 809, 811, 813, 815, 817, 821, 825, 827, 829, 831, 833, 835, 837, 841, 844, 848, 850, 852, 855, 859, 861, 864, 867, 869, 874, 879, 883, 887, 889, 891, 894, 896, 898, 901, 904, 906, 908, 910, 914, 916, 918, 920, 922, 924, 927, 929, 931, 934, 939, 942, 946, 948, 951, 956, 962, 964, 970, 973, 976, 979, 981, 983, 985, 987, 989, 991, 993, 995, 997, 999, 1015, 1017, 1019, 1022, 1025, 1028, 1031, 1034, 1036, 1039, 1041, 1044, 1046, 1048, 1050, 1052, 1054, 1056, 1058, 1060, 1064, 1066, 1068, 1071, 1074, 1077, 1081, 1084, 1086, 1088, 1090, 1092, 1094, 1097, 1099, 1102, 1104, 1107, 1109, 1111, 1113, 1117, 1119, 1124, 1126, 1132, 1135, 1138, 1146, 1157, 1162, 1164, 1179, 1189, 1192, 1203, 1208, 1214, 1216, 1222, 1229, 1232, 1242, 1244, 1246, 1248, 1253, 1256, 1260, 1262, 1265, 1273, 1277, 1279, 1281, 1287, 1290, 1332, 1338, 1340, 1342, 1344, 1346, 1351, 1353, 1355, 1357, 1359, 1361, 1363, 1365, 1367, 1369, 1373, 1376, 1380, 1382, 1385, 1387, 1391, 1398, 1401, 1404, 1406, 1411, 1419, 1421, 1423, 1425, 1427, 1429, 1431, 1437, 1439, 1441, 1445, 1448, 1451, 1455, 1458, 1461, 1464, 1469, 1472, 1474, 1476, 1484, 1486, 1488, 1490, 1494, 1497, 1500, 1502, 1505, 1507, 1509, 1512, 1515, 1522, 1525, 1527, 1533, 1535, 1540, 1543, 1546, 1549, 1551, 1554, 1560, 1562, 1566, 1569, 1572, 1574, 1577, 1579, 1581, 1584, 1586, 1588, 1591, 1594, 1596, 1598, 1601, 1607, 1614, 1617, 1627, 1630, 1632, 1635, 1638, 1644, 1740, 1742, 1744, 1746, 1757, 1759, 1761, 1765, 1768, 1771, 1775, 1777, 1784, 1793, 1795, 1797, 1800, 1803, 1805, 1807, 1811, 1813, 1816, 1818, 1820, 1823, 1825, 1831, 1833, 1836, 1838, 1842, 1845, 1848, 1850, 1853, 1855, 1857, 1859, 1864, 1954, 1959, 1961, 1963, 1965, 1969, 1971, 1977, 1979, 1981, 1983, 1987, 1989, 1992, 1994, 1996, 1998, 2000, 2002, 2004, 2006, 2008, 2010, 2012, 2014, 2016, 2018, 2020, 2022, 2028, 2030, 2032, 2034, 2036, 2038, 2040, 2042, 2044, 2046, 2050, 2058, 2060, 2062, 2064, 2066, 2068, 2070, 2072, 2074, 2076, 2078, 2081, 2083, 2085, 2087, 2089, 2091, 2094, 2096, 2099, 2123, 2125, 2127, 2130, 2132, 2134, 2138, 2140, 2143, 2149, 2151, 2153, 2156, 2158, 2162, 2164, 2167, 2169, 2171, 2176, 2178, 2180, 2182, 2185, 2187, 2190, 2195, 2198, 2203, 2205, 2209, 2213, 2216, 2221, 2223, 2227, 2229, 2233, 2243, 2255, 2270, 2272, 2275, 2277, 2279, 2282, 2284, 2287, 2289, 2291, 2293, 2295, 2298, 2300, 2302, 2304, 2306, 2308, 2310, 2312, 2315, 2319, 2321, 2323, 2325, 2328, 2330, 2332, 2334, 2336, 2338, 2340, 2343, 2346, 2350, 2352, 2354, 2356, 2358, 2360, 2362, 2364, 2366, 2370, 2372, 2374, 2376, 2378, 2380, 2382, 2384, 2387, 2389, 2392, 2394, 2396, 2398, 2401, 2403, 2406, 2408, 2410, 2412, 2414, 2416, 2418, 2420, 2422, 2424, 2427, 2429, 2432, 2434, 2436, 2441, 2443, 2446, 2448, 2450, 2452, 2454, 2456, 2458, 2460, 2462, 2469, 2471, 2473, 2475, 2477, 2480, 2483, 2486, 2492, 2499, 2511, 2516, 2532, 2537, 2543, 2549, 2552, 2554, 2559, 2561, 2563, 2565, 2574, 2580, 2582, 2586, 2603, 2612, 2614, 2616, and 2618, or a fragment thereof. A plant produced from the plant cell has a difference in the level of biomass as compared to the corresponding level of a control plant that does not include the nucleic acid.

This document also features a plant cell that includes an exogenous nucleic acid, the exogenous nucleic acid comprising a regulatory region operably linked to a nucleotide sequence encoding a polypeptide, wherein the HMM bit score of the amino acid sequence of the polypeptide is greater than about 65, the HMM based on the amino acid sequences depicted in one of FIGS. 1-38, and wherein the plant has a difference in the level of biomass as compared to the corresponding level of a control plant that does not include the nucleic acid. For example, the plant can have an increased level of biomass relative to the control plant.

In another aspect, this document features a plant cell that includes an exogenous nucleic acid. The exogenous nucleic acid includes a regulatory region operably linked to a nucleotide sequence encoding a polypeptide having 80 percent or greater sequence identity to an amino acid sequence selected from the group consisting of SEQ ID NO: 2, 4, 6-9, 11, 13-15, 17, 18, 20-27, 29, 31-33, 35, 36, 38-51, 53, 54, 56-61, 63-67, 69, 70, 72-76, 78, 80-83, 85, 86, 88-91, 93-97, 99-103, 105, 107, 109, 110, 112, 113, 115, 117, 119-152, 154, 156, 158, 159, 161, 163, 165, 167, 168, 170, 172, 174, 176, 178, 180-185, 187, 188, 190, 192-194, 196, 198, 200, 202, 203, 205, 207-211, 213-251, 253, 255, 257, 258, 260-262, 264, 265, 267-272, 274-279, 281-283, 285, 287-292, 294, 295-297, 299, 301, 303-305, 307, 309, 310, 312, 314, 316-318, 320, 321, 323, 325, 327-329, 331, 332, 334, 335, 337-339, 341, 342, 344, 345, 347, 349, 351, 353, 355, 357, 359, 361-366, 368, 370, 372, 373, 375-378, 380, 382-387, 389, 391, 393, 395, 396, 398-404, 406-414, 416, 418, 420, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497-502, 504, 506, 508, 509, 511-517, 519, 521, 522, 524-527, 529, 530, 532, 533, 535, 536, 537, 539, 541, 543, 545, 546, 548, 550, 552-555, 557, 558, 560, 562, 564, 566, 568, 570-578, 580, 582, 584, 585, 587, 589, 591, 592, 594-596, 598, 600, 601, 603, 604, 606-608, 610, 611, 613, 615, 617, 619, 621, 623, 625, 626, 628-632, 634, 636, 638, 640, 642, 643, 645, 647, 649, 651, 653, 655, 657, 659, 661, 663, 665, 667-670, 672, 674, 675, 677, 679-682, 684, 685, 687, 689-692, 694-698, 700-704, 706, 707, 709-718, 720, 722, 724, 726-728, 730, 731, 733-739, 741, 743, 745, 746, 748, 750, 752, 754, 756, 758, 760-764, 766, 768, 770, 772, 774, 776, 778, 780, 782, 784, 785, 787, 789, 791, 793-795, 797, 799, 801, 803, 805, 806, 808, 810, 812, 814, 816, 818-820, 822-824, 826, 828, 830, 832, 834, 836, 838-840, 842, 843, 845-847, 849, 851, 853, 854, 856-858, 860, 862, 863, 865, 866, 868, 870-873, 875-878, 880-882, 884-886, 888, 890, 892, 893, 895, 897, 899, 900, 902, 903, 905, 907, 909, 911, 912, 913, 915, 917, 919, 921, 923, 925, 926, 928, 930, 932, 933, 935, 936-938, 940, 941, 943-945, 947, 949, 950, 952-955, 957-961, 963, 965-969, 971, 972, 974, 975, 977, 978, 980, 982, 984, 986, 988, 990, 992, 994, 996, 998, 1000-1014, 1016, 1018, 1020, 1021, 1023, 1024, 1026, 1027, 1029, 1030, 1032, 1033, 1035, 1037, 1038, 1040, 1042, 1043, 1045, 1047, 1049, 1051, 1053, 1055, 1057, 1059, 1061-1063, 1065, 1067, 1069, 1070, 1072, 1073, 1075, 1076, 1078-1080, 1082, 1083, 1085, 1087, 1089, 1091, 1093, 1095, 1096, 1098, 1100, 1101, 1103, 1105, 1106, 1108, 1110, 1112, 1114-1116, 1118, 1120-1123, 1125, 1127-1131, 1133, 1134, 1136, 1137, 1139-1145, 1147-1156, 1158-1161, 1163, 1165-1178, 1180-1188, 1190, 1191, 1193-1202, 1204, 1205-1207, 1209-1213, 1215, 1217-1221, 1223-1228, 1230, 1231, 1233-1241, 1243, 1245, 1247, 1249-1252, 1254, 1255, 1257-1259, 1261, 1263, 1264, 1266-1272, 1274-1276, 1278, 1280, 1282-1286, 1288, 1289, 1291-1331, 1333-1337, 1339, 1341, 1343, 1345, 1347-1350, 1352, 1354, 1356, 1358, 1360, 1362, 1364, 1366, 1368, 1370-1372, 1374, 1375, 1377-1379, 1381, 1383, 1384, 1386, 1388-1390, 1392-1397, 1399, 1400, 1402, 1403, 1405, 1407-1410, 1412-1418, 1420, 1422, 1424, 1426, 1428, 1430, 1432-1436, 1438, 1440, 1442-1444, 1446, 1447, 1449, 1450, 1452-1454, 1456, 1457, 1459, 1460, 1462, 1463, 1465-1468, 1470, 1471, 1473, 1475, 1477-1483, 1485, 1487, 1489, 1491-1493, 1495, 1496, 1498, 1499, 1501, 1503, 1504, 1506, 1508, 1510, 1511, 1513, 1514, 1516-1521, 1523, 1524, 1526, 1528-1532, 1534, 1536-1539, 1541, 1542, 1544, 1545, 1547, 1548, 1550, 1552, 1553, 1555-1559, 1561, 1563-1565, 1567, 1568, 1570, 1571, 1573, 1575, 1576, 1578, 1580, 1582, 1583, 1585, 1587, 1589, 1590, 1592, 1593, 1595, 1597, 1599, 1600, 1602-1606, 1608-1613, 1615, 1616, 1618-1626, 1628, 1629, 1631, 1633, 1634, 1636, 1637, 1639-1643, 1645, 1646-1739, 1741, 1743, 1745, 1747-1756, 1758, 1760, 1762-1764, 1766, 1767, 1769, 1770, 1772-1774, 1776, 1778-1783, 1785-1792, 1794, 1796, 1798, 1799, 1801, 1802, 1804, 1806, 1808-1810, 1812, 1814, 1815, 1817, 1819, 1821, 1822, 1824, 1826-1830, 1832, 1834, 1835, 1837, 1839-1841, 1843, 1844, 1846, 1847, 1849, 1851, 1852, 1854, 1856, 1858, 1860-1863, 1865-1953, 1955-1958, 1960, 1962, 1964, 1966-1968, 1970, 1972-1976, 1978, 1980, 1982, 1984-1986, 1988, 1990, 1991, 1993, 1995, 1997, 1999, 2001, 2003, 2005, 2007, 2009, 2011, 2013, 2015, 2017, 2019, 2021, 2023-2027, 2029, 2031, 2033, 2035, 2037, 2039, 2041, 2043, 2045, 2047-2049, 2051-2057, 2059, 2061, 2063, 2065, 2067, 2069, 2071, 2073, 2075, 2077, 2079, 2080, 2082, 2084, 2086, 2088, 2090, 2092, 2093, 2095, 2097, 2098, 2100-2122, 2124, 2126, 2128, 2129, 2131, 2133, 2135-2137, 2139, 2141, 2142, 2144-2148, 2150, 2152, 2154, 2155, 2157, 2159-2161, 2163, 2165, 2166, 2168, 2170, 2172-2175, 2177, 2179, 2181, 2183, 2184, 2186, 2188, 2189, 2191-2194, 2196, 2197, 2199-2202, 2204, 2206-2208, 2210-2212, 2214, 2215, 2217-2220, 2222, 2224-2226, 2228, 2230-2232, 2234-2242, 2244-2254, 2256-2269, 2271, 2273, 2274, 2276, 2278, 2280, 2281, 2283, 2285, 2286, 2288, 2290, 2292, 2294, 2296, 2297, 2299, 2301, 2303, 2305, 2307, 2309, 2311, 2313, 2314, 2316-2318, 2320, 2322, 2324, 2326, 2327, 2329, 2331, 2333, 2335, 2337, 2339, 2341, 2342, 2344, 2345, 2347-2349, 2351, 2353, 2355, 2357, 2359, 2361, 2363, 2365, 2367-2369, 2371, 2373, 2375, 2377, 2379, 2381, 2383, 2385, 2386, 2388, 2390, 2391, 2393, 2395, 2397, 2399, 2400, 2402, 2404, 2405, 2407, 2409, 2411, 2413, 2415, 2417, 2419, 2421, 2423, 2425, 2426, 2428, 2430, 2431, 2433, 2435, 2437, 2438-2440, 2442, 2444, 2445, 2447, 2449, 2451, 2453, 2455, 2457, 2459, 2461, 2463-2468, 2470, 2472, 2474, 2476, 2478, 2479, 2481, 2482, 2484, 2485, 2487-2491, 2493-2498, 2500-2510, 2512-2515, 2517-2531, 2533-2536, 2538-2542, 2544-2548, 2550, 2551, 2553, 2555-2558, 2560, 2562, 2564, 2566-2573, 2575-2579, 2581, 2583-2585, 2587-2602, 2604-2611, 2613, 2615, 2617, and 2619-2623, wherein a plant produced from said plant cell has a difference in the level of biomass as compared to the corresponding level of a control plant that does not comprise said nucleic acid. For example, the plant can have an increased level of biomass relative to the control plant.

This document also features a plant cell that includes an exogenous nucleic acid. The exogenous nucleic acid includes a regulatory region operably linked to a nucleotide sequence having 80 percent or greater sequence identity to a nucleotide sequence selected from the group consisting of SEQ ID NO: 1, 3, 5, 10, 12, 16, 19, 28, 30, 34, 37, 52, 55, 62, 68, 71, 77, 79, 84, 87, 92, 98, 104, 106, 108, 111, 114, 116, 118, 153, 155, 157, 160, 162, 164, 166, 169, 171, 173, 175, 177, 179, 186, 189, 191, 195, 197, 199, 201, 204, 206, 212, 252, 254, 256, 259, 263, 266, 273, 280, 284, 286, 293, 298, 300, 302, 306, 308, 311, 313, 315, 319, 322, 324, 326, 330, 333, 336, 340, 343, 346, 348, 350, 352, 354, 356, 358, 360, 367, 369, 371, 374, 379, 381, 388, 390, 392, 394, 397, 405, 415, 417, 419, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 503, 505, 507, 510, 518, 520, 523, 528, 531, 534, 538, 540, 542, 544, 547, 549, 551, 556, 559, 561, 563, 565, 567, 569, 579, 581, 583, 586, 588, 590, 593, 597, 599, 602, 605, 609, 612, 614, 616, 618, 620, 622, 624, 627, 633, 635, 637, 639, 641, 644, 646, 648, 650, 652, 654, 656, 658, 660, 662, 664, 666, 671, 673, 676, 678, 683, 686, 688, 693, 699, 705, 708, 719, 721, 723, 725, 729, 732, 740, 742, 744, 747, 749, 751, 753, 755, 757, 759, 765, 767, 769, 771, 773, 775, 777, 779, 781, 783, 786, 788, 790, 792, 796, 798, 800, 802, 804, 807, 809, 811, 813, 815, 817, 821, 825, 827, 829, 831, 833, 835, 837, 841, 844, 848, 850, 852, 855, 859, 861, 864, 867, 869, 874, 879, 883, 887, 889, 891, 894, 896, 898, 901, 904, 906, 908, 910, 914, 916, 918, 920, 922, 924, 927, 929, 931, 934, 939, 942, 946, 948, 951, 956, 962, 964, 970, 973, 976, 979, 981, 983, 985, 987, 989, 991, 993, 995, 997, 999, 1015, 1017, 1019, 1022, 1025, 1028, 1031, 1034, 1036, 1039, 1041, 1044, 1046, 1048, 1050, 1052, 1054, 1056, 1058, 1060, 1064, 1066, 1068, 1071, 1074, 1077, 1081, 1084, 1086, 1088, 1090, 1092, 1094, 1097, 1099, 1102, 1104, 1107, 1109, 1111, 1113, 1117, 1119, 1124, 1126, 1132, 1135, 1138, 1146, 1157, 1162, 1164, 1179, 1189, 1192, 1203, 1208, 1214, 1216, 1222, 1229, 1232, 1242, 1244, 1246, 1248, 1253, 1256, 1260, 1262, 1265, 1273, 1277, 1279, 1281, 1287, 1290, 1332, 1338, 1340, 1342, 1344, 1346, 1351, 1353, 1355, 1357, 1359, 1361, 1363, 1365, 1367, 1369, 1373, 1376, 1380, 1382, 1385, 1387, 1391, 1398, 1401, 1404, 1406, 1411, 1419, 1421, 1423, 1425, 1427, 1429, 1431, 1437, 1439, 1441, 1445, 1448, 1451, 1455, 1458, 1461, 1464, 1469, 1472, 1474, 1476, 1484, 1486, 1488, 1490, 1494, 1497, 1500, 1502, 1505, 1507, 1509, 1512, 1515, 1522, 1525, 1527, 1533, 1535, 1540, 1543, 1546, 1549, 1551, 1554, 1560, 1562, 1566, 1569, 1572, 1574, 1577, 1579, 1581, 1584, 1586, 1588, 1591, 1594, 1596, 1598, 1601, 1607, 1614, 1617, 1627, 1630, 1632, 1635, 1638, 1644, 1740, 1742, 1744, 1746, 1757, 1759, 1761, 1765, 1768, 1771, 1775, 1777, 1784, 1793, 1795, 1797, 1800, 1803, 1805, 1807, 1811, 1813, 1816, 1818, 1820, 1823, 1825, 1831, 1833, 1836, 1838, 1842, 1845, 1848, 1850, 1853, 1855, 1857, 1859, 1864, 1954, 1959, 1961, 1963, 1965, 1969, 1971, 1977, 1979, 1981, 1983, 1987, 1989, 1992, 1994, 1996, 1998, 2000, 2002, 2004, 2006, 2008, 2010, 2012, 2014, 2016, 2018, 2020, 2022, 2028, 2030, 2032, 2034, 2036, 2038, 2040, 2042, 2044, 2046, 2050, 2058, 2060, 2062, 2064, 2066, 2068, 2070, 2072, 2074, 2076, 2078, 2081, 2083, 2085, 2087, 2089, 2091, 2094, 2096, 2099, 2123, 2125, 2127, 2130, 2132, 2134, 2138, 2140, 2143, 2149, 2151, 2153, 2156, 2158, 2162, 2164, 2167, 2169, 2171, 2176, 2178, 2180, 2182, 2185, 2187, 2190, 2195, 2198, 2203, 2205, 2209, 2213, 2216, 2221, 2223, 2227, 2229, 2233, 2243, 2255, 2270, 2272, 2275, 2277, 2279, 2282, 2284, 2287, 2289, 2291, 2293, 2295, 2298, 2300, 2302, 2304, 2306, 2308, 2310, 2312, 2315, 2319, 2321, 2323, 2325, 2328, 2330, 2332, 2334, 2336, 2338, 2340, 2343, 2346, 2350, 2352, 2354, 2356, 2358, 2360, 2362, 2364, 2366, 2370, 2372, 2374, 2376, 2378, 2380, 2382, 2384, 2387, 2389, 2392, 2394, 2396, 2398, 2401, 2403, 2406, 2408, 2410, 2412, 2414, 2416, 2418, 2420, 2422, 2424, 2427, 2429, 2432, 2434, 2436, 2441, 2443, 2446, 2448, 2450, 2452, 2454, 2456, 2458, 2460, 2462, 2469, 2471, 2473, 2475, 2477, 2480, 2483, 2486, 2492, 2499, 2511, 2516, 2532, 2537, 2543, 2549, 2552, 2554, 2559, 2561, 2563, 2565, 2574, 2580, 2582, 2586, 2603, 2612, 2614, 2616, and 2618, or a fragment thereof. A plant produced from the plant cell has a difference in the level of biomass as compared to the corresponding level of a control plant that does not include the nucleic acid. For example, the plant can have an increased level of biomass relative to the control plant.

This document also features a transgenic plant that includes any of the plant cells described herein and seed product comprising embryonic tissue from such a transgenic plant. The plant can be a member of a species selected from the group consisting of *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In another aspect, this document features an isolated nucleic acid comprising a nucleotide sequence having 85% or greater sequence identity to the nucleotide sequence set forth in SEQ ID NO: 1, 10, 30, 34, 55, 71, 84, 87, 92, 98, 162, 164, 171, 173, 179, 191, 206, 212, 259, 263, 273, 280, 284, 286, 298, 302, 306, 311, 326, 330, 340, 343, 348, 354, 374, 379, 390, 392, 394, 397, 417, 424, 452, 462, 470, 484, 496, 507, 510, 518, 540, 544, 549, 556, 561, 565, 567, 569, 588, 599, 614, 618, 646, 671, 673, 683, 688, 693, 848, 869, 894, 896, 920, 922, 1034, 1039, 1041, 1044, 1048, 1050, 1056, 1157, 1229, 1260, 1262, 1265, 1273, 1281, 1373, 1406, 1421, 1423, 1427, 1431, 1439, 1448, 1458, 1469, 1472, 1474, 1494, 1502, 1505, 1522, 1525, 1527, 1535, 1551, 1554, 1560, 1569, 1574, 1577, 1581, 1584, 1614, 1632, or 1635.

This document also features an isolated nucleic acid that includes a nucleotide sequence encoding a polypeptide having 80% or greater sequence identity to the amino acid sequence set forth in SEQ ID NO: 2, 8, 9, 11, 14, 15, 18, 21, 22, 23, 24, 25, 26, 27, 31, 32, 35, 40, 41, 47, 48, 49, 50, 51, 56, 72, 83, 99, 100, 102, 121, 129, 132, 135, 137, 139, 140, 141, 142, 143, 144, 145, 146, 147, 152, 159, 163, 165, 168, 172, 174, 180, 181, 184, 185, 192, 193, 207, 208, 209, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 258, 260, 261, 262, 264, 268, 269, 270, 274, 275, 276, 277, 278, 279, 281, 282, 283, 285, 287, 288, 289, 290, 291, 295, 296, 299, 303, 305, 307, 312, 317, 327, 331, 338, 339, 341, 342, 344, 349, 355, 362, 366, 373, 375, 376, 377, 378, 380, 384, 386, 387, 391, 393, 395, 396, 398, 399, 400, 401, 402, 403, 404, 407, 408, 409, 410, 411, 412, 414, 418, 421, 425, 453, 463, 471, 485, 497, 501, 511, 512, 514, 516, 519, 522, 525, 533, 536, 537, 541, 545, 546, 550, 553, 554, 557, 558, 562, 566, 568, 570, 573, 575, 576, 578, 589, 592, 595, 596, 601, 607, 608, 611, 615, 619, 626, 629, 668, 670, 672, 674, 675, 680, 682, 684, 685, 689, 690, 691, 692, 694, 695, 696, 698, 701, 702, 703, 704, 710, 713, 715, 727, 728, 731, 737, 738, 739, 787, 849, 866, 868, 870, 881, 895, 897, 900, 923, 926, 978, 1004, 1006, 1008, 1009, 1013, 1030, 1033, 1035, 1038, 1040, 1042, 1043, 1045, 1049, 1051, 1057, 1061, 1063, 1083, 1096, 1115, 1121, 1122, 1123, 1144, 1152, 1153, 1156, 1166, 1167, 1168, 1169, 1170, 1176, 1177, 1178, 1184, 1191, 1194, 1195, 1199, 1202, 1206, 1207, 1219, 1221, 1224, 1225, 1226, 1227, 1228, 1230, 1231, 1237, 1238, 1239, 1240, 1241, 1258, 1259, 1261, 1263, 1264, 1266, 1267, 1269, 1270, 1271, 1272, 1274, 1276, 1282, 1284, 1285, 1286, 1289, 1292, 1293, 1294, 1295, 1296, 1297, 1298, 1299, 1300, 1301, 1302, 1303, 1304, 1305, 1311, 1314, 1319, 1322, 1323, 1327, 1329, 1371, 1372, 1374, 1378, 1384, 1390, 1393, 1395, 1396, 1400, 1403, 1407, 1408, 1409, 1410, 1413, 1414, 1415, 1416, 1417, 1422, 1424, 1428, 1432, 1433, 1434, 1435, 1436, 1440, 1443, 1444, 1449, 1450, 1457, 1459, 1467, 1468, 1470, 1473, 1475, 1479, 1480, 1481, 1482, 1483, 1492, 1495, 1496, 1499, 1503, 1506, 1518, 1519, 1521, 1523, 1524, 1526, 1528, 1529, 1530, 1532, 1536, 1537, 1548, 1552, 1553, 1555, 1557, 1558, 1559, 1561, 1570, 1575, 1576, 1578, 1582, 1583, 1585, 1593, 1603, 1604, 1609, 1610, 1611, 1612, 1613, 1615, 1616, 1622, 1623, 1624, 1625, 1626, 1629, 1633, 1634, 1636, 1641, 1642, 1643, 1646, 1647, 1648, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, or 1731.

This document also features an isolated nucleic acid that includes a nucleotide sequence encoding a polypeptide having 80% or greater sequence identity to the amino acid sequence set forth in SEQ ID NO: 599, 1759, 1765, 1797, 1807, 1818, 1833, 1836, 1845, 1853, 1855, 1857, 1959, 1963, 1965, 1994, 1996, 2000, 2004, 2040, 2064, 2066, 2070, 2072, 2081, 2083, 2085, 2091, 2151, 2164, 2176, 2190, 2198, 2203, 2205, 2221, 2223, 2227, 2229, 2255, 2291, 2300, 2310, 2325, 2330, 2334, 2338, 2346, 2354, 2376, 2389, 2394, 2396, 2429, 2432, 2436, 2443, 2450, 2452, 2456, 2458, 2469, 2473, 2475, 2477, 2480, 2483, 2499, 2532, 2543, 2549, 2552, or 2574.

In some embodiments, this document features an isolated nucleic acid that includes a nucleotide sequence encoding a polypeptide having 80% or greater sequence identity to the amino acid sequence set forth in SEQ ID NO:1061, 1593, 1751, 1815, 1819, 1822, 1827, 1829, 1834, 1837, 1840, 1841, 1846, 1852, 1854, 1856, 1858, 1861, 1862, 1863, 1866, 1867, 1868, 1869 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1960, 1964, 1966, 1974, 1975, 1985, 1986, 1995, 2001, 2005, 2007, 2024, 2026, 2052, 2054, 2055, 2092, 2098, 2101, 2102, 2103, 2104, 2105, 2106, 2107, 2109, 2110, 2111, 2112, 2113, 2114, 2115, 2116, 2117, 2118, 2119, 2120, 2121, 2122, 2129, 2145, 2146, 2147, 2148, 2152, 2155, 2165, 2177, 2189, 2192, 2194, 2199, 2200, 2201, 2202, 2206, 2218, 2219, 2222, 2224, 2230, 2232, 2235, 2245, 2246, 2248, 2249, 2250, 2251, 2252, 2253, 2254, 2256, 2257, 2258, 2259, 2260, 2261, 2262, 2263, 2264, 2265, 2266, 2267, 2268, 2269, 2274, 2281, 2286, 2292, 2301, 2311, 2314, 2317, 2326, 2327, 2331, 2335, 2339, 2349, 2377, 2390, 2395, 2397, 2405, 2426, 2430, 2431, 2433, 2437, 2440, 2444, 2445, 2451, 2453, 2457, 2459, 2470, 2474, 2476, 2478, 2481, 2482, 2484, 2491, 2494, 2495, 2496, 2497, 2498, 2500, 2501, 2502, 2503, 2504, 2505, 2506, 2507, 2508, 2509, 2518, 2519, 2520, 2521, 2522, 2523, 2524, 2525, 2526, 2527, 2528, 2529, 2530, 2531, 2533, 2534, 2535, 2536, 2539, 2540, 2541, 2542, 2544, 2545, 2546, 2547, 2548, 2550, 2551, 2553, 2556, 2557, 2558, 2568, 2569, 2570, 2576, or 2577.

In another aspect, this document features a method of identifying whether a polymorphism is associated with variation in a trait (e.g., dry matter yield). The method includes determining whether one or more genetic polymorphisms in a population of plants (e.g., switchgrass plants) is associated with the locus for a polypeptide selected from the group consisting of the polypeptides depicted in FIGS. 1-38 and functional homologs thereof; and measuring the correlation between variation in the trait in plants of the population and the presence of the one or more genetic polymorphisms in plants of the population, thereby identifying whether or not the one or more genetic polymorphisms are associated with variation in the trait.

A method of making a plant line also is featured. The method includes determining whether one or more genetic polymorphisms in a population of plants (e.g., switchgrass plants) is associated with the locus for a polypeptide selected from the group consisting of the polypeptides depicted in FIGS. 1-38 and functional homologs thereof; identifying one or more plants in the population in which the presence of at least one of the genetic polymorphisms is associated with variation in a biomass trait (e.g., dry matter yield); crossing one or more of the identified plants with itself or a different plant to produce seed; crossing at least one progeny plant grown from the seed with itself or a different plant; and repeating the crossing steps for an additional 0-5 generations to make the plant line, wherein at least one of the genetic polymorphisms is present in the plant line.

This document also features a method of producing a plant. The method includes growing a plant cell comprising an exogenous nucleic acid, the exogenous nucleic acid comprising a regulatory region operably linked to a nucleotide sequence encoding a polypeptide, wherein the HMM bit score of the amino acid sequence of the polypeptide is greater than about 65, the HMM based on the amino acid sequences depicted in one of FIG. 15, 16, 18, 19, 23, 24, or 25, and wherein the plant has an increase in panicle weight as compared to the corresponding level of a control plant that does not comprise the nucleic acid.

A method of producing a plant also is featured. The method includes growing a plant cell comprising an exogenous nucleic acid, the exogenous nucleic acid comprising a regulatory region operably linked to a nucleotide sequence encoding a polypeptide having 80 percent or greater sequence identity to an amino acid sequence selected from the group consisting of SEQ ID NOs:154, 368, 634, 851, 1016, 1035, 1580, and 1592, wherein a plant produced from the plant cell has an increase in panicle weight as compared to the corresponding level of a control plant that does not include the nucleic acid.

This document also features a method of producing a plant that includes growing a plant cell comprising an exogenous nucleic acid, the exogenous nucleic acid comprising a regulatory region operably linked to a nucleotide sequence having 80 percent or greater sequence identity to a nucleotide sequence selected from the group consisting of SEQ ID NOs: 153, 367, 633, 850, 1015, 1034, 1579, 1591, or a fragment thereof, wherein a plant produced from the plant cell has an increased in panicle weight as compared to the corresponding level of a control plant that does not include the nucleic acid.

In another aspect, this document features a method of altering the level of biomass in a plant. The method includes modifying an endogenous biomass-modulating nucleic acid, the nucleic acid comprising a nucleotide sequence with an open reading frame having 80 percent or greater sequence identity (e.g., 90% or 95% sequence identity) to the nucleotide sequence selected from the group consisting of SEQ ID NO: 1, 3, 5, 10, 12, 16, 19, 28, 30, 34, 37, 52, 55, 62, 68, 71, 77, 79, 84, 87, 92, 98, 104, 106, 108, 111, 114, 116, 118, 153, 155, 157, 160, 162, 164, 166, 169, 171, 173, 175, 177, 179, 186, 189, 191, 195, 197, 199, 201, 204, 206, 212, 252, 254, 256, 259, 263, 266, 273, 280, 284, 286, 293, 298, 300, 302, 306, 308, 311, 313, 315, 319, 322, 324, 326, 330, 333, 336, 340, 343, 346, 348, 350, 352, 354, 356, 358, 360, 367, 369, 371, 374, 379, 381, 388, 390, 392, 394, 397, 405, 415, 417, 419, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 503, 505, 507, 510, 518, 520, 523, 528, 531, 534, 538, 540, 542, 544, 547, 549, 551, 556, 559, 561, 563, 565, 567, 569, 579, 581, 583, 586, 588, 590, 593, 597, 599, 602, 605, 609, 612, 614, 616, 618, 620, 622, 624, 627, 633, 635, 637, 639, 641, 644, 646, 648, 650, 652, 654, 656, 658, 660, 662, 664, 666, 671, 673, 676, 678, 683, 686, 688, 693, 699, 705, 708, 719, 721, 723, 725, 729, 732, 740, 742, 744, 747, 749, 751, 753, 755, 757, 759, 765, 767, 769, 771, 773, 775, 777, 779, 781, 783, 786, 788, 790, 792, 796, 798, 800, 802, 804, 807, 809, 811, 813, 815, 817, 821, 825, 827, 829, 831, 833, 835, 837, 841, 844, 848, 850, 852, 855, 859, 861, 864, 867, 869, 874, 879, 883, 887, 889, 891, 894, 896, 898, 901, 904, 906, 908, 910, 914, 916, 918, 920, 922, 924, 927, 929, 931, 934, 939, 942, 946, 948, 951, 956, 962, 964, 970, 973, 976, 979, 981, 983, 985, 987, 989, 991, 993, 995, 997, 999, 1015, 1017, 1019, 1022, 1025, 1028, 1031, 1034, 1036, 1039, 1041, 1044, 1046, 1048, 1050, 1052, 1054, 1056, 1058, 1060, 1064, 1066, 1068, 1071, 1074, 1077, 1081, 1084, 1086, 1088, 1090, 1092, 1094, 1097, 1099, 1102, 1104, 1107, 1109, 1111, 1113, 1117, 1119, 1124, 1126, 1132, 1135, 1138, 1146, 1157, 1162, 1164, 1179, 1189, 1192, 1203, 1208, 1214, 1216, 1222, 1229, 1232, 1242, 1244, 1246, 1248, 1253, 1256, 1260, 1262, 1265, 1273, 1277, 1279, 1281, 1287, 1290, 1332, 1338, 1340, 1342, 1344, 1346, 1351, 1353, 1355, 1357, 1359, 1361, 1363, 1365, 1367, 1369, 1373, 1376, 1380, 1382, 1385, 1387, 1391, 1398, 1401, 1404, 1406, 1411, 1419, 1421, 1423, 1425, 1427, 1429, 1431, 1437, 1439, 1441, 1445, 1448, 1451, 1455, 1458, 1461, 1464, 1469, 1472, 1474, 1476, 1484, 1486, 1488, 1490, 1494, 1497, 1500, 1502, 1505, 1507, 1509, 1512, 1515, 1522, 1525, 1527, 1533, 1535, 1540, 1543, 1546, 1549, 1551, 1554, 1560, 1562, 1566, 1569, 1572, 1574, 1577, 1579, 1581, 1584, 1586, 1588, 1591, 1594, 1596, 1598, 1601, 1607, 1614, 1617, 1627, 1630, 1632, 1635, 1638, 1644, 1740, 1742, 1744, 1746, 1757, 1759, 1761, 1765, 1768, 1771, 1775, 1777, 1784, 1793, 1795, 1797, 1800, 1803, 1805, 1807, 1811, 1813, 1816, 1818, 1820, 1823, 1825, 1831, 1833, 1836, 1838, 1842, 1845, 1848, 1850, 1853, 1855, 1857, 1859, 1864, 1954, 1959, 1961, 1963, 1965, 1969, 1971, 1977, 1979, 1981, 1983, 1987, 1989, 1992, 1994, 1996, 1998, 2000, 2002, 2004, 2006, 2008, 2010, 2012, 2014, 2016, 2018, 2020, 2022, 2028, 2030, 2032, 2034, 2036, 2038, 2040, 2042, 2044, 2046, 2050, 2058, 2060, 2062, 2064, 2066, 2068, 2070, 2072, 2074, 2076, 2078, 2081, 2083, 2085, 2087, 2089, 2091, 2094, 2096, 2099, 2123, 2125, 2127, 2130, 2132, 2134, 2138, 2140, 2143, 2149, 2151, 2153, 2156, 2158, 2162, 2164, 2167, 2169, 2171, 2176, 2178, 2180, 2182, 2185, 2187, 2190, 2195, 2198, 2203, 2205, 2209, 2213, 2216, 2221, 2223, 2227, 2229, 2233, 2243, 2255, 2270, 2272, 2275, 2277, 2279, 2282, 2284, 2287, 2289, 2291, 2293, 2295, 2298, 2300, 2302, 2304, 2306, 2308, 2310, 2312, 2315, 2319, 2321, 2323, 2325, 2328, 2330, 2332, 2334, 2336, 2338, 2340, 2343, 2346, 2350, 2352, 2354, 2356, 2358, 2360, 2362, 2364, 2366, 2370, 2372, 2374, 2376, 2378, 2380, 2382, 2384, 2387, 2389, 2392, 2394, 2396, 2398, 2401, 2403, 2406, 2408, 2410, 2412, 2414, 2416, 2418, 2420, 2422, 2424, 2427, 2429, 2432, 2434, 2436, 2441, 2443, 2446, 2448, 2450, 2452, 2454, 2456, 2458, 2460, 2462, 2469, 2471, 2473, 2475, 2477, 2480, 2483, 2486, 2492, 2499, 2511, 2516, 2532, 2537, 2543, 2549, 2552, 2554, 2559, 2561, 2563, 2565, 2574, 2580, 2582, 2586, 2603, 2612, 2614, 2616, and 2618. The plant has a difference in the level of biomass as compared to the corresponding level of a control plant where the nucleic acid has not been modified. The modification can be effected by introducing a genetic modification in the locus comprising the nucleic acid. The method further can include selecting for plants having altered biomass.

The endogenous nucleic acid can encode a polypeptide having 80 percent or greater sequence identity to an amino acid sequence selected from the group consisting of SEQ ID NO: 2, 4, 6-9, 11, 13-15, 17, 18, 20-27, 29, 31-33, 35, 36, 38-51, 53, 54, 56-61, 63-67, 69, 70, 72-76, 78, 80-83, 85, 86, 88-91, 93-97, 99-103, 105, 107, 109, 110, 112, 113, 115, 117, 119-152, 154, 156, 158, 159, 161, 163, 165, 167, 168, 170, 172, 174, 176, 178, 180-185, 187, 188, 190, 192-194, 196, 198, 200, 202, 203, 205, 207-211, 213-251, 253, 255, 257, 258, 260-262, 264, 265, 267-272, 274-279, 281-283, 285, 287-292, 294, 295-297, 299, 301, 303-305, 307, 309, 310, 312, 314, 316-318, 320, 321, 323, 325, 327-329, 331, 332, 334, 335, 337-339, 341, 342, 344, 345, 347, 349, 351, 353, 355, 357, 359, 361-366, 368, 370, 372, 373, 375-378, 380, 382-387, 389, 391, 393, 395, 396, 398-404, 406-414, 416, 418, 420, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497-502, 504, 506, 508, 509, 511-517, 519, 521, 522, 524-527, 529, 530, 532, 533, 535, 536, 537, 539, 541, 543, 545, 546, 548, 550, 552-555, 557, 558, 560, 562, 564, 566, 568, 570-578, 580, 582, 584, 585, 587, 589, 591, 592, 594-596, 598, 600, 601, 603, 604, 606-608, 610, 611, 613, 615, 617, 619, 621, 623, 625, 626, 628-632, 634, 636, 638, 640, 642, 643, 645, 647, 649, 651, 653, 655, 657, 659, 661, 663, 665, 667-670, 672, 674, 675, 677, 679-682, 684, 685, 687, 689-692, 694-698, 700-704, 706, 707, 709-718, 720, 722, 724, 726-728, 730, 731, 733-739, 741, 743, 745, 746, 748, 750, 752, 754, 756, 758, 760-764, 766, 768, 770, 772, 774, 776, 778, 780, 782, 784, 785, 787, 789, 791, 793-795, 797, 799, 801, 803, 805, 806, 808, 810, 812, 814, 816, 818-820, 822-824, 826, 828, 830, 832, 834, 836, 838-840, 842, 843, 845-847, 849, 851, 853, 854, 856-858, 860, 862, 863, 865, 866, 868, 870-873, 875-878, 880-882, 884-886, 888, 890, 892, 893, 895, 897, 899, 900, 902, 903, 905, 907, 909, 911, 912, 913, 915, 917, 919, 921, 923, 925, 926, 928, 930, 932, 933, 935, 936-938, 940, 941, 943-945, 947, 949, 950, 952-955, 957-961, 963, 965-969, 971, 972, 974, 975, 977, 978, 980, 982, 984, 986, 988, 990, 992, 994, 996, 998, 1000-1014, 1016, 1018, 1020, 1021, 1023, 1024, 1026, 1027, 1029, 1030, 1032, 1033, 1035, 1037, 1038, 1040, 1042, 1043, 1045, 1047, 1049, 1051, 1053, 1055, 1057, 1059, 1061-1063, 1065, 1067, 1069, 1070, 1072, 1073, 1075, 1076, 1078-1080, 1082, 1083, 1085, 1087, 1089, 1091, 1093, 1095, 1096, 1098, 1100, 1101, 1103, 1105, 1106, 1108, 1110, 1112, 1114-1116, 1118, 1120-1123, 1125, 1127-1131, 1133, 1134, 1136, 1137, 1139-1145, 1147-1156, 1158-1161, 1163, 1165-1178, 1180-1188, 1190, 1191, 1193-1202, 1204, 1205-1207, 1209-1213, 1215, 1217-1221, 1223-1228, 1230, 1231, 1233-1241, 1243, 1245, 1247, 1249-1252, 1254, 1255, 1257-1259, 1261, 1263, 1264, 1266-1272, 1274-1276, 1278, 1280, 1282-1286, 1288, 1289, 1291-1331, 1333-1337, 1339, 1341, 1343, 1345, 1347-1350, 1352, 1354, 1356, 1358, 1360, 1362, 1364, 1366, 1368, 1370-1372, 1374, 1375, 1377-1379, 1381, 1383, 1384, 1386, 1388-1390, 1392-1397, 1399, 1400, 1402, 1403, 1405, 1407-1410, 1412-1418, 1420, 1422, 1424, 1426, 1428, 1430, 1432-1436, 1438, 1440, 1442-1444, 1446, 1447, 1449, 1450, 1452-1454, 1456, 1457, 1459, 1460, 1462, 1463, 1465-1468, 1470, 1471, 1473, 1475, 1477-1483, 1485, 1487, 1489, 1491-1493, 1495, 1496, 1498, 1499, 1501, 1503, 1504, 1506, 1508, 1510, 1511, 1513, 1514, 1516-1521, 1523, 1524, 1526, 1528-1532, 1534, 1536-1539, 1541, 1542, 1544, 1545, 1547, 1548, 1550, 1552, 1553, 1555-1559, 1561, 1563-1565, 1567, 1568, 1570, 1571, 1573, 1575, 1576, 1578, 1580, 1582, 1583, 1585, 1587, 1589, 1590, 1592, 1593, 1595, 1597, 1599, 1600, 1602-1606, 1608-1613, 1615, 1616, 1618-1626, 1628, 1629, 1631, 1633, 1634, 1636, 1637, 1639-1643, 1645, 1646-1739, 1741, 1743, 1745, 1747-1756, 1758, 1760, 1762-1764, 1766, 1767, 1769, 1770, 1772-1774, 1776, 1778-1783, 1785-1792, 1794, 1796, 1798, 1799, 1801, 1802, 1804, 1806, 1808-1810, 1812, 1814, 1815, 1817, 1819, 1821, 1822, 1824, 1826-1830, 1832, 1834, 1835, 1837, 1839-1841, 1843, 1844, 1846, 1847, 1849, 1851, 1852, 1854, 1856, 1858, 1860-1863, 1865-1953, 1955-1958, 1960, 1962, 1964, 1966-1968, 1970, 1972-1976, 1978, 1980, 1982, 1984-1986, 1988, 1990, 1991, 1993, 1995, 1997, 1999, 2001, 2003, 2005, 2007, 2009, 2011, 2013, 2015, 2017, 2019, 2021, 2023-2027, 2029, 2031, 2033, 2035, 2037, 2039, 2041, 2043, 2045, 2047-2049, 2051-2057, 2059, 2061, 2063, 2065, 2067, 2069, 2071, 2073, 2075, 2077, 2079, 2080, 2082, 2084, 2086, 2088, 2090, 2092, 2093, 2095, 2097, 2098, 2100-2122, 2124, 2126, 2128, 2129, 2131, 2133, 2135-2137, 2139, 2141, 2142, 2144-2148, 2150, 2152, 2154, 2155, 2157, 2159-2161, 2163, 2165, 2166, 2168, 2170, 2172-2175, 2177, 2179, 2181, 2183, 2184, 2186, 2188, 2189, 2191-2194, 2196, 2197, 2199-2202, 2204, 2206-2208, 2210-2212, 2214, 2215, 2217-2220, 2222, 2224-2226, 2228, 2230-2232, 2234-2242, 2244-2254, 2256-2269, 2271, 2273, 2274, 2276, 2278, 2280, 2281, 2283, 2285, 2286, 2288, 2290, 2292, 2294, 2296, 2297, 2299, 2301, 2303, 2305, 2307, 2309, 2311, 2313, 2314, 2316-2318, 2320, 2322, 2324, 2326, 2327, 2329, 2331, 2333, 2335, 2337, 2339, 2341, 2342, 2344, 2345, 2347-2349, 2351, 2353, 2355, 2357, 2359, 2361, 2363, 2365, 2367-2369, 2371, 2373, 2375, 2377, 2379, 2381, 2383, 2385, 2386, 2388, 2390, 2391, 2393, 2395, 2397, 2399, 2400, 2402, 2404, 2405, 2407, 2409, 2411, 2413, 2415, 2417, 2419, 2421, 2423, 2425, 2426, 2428, 2430, 2431, 2433, 2435, 2437, 2438-2440, 2442, 2444, 2445, 2447, 2449, 2451, 2453, 2455, 2457, 2459, 2461, 2463-2468, 2470, 2472, 2474, 2476, 2478, 2479, 2481, 2482, 2484, 2485, 2487-2491, 2493-2498, 2500-2510, 2512-2515, 2517-2531, 2533-2536, 2538-2542, 2544-2548, 2550, 2551, 2553, 2555-2558, 2560, 2562, 2564, 2566-2573, 2575-2579, 2581, 2583-2585, 2587-2602, 2604-2611, 2613, 2615, 2617, and 2619-2623.

This document also features a method of producing a plant. The method includes growing a plant cell containing a modified endogenous nucleic acid encoding a polypeptide, wherein the HMM bit score of the amino acid sequence of the polypeptide is greater than about 65, the HMM based on the amino acid sequences depicted in one of FIGS. 1-38. The plant has a difference in the level of biomass as compared to the corresponding level of a control plant where the nucleic acid has not been modified.

In another aspect, this document features a plant cell containing a modified endogenous nucleic acid encoding a polypeptide, wherein the HMM bit score of the amino acid sequence of the polypeptide is greater than about 65, the HMM based on the amino acid sequences depicted in one of FIGS. 1-38. A plant produced from the plant cell has a difference in the level of biomass as compared to the corresponding level of a control plant where said nucleic acid has not been modified.

A plant cell also is featured that contains a modified biomass-modulating endogenous nucleic acid. The nucleic acid includes a nucleotide sequence with an open reading frame having 80 percent or greater sequence identity to the nucleotide sequence selected from the group consisting of SEQ ID NO: 1, 3, 5, 10, 12, 16, 19, 28, 30, 34, 37, 52, 55, 62, 68, 71, 77, 79, 84, 87, 92, 98, 104, 106, 108, 111, 114, 116, 118, 153, 155, 157, 160, 162, 164, 166, 169, 171, 173, 175, 177, 179, 186, 189, 191, 195, 197, 199, 201, 204, 206, 212, 252, 254, 256, 259, 263, 266, 273, 280, 284, 286, 293, 298, 300, 302, 306, 308, 311, 313, 315, 319, 322, 324, 326, 330, 333, 336, 340, 343, 346, 348, 350, 352, 354, 356, 358, 360, 367, 369, 371, 374, 379, 381, 388, 390, 392, 394, 397, 405, 415, 417, 419, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 503, 505, 507, 510, 518, 520, 523, 528, 531, 534, 538, 540, 542, 544, 547, 549, 551, 556, 559, 561, 563, 565, 567, 569, 579, 581, 583, 586, 588, 590, 593, 597, 599, 602, 605, 609, 612, 614, 616, 618, 620, 622, 624, 627, 633, 635, 637, 639, 641, 644, 646, 648, 650, 652, 654, 656, 658, 660, 662, 664, 666, 671, 673, 676, 678, 683, 686, 688, 693, 699, 705, 708, 719, 721, 723, 725, 729, 732, 740, 742, 744, 747, 749, 751, 753, 755, 757, 759, 765, 767, 769, 771, 773, 775, 777, 779, 781, 783, 786, 788, 790, 792, 796, 798, 800, 802, 804, 807, 809, 811, 813, 815, 817, 821, 825, 827, 829, 831, 833, 835, 837, 841, 844, 848, 850, 852, 855, 859, 861, 864, 867, 869, 874, 879, 883, 887, 889, 891, 894, 896, 898, 901, 904, 906, 908, 910, 914, 916, 918, 920, 922, 924, 927, 929, 931, 934, 939, 942, 946, 948, 951, 956, 962, 964, 970, 973, 976, 979, 981, 983, 985, 987, 989, 991, 993, 995, 997, 999, 1015, 1017, 1019, 1022, 1025, 1028, 1031, 1034, 1036, 1039, 1041, 1044, 1046, 1048, 1050, 1052, 1054, 1056, 1058, 1060, 1064, 1066, 1068, 1071, 1074, 1077, 1081, 1084, 1086, 1088, 1090, 1092, 1094, 1097, 1099, 1102, 1104, 1107, 1109, 1111, 1113, 1117, 1119, 1124, 1126, 1132, 1135, 1138, 1146, 1157, 1162, 1164, 1179, 1189, 1192, 1203, 1208, 1214, 1216, 1222, 1229, 1232, 1242, 1244, 1246, 1248, 1253, 1256, 1260, 1262, 1265, 1273, 1277, 1279, 1281, 1287, 1290, 1332, 1338, 1340, 1342, 1344, 1346, 1351, 1353, 1355, 1357, 1359, 1361, 1363, 1365, 1367, 1369, 1373, 1376, 1380, 1382, 1385, 1387, 1391, 1398, 1401, 1404, 1406, 1411, 1419, 1421, 1423, 1425, 1427, 1429, 1431, 1437, 1439, 1441, 1445, 1448, 1451, 1455, 1458, 1461, 1464, 1469, 1472, 1474, 1476, 1484, 1486, 1488, 1490, 1494, 1497, 1500, 1502, 1505, 1507, 1509, 1512, 1515, 1522, 1525, 1527, 1533, 1535, 1540, 1543, 1546, 1549, 1551, 1554, 1560, 1562, 1566, 1569, 1572, 1574, 1577, 1579, 1581, 1584, 1586, 1588, 1591, 1594, 1596, 1598, 1601, 1607, 1614, 1617, 1627, 1630, 1632, 1635, 1638, 1644, 1740, 1742, 1744, 1746, 1757, 1759, 1761, 1765, 1768, 1771, 1775, 1777, 1784, 1793, 1795, 1797, 1800, 1803, 1805, 1807, 1811, 1813, 1816, 1818, 1820, 1823, 1825, 1831, 1833, 1836, 1838, 1842, 1845, 1848, 1850, 1853, 1855, 1857, 1859, 1864, 1954, 1959, 1961, 1963, 1965, 1969, 1971, 1977, 1979, 1981, 1983, 1987, 1989, 1992, 1994, 1996, 1998, 2000, 2002, 2004, 2006, 2008, 2010, 2012, 2014, 2016, 2018, 2020, 2022, 2028, 2030, 2032, 2034, 2036, 2038, 2040, 2042, 2044, 2046, 2050, 2058, 2060, 2062, 2064, 2066, 2068, 2070, 2072, 2074, 2076, 2078, 2081, 2083, 2085, 2087, 2089, 2091, 2094, 2096, 2099, 2123, 2125, 2127, 2130, 2132, 2134, 2138, 2140, 2143, 2149, 2151, 2153, 2156, 2158, 2162, 2164, 2167, 2169, 2171, 2176, 2178, 2180, 2182, 2185, 2187, 2190, 2195, 2198, 2203, 2205, 2209, 2213, 2216, 2221, 2223, 2227, 2229, 2233, 2243, 2255, 2270, 2272, 2275, 2277, 2279, 2282, 2284, 2287, 2289, 2291, 2293, 2295, 2298, 2300, 2302, 2304, 2306, 2308, 2310, 2312, 2315, 2319, 2321, 2323, 2325, 2328, 2330, 2332, 2334, 2336, 2338, 2340, 2343, 2346, 2350, 2352, 2354, 2356, 2358, 2360, 2362, 2364, 2366, 2370, 2372, 2374, 2376, 2378, 2380, 2382, 2384, 2387, 2389, 2392, 2394, 2396, 2398, 2401, 2403, 2406, 2408, 2410, 2412, 2414, 2416, 2418, 2420, 2422, 2424, 2427, 2429, 2432, 2434, 2436, 2441, 2443, 2446, 2448, 2450, 2452, 2454, 2456, 2458, 2460, 2462, 2469, 2471, 2473, 2475, 2477, 2480, 2483, 2486, 2492, 2499, 2511, 2516, 2532, 2537, 2543, 2549, 2552, 2554, 2559, 2561, 2563, 2565, 2574, 2580, 2582, 2586, 2603, 2612, 2614, 2616, and 2618, and wherein a plant produced from said plant cell has a difference in the level of biomass as compared to the corresponding level of a control plant where said nucleic acid has not been modified.

The endogenous nucleic acid can encode a polypeptide having 80 percent or greater sequence identity to an amino acid sequence selected from the group consisting of SEQ ID NO: 2, 4, 6-9, 11, 13-15, 17, 18, 20-27, 29, 31-33, 35, 36, 38-51, 53, 54, 56-61, 63-67, 69, 70, 72-76, 78, 80-83, 85, 86, 88-91, 93-97, 99-103, 105, 107, 109, 110, 112, 113, 115, 117, 119-152, 154, 156, 158, 159, 161, 163, 165, 167, 168, 170, 172, 174, 176, 178, 180-185, 187, 188, 190, 192-194, 196, 198, 200, 202, 203, 205, 207-211, 213-251, 253, 255, 257, 258, 260-262, 264, 265, 267-272, 274-279, 281-283, 285, 287-292, 294, 295-297, 299, 301, 303-305, 307, 309, 310, 312, 314, 316-318, 320, 321, 323, 325, 327-329, 331, 332, 334, 335, 337-339, 341, 342, 344, 345, 347, 349, 351, 353, 355, 357, 359, 361-366, 368, 370, 372, 373, 375-378, 380, 382-387, 389, 391, 393, 395, 396, 398-404, 406-414, 416, 418, 420, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497-502, 504, 506, 508, 509, 511-517, 519, 521, 522, 524-527, 529, 530, 532, 533, 535, 536, 537, 539, 541, 543, 545, 546, 548, 550, 552-555, 557, 558, 560, 562, 564, 566, 568, 570-578, 580, 582, 584, 585, 587, 589, 591, 592, 594-596, 598, 600, 601, 603, 604, 606-608, 610, 611, 613, 615, 617, 619, 621, 623, 625, 626, 628-632, 634, 636, 638, 640, 642, 643, 645, 647, 649, 651, 653, 655, 657, 659, 661, 663, 665, 667-670, 672, 674, 675, 677, 679-682, 684, 685, 687, 689-692, 694-698, 700-704, 706, 707, 709-718, 720, 722, 724, 726-728, 730, 731, 733-739, 741, 743, 745, 746, 748, 750, 752, 754, 756, 758, 760-764, 766, 768, 770, 772, 774, 776, 778, 780, 782, 784, 785, 787, 789, 791, 793-795, 797, 799, 801, 803, 805, 806, 808, 810, 812, 814, 816, 818-820, 822-824, 826, 828, 830, 832, 834, 836, 838-840, 842, 843, 845-847, 849, 851, 853, 854, 856-858, 860, 862, 863, 865, 866, 868, 870-873, 875-878, 880-882, 884-886, 888, 890, 892, 893, 895, 897, 899, 900, 902, 903, 905, 907, 909, 911, 912, 913, 915, 917, 919, 921, 923, 925, 926, 928, 930, 932, 933, 935, 936-938, 940, 941, 943-945, 947, 949, 950, 952-955, 957-961, 963, 965-969, 971, 972, 974, 975, 977, 978, 980, 982, 984, 986, 988, 990, 992, 994, 996, 998, 1000-1014, 1016, 1018, 1020, 1021, 1023, 1024, 1026, 1027, 1029, 1030, 1032, 1033, 1035, 1037, 1038, 1040, 1042, 1043, 1045, 1047, 1049, 1051, 1053, 1055, 1057, 1059, 1061-1063, 1065, 1067, 1069, 1070, 1072, 1073, 1075, 1076, 1078-1080, 1082, 1083, 1085, 1087, 1089, 1091, 1093, 1095, 1096, 1098, 1100, 1101, 1103, 1105, 1106, 1108, 1110, 1112, 1114-1116, 1118, 1120-1123, 1125, 1127-1131, 1133, 1134, 1136, 1137, 1139-1145, 1147-1156, 1158-1161, 1163, 1165-1178, 1180-1188, 1190, 1191, 1193-1202, 1204, 1205-1207, 1209-1213, 1215, 1217-1221, 1223-1228, 1230, 1231, 1233-1241, 1243, 1245, 1247, 1249-1252, 1254, 1255, 1257-1259, 1261, 1263, 1264, 1266-1272, 1274-1276, 1278, 1280, 1282-1286, 1288, 1289, 1291-1331, 1333-1337, 1339, 1341, 1343, 1345, 1347-1350, 1352, 1354, 1356, 1358, 1360, 1362, 1364, 1366, 1368, 1370-1372, 1374, 1375, 1377-1379, 1381, 1383, 1384, 1386, 1388-1390, 1392-1397, 1399, 1400, 1402, 1403, 1405, 1407-1410, 1412-1418, 1420, 1422, 1424, 1426, 1428, 1430, 1432-1436, 1438, 1440, 1442-1444, 1446, 1447, 1449, 1450, 1452-1454, 1456, 1457, 1459, 1460, 1462, 1463, 1465-1468, 1470, 1471, 1473, 1475, 1477-1483, 1485, 1487, 1489, 1491-1493, 1495, 1496, 1498, 1499, 1501, 1503, 1504, 1506, 1508, 1510, 1511, 1513, 1514, 1516-1521, 1523, 1524, 1526, 1528-1532, 1534, 1536-1539, 1541, 1542, 1544, 1545, 1547, 1548, 1550, 1552, 1553, 1555-1559, 1561, 1563-1565, 1567, 1568, 1570, 1571, 1573, 1575, 1576, 1578, 1580, 1582, 1583, 1585, 1587, 1589, 1590, 1592, 1593, 1595, 1597, 1599, 1600, 1602-1606, 1608-1613, 1615, 1616, 1618-1626, 1628, 1629, 1631, 1633, 1634, 1636, 1637, 1639-1643, 1645, 1646-1739, 1741, 1743, 1745, 1747-1756, 1758, 1760, 1762-1764, 1766, 1767, 1769, 1770, 1772-1774, 1776, 1778-1783, 1785-1792, 1794, 1796, 1798, 1799, 1801, 1802, 1804, 1806, 1808-1810, 1812, 1814, 1815, 1817, 1819, 1821, 1822, 1824, 1826-1830, 1832, 1834, 1835, 1837, 1839-1841, 1843, 1844, 1846, 1847, 1849, 1851, 1852, 1854, 1856, 1858, 1860-1863, 1865-1953, 1955-1958, 1960, 1962, 1964, 1966-1968, 1970, 1972-1976, 1978, 1980, 1982, 1984-1986, 1988, 1990, 1991, 1993, 1995, 1997, 1999, 2001, 2003, 2005, 2007, 2009, 2011, 2013, 2015, 2017, 2019, 2021, 2023-2027, 2029, 2031, 2033, 2035, 2037, 2039, 2041, 2043, 2045, 2047-2049, 2051-2057, 2059, 2061, 2063, 2065, 2067, 2069, 2071, 2073, 2075, 2077, 2079, 2080, 2082, 2084, 2086, 2088, 2090, 2092, 2093, 2095, 2097, 2098, 2100-2122, 2124, 2126, 2128, 2129, 2131, 2133, 2135-2137, 2139, 2141, 2142, 2144-2148, 2150, 2152, 2154, 2155, 2157, 2159-2161, 2163, 2165, 2166, 2168, 2170, 2172-2175, 2177, 2179, 2181, 2183, 2184, 2186, 2188, 2189, 2191-2194, 2196, 2197, 2199-2202, 2204, 2206-2208, 2210-2212, 2214, 2215, 2217-2220, 2222, 2224-2226, 2228, 2230-2232, 2234-2242, 2244-2254, 2256-2269, 2271, 2273, 2274, 2276, 2278, 2280, 2281, 2283, 2285, 2286, 2288, 2290, 2292, 2294, 2296, 2297, 2299, 2301, 2303, 2305, 2307, 2309, 2311, 2313, 2314, 2316-2318, 2320, 2322, 2324, 2326, 2327, 2329, 2331, 2333, 2335, 2337, 2339, 2341, 2342, 2344, 2345, 2347-2349, 2351, 2353, 2355, 2357, 2359, 2361, 2363, 2365, 2367-2369, 2371, 2373, 2375, 2377, 2379, 2381, 2383, 2385, 2386, 2388, 2390, 2391, 2393, 2395, 2397, 2399, 2400, 2402, 2404, 2405, 2407, 2409, 2411, 2413, 2415, 2417, 2419, 2421, 2423, 2425, 2426, 2428, 2430, 2431, 2433, 2435, 2437, 2438-2440, 2442, 2444, 2445, 2447, 2449, 2451, 2453, 2455, 2457, 2459, 2461, 2463-2468, 2470, 2472, 2474, 2476, 2478, 2479, 2481, 2482, 2484, 2485, 2487-2491, 2493-2498, 2500-2510, 2512-2515, 2517-2531, 2533-2536, 2538-2542, 2544-2548, 2550, 2551, 2553, 2555-2558, 2560, 2562, 2564, 2566-2573, 2575-2579, 2581, 2583-2585, 2587-2602, 2604-2611, 2613, 2615, 2617, and 2619-2623. A plant produced from the plant cell has a difference in the level of biomass as compared to the corresponding level of a control plant where the nucleic acid has not been modified.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF DRAWINGS

FIGS. 1A-1B are an alignment of the amino acid sequence of CeresClone:1871521 (SEQ ID NO: 1333) with homologous and/or orthologous amino acid sequences. In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE version 3.52.

Figure 2C:
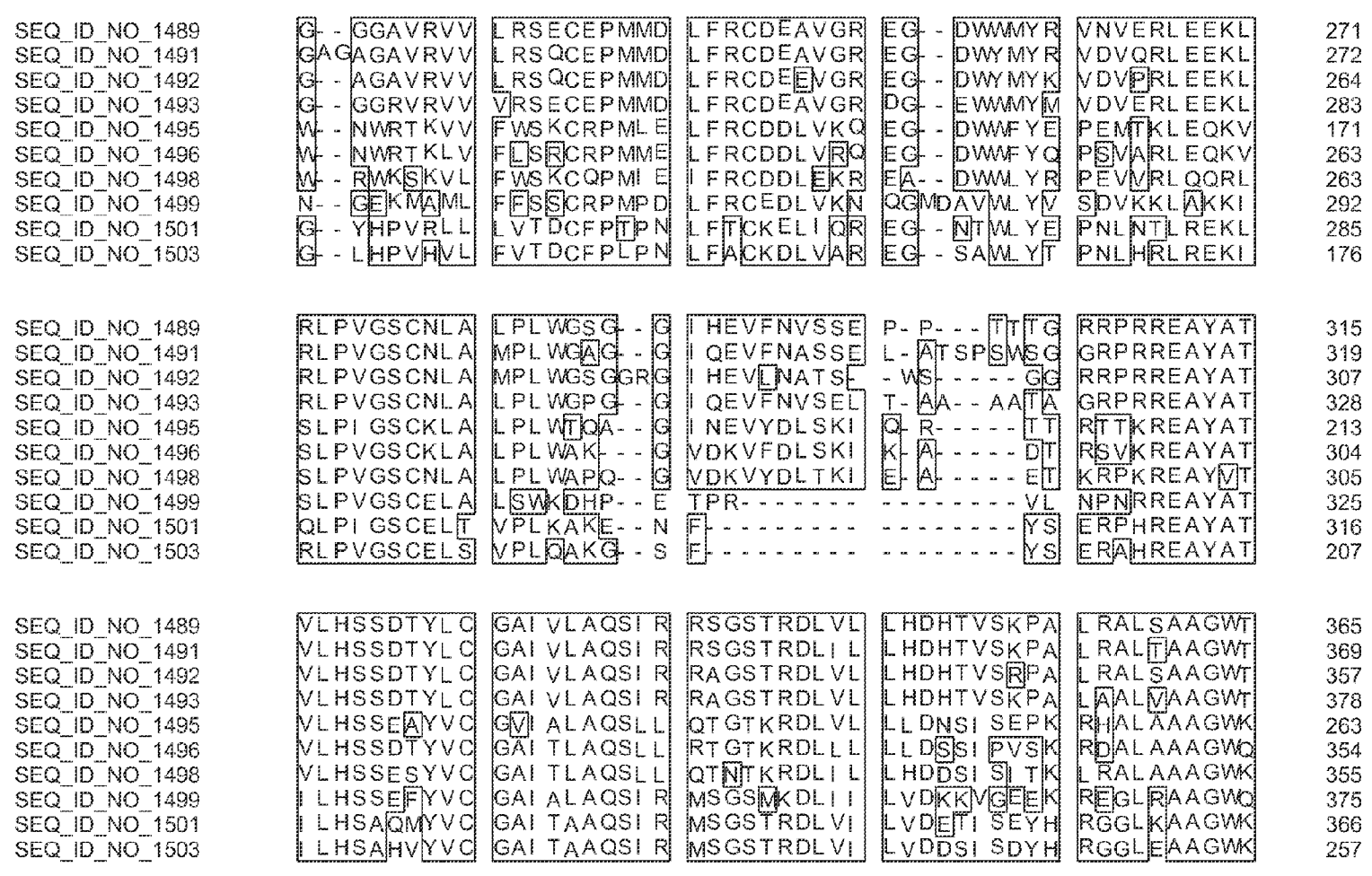
Figure 2D:
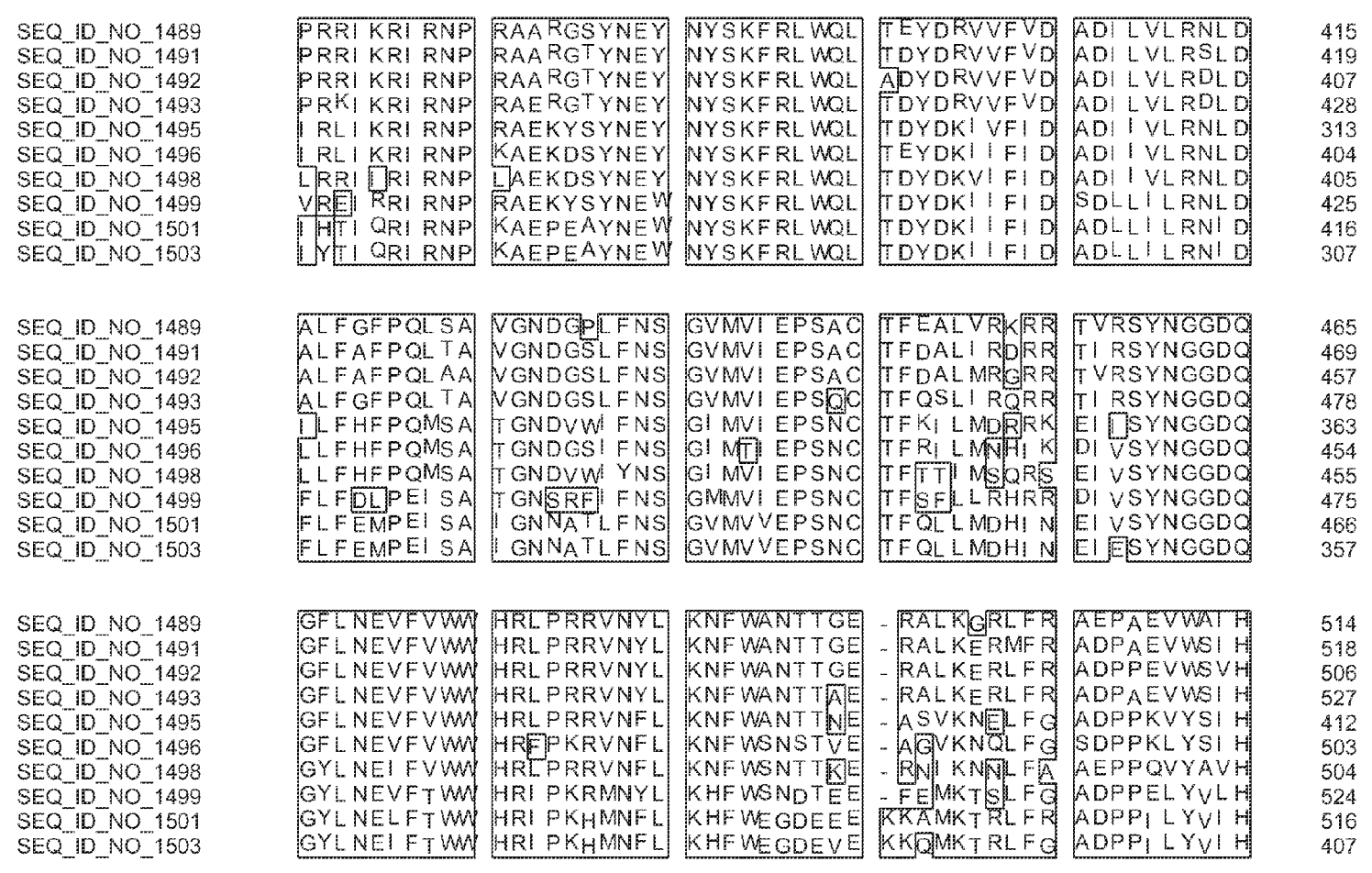
Figure 2E:
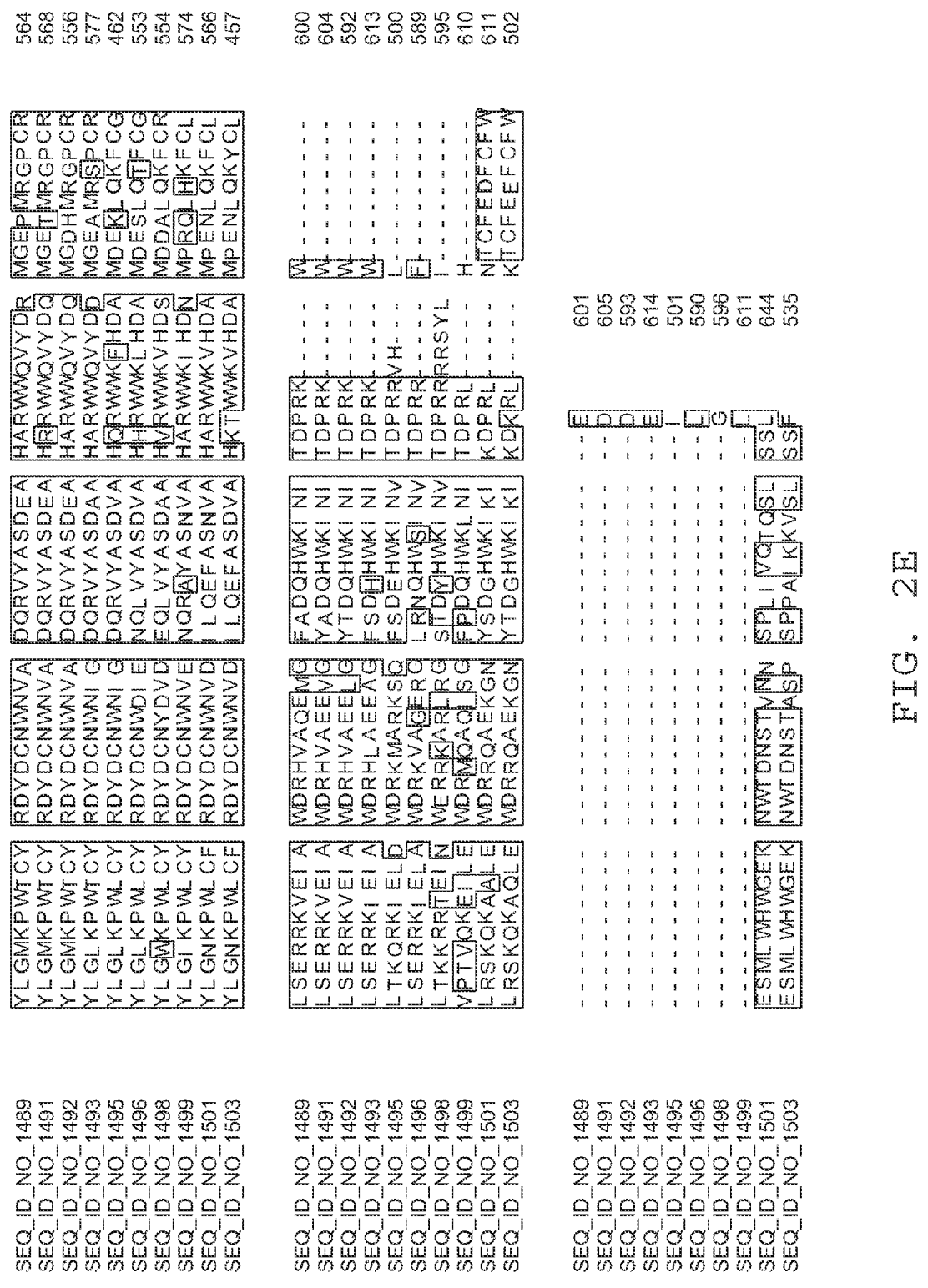

FIGS. 2A-2E are an alignment of the amino acid sequence of CeresClone:1909354 (SEQ ID NO: 1489) with homologous and/or orthologous amino acid sequences.

Figure 3A:
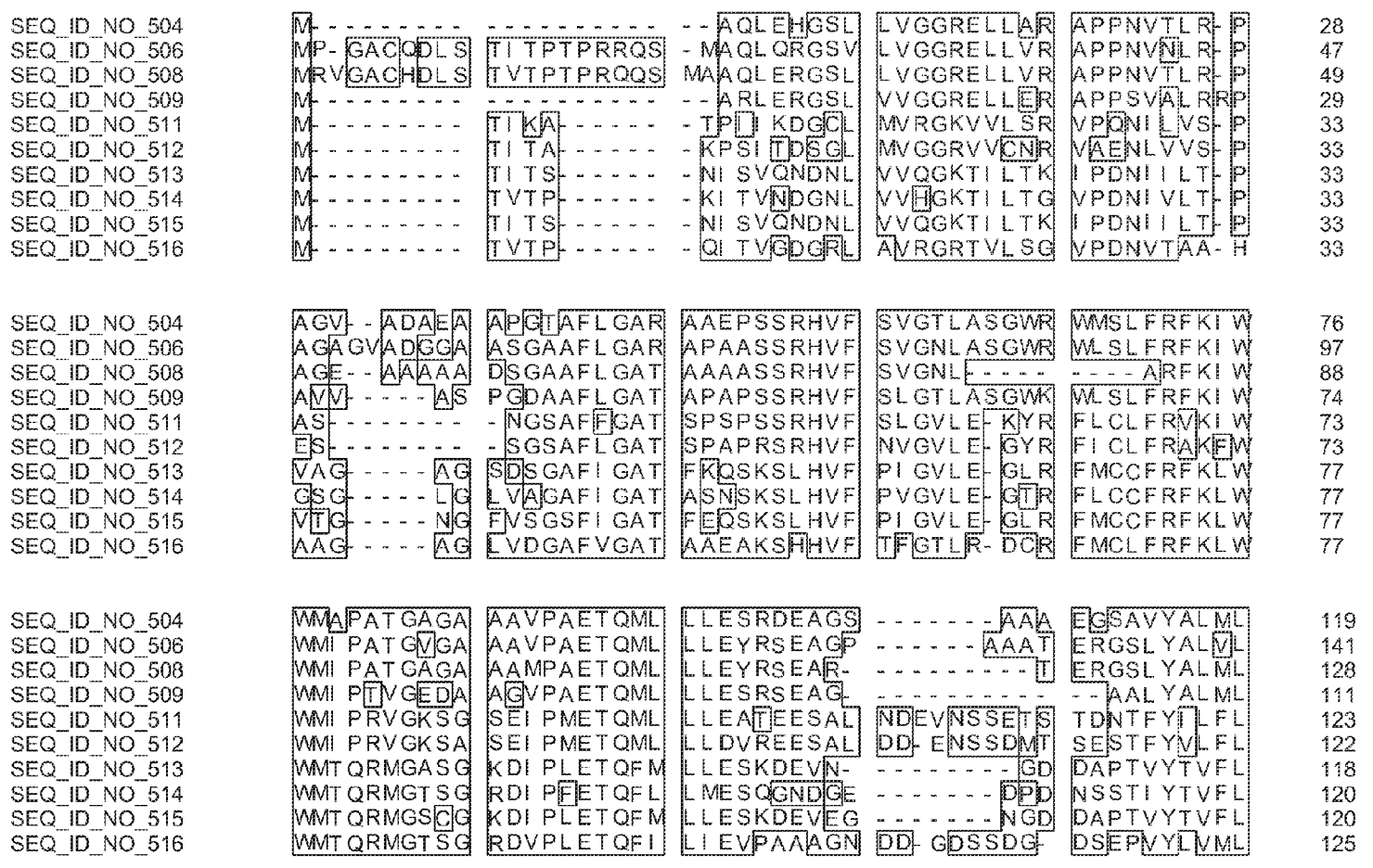
Figure 3B:
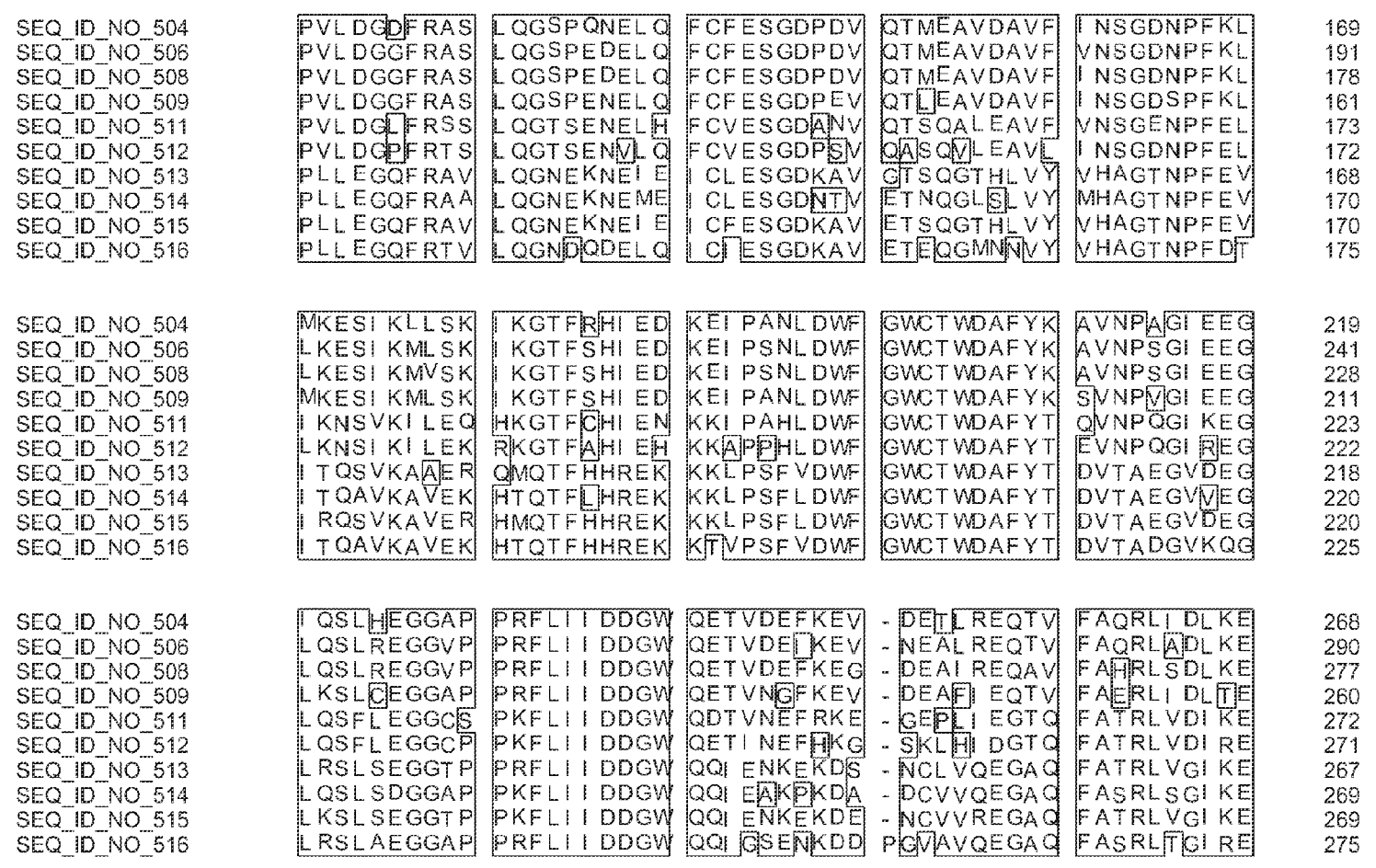
Figure 3D:
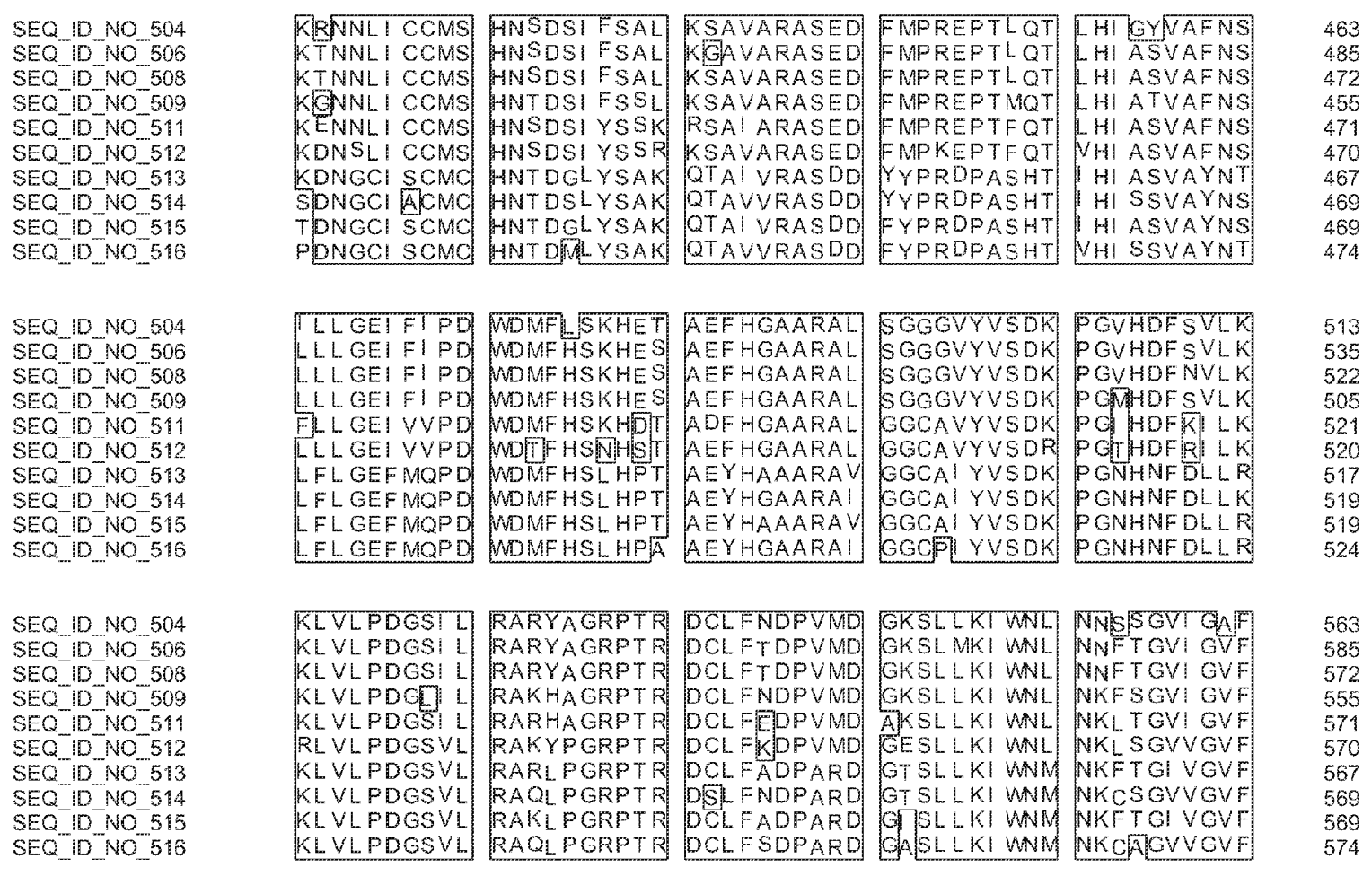
Figure 3E:
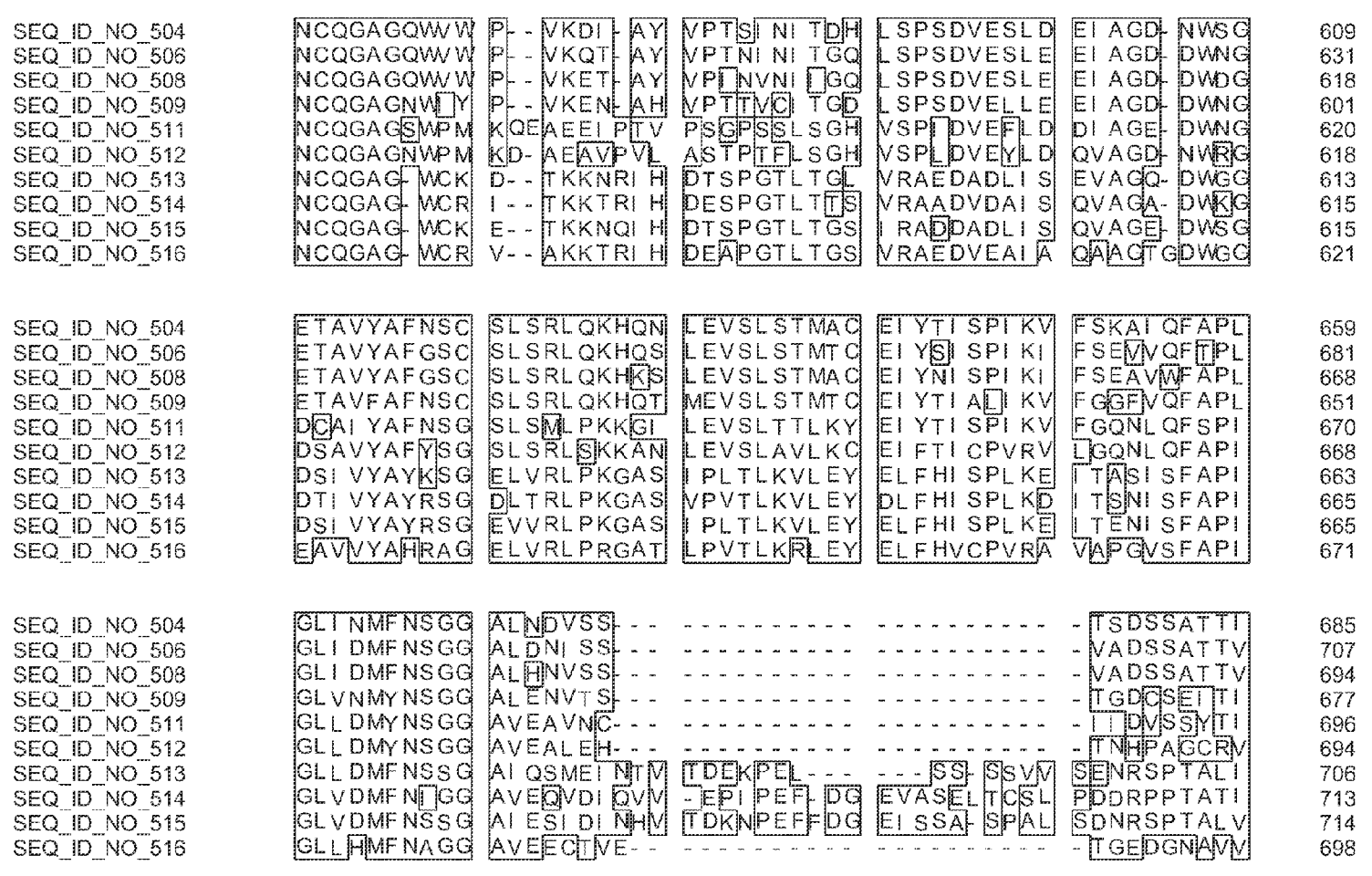
Figure 3F:
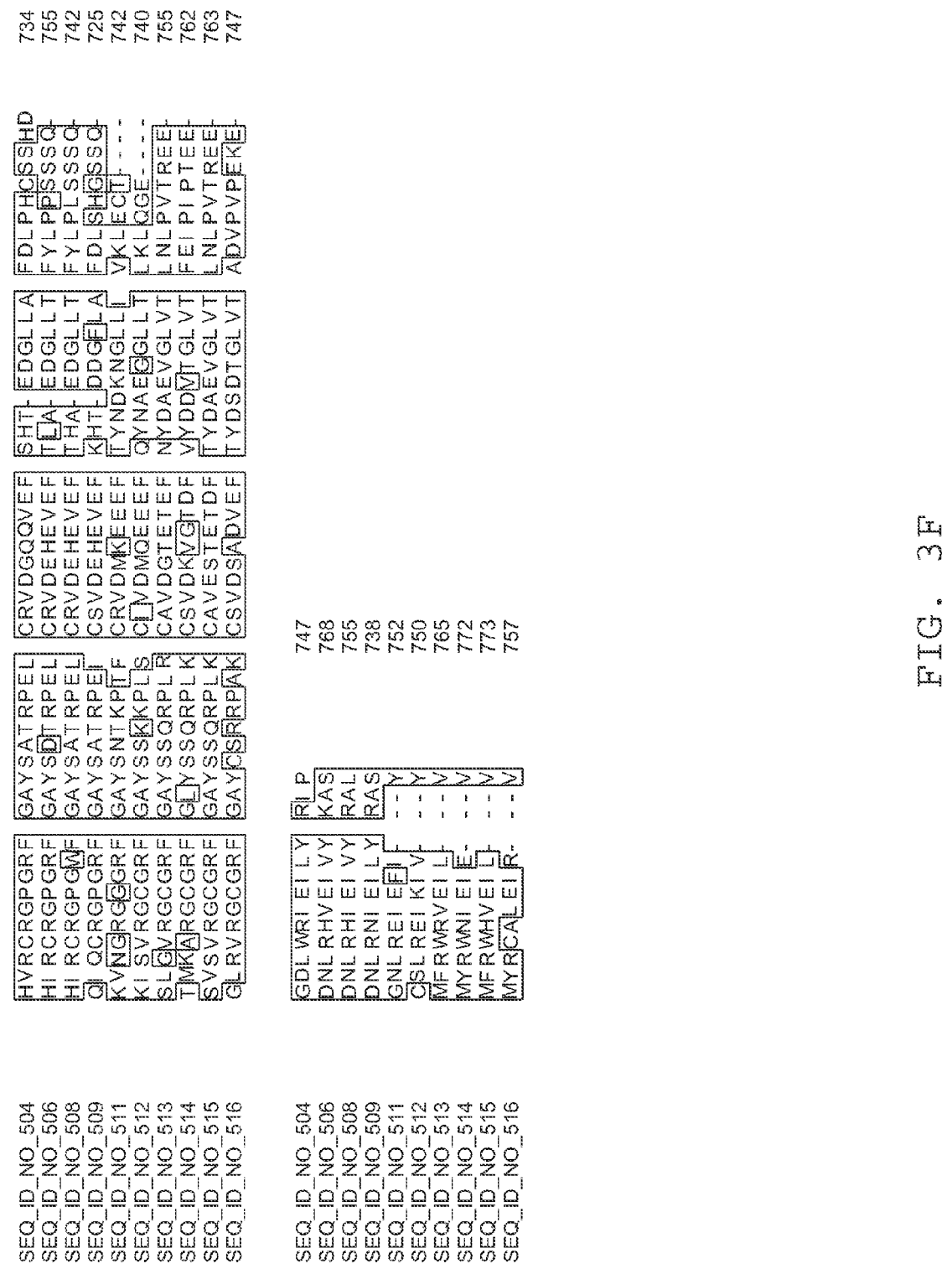

FIGS. 3A-3F are an alignment of the amino acid sequence of CeresClone:1882035 (SEQ ID NO: 504) with homologous and/or orthologous amino acid sequences.

FIGS. 4A-4C are an alignment of the amino acid sequence of CeresClone:1819917 (SEQ ID NO:198) with homologous and/or orthologous amino acid sequences.

Figure 5A:
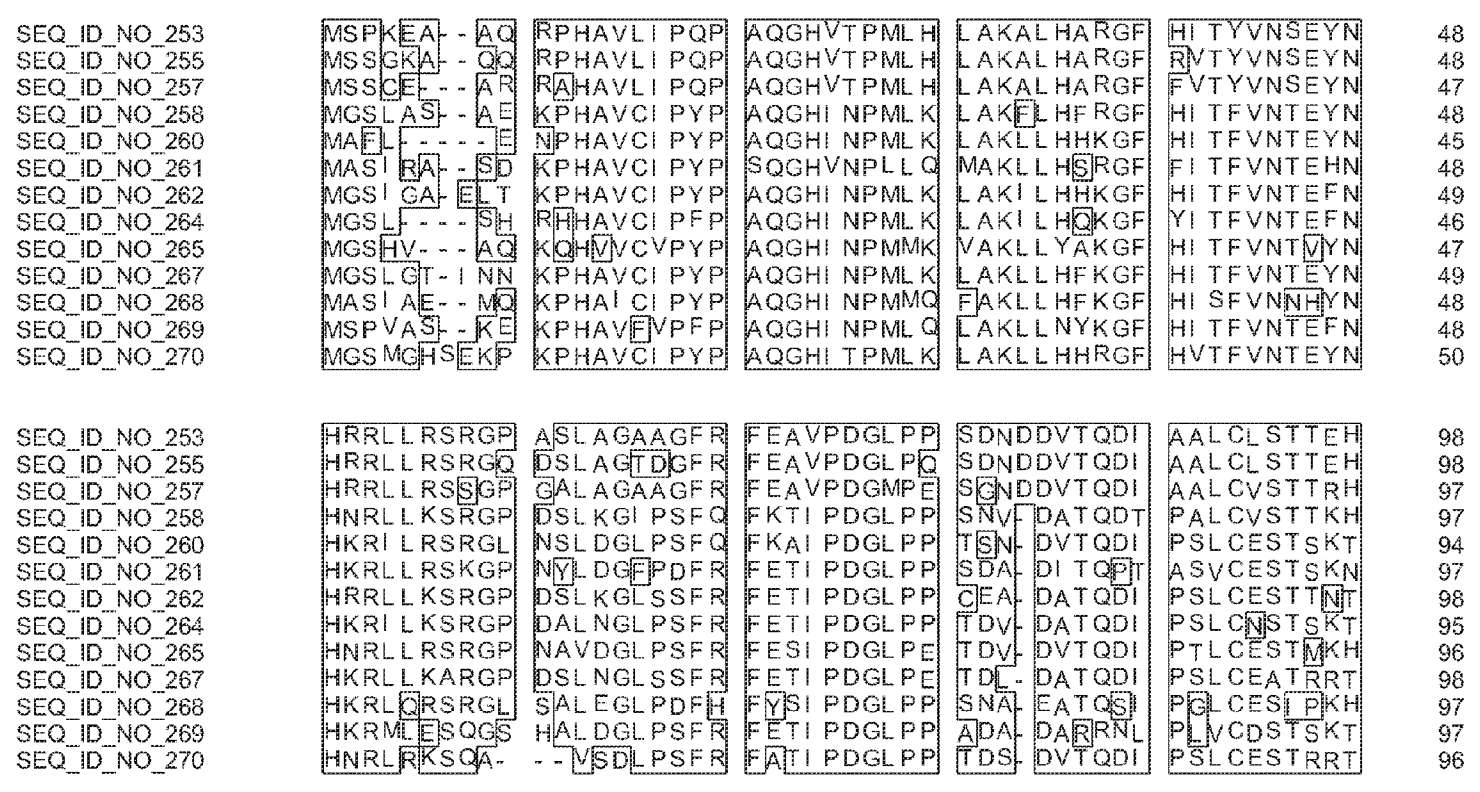
Figure 5C:
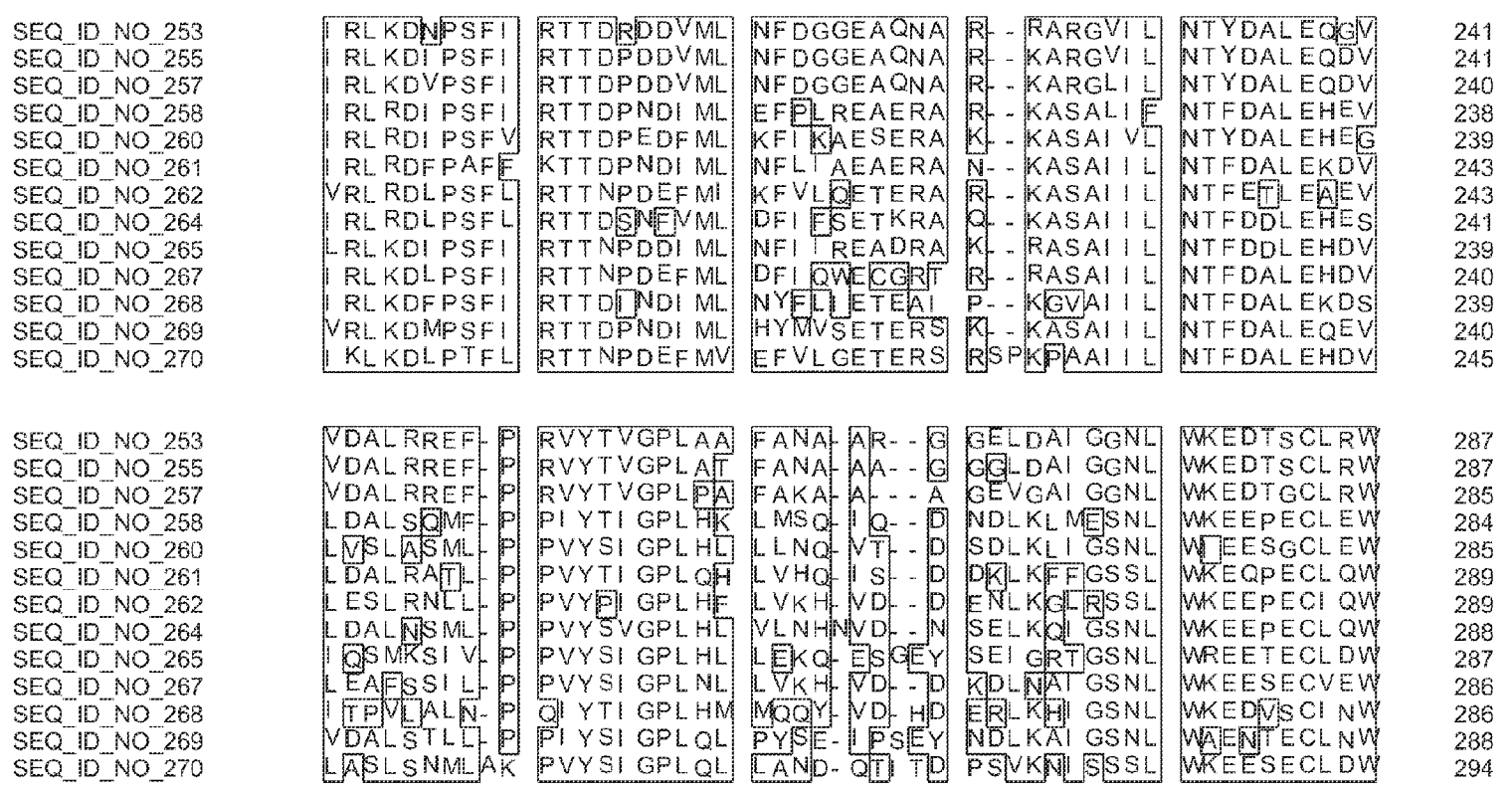

FIGS. 5A-5F are an alignment of the amino acid sequence of CeresClone:1815762 (SEQ ID NO: 253) with homologous and/or orthologous amino acid sequences.

FIGS. 6A-6C are an alignment of the amino acid sequence of CeresClone:1792015 (SEQ ID NO: 1541) with homologous and/or orthologous amino acid sequences.

FIGS. 7A-7D are an alignment of the amino acid sequence of CeresClone:1791384 (SEQ ID NO: 663) with homologous and/or orthologous amino acid sequences.

FIGS. 8A-8D are an alignment of the amino acid sequence of CeresClone:1786268 (SEQ ID NO: 1366) with homologous and/or orthologous amino acid sequences.

Figure 9A:
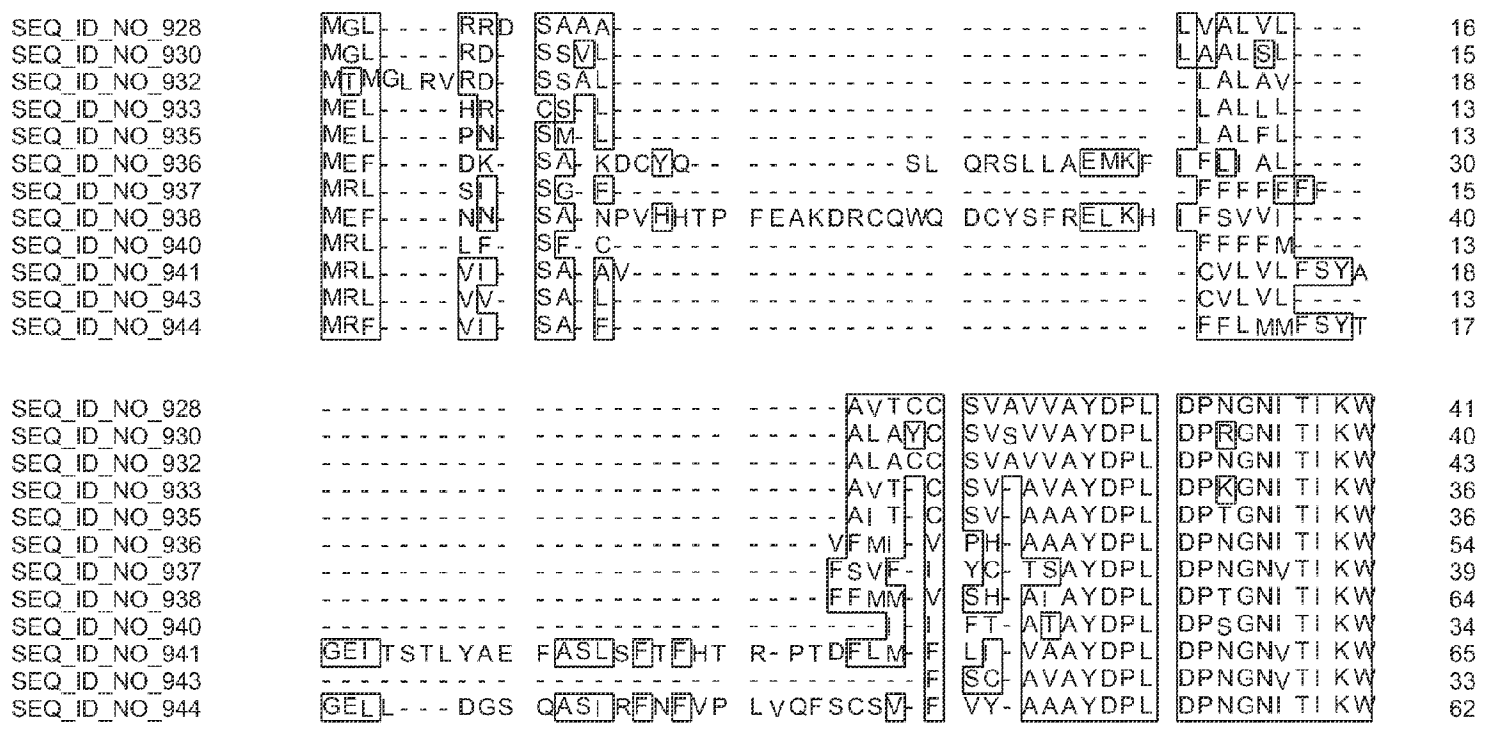
Figure 9B:
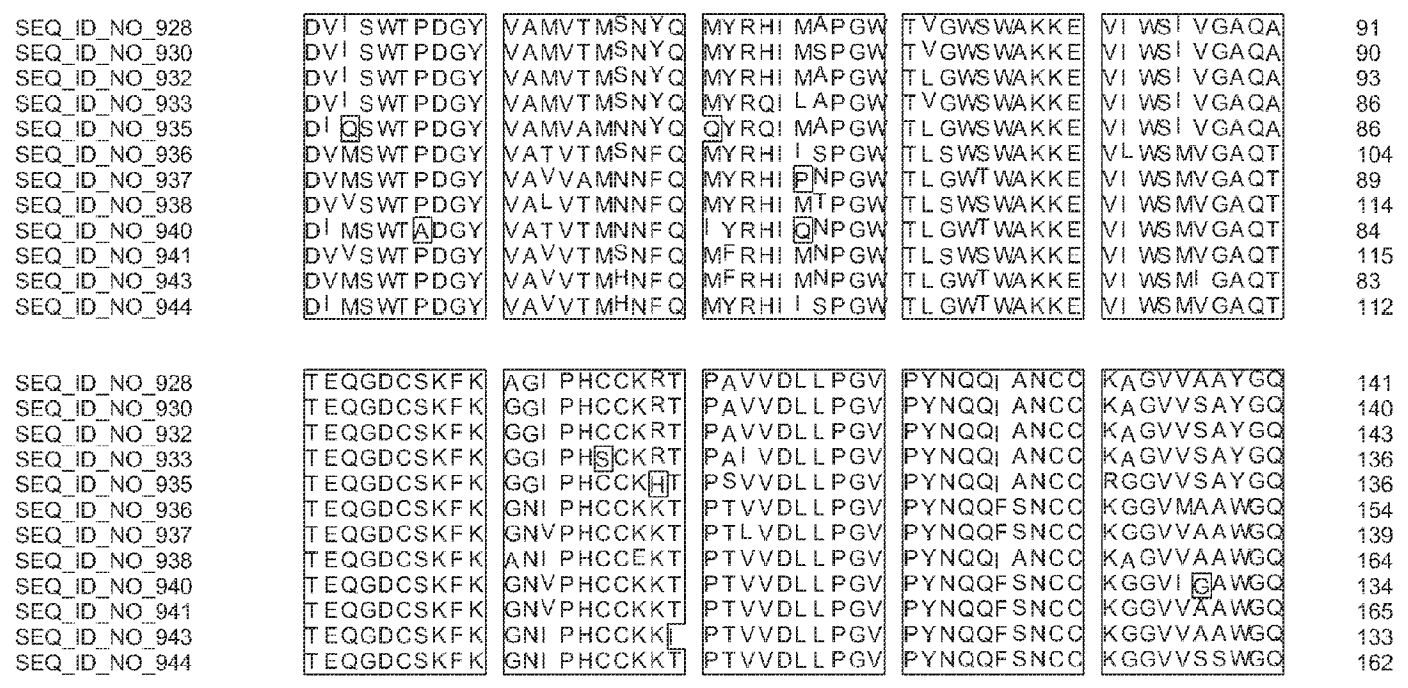
Figure 9D:
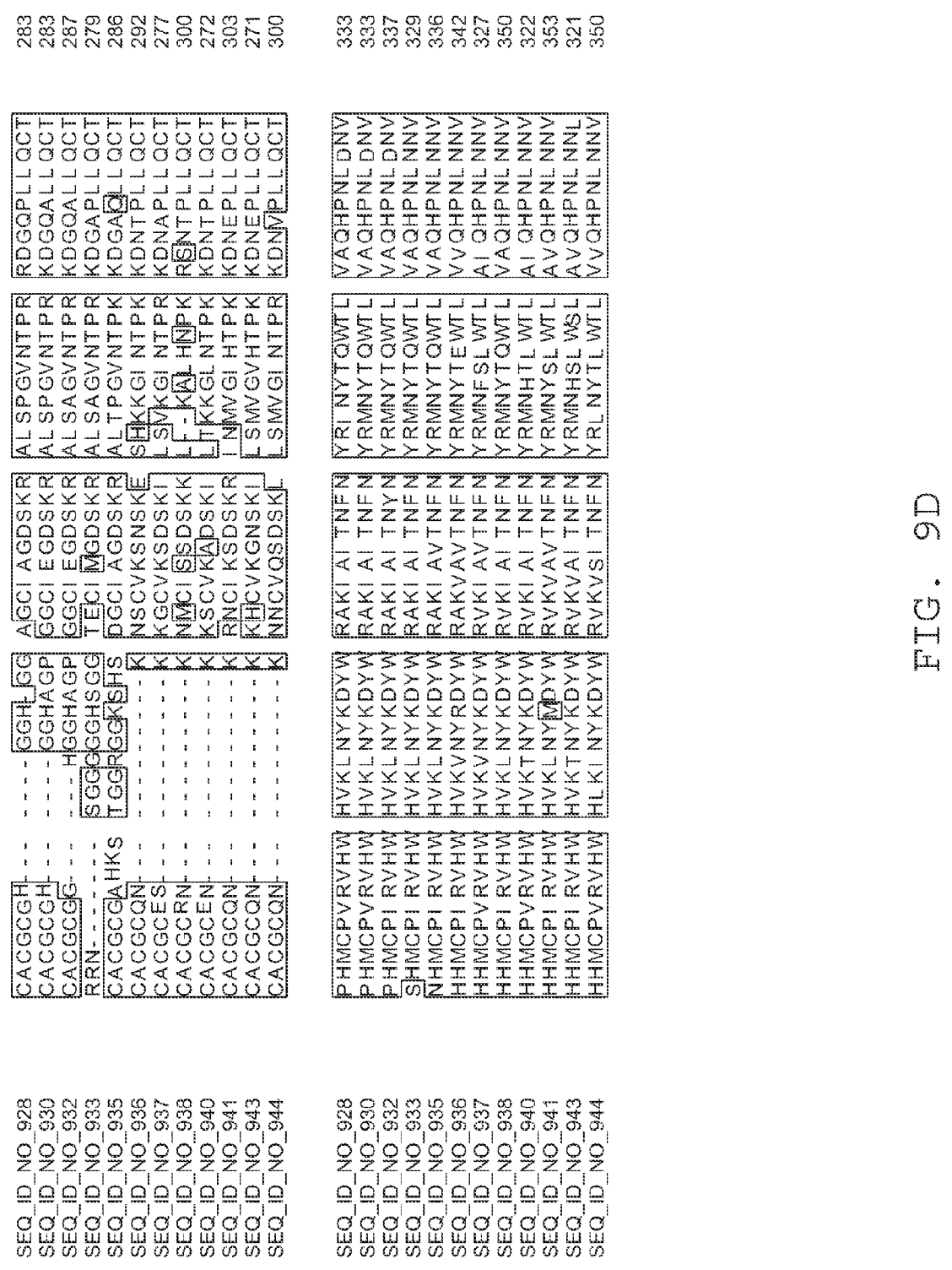
Figure 9E:
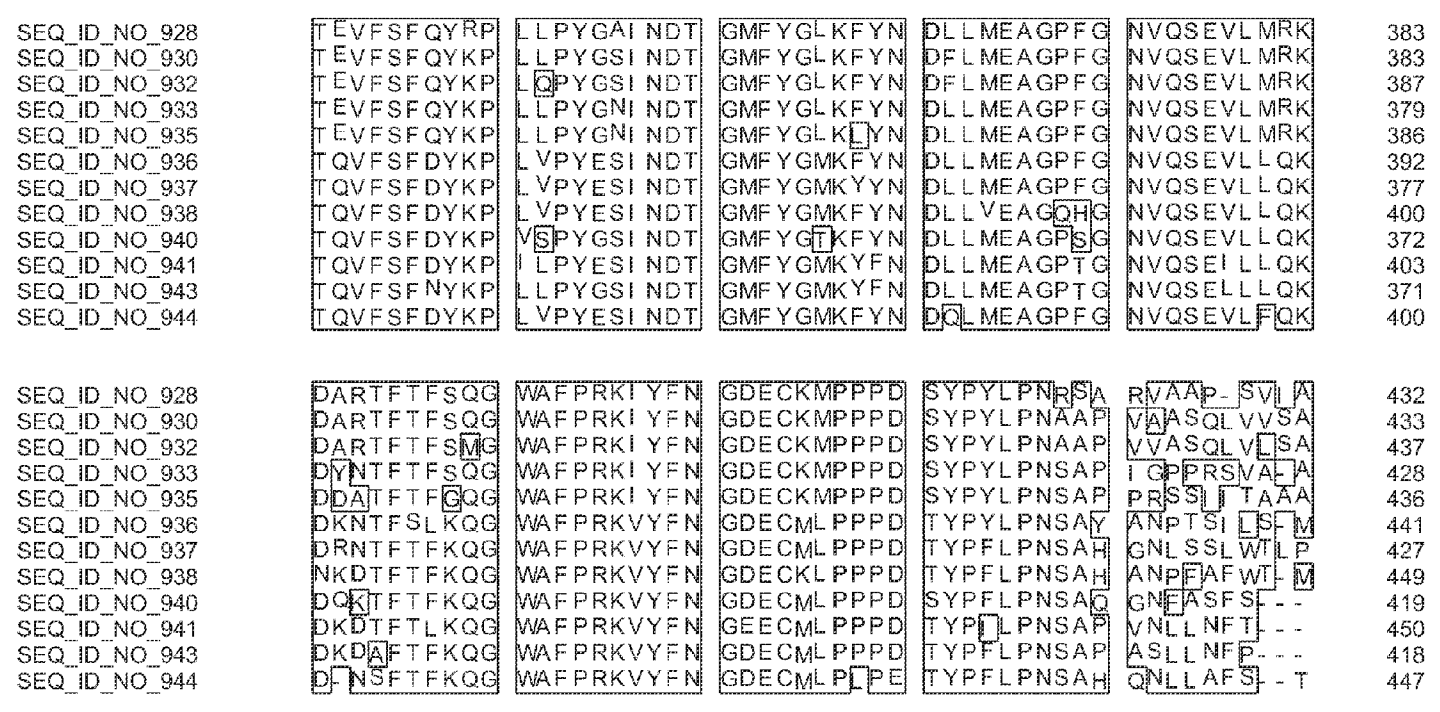

FIGS. 9A-9F are an alignment of the amino acid sequence of CeresClone:1781794 (SEQ ID NO: 928) with homologous and/or orthologous amino acid sequences.

Figure 10A:
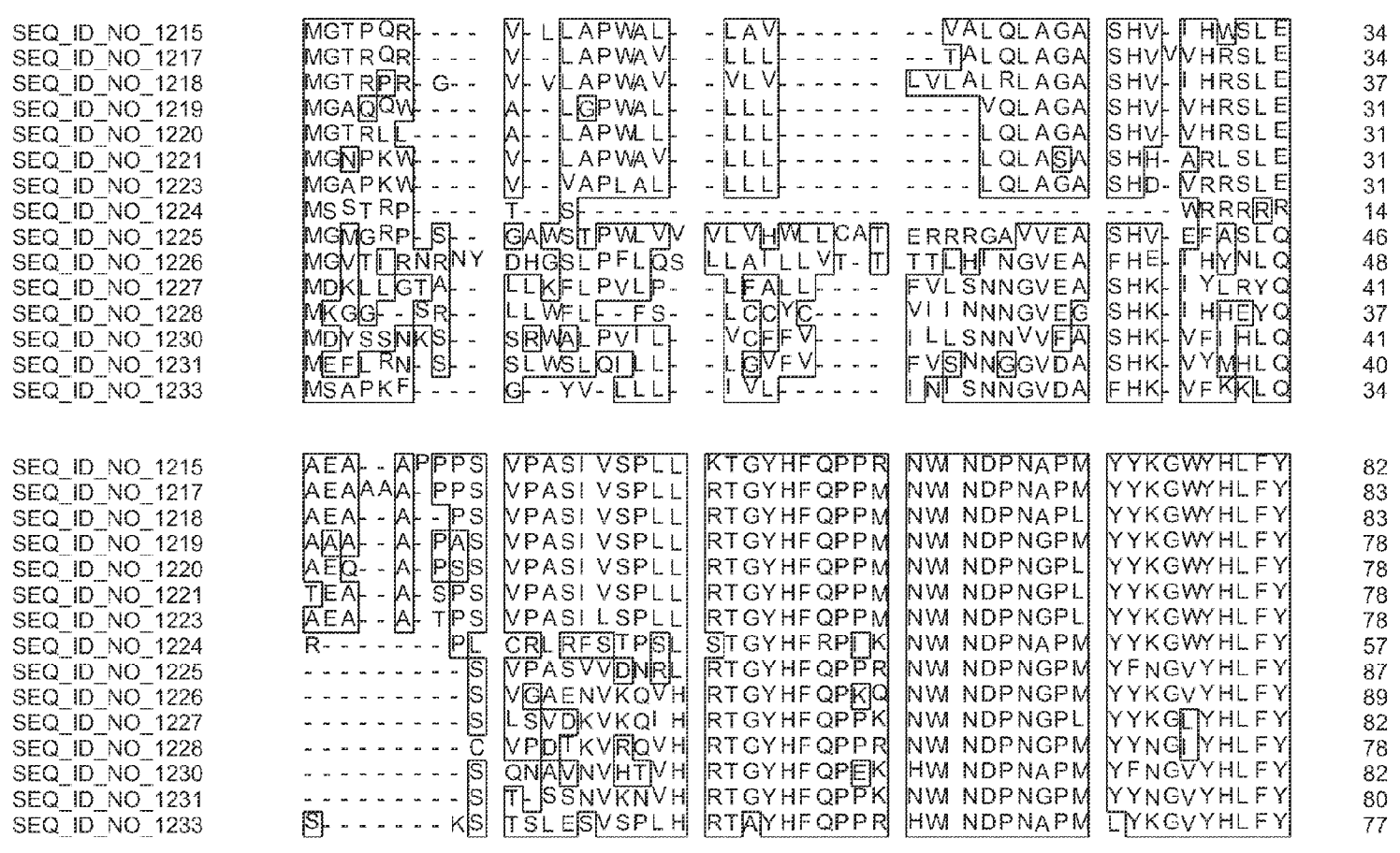
Figure 10D:
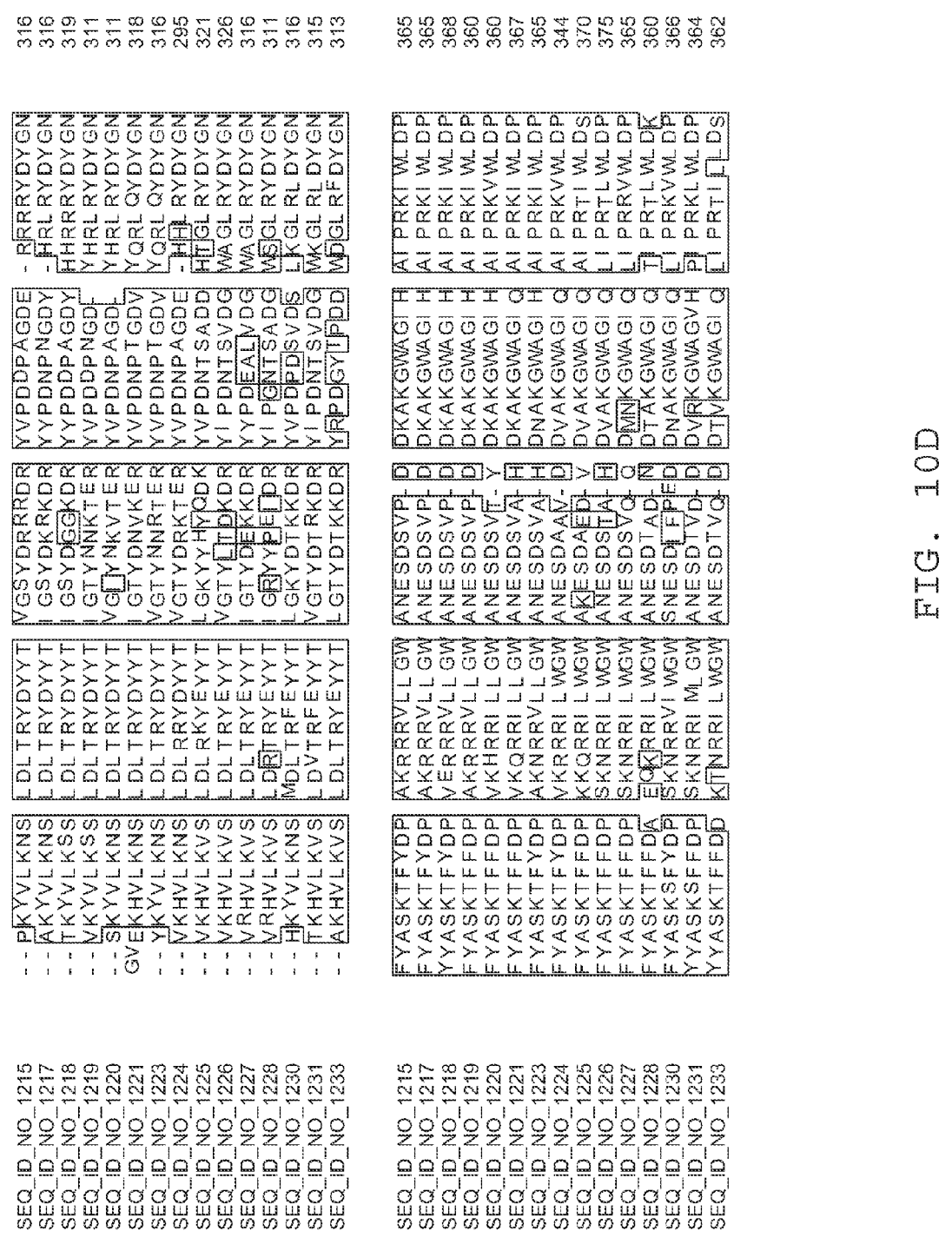

FIGS. 10A-10G are an alignment of the amino acid sequence of CeresClone:1769374 (SEQ ID NO:1215) with homologous and/or orthologous amino acid sequences.

Figure 11B:
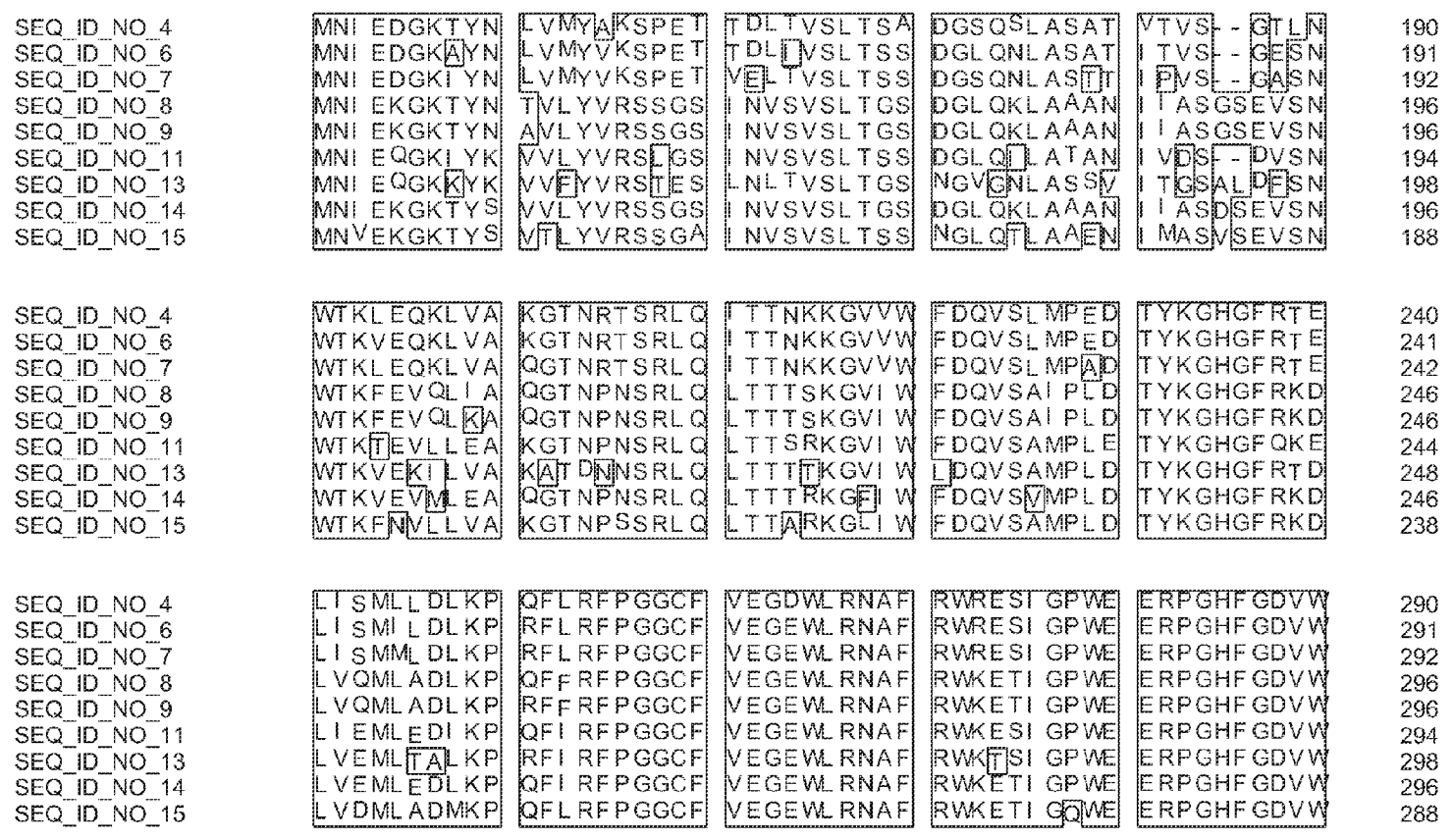
Figure 11E:
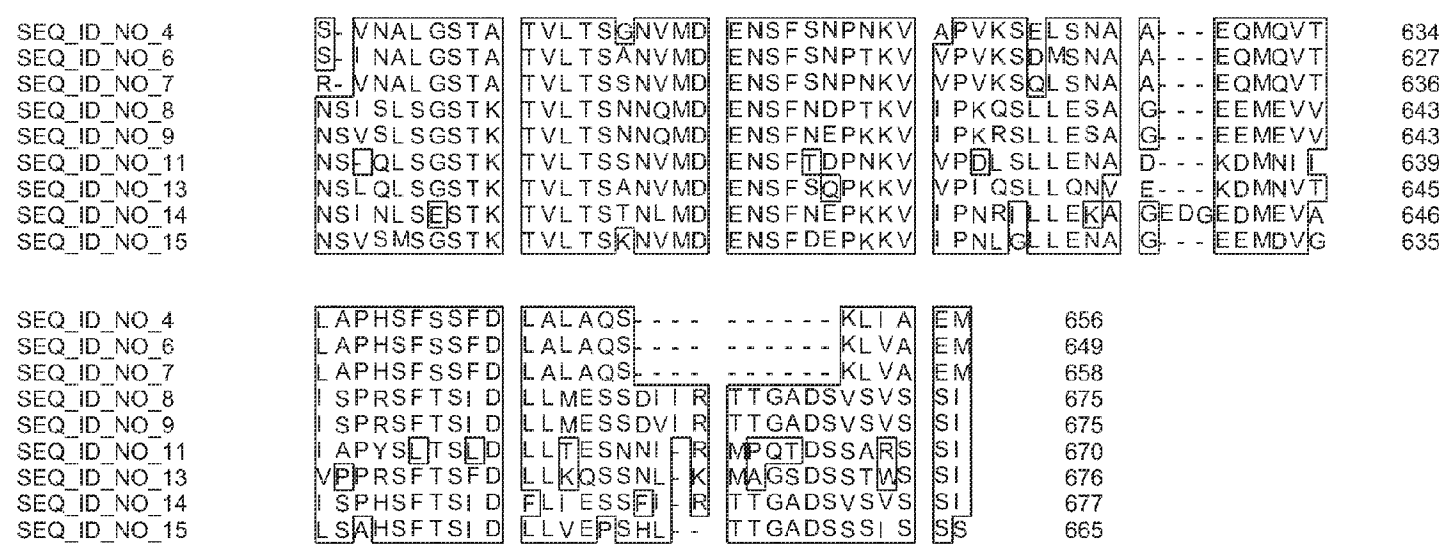

FIGS. 11A-11E are an alignment of the amino acid sequence of CeresClone:1753603 (SEQ ID NO: 4) with homologous and/or orthologous amino acid sequences.

FIGS. 12A-12B are an alignment of the amino acid sequence of CeresClone:1724480 (SEQ ID NO: 580) with homologous and/or orthologous amino acid sequences.

FIGS. 13A-13B are an alignment of the amino acid sequence of CeresAnnot:1514289 (SEQ ID NO: 53) with homologous and/or orthologous amino acid sequences.

FIGS. 14A-14B are an alignment of the amino acid sequence of CeresClone:466497 (SEQ ID NO: 1112) with homologous and/or orthologous amino acid sequences.

FIG. 15 is an alignment of the amino acid sequence of CeresClone:1841236_CW00741 (SEQ ID NO: 634) with homologous and/or orthologous amino acid sequences.

FIGS. 16A-16C are an alignment of the amino acid sequence of CeresClone:1790897_CW00776 (SEQ ID NO: 368) with homologous and/or orthologous amino acid sequences.

Figure 17A:
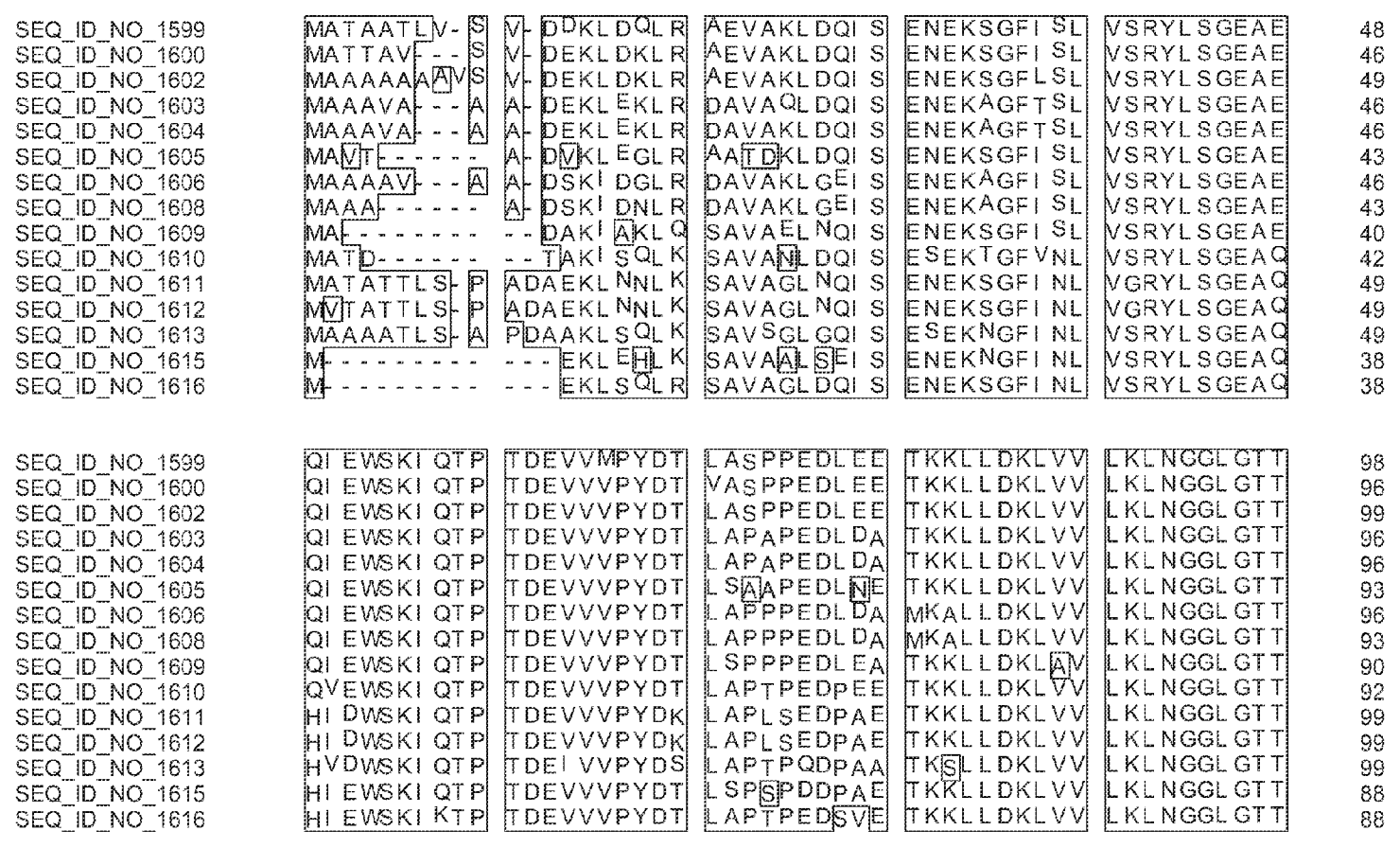
Figure 17C:
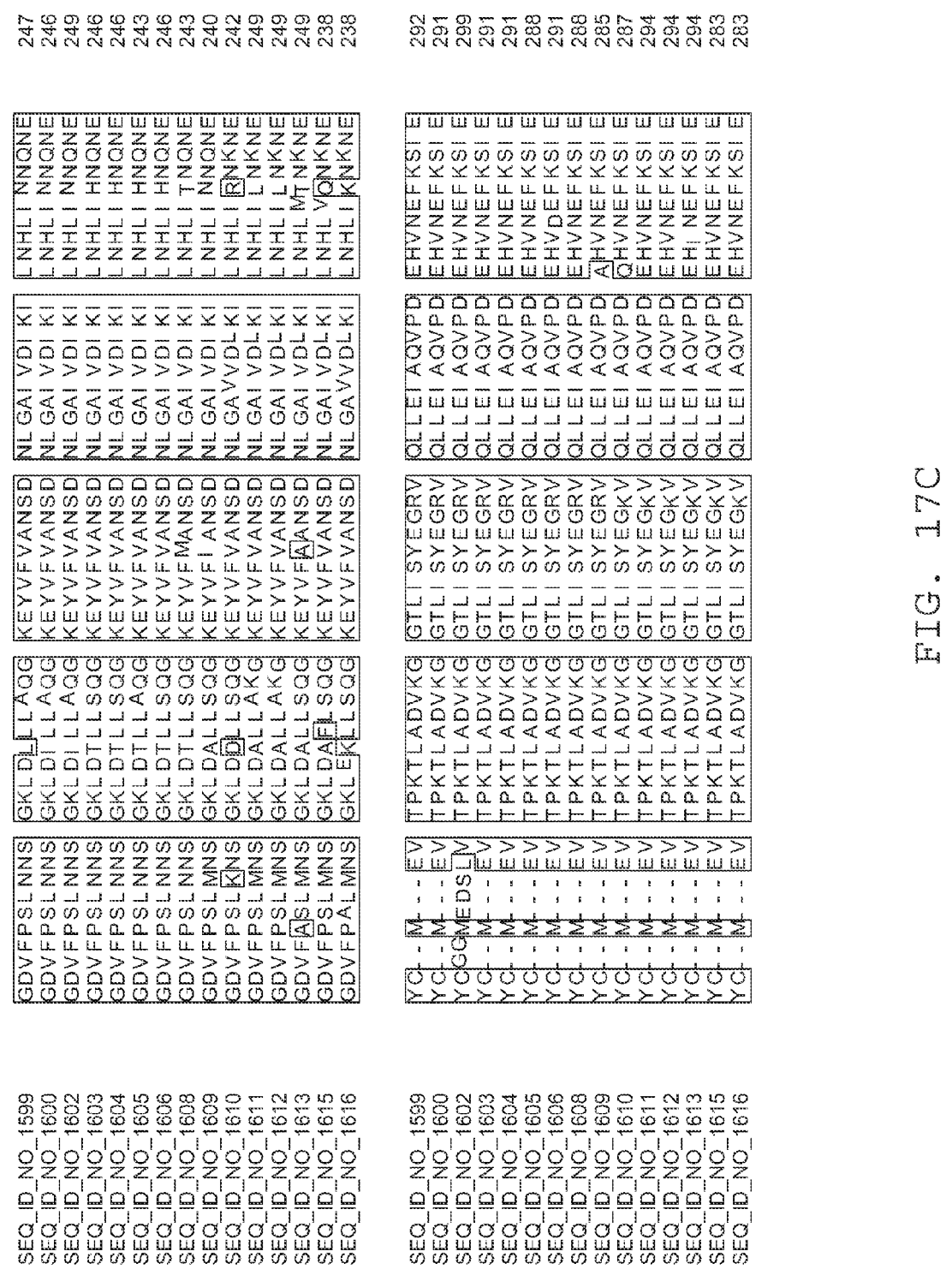
Figure 17D:
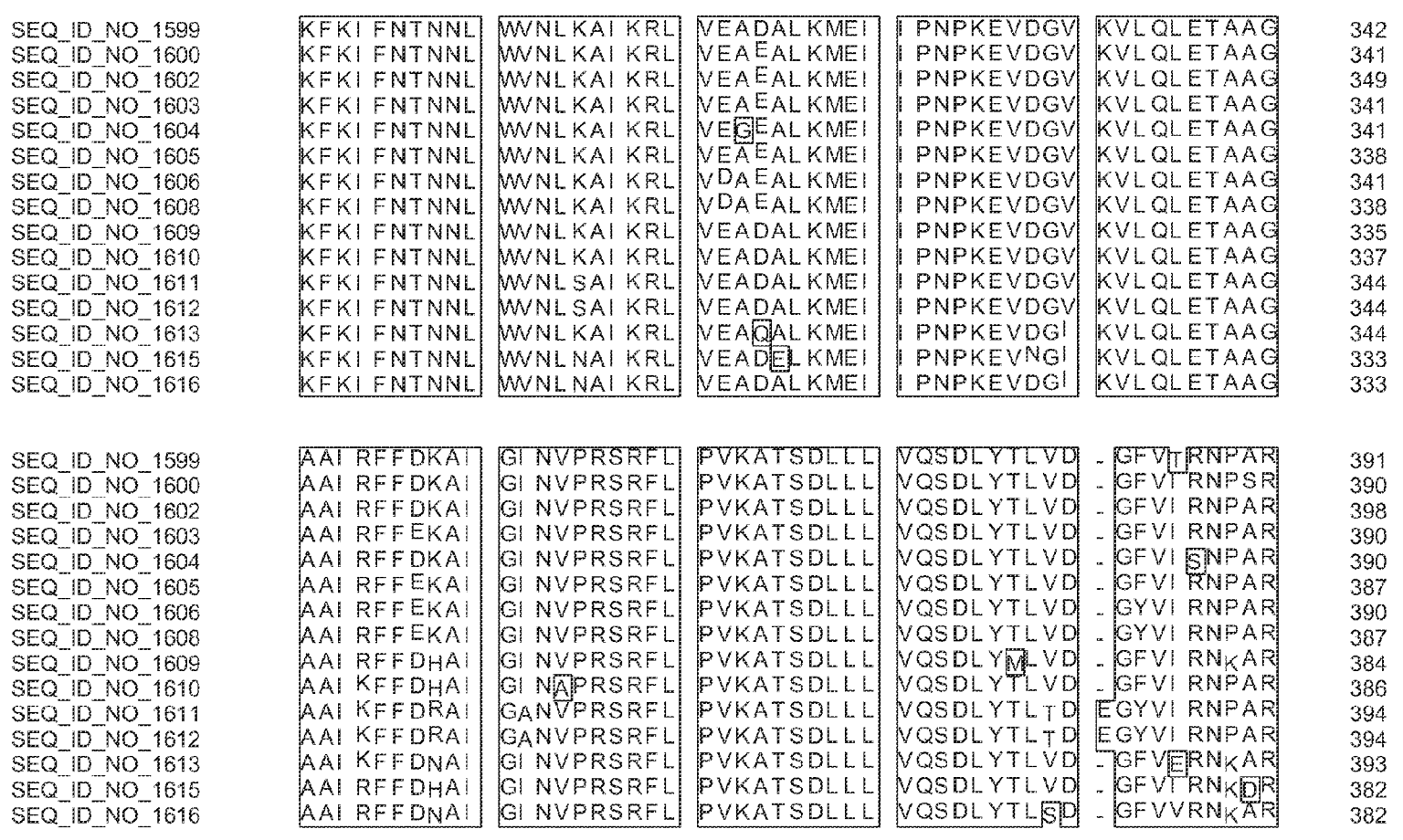
Figure 17E:
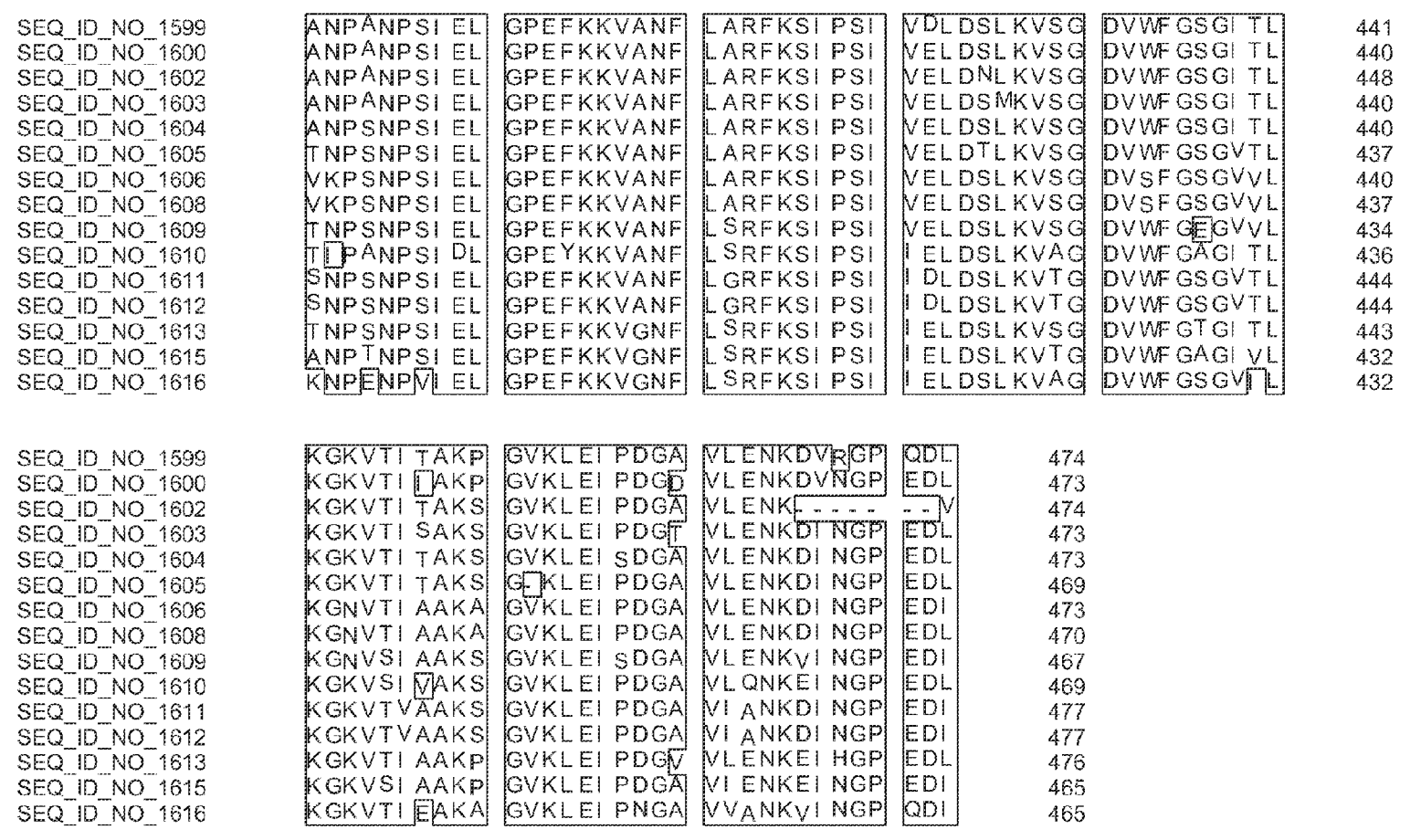

FIGS. 17A-17E are an alignment of the amino acid sequence of CeresClone:1780416_CW00778 (SEQ ID NO: 1599) with homologous and/or orthologous amino acid sequences.

FIG. 18 is an alignment of the amino acid sequence of CeresClone:1773290_CW00761 (SEQ ID NO: 154) with homologous and/or orthologous amino acid sequences.

FIG. 19 is an alignment of the amino acid sequence of CeresClone:1744499_CW00813 (SEQ ID NO: 1035) with homologous and/or orthologous amino acid sequences.

FIG. 20 is an alignment of the amino acid sequence of CeresClone:896483_CW00787 (SEQ ID NO: 741) with homologous and/or orthologous amino acid sequences.

FIGS. 21A-21B are an alignment of the amino acid sequence of CeresClone:225681_CW00792 (SEQ ID NO:187) with homologous and/or orthologous amino acid sequences.

Figure 22D:
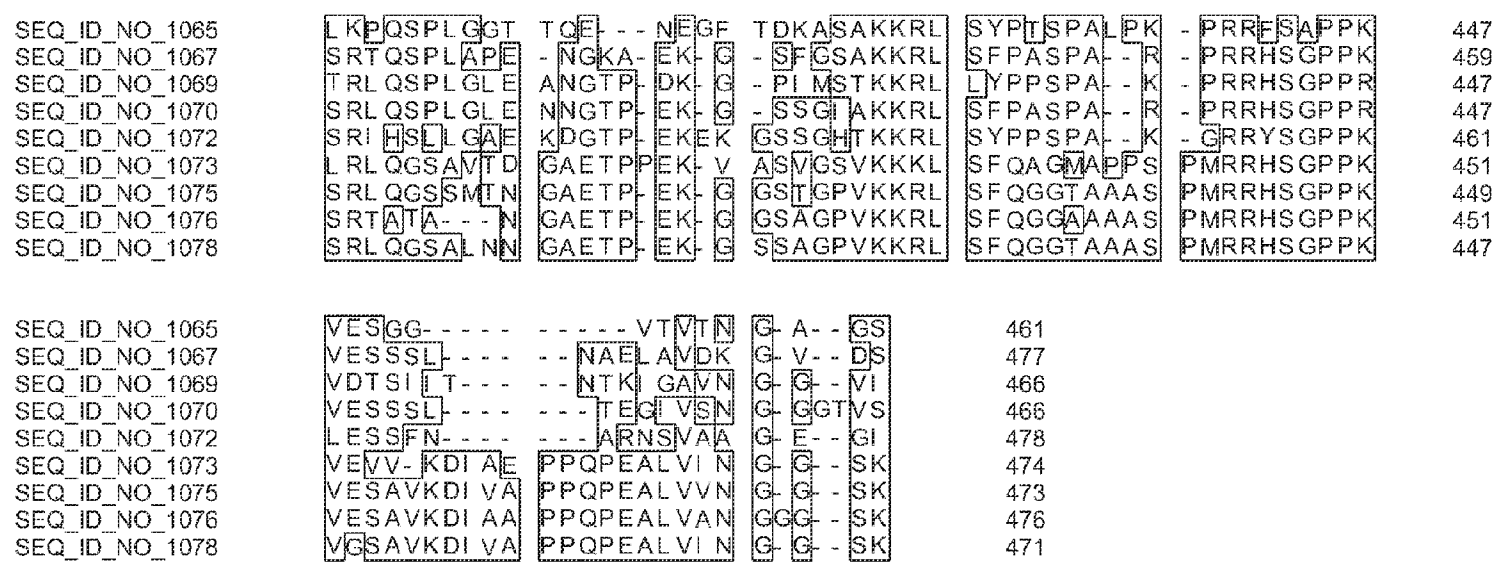

FIGS. 22A-22D are an alignment of the amino acid sequence of CeresClone:106263_CW00780 (SEQ ID NO: 1065) with homologous and/or orthologous amino acid sequences.

FIGS. 23A-23B are an alignment of the amino acid sequence of CeresAnnot:1310682 (SEQ ID NO: 1592) with homologous and/or orthologous amino acid sequences.

FIGS. 24A-24C are an alignment of the amino acid sequence of CeresAnnot:838049_CW00759 (SEQ ID NO: 851) with homologous and/or orthologous amino acid sequences.

FIGS. 25A-25B are an alignment of the amino acid sequence of CeresAnnot:553111_CW00758 (SEQ ID NO: 1016) with homologous and/or orthologous amino acid sequences.

FIG. 26 is an alignment of the amino acid sequence of CeresClone:1238706 (SEQ ID NO: 2186) with homologous and/or orthologous amino acid sequences.

Figure 27A:
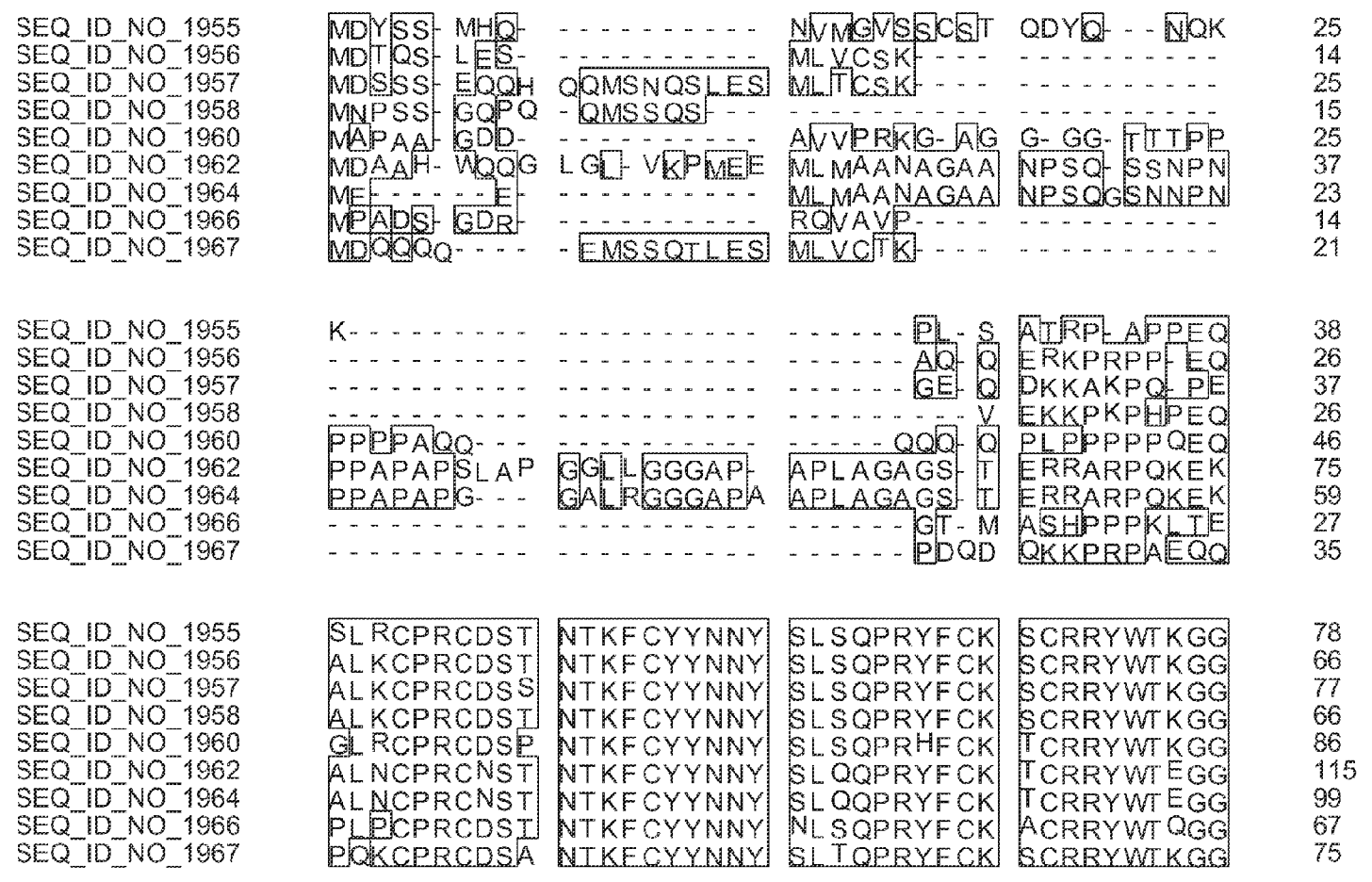
Figure 27B:
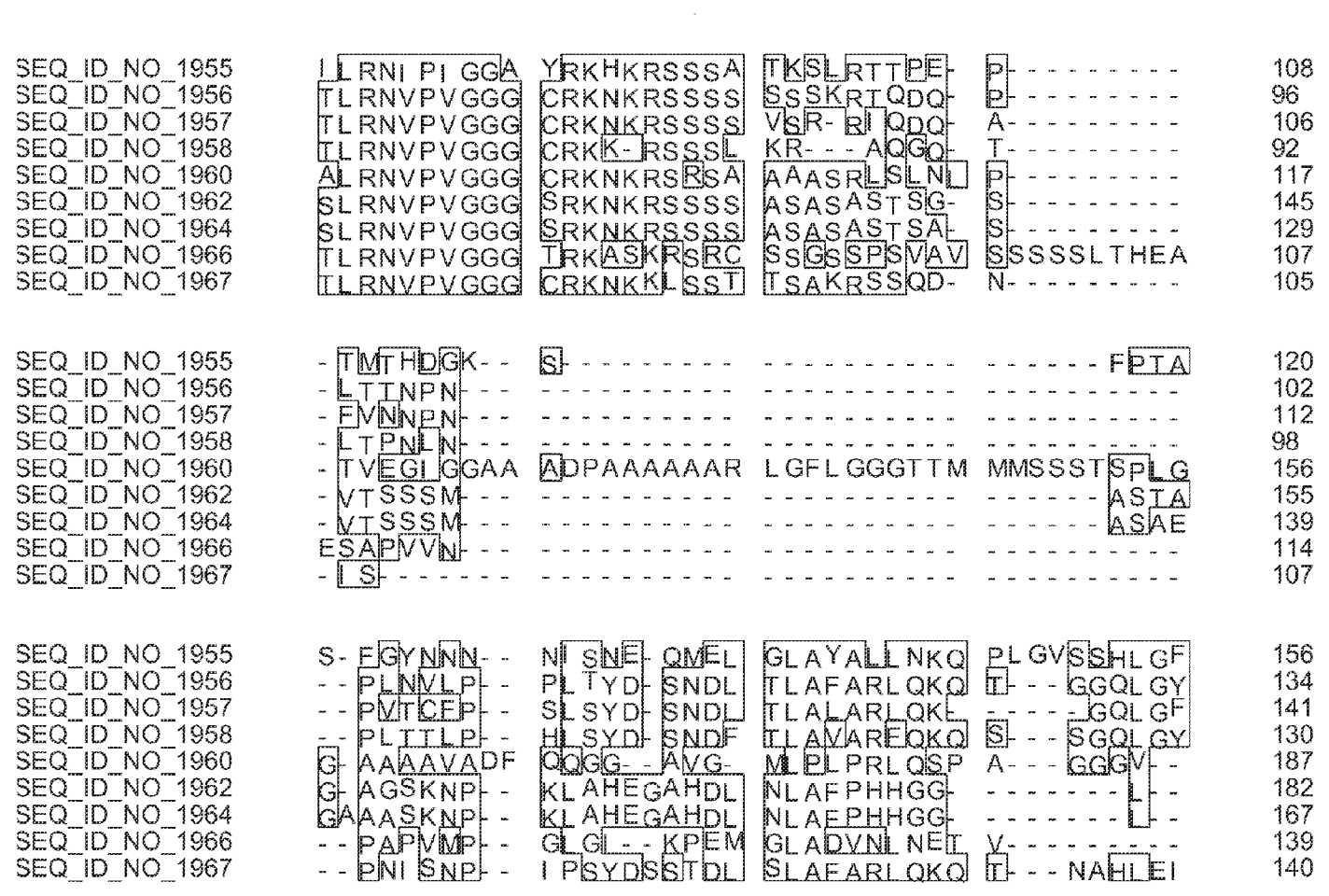
Figure 27C:
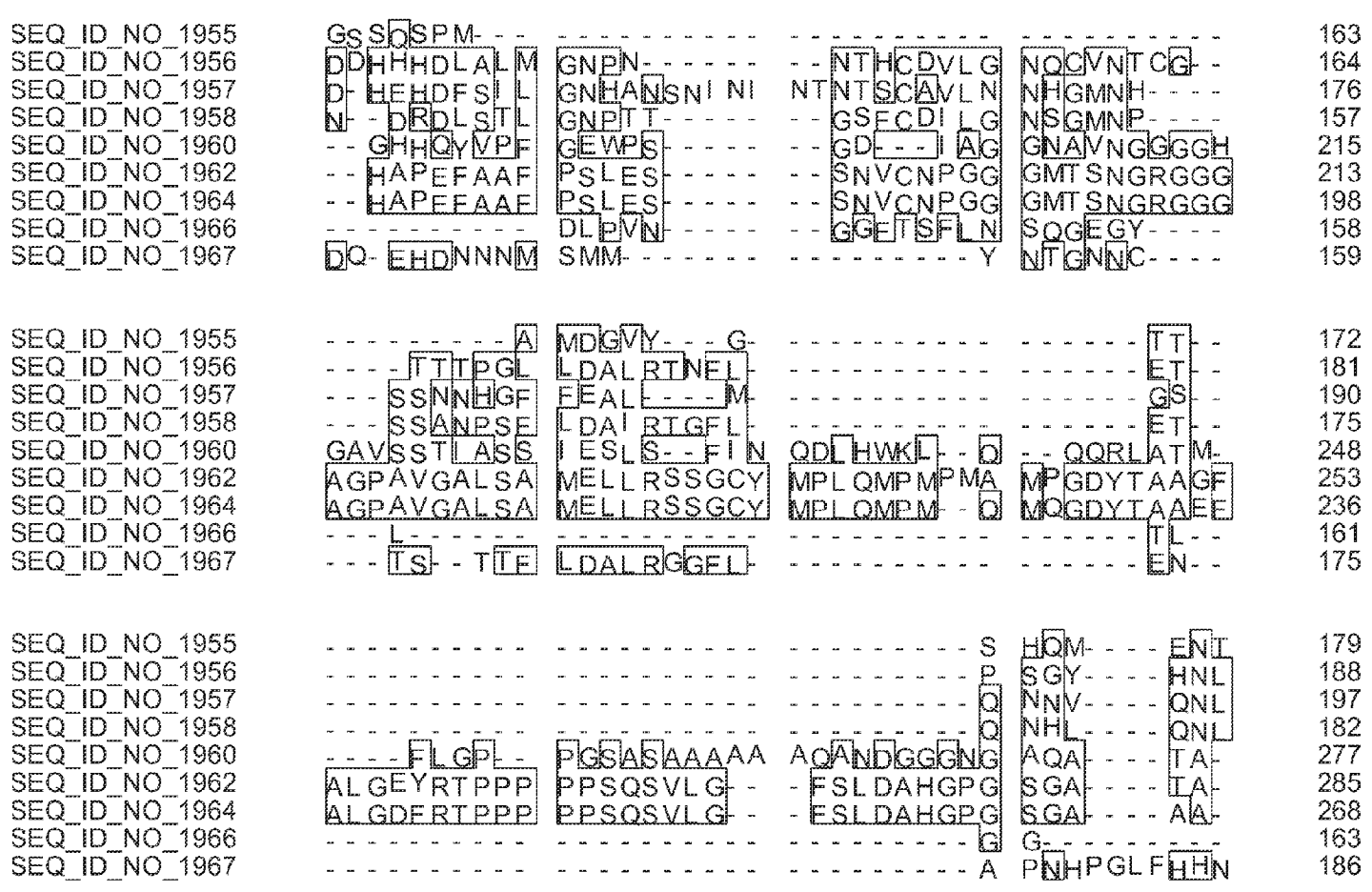
Figure 27D:
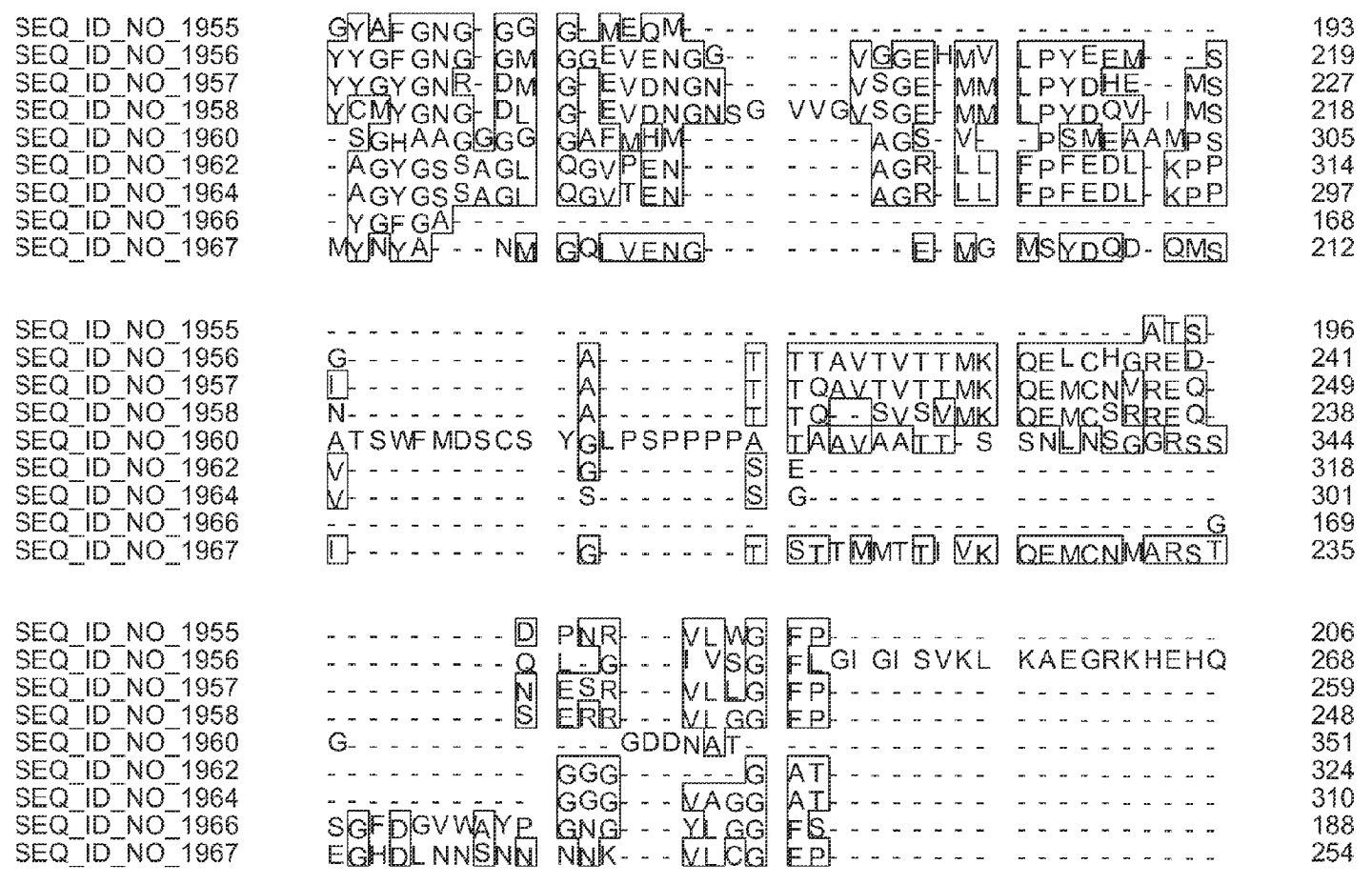
Figure 27E:
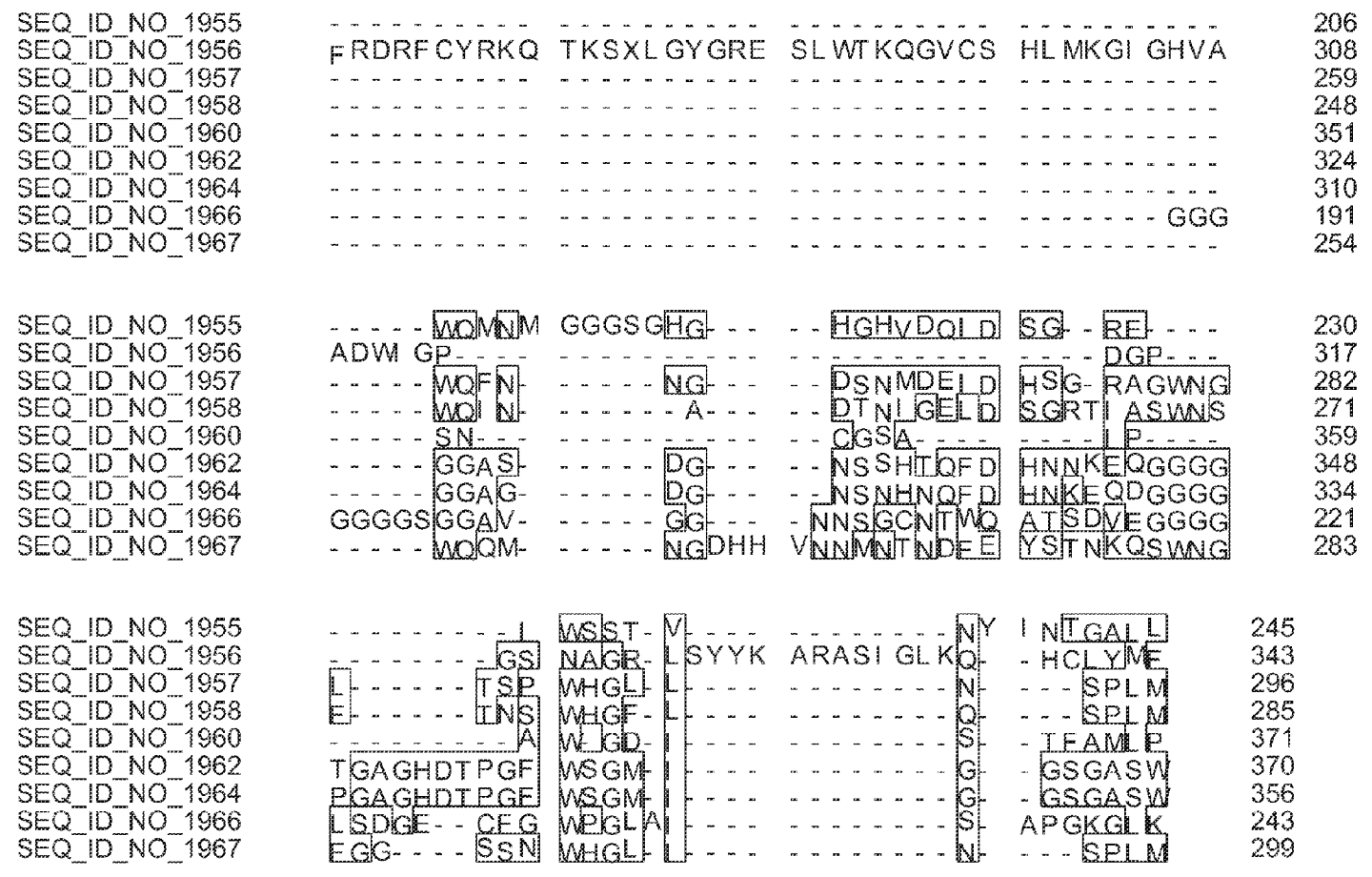

FIGS. 27A-27E are an alignment of the amino acid sequence of CeresAnnot:529860 (SEQ ID NO: 1955) with homologous and/or orthologous amino acid sequences.

FIG. 28 is an alignment of the amino acid sequence of CeresAnnot:851842 (SEQ ID NO: 2566) with homologous and/or orthologous amino acid sequences.

Figure 29A:
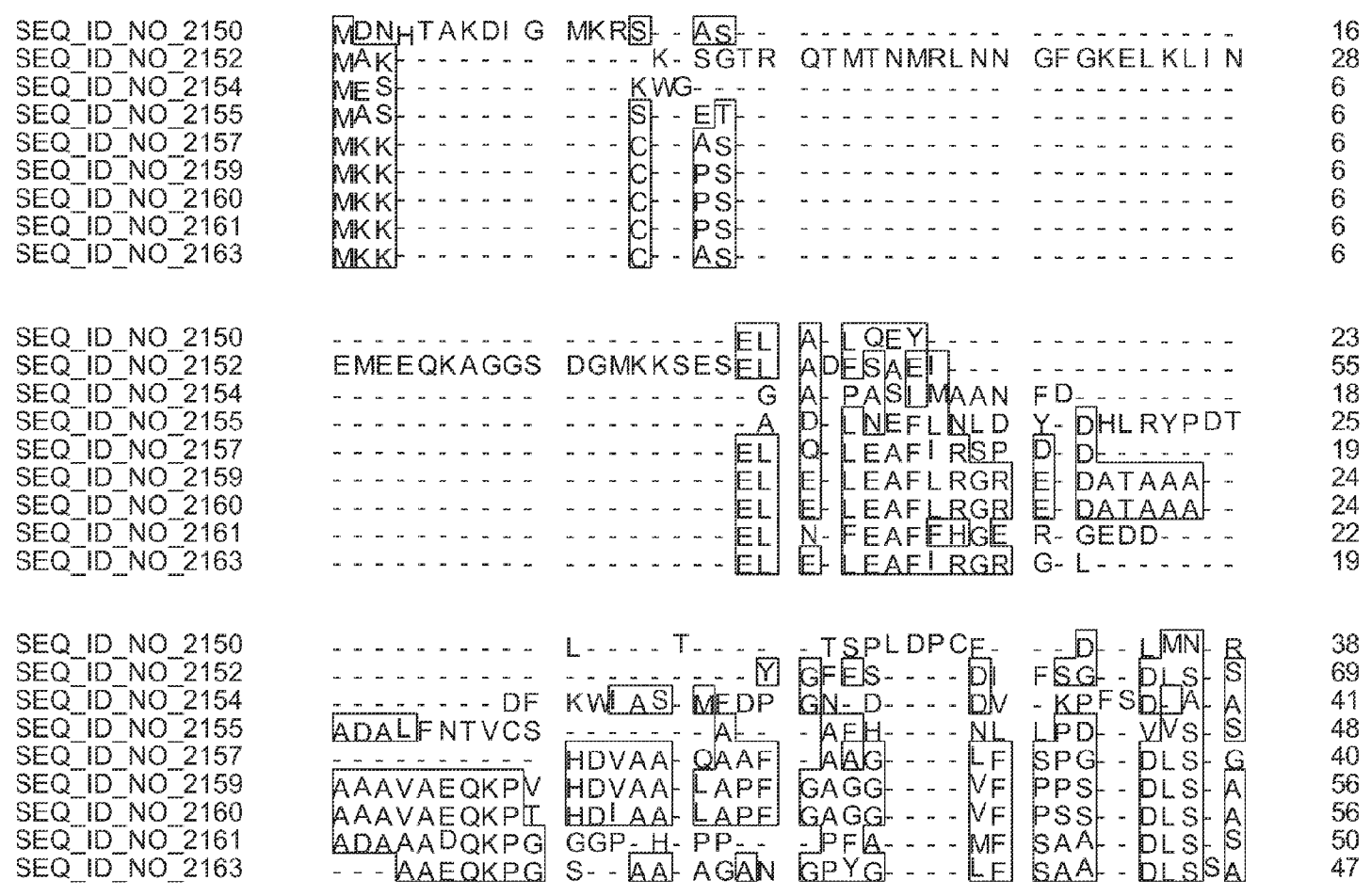
Figure 29C:
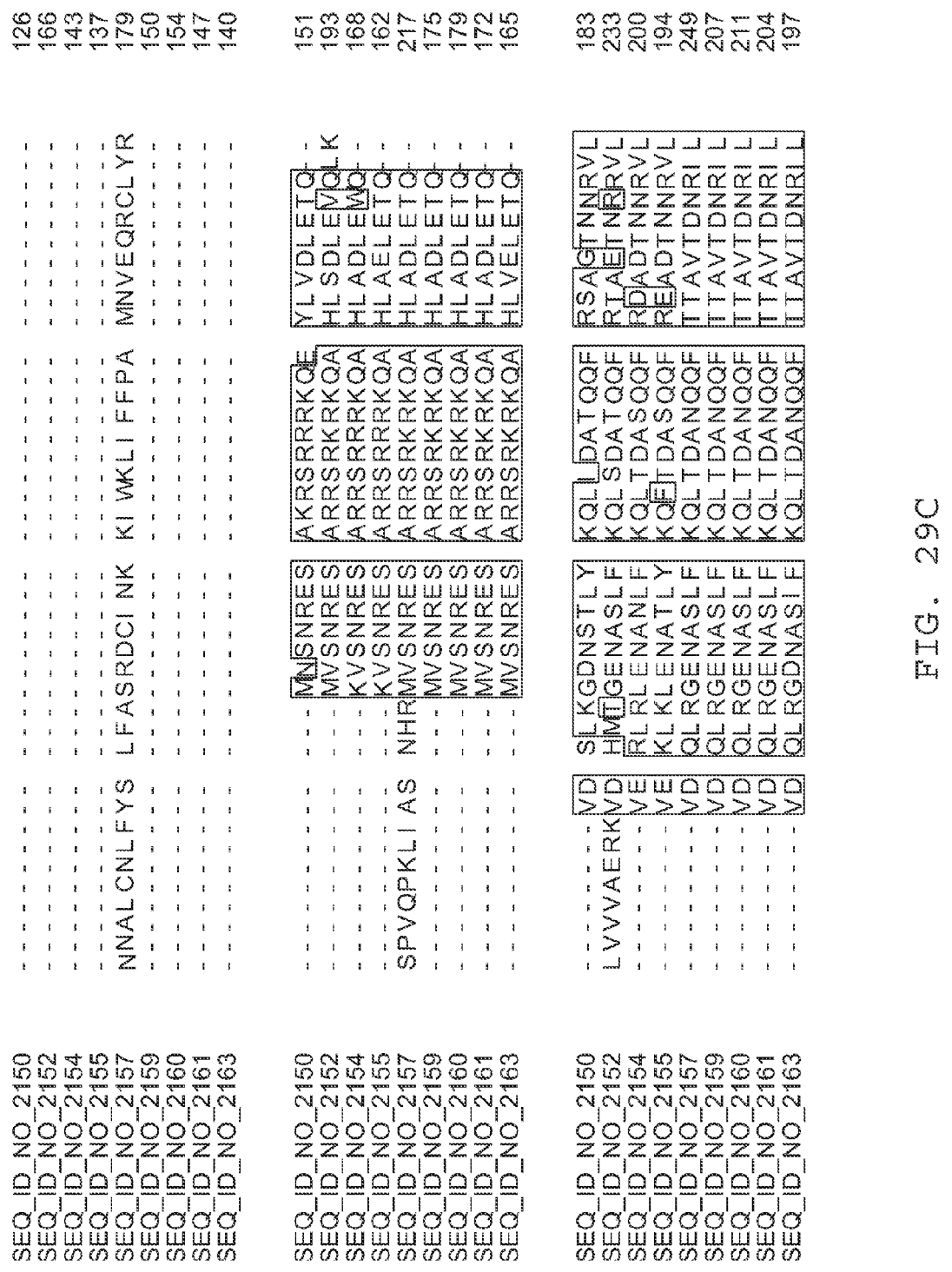
Figure 29D:
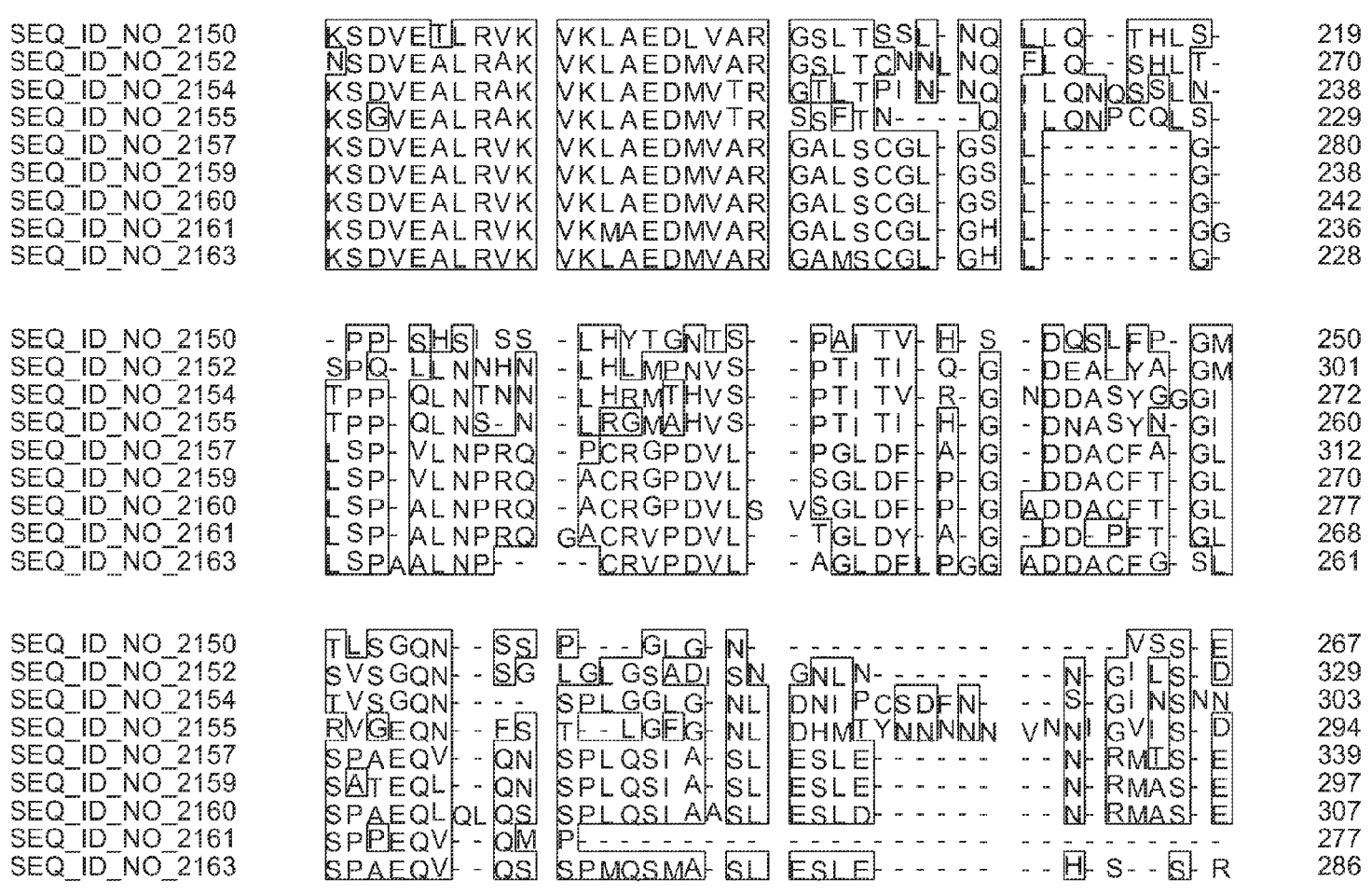

FIGS. 29A-29E are an alignment of the amino acid sequence of CeresAnnot:853198 (SEQ ID NO: 2150) with homologous and/or orthologous amino acid sequences.

Figure 30D:
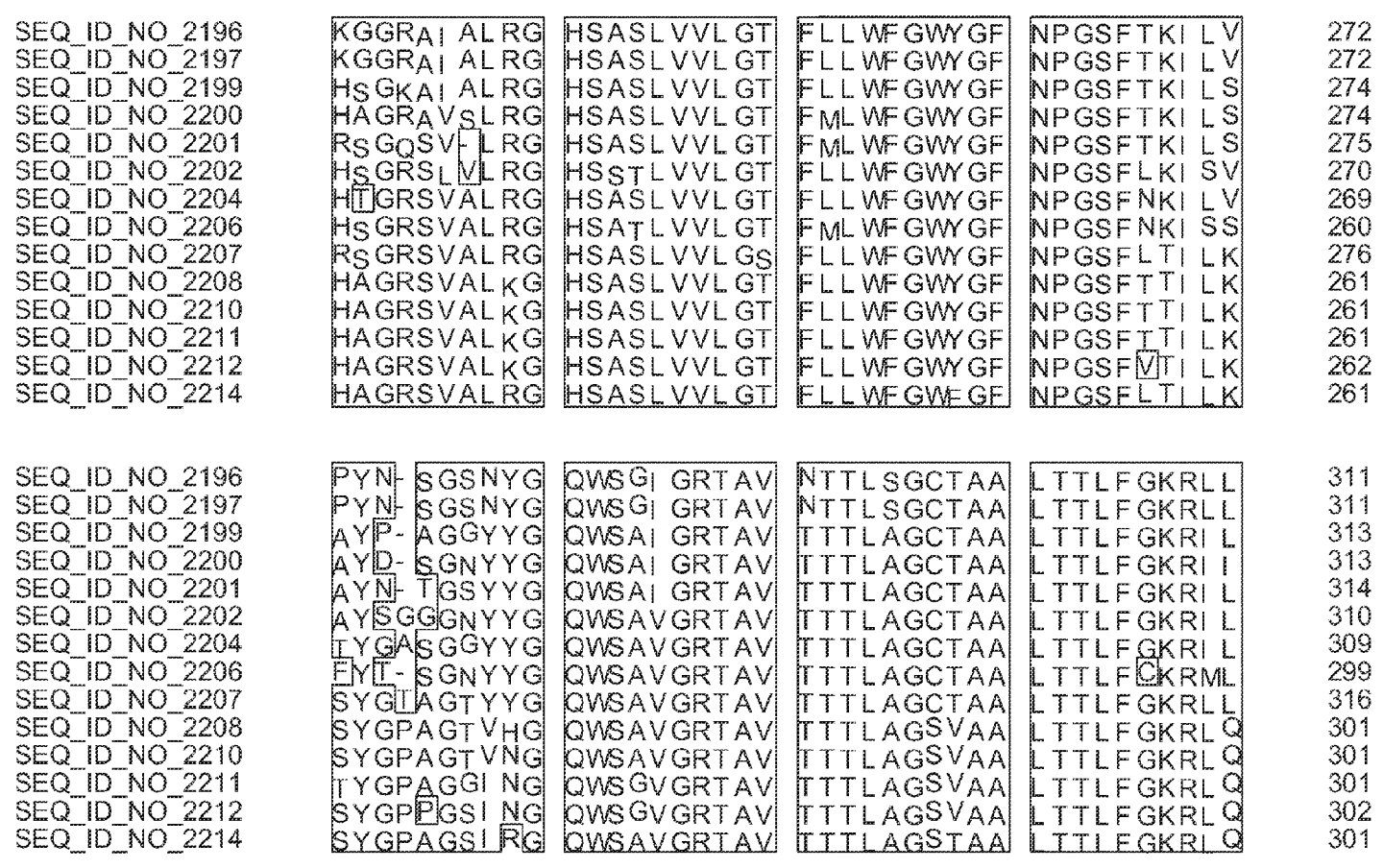
Figure 30E:
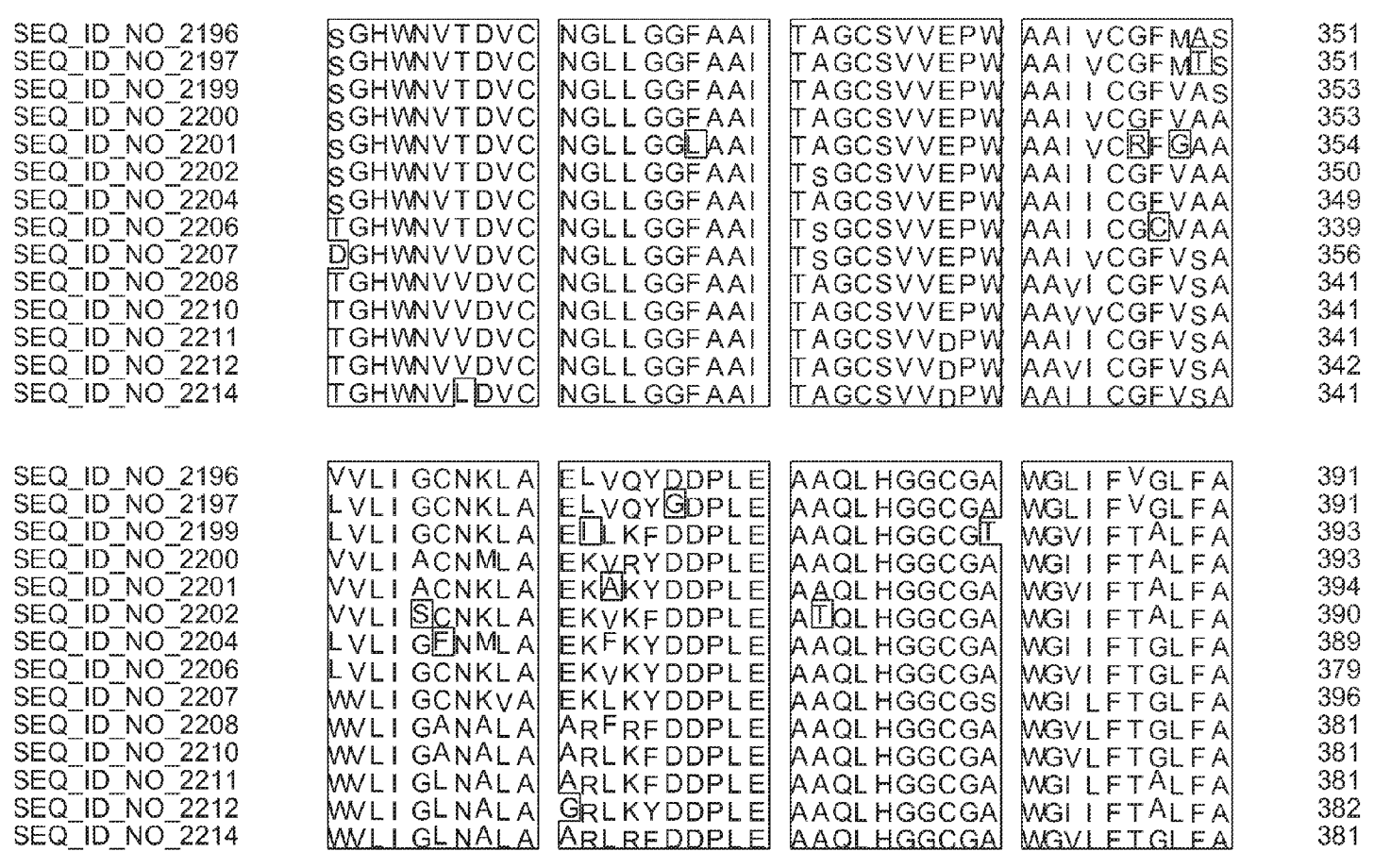
Figure 30F:
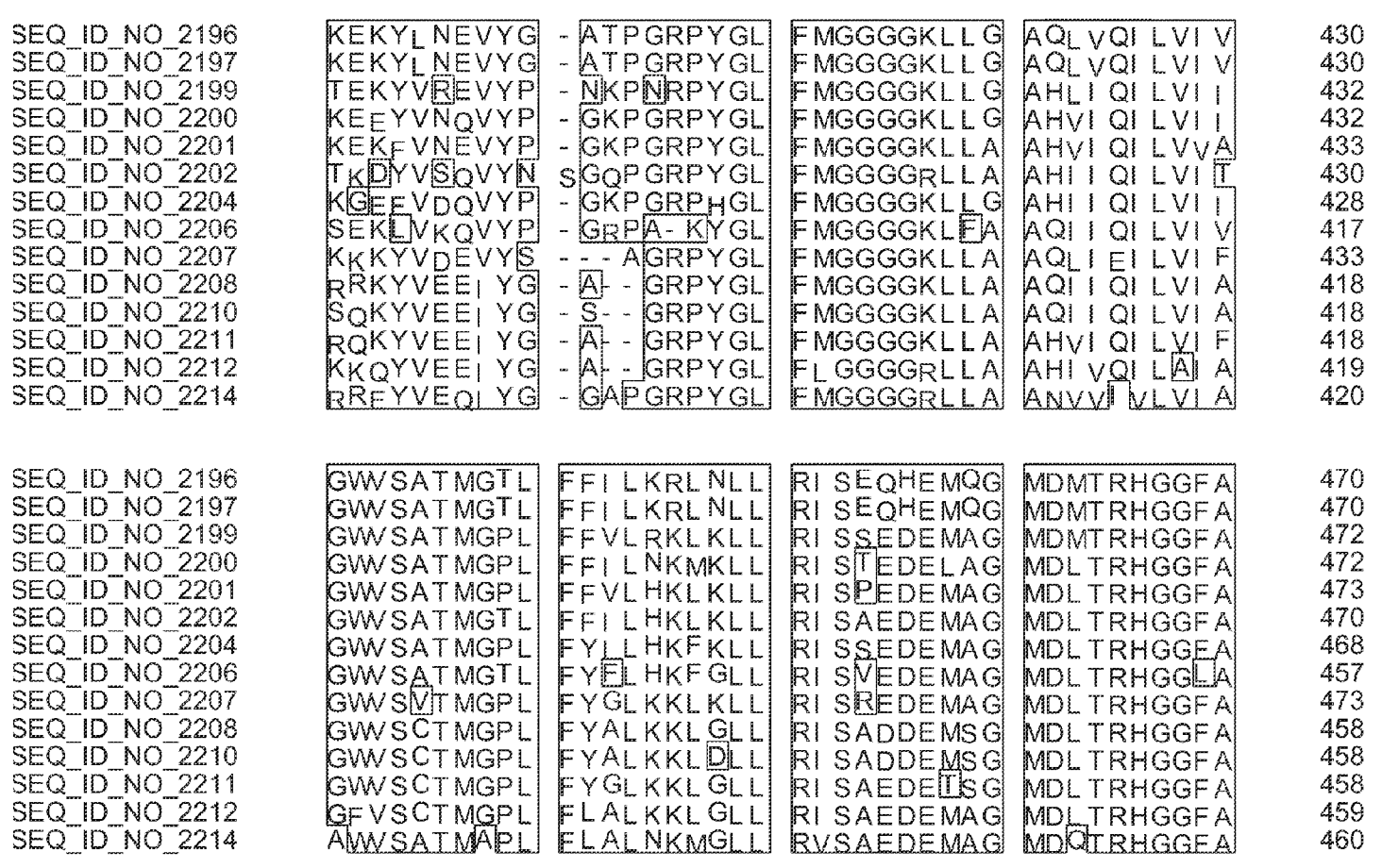
Figure 30G:
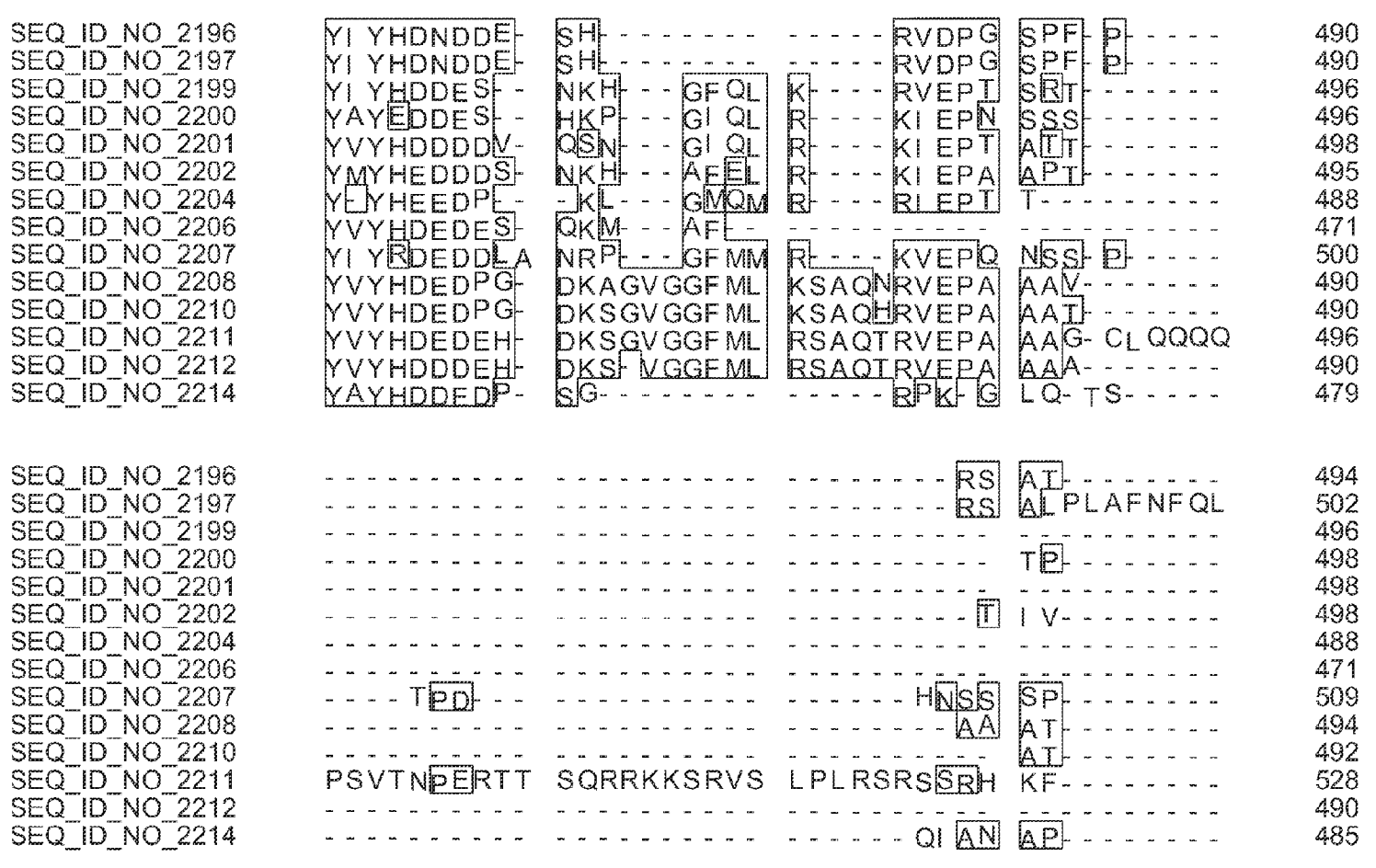
Figure 30H:
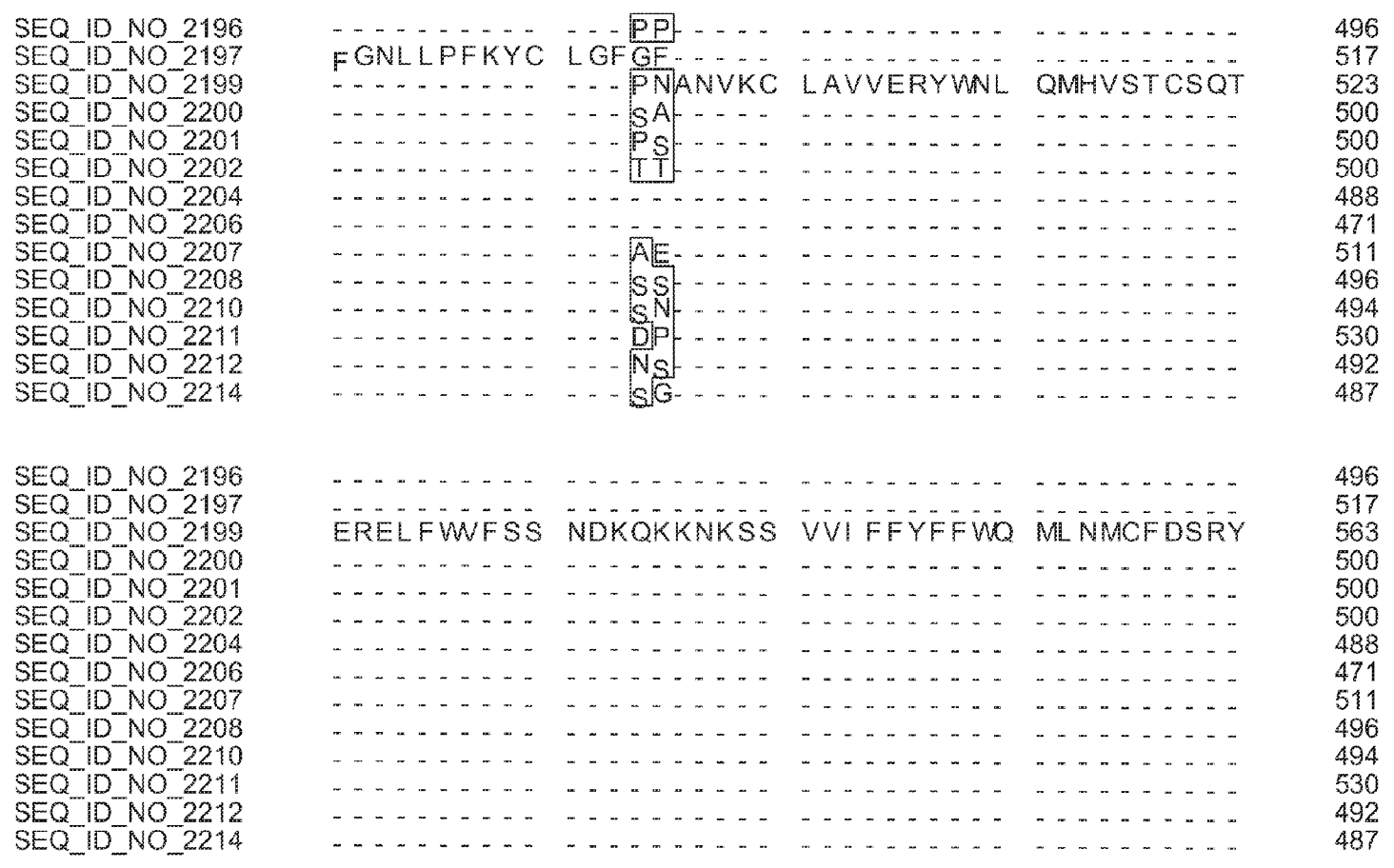
Figure 30L:
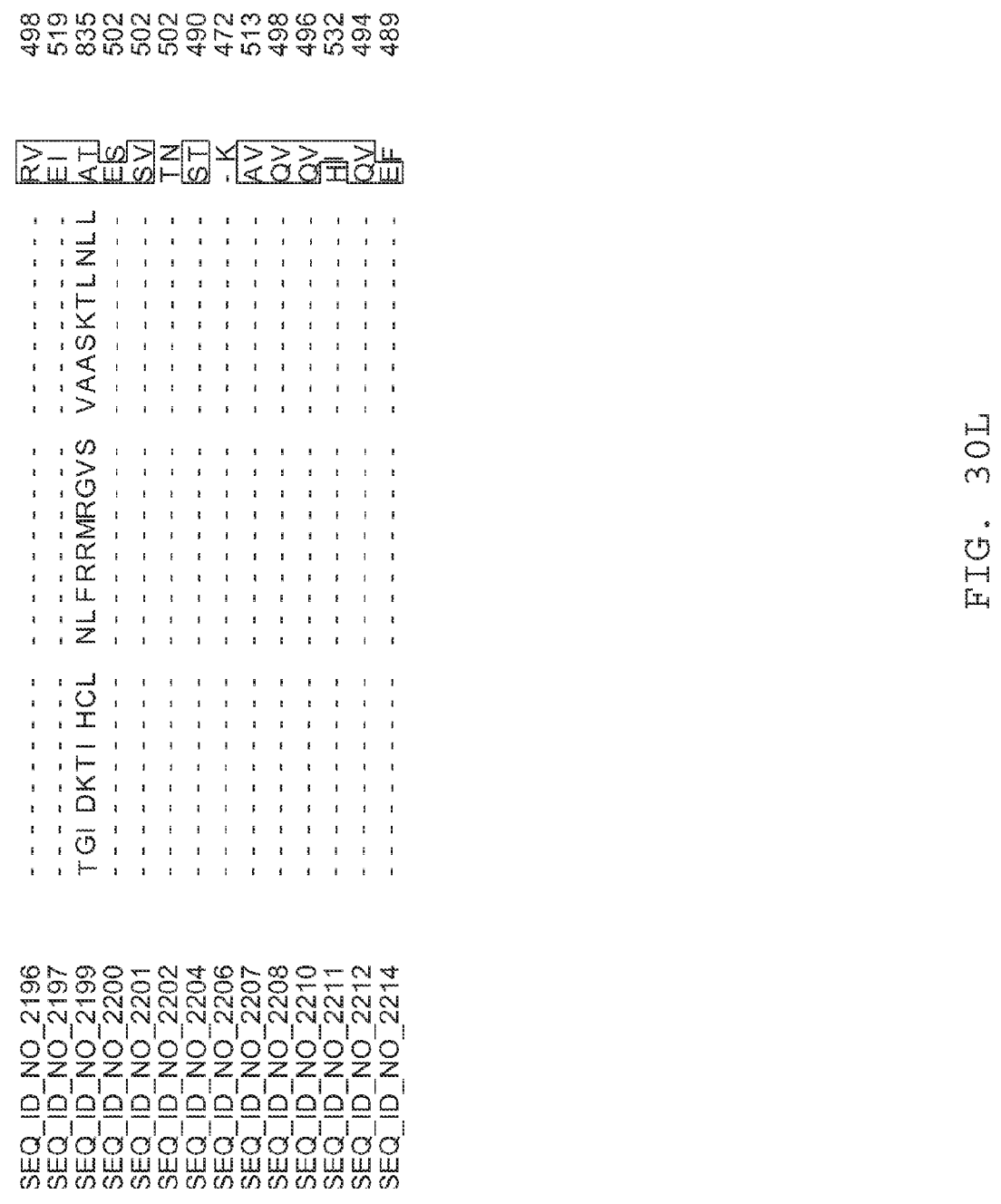

FIGS. 30A-30L are an alignment of the amino acid sequence of CeresAnnot:873343 (SEQ ID NO: 2196) with homologous and/or orthologous amino acid sequences.

FIGS. 31A-31K are an alignment of the amino acid sequence of CeresAnnot:878887 (SEQ ID NO: 2493) with homologous and/or orthologous amino acid sequences.

FIGS. 32A-32C are an alignment of the amino acid sequence of CeresAnnot:1440417 (SEQ ID NO: 2271) with homologous and/or orthologous amino acid sequences.

Figure 33A:
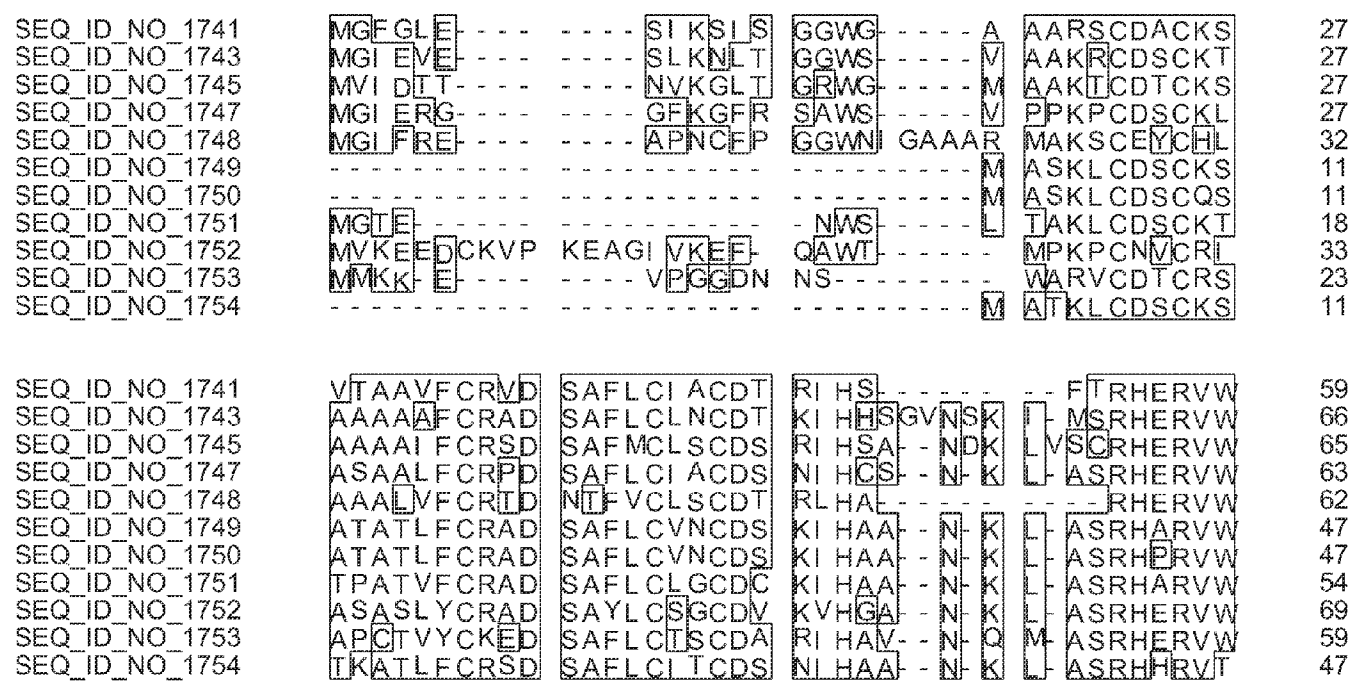
Figure 33B:
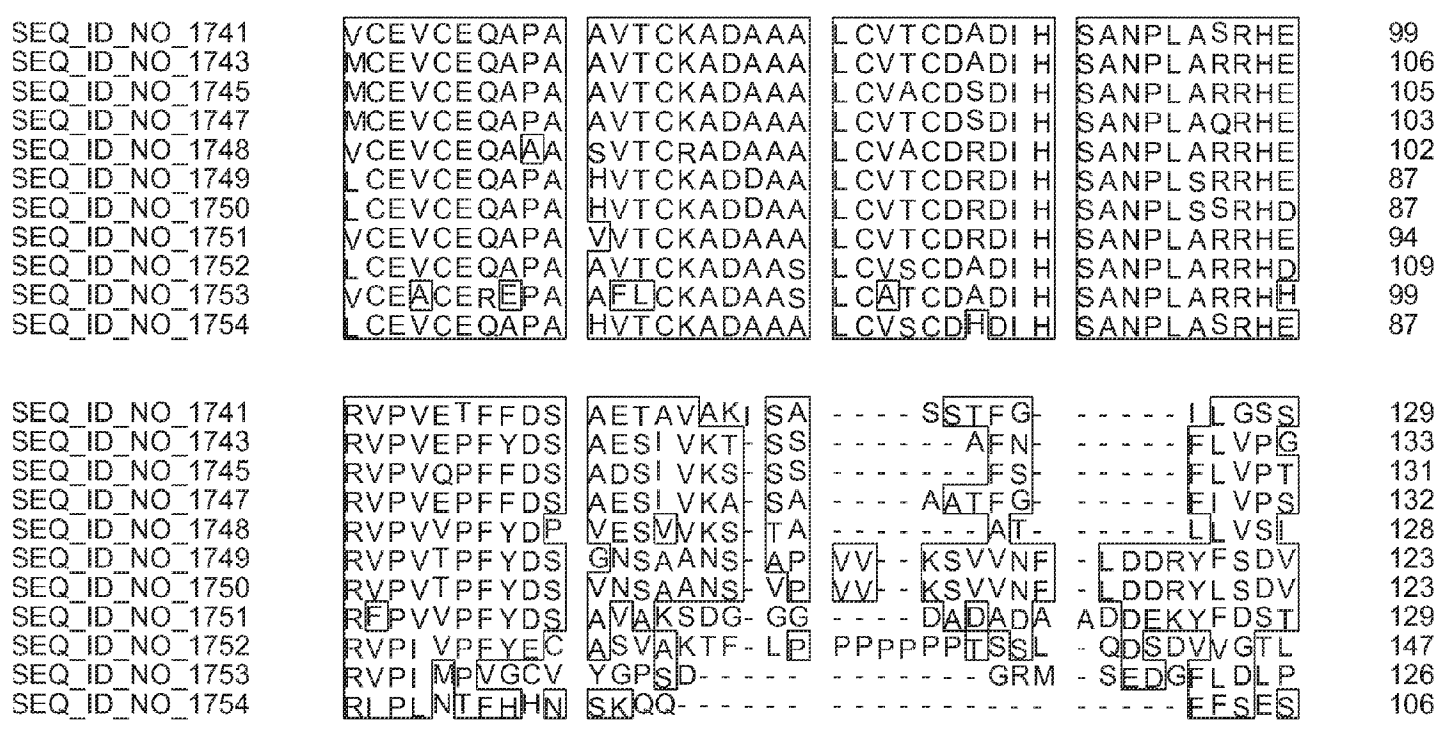
Figure 33C:
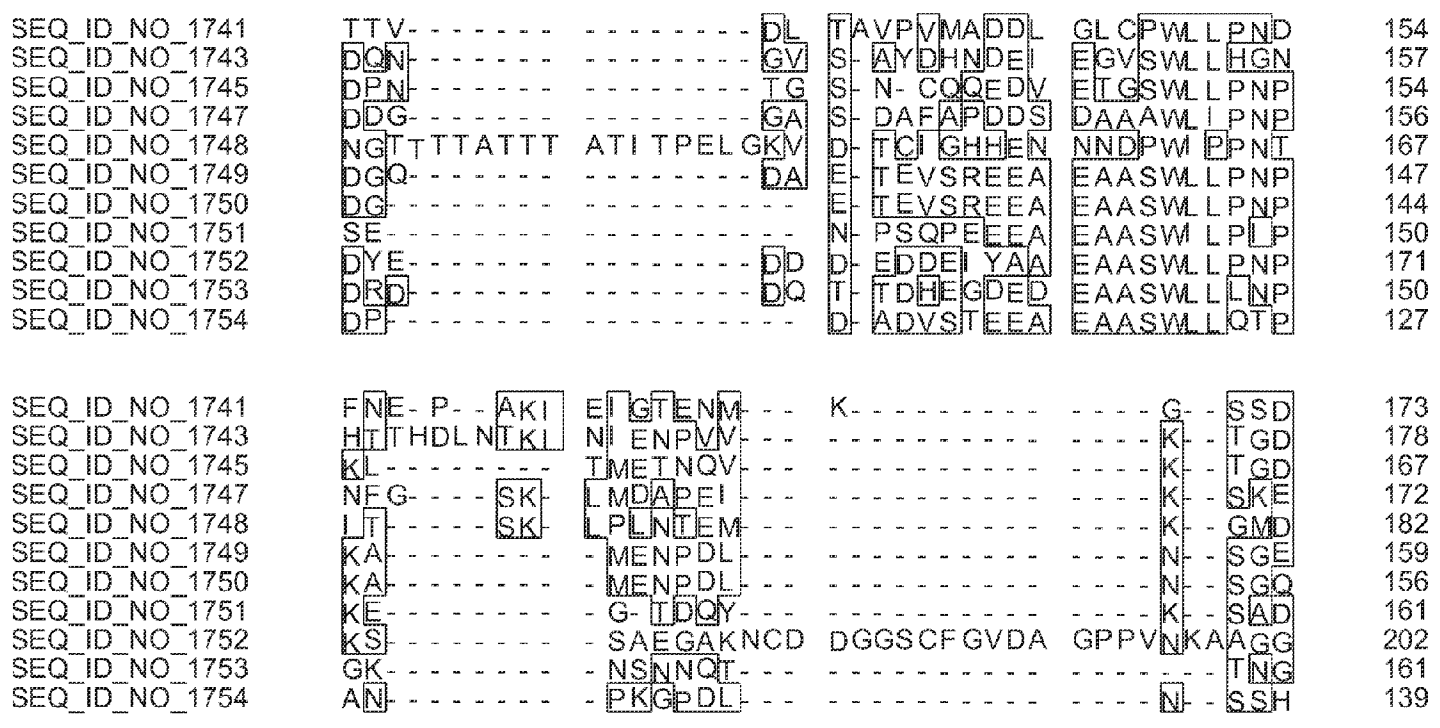
Figure 33D:
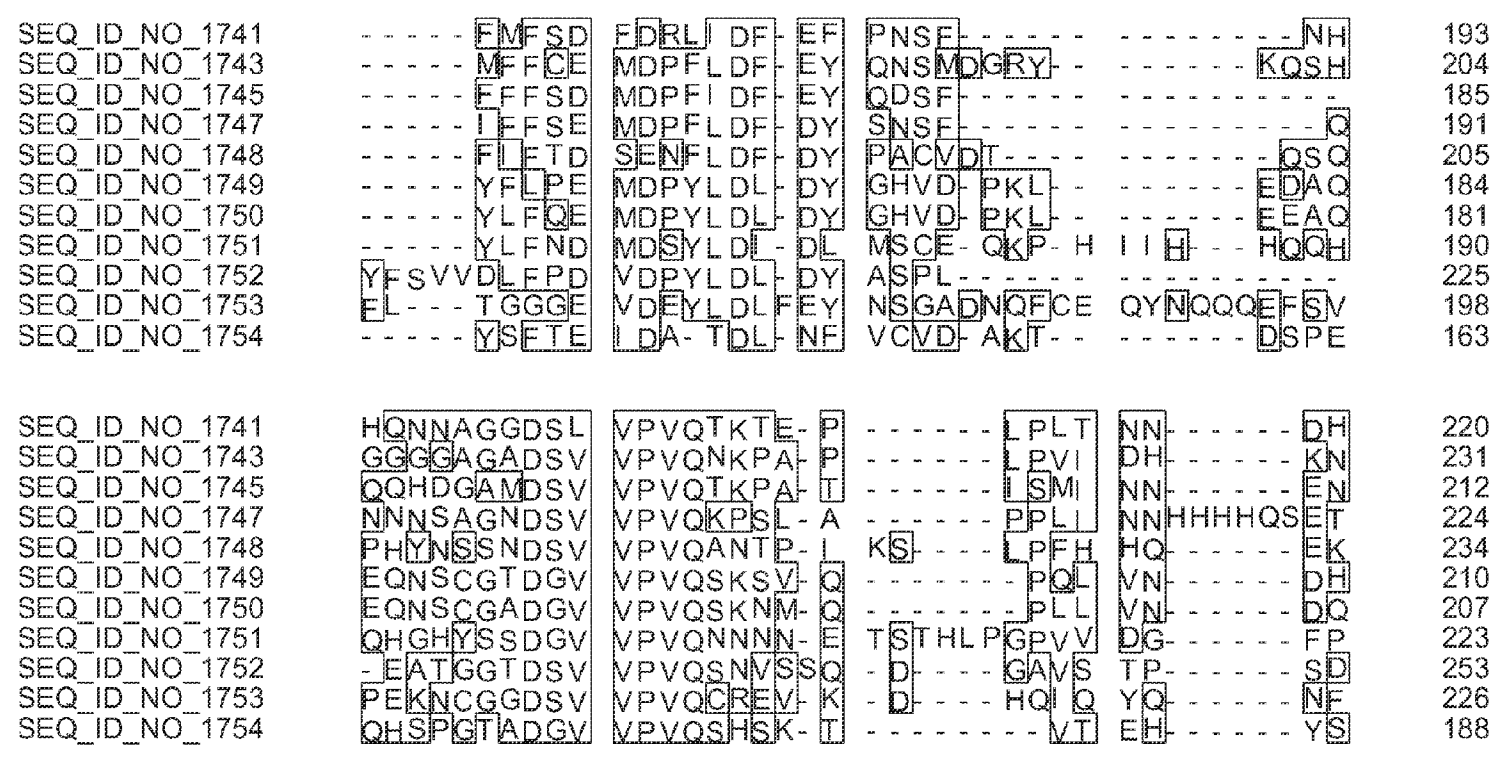
Figure 33F:
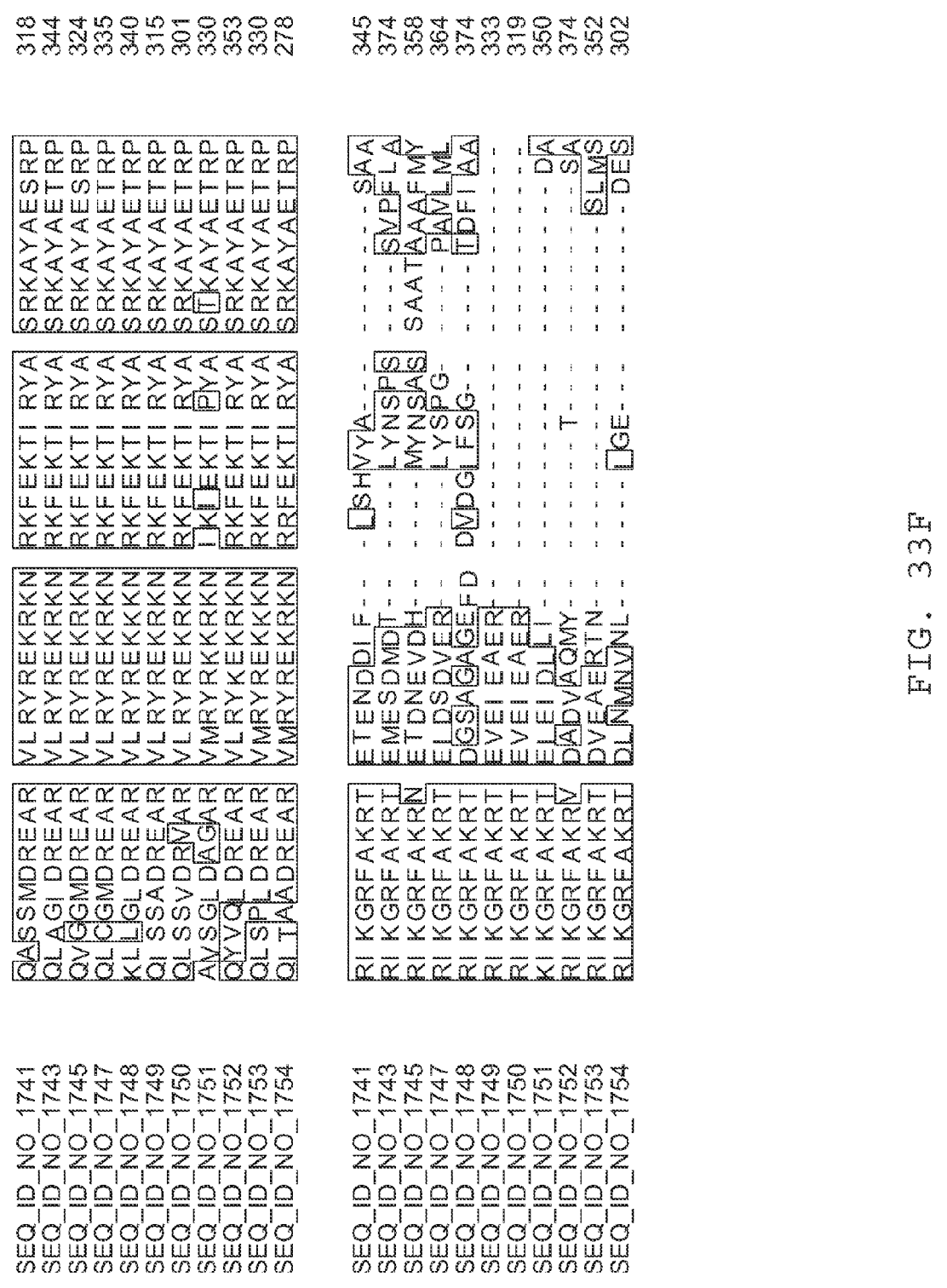

FIGS. 33A-33G are an alignment of the amino acid sequence of CeresClone:6639 (SEQ ID NO: 1741) with homologous and/or orthologous amino acid sequences.

FIG. 34 is an alignment of the amino acid sequence of CeresClone:11830 (SEQ ID NO: 1980) with homologous and/or orthologous amino acid sequences.

FIGS. 35A-35D are an alignment of the amino acid sequence of CeresClone:32753 (SEQ ID NO: 1812) with homologous and/or orthologous amino acid sequences.

FIGS. 36A-36C are an alignment of the amino acid sequence of CeresClone:39378 (SEQ ID NO: 2124) with homologous and/or orthologous amino acid sequences.

FIGS. 37A-37D are an alignment of the amino acid sequence of CeresClone:93867 (SEQ ID NO: 2035) with homologous and/or orthologous amino acid sequences.

Figure 38A:
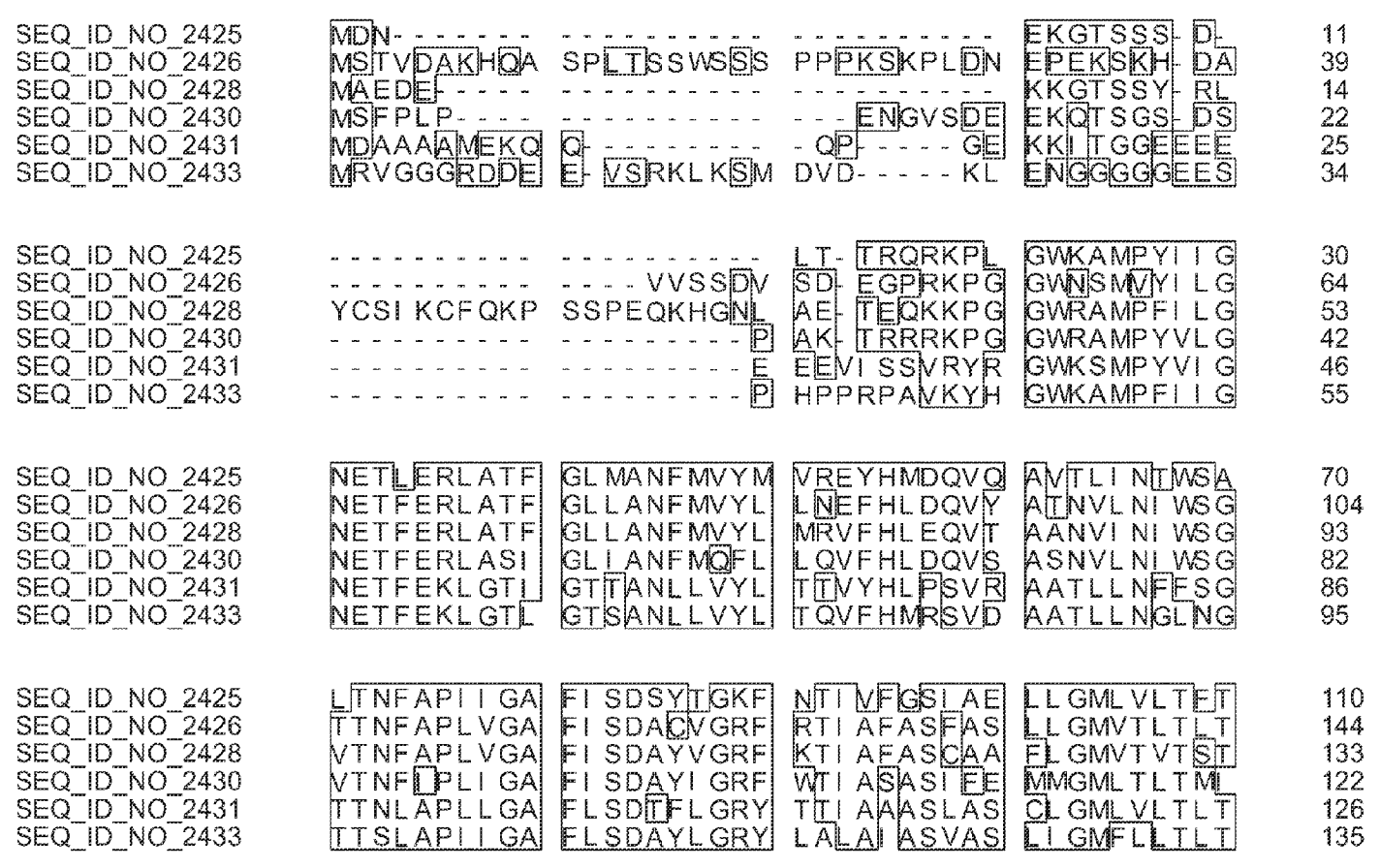
Figure 38C:
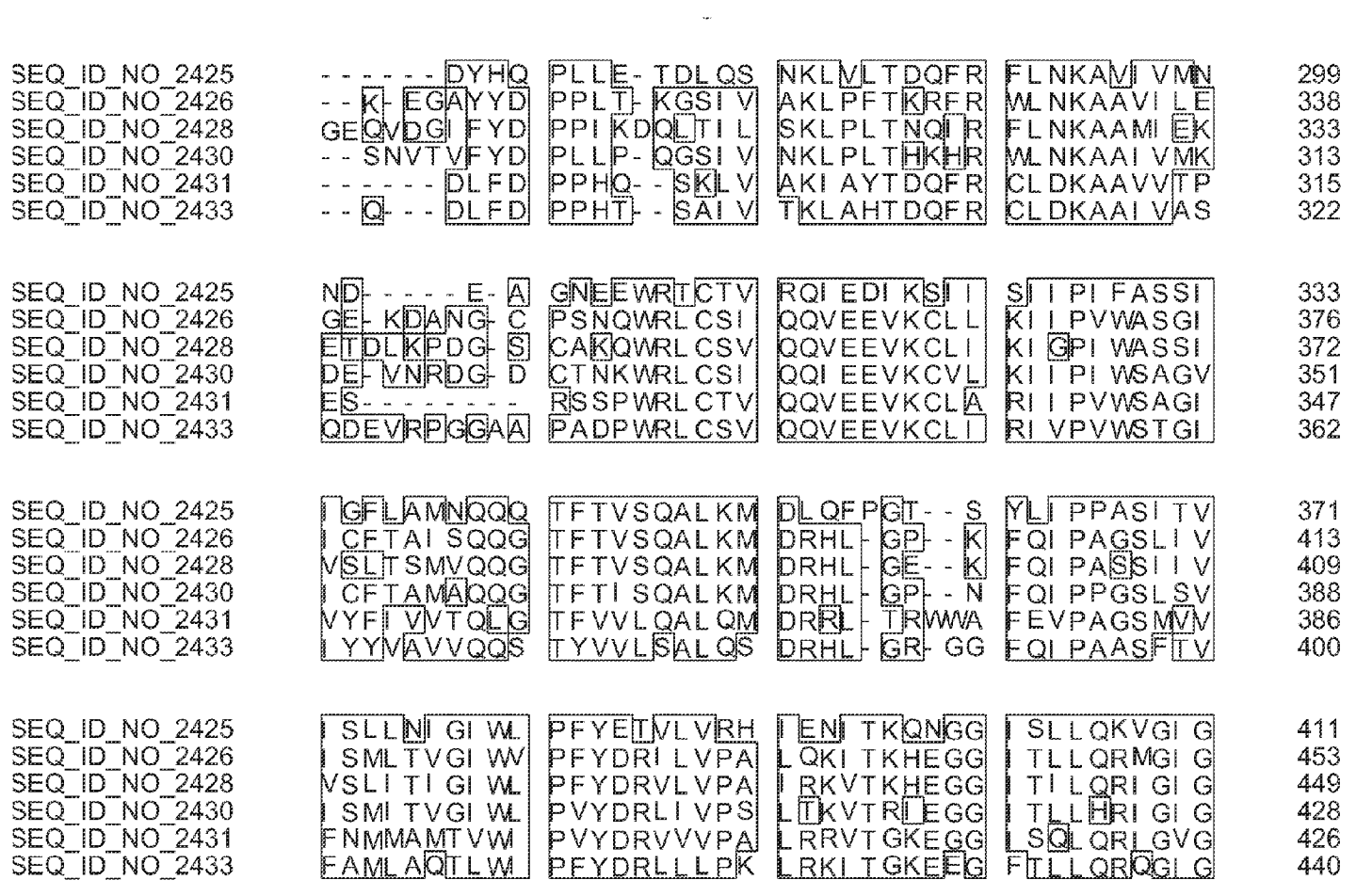
Figure 38D:
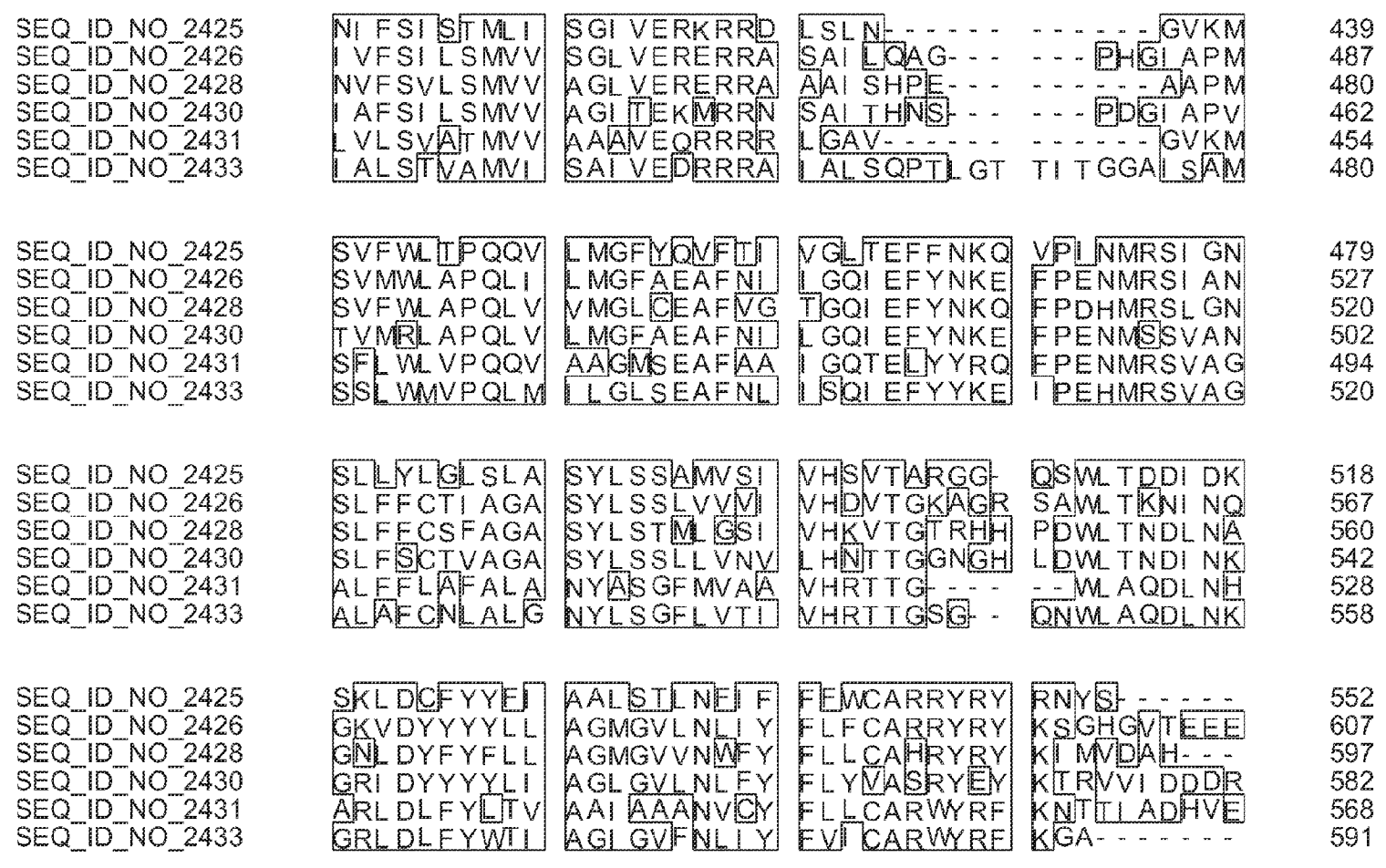

FIGS. 38A-38E are an alignment of the amino acid sequence of CeresAnnot:837788 (SEQ ID NO: 2425) with homologous and/or orthologous amino acid sequences.

DETAILED DESCRIPTION

The invention features methods and materials related to modulating biomass levels in plants. In some embodiments, the plants may also have modulated levels of, for example, lignin, modified root architecture, modified herbicide resistance, modified carotenoid biosynthesis, or modulated cell wall content. The methods can include transforming a plant cell with a nucleic acid encoding a biomass-modulating polypeptide, wherein expression of the polypeptide results in a modulated level of biomass. Plant cells produced using such methods can be grown to produce plants having an increased or decreased biomass. Such plants, and the seeds of such plants, may be used to produce, for example, biomass having an increased value as a biofuel feedstock.

I. Definitions

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic Panicum virgatum plant transformed with and expressing the coding sequence for a nitrogen transporter polypeptide from a Zea mays plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Modulation" of the level of biomass refers to the change in the level of the biomass that is observed as a result of expression of, or transcription from, an exogenous nucleic acid in a plant cell and/or plant. The change in level is measured relative to the corresponding level in control plants.

"Nucleic acid" and "polynucleotide" are used interchangeably herein, and refer to both RNA and DNA, including cDNA, genomic DNA, synthetic DNA, and DNA or RNA containing nucleic acid analogs. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., The Plant Cell, 1:977-984 (1989).

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. Polypeptides

Polypeptides described herein include biomass-modulating polypeptides. Biomass-modulating polypeptides can be effective to modulate biomass levels when expressed in a plant or plant cell. Such polypeptides typically contain at least one domain indicative of biomass-modulating polypeptides, as described in more detail herein. Biomass-modulating polypeptides typically have an HMM bit score that is greater than 65 as described in more detail herein. In some embodiments, biomass-modulating polypeptides have greater than 80% identity to SEQ ID NOs: 2, 4, 6-9, 11, 13-15, 17, 18, 20-27, 29, 31-33, 35, 36, 38-51, 53, 54, 56-61, 63-67, 69, 70, 72-76, 78, 80-83, 85, 86, 88-91, 93-97, 99-103, 105, 107, 109, 110, 112, 113, 115, 117, 119-152, 154, 156, 158, 159, 161, 163, 165, 167, 168, 170, 172, 174, 176, 178, 180-185, 187, 188, 190, 192-194, 196, 198, 200, 202, 203, 205, 207-211, 213-251, 253, 255, 257, 258, 260-262, 264, 265, 267-272, 274-279, 281-283, 285, 287-292, 294, 295-297, 299, 301, 303-305, 307, 309, 310, 312, 314, 316-318, 320, 321, 323, 325, 327-329, 331, 332, 334, 335, 337-339, 341, 342, 344, 345, 347, 349, 351, 353, 355, 357, 359, 361-366, 368, 370, 372, 373, 375-378, 380, 382-387, 389, 391, 393, 395, 396, 398-404, 406-414, 416, 418, 420, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497-502, 504, 506, 508, 509, 511-517, 519, 521, 522, 524-527, 529, 530, 532, 533, 535, 536, 537, 539, 541, 543, 545, 546, 548, 550, 552-555, 557, 558, 560, 562, 564, 566, 568, 570-578, 580, 582, 584, 585, 587, 589, 591, 592, 594-596, 598, 600, 601, 603, 604, 606-608, 610, 611, 613, 615, 617, 619, 621, 623, 625, 626, 628-632, 634, 636, 638, 640, 642, 643, 645, 647, 649, 651, 653, 655, 657, 659, 661, 663, 665, 667-670, 672, 674, 675, 677, 679-682, 684, 685, 687, 689-692, 694-698, 700-704, 706, 707, 709-718, 720, 722, 724, 726-728, 730, 731, 733-739, 741, 743, 745, 746, 748, 750, 752, 754, 756, 758, 760-764, 766, 768, 770, 772, 774, 776, 778, 780, 782, 784, 785, 787, 789, 791, 793-795, 797, 799, 801, 803, 805, 806, 808, 810, 812, 814, 816, 818-820, 822-824, 826, 828, 830, 832, 834, 836, 838-840, 842, 843, 845-847, 849, 851, 853, 854, 856-858, 860, 862, 863, 865, 866, 868, 870-873, 875-878, 880-882, 884-886, 888, 890, 892, 893, 895, 897, 899, 900, 902, 903, 905, 907, 909, 911, 912, 913, 915, 917, 919, 921, 923, 925, 926, 928, 930, 932, 933, 935, 936-938, 940, 941, 943-945, 947, 949, 950, 952-955, 957-961, 963, 965-969, 971, 972, 974, 975, 977, 978, 980, 982, 984, 986, 988, 990, 992, 994, 996, 998, 1000-1014, 1016, 1018, 1020, 1021, 1023, 1024, 1026, 1027, 1029, 1030, 1032, 1033, 1035, 1037, 1038, 1040, 1042, 1043, 1045, 1047, 1049, 1051, 1053, 1055, 1057, 1059, 1061-1063, 1065, 1067, 1069, 1070, 1072, 1073, 1075, 1076, 1078-1080, 1082, 1083, 1085, 1087, 1089, 1091, 1093, 1095, 1096, 1098, 1100, 1101, 1103, 1105, 1106, 1108, 1110, 1112, 1114-1116, 1118, 1120-1123, 1125, 1127-1131, 1133, 1134, 1136, 1137, 1139-1145, 1147-1156, 1158-1161, 1163, 1165-1178, 1180-1188, 1190, 1191, 1193-1202, 1204, 1205-1207, 1209-1213, 1215, 1217-1221, 1223-1228, 1230, 1231, 1233-1241, 1243, 1245, 1247, 1249-1252, 1254, 1255, 1257-1259, 1261, 1263, 1264, 1266-1272, 1274-1276, 1278, 1280, 1282-1286, 1288, 1289, 1291-1331, 1333-1337, 1339, 1341, 1343, 1345, 1347-1350, 1352, 1354, 1356, 1358, 1360, 1362, 1364, 1366, 1368, 1370-1372, 1374, 1375, 1377-1379, 1381, 1383, 1384, 1386, 1388-1390, 1392-1397, 1399, 1400, 1402, 1403, 1405, 1407-1410, 1412-1418, 1420, 1422, 1424, 1426, 1428, 1430, 1432-1436, 1438, 1440, 1442-1444, 1446, 1447, 1449, 1450, 1452-1454, 1456, 1457, 1459, 1460, 1462, 1463, 1465-1468, 1470, 1471, 1473, 1475, 1477-1483, 1485, 1487, 1489, 1491-1493, 1495, 1496, 1498, 1499, 1501, 1503, 1504, 1506, 1508, 1510, 1511, 1513, 1514, 1516-1521, 1523, 1524, 1526, 1528-1532, 1534, 1536-1539, 1541, 1542, 1544, 1545, 1547, 1548, 1550, 1552, 1553, 1555-1559, 1561, 1563-1565, 1567, 1568, 1570, 1571, 1573, 1575, 1576, 1578, 1580, 1582, 1583, 1585, 1587, 1589, 1590, 1592, 1593, 1595, 1597, 1599, 1600, 1602-1606, 1608-1613, 1615, 1616, 1618-1626, 1628, 1629, 1631, 1633, 1634, 1636, 1637, 1639-1643, 1645, 1646-1739, 1741, 1743, 1745, 1747-1756, 1758, 1760, 1762-1764, 1766, 1767, 1769, 1770, 1772-1774, 1776, 1778-1783, 1785-1792, 1794, 1796, 1798, 1799, 1801, 1802, 1804, 1806, 1808-1810, 1812, 1814, 1815, 1817, 1819, 1821, 1822, 1824, 1826-1830, 1832, 1834, 1835, 1837, 1839-1841, 1843, 1844, 1846, 1847, 1849, 1851, 1852, 1854, 1856, 1858, 1860-1863, 1865-1953, 1955-1958, 1960, 1962, 1964, 1966-1968, 1970, 1972-1976, 1978, 1980, 1982, 1984-1986, 1988, 1990, 1991, 1993, 1995, 1997, 1999, 2001, 2003, 2005, 2007, 2009, 2011, 2013, 2015, 2017, 2019, 2021, 2023-2027, 2029, 2031, 2033, 2035, 2037, 2039, 2041, 2043, 2045, 2047-2049, 2051-2057, 2059, 2061, 2063, 2065, 2067, 2069, 2071, 2073, 2075, 2077, 2079, 2080, 2082, 2084, 2086, 2088, 2090, 2092, 2093, 2095, 2097, 2098, 2100-2122, 2124, 2126, 2128, 2129, 2131, 2133, 2135-2137, 2139, 2141, 2142, 2144-2148, 2150, 2152, 2154, 2155, 2157, 2159-2161, 2163, 2165, 2166, 2168, 2170, 2172-2175, 2177, 2179, 2181, 2183, 2184, 2186, 2188, 2189, 2191-2194, 2196, 2197, 2199-2202, 2204, 2206-2208, 2210-2212, 2214, 2215, 2217-2220, 2222, 2224-2226, 2228, 2230-2232, 2234-2242, 2244-2254, 2256-2269, 2271, 2273, 2274, 2276, 2278, 2280, 2281, 2283, 2285, 2286, 2288, 2290, 2292, 2294, 2296, 2297, 2299, 2301, 2303, 2305, 2307, 2309, 2311, 2313, 2314, 2316-2318, 2320, 2322, 2324, 2326, 2327, 2329, 2331, 2333, 2335, 2337, 2339, 2341, 2342, 2344, 2345, 2347-2349, 2351, 2353, 2355, 2357, 2359, 2361, 2363, 2365, 2367-2369, 2371, 2373, 2375, 2377, 2379, 2381, 2383, 2385, 2386, 2388, 2390, 2391, 2393, 2395, 2397, 2399, 2400, 2402, 2404, 2405, 2407, 2409, 2411, 2413, 2415, 2417, 2419, 2421, 2423, 2425, 2426, 2428, 2430, 2431, 2433, 2435, 2437, 2438-2440, 2442, 2444, 2445, 2447, 2449, 2451, 2453, 2455, 2457, 2459, 2461, 2463-2468, 2470, 2472, 2474, 2476, 2478, 2479, 2481, 2482, 2484, 2485, 2487-2491, 2493-2498, 2500-2510, 2512-2515, 2517-2531, 2533-2536, 2538-2542, 2544-2548, 2550, 2551, 2553, 2555-2558, 2560, 2562, 2564, 2566-2573, 2575-2579, 2581, 2583-2585, 2587-2602, 2604-2611, 2613, 2615, 2617, or 2619-2623 as described in more detail herein.

A. Domains Indicative of Biomass-Modulating Polypeptides

A biomass-modulating polypeptide can contain a methyltransferase_2 domain and a dimerization domain, which are predicted to be characteristic of a biomass-modulating polypeptide. SEQ ID NO: 1333 sets forth the amino acid sequence of a *Panicum virgatum* clone, identified herein as CeresClone:1871521 (SEQ ID NO:1332), that is predicted to encode a polypeptide containing methyltransferase_2 and dimerization domains. For example, a biomass-modulating polypeptide can comprise a methyltransferase_2 domain having 60 percent or greater (e.g., 65, 70, 75, 80, 85, 90, 95, 97, 98, 99, or 100%) sequence identity to residues 94 to 340 of SEQ ID NO: 1333 or can comprise a dimerization domain having 60 percent or greater (e.g., 65, 70, 75, 80, 85, 90, 95, 97, 98, 99, or 100%) sequence identity to residues 33 to 85 of SEQ ID NO:1333. In some embodiments, a biomass-modulating polypeptide can comprise a methyltransferase_2 domain and a dimerization domain having 60 percent or greater (e.g., 65, 70, 75, 80, 85, 90, 95, 97, 98, 99, or 100%)

sequence identity to the methyltransferase_2 and dimerization domains of one or more of the polypeptides set forth in SEQ ID NOs: 1334, 1335, 1336, 1337, 1339, 1341, 1343, 1345, 1347, 1348, 1349, 1350, 1352, 1354, 1356, 1358, 1360, 1362, or 1364. The methyltransferase_2 and dimerization domains of such sequences are set forth in the Sequence Listing. The methyltransferase_2 domain and dimerization domain are characteristic of O-methyltransferases, which catalyze the transfer of a methyl group from S-adenosyl-L-methionine (AdoMet) to either nitrogen, oxygen or carbon atoms of DNA, RNA, proteins, or small molecules. The dimerization domain typically is found at the N-terminus and mediates dimerization of the O-methyltransferases.

A biomass-modulating polypeptide can contain a glycosyl transferase family 8 domain, which is predicted to be characteristic of a biomass-modulating polypeptide. SEQ ID NO: 1489 sets forth the amino acid sequence of a *Panicum virgatum* clone, identified herein as CeresClone:1909354 (SEQ ID NO: 1488) that is predicted to encode a polypeptide containing a glycosyl transferase family 8 domain. For example, a biomass-modulating polypeptide can comprise a glycosyl transferase family 8 domain having 60 percent or greater (e.g., 65, 70, 75, 80, 85, 90, 95, 97, 98, 99, or 100%) sequence identity to residues 314 to 525 of SEQ ID NO: 1489. In some embodiments, a biomass-modulating polypeptide can comprise a glycosyl transferase family 8 domain having 60 percent or greater (e.g., 65, 70, 75, 80, 85, 90, 95, 97, 98, 99, or 100%) sequence identity to the glycosyl transferase family 8 domain of one or more of the polypeptides set forth in SEQ ID NOs: 1491, 1492, 1493, 1495, 1496, 1498, 1499, 1501, 1503, 1504, 1506, 1508, 1510, 1511, 1513, 1514, 1516, 1517, 1518, 1519, 1520, 1521, 1523, 1524, 1526, 1528, 1529, 1530, 1531, 1532, 1534, 1536, 1537, 1538, or 1539. The glycosyl transferase family 8 domain of such sequences are set forth in the Sequence Listing. The glycosyl transferase family 8 domain is found in a family of enzymes that transfer sugar residues to donor molecules. Members of the glycosyl transferase 8 family are involved in lipopolysaccharide biosynthesis and glycogen synthesis, and include lipopolysaccharide galactosyltransferase, lipopolysaccharide glucosyltransferase, and glycogenin glucosyltransferase.

A biomass-modulating polypeptide can contain a raffinose synthase domain, which is predicted to be characteristic of a biomass-modulating polypeptide. SEQ ID NO: 504 sets forth the amino acid sequence of a *Panicum virgatum* clone, identified herein as CeresClone:1882035 (SEQ ID NO:503) that is predicted to encode a polypeptide containing a raffinose synthase domain. For example, a biomass-modulating polypeptide can comprise a raffinose synthase domain having 60 percent or greater (e.g., 65, 70, 75, 80, 85, 90, 95, 97, 98, 99, or 100%) sequence identity to residues 2-727 of SEQ ID NO: 504. In some embodiments, a biomass-modulating polypeptide can comprise a raffinose synthase domain having 60 percent or greater (e.g., 65, 70, 75, 80, 85, 90, 95, 97, 98, 99, or 100%) sequence identity to the raffinose synthase domain of one or more of the polypeptides set forth in SEQ ID NOs: 506, 508, 509, 511, 512, 513, 514, 515, 516, 517, 519, 521, 522, 524, 525, 526, 527, 529, 530, 532, 533, 535, 536, 537, 539, 541, 543, 545, 546, 548, 550, 552, 553, 554, 555, 557, 558, 560, 562, 564, 566, 568, 570, 571, 572, 573, 574, 575, 576, 577, or 578. Raffinose family oligosaccharides (RFOs) are synthesized by a set of galactosyltransferases, which sequentially add galactose units from galactinol to sucrose. Raffinose synthase (EC 2.4.1.82) (also known as seed imbibition (Sip1) protein) produces raffinose by transferring a galactose unit from galactinol to sucrose. RFOs may act as protective agents during desiccation and storage of seeds in the dry state, and also may function as prebiotics, by specifically stimulating growth of remedial gut bacteria. See, Peterbauer et al., *Plant Physiol.* 127(4): 1764-1772 (2001).

A biomass-modulating polypeptide can contain an LpxC domain, which is predicted to be characteristic of a biomass-modulating polypeptide. SEQ ID NO: 198 sets forth the amino acid sequence of a *Panicum virgatum* clone, identified herein as CeresClone:1819917 (SEQ ID NO: 197), that is predicted to encode a polypeptide containing an LpxC domain. For example, a biomass-modulating polypeptide can comprise an LpxC domain having 60 percent or greater (e.g., 65, 70, 75, 80, 85, 90, 95, 97, 98, 99, or 100%) sequence identity to residues 24 to 315 of SEQ ID NO: 198. In some embodiments, a biomass-modulating polypeptide can comprise an LpxC domain having 60 percent or greater (e.g., 65, 70, 75, 80, 85, 90, 95, 97, 98, 99, or 100%) sequence identity to the LpxC domain of one or more of the polypeptides set forth in SEQ ID NOs: 200, 202, 203, 205, 207, 208, 209, 210, 211, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, or 251. The LpxC domains of such sequences are set forth in the Sequence Listing. Enzymes within the LpxC family are UDP-3-O— N-acetylglucosamine deacetylases, zinc-dependent metalloamidases that catalyse the second and committed step in the biosynthesis of Lipid A, which anchors lipopolysaccharide into the membrane in Gram negative bacteria. Orthologs of the *E. coli* LpxC genes are found in higher plants, which may synthesize Lipid A like substances. Such Lipid A like substances may be structural components of chloroplast outer membranes or may function as a signaling molecule in plants. See, Raetz and Whitfield, *Annu Rev Biochem.* 71: 635-700 (2002).

A biomass-modulating polypeptide can contain a UDP-glucoronosyl and UDP-glucosyl transfer (UDPGT) domain, which is predicted to be characteristic of a biomass-modulating polypeptide. SEQ ID NO: 253 sets forth the amino acid sequence of a *Panicum virgatum* clone, identified herein as CeresClone:1815762 (SEQ ID NO: 252), that is predicted to encode a polypeptide containing a UDPGT domain. For example, a biomass-modulating polypeptide can comprise a UDPGT domain having 60 percent or greater (e.g., 65, 70, 75, 80, 85, 90, 95, 97, 98, 99, or 100%) sequence identity to residues 11 to 480 of SEQ ID NO: 253. In some embodiments, a biomass-modulating polypeptide can comprise a UDPGT domain having 60 percent or greater (e.g., 65, 70, 75, 80, 85, 90, 95, 97, 98, 99, or 100%) sequence identity to the UDPGT domain of one or more of the polypeptides set forth in SEQ ID NOs: 255, 257, 258, 260, 261, 262, 264, 265, 267, 268, 269, 270, 271, 272, 274, 275, 276, 277, 278, 279, 281, 282, 283, 285, 287, 288, 289, 290, 291, 292, 294, 295, 296, 297, 299, 301, 303, 304, 305, 307, 309, 310, 312, 314, 316, 317, 318, 320, 321, 323, 325, 327, 328, 329, 331, 332, 334, 335, 337, 338, 339, 341, 342, 344, 345, 347, 349, 351, 353, 355, 357, 359, 361, 362, 363, 364, 365, or 366. The UDPGT domains of such sequences are set forth in the Sequence Listing. UDP-glucuronosyl transferases (EC:2.4.1.17) are part of a large family of membrane-bound microsomal enzymes that catalyze the transfer of glucuronic acid to exogenous and endogenous lipophilic substrates. Another enzyme in the UDPGT family is flavonol O(3)-glucosyltransferase (EC:2.4.1.91), which catalyzes the transfer of glucose from UDP-glucose to a flavanol.

A biomass-modulating polypeptide can contain a Glyco_hydro_18 domain, which is predicted to be characteristic of a biomass-modulating polypeptide. SEQ ID NO: 1541 sets forth the amino acid sequence of a *Panicum virgatum* clone, identified herein as CeresClone:1792015 (SEQ ID NO: 1540), that is predicted to encode a polypeptide containing a Glyco_hydro_18 domain. For example, a biomass-modulating polypeptide can comprise a Glyco_hydro_18 domain having 60 percent or greater (e.g., 65, 70, 75, 80, 85, 90, 95, 97, 98, 99, or 100%) sequence identity to residues 36 to 287 of SEQ ID NO: 1541. In some embodiments, a biomass-modulating polypeptide can comprise a Glyco_hydro_18 domain having 60 percent or greater (e.g., 65, 70, 75, 80, 85, 90, 95, 97, 98, 99, or 100%) sequence identity to the Glyco_hydro_18 domain of one or more of the polypeptides set forth in SEQ ID NOs: 1542, 1544, 1545, 1547, 1548, 1550, 1552, 1553, 1555, 1556, 1557, 1558, 1559, 1561, 1563, 1564, 1565, 1567, 1568, 1570, 1571, 1573, 1575, 1576, or 1578. The alpha/beta hydrolase fold domains of such sequences are set forth in the Sequence Listing. The Glyco_hydro_18 domain is found in O-glycosyl hydrolases, a group of enzymes that hydrolyse the glycosidic bond between two or more carbohydrates.

A biomass-modulating polypeptide can contain a Glyco_transf_34 domain, which is predicted to be characteristic of a biomass-modulating polypeptide. SEQ ID NO: 663 sets forth the amino acid sequence of a *Panicum virgatum* clone, identified herein as CeresClone:1791384 (SEQ ID NO: 662), that is predicted to encode a polypeptide containing a Glyco_transf_34 domain. For example, a biomass-modulating polypeptide can comprise a Glyco_transf_34 domain having 60 percent or greater (e.g., 65, 70, 75, 80, 85, 90, 95, 97, 98, 99, or 100%) sequence identity to residues 136 to 380 of SEQ ID NO: 663. In some embodiments, a biomass-modulating polypeptide can comprise a Glyco_transf_34 domain having 60 percent or greater (e.g., 65, 70, 75, 80, 85, 90, 95, 97, 98, 99, or 100%) sequence identity to the Glyco_transf_34 domain of one or more of the polypeptides set forth in SEQ ID NOs: 665, 667, 668, 669, 670, 672, 674, 675, 677, 679, 680, 681, 682, 684, 685, 687, 689, 690, 691, 692, 694, 695, 696, 697, 698, 700, 701, 702, 703, 704, 706, 707, 709, 710, 711, 712, 713, 714, 715, 716, 717, 718, 720, 722, 724, 726, 727, 728, 730, 731, 733, 734, 735, 736, 737, 738, or 739. The Glyco_transf_34 domains of such sequences are set forth in the Sequence Listing. Glyco_transf_34 domains are found within enzymes of the galactosyl transferase GMA12/MNN10 family. Many of the galactosyl transferases within this family contain a DXD motif.

A biomass-modulating polypeptide can contain a branch domain, which is predicted to be characteristic of a biomass-modulating polypeptide. SEQ ID NO: 1366 sets forth the amino acid sequence of a *Panicum virgatum* clone, identified herein as CeresClone:1786268 (SEQ ID NO: 1365), that is predicted to encode a polypeptide containing a branch domain. For example, a biomass-modulating polypeptide can comprise a branch domain having 60 percent or greater (e.g., 65, 70, 75, 80, 85, 90, 95, 97, 98, 99, or 100%) sequence identity to residues 75 to 300 of SEQ ID NO: 1366. In some embodiments, a biomass-modulating polypeptide can comprise a branch domain having 60 percent or greater (e.g., 65, 70, 75, 80, 85, 90, 95, 97, 98, 99, or 100%) sequence identity to the branch domain of one or more of the polypeptides set forth in SEQ ID NOs: 1368, 1370, 1371, 1372, 1374, 1375, 1377, 1378, 1379, 1381, 1383, 1384, 1386, 1388-1390, 1392, 1393, 1394, 1395, 1396, 1397, 1399, 1400, 1402, 1403, 1405, 1407, 1408, 1409, 1410, 1412, 1413, 1414, 1415, 1416, 1417, 1418, 1420, 1422, 1424, 1426, 1428, 1430, 1432, 1433, 1434, 1435, 1436, 1438, 1440, 1442, 1443, 1444, 1446, 1447, 1449, 1450, 1452, 1453, 1454, 1456, 1457, 1459, 1460, 1462, 1463, 1465, 1466, 1467, 1468, 1470, 1471, 1473, 1475, 1477, 1478, 1479, 1480, 1481, 1482, 1483, 1485, or 1487. The branch domains of such sequences are set forth in the Sequence Listing. The branch domain is found in a family of two different beta-1,6-N-acetylglucosaminyltransferase enzymes, 1-branching enzyme and core-2 branching enzyme, which are both integral membrane proteins. The I-branching enzyme converts linear into branched poly-N-acetyllactosaminoglycans in the glycosylation pathway while core-2 branching enzyme forms side-chain branches in O-glycans in the glycosylation pathway.

A biomass-modulating polypeptide can contain a COBRA domain, which is predicted to be characteristic of a biomass-modulating polypeptide. SEQ ID NO: 928 sets forth the amino acid sequence of a *Panicum virgatum* clone, identified herein as CeresClone:1781794 (SEQ ID NO: 927), that is predicted to encode a polypeptide containing a COBRA domain. For example, a biomass-modulating polypeptide can comprise a COBRA domain having 60 percent or greater (e.g., 65, 70, 75, 80, 85, 90, 95, 97, 98, 99, or 100%) sequence identity to residues 51 to 215 of SEQ ID NO: 928. In some embodiments, a biomass-modulating polypeptide can comprise a COBRA domain having 60 percent or greater (e.g., 65, 70, 75, 80, 85, 90, 95, 97, 98, 99, or 100%) sequence identity to the COBRA domain of one or more of the polypeptides set forth in SEQ ID NOs: 930, 932, 933, 935, 936. 937, 938, 940, 941, 943, 944, 945, 947, 949, 950, 952, 953, 954, 955, 957, 958, 959, 960, 961, 963, 965, 966, 967, 968, 969, 971, 972, 974, 975, 977, 978, 980, 982, 984, 986, 988, 990, 992, 994, 996, 998, 1000, 1001, 1002, 1003, 1004, 1005, 1006, 1007, 1008, 1009, 1010, 1011, 1012, 1013, or 1014. The COBRA domains of such sequences are set forth in the Sequence Listing. COBRA domains are found within a family of plant proteins designated COBRA-like (COBL) proteins. Members of the family are extracellular glycosyl-phosphatidyl inositol-anchored proteins (GPI-linked). COBRA is involved in determining the orientation of cell expansion, probably by playing an important role in cellulose deposition. It may act by recruiting cellulose synthesizing complexes to discrete positions on the cell surface. See Roudier et al., *Plant Cell.* 17(6):1749-63 (2005), Epub 2005 Apr. 22.

A biomass-modulating polypeptide can contain glycosyl hydrolase family 32 N and C-terminal domains, which are predicted to be characteristic of a biomass-modulating polypeptide. SEQ ID NO: 1215 sets forth the amino acid sequence of a *Panicum virgatum* clone, identified herein as CeresClone:1769374 (SEQ ID NO: 1214), that is predicted to encode a polypeptide containing glycosyl hydrolase family 32 N and C-terminal domains. For example, a biomass-modulating polypeptide can comprise a glycosyl hydrolase family 32 N-terminal domain having 60 percent or greater (e.g., 65, 70, 75, 80, 85, 90, 95, 97, 98, 99, or 100%) sequence identity to residues 57 to 374 of SEQ ID NO: 1215 and a glycosyl hydrolase family 32 C-terminal domain having 60 percent or greater (e.g., 65, 70, 75, 80, 85, 90, 95, 97, 98, 99, or 100%) sequence identity to residues 415 to 533 of SEQ ID NO: 1215. In some embodiments, a biomass-modulating polypeptide can comprise glycosyl hydrolase family 32 N and C-terminal domains having 60 percent or greater (e.g., 65, 70, 75, 80, 85, 90, 95, 97, 98, 99, or 100%) sequence identity to the glycosyl hydrolase family 32 N and C-terminal domains of one or more of the polypeptides set forth in SEQ ID NOs: 1217, 1218, 1219, 1220, 1221, 1223, 1224, 1225, 1226, 1227, 1228, 1230, 1231, 1233, 1234, 1235, 1236, 1237, 1238, 1239, 1240, 1241, 1243, 1245, 1247, 1249, 1250, 1251, 1252, 1254, 1255, 1257, 1258, 1259, 1261, 1263, 1264, 1266, 1267, 1268, 1269, 1270, 1271, 1272, 1274, 1275, 1276, 1278, 1280, 1282, 1283, 1284, 1285, 1286, 1288, 1289, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, or 1331. The glycosyl hydrolase family 32 N and C-terminal domains of such sequences are set forth in the Sequence Listing. The N-terminal domain of glycosyl hydrolase family 32 forms a five bladed beta propeller structure. The C-terminal domain of glycosyl hydrolase family 32 forms a five beta sandwich module. See Alberto et al., *J Biol. Chem.* 79(18):18903-10 (2004); Epub 2004 Feb. 18.

A biomass-modulating polypeptide can contain an Alpha-L-AF_C domain and a CBM_4_9 domain, which are predicted to be characteristic of a biomass-modulating polypeptide. SEQ ID NO: 4 sets forth the amino acid sequence of a *Panicum virgatum* clone, identified herein as CeresClone:1753603 (SEQ ID NO: 3), that is predicted to encode a polypeptide containing Alpha-L-AF_C and CBM_4_9 domains. For example, a biomass-modulating polypeptide can comprise an Alpha-L-AF_C domain having 60 percent or greater (e.g., 65, 70, 75, 80, 85, 90, 95, 97, 98, 99, or 100%) sequence identity to residues 454 to 639 of SEQ ID NO: 4 and a CBM_4_9 domain having 60 percent or greater (e.g., 65, 70, 75, 80, 85, 90, 95, 97, 98, 99, or 100%) sequence identity to residues 71 to 229 of SEQ ID NO: 4. In some embodiments, a biomass-modulating polypeptide can comprise Alpha-L-AF_C and CBM_4_9 domains having 60 percent or greater (e.g., 65, 70, 75, 80, 85, 90, 95, 97, 98, 99, or 100%) sequence identity to the Alpha-L-AF_C and CBM_4_9 domains of one or more of the polypeptides set forth in SEQ ID NOs: 6, 7, 8, 9, 11, 13, 14, 15, 17, 18, 20, 21, 22, 23, 24, 25, 26, 27, 29, 31, 32, 33, 35, 36, 38, 39, 40, 41, 42, 43, 44, 45, 46, 47, 48, 49, 50, or 51. The Alpha-L-AF_C and CBM_4_9 domains of such sequences are set forth in the Sequence Listing. The Alpha-L-AF_C domain represents the approximately 200 C-terminal residues of bacterial and eukaryotic alpha-L-arabinofuranosidase (EC: 3.2.1.55), which catalyzes the hydrolysis of nonreducing terminal alpha-L-arabinofuranosidic linkages in L-arabinose-containing polysaccharides. The CBM_4_9 domain is a carbohydrate binding domain.

A biomass-modulating polypeptide can contain an EMP24_GP25L domain, which is predicted to be characteristic of a biomass-modulating polypeptide. SEQ ID NO: 580 sets forth the amino acid sequence of a *Panicum virgatum* clone, identified herein as CeresClone:1724480 (SEQ ID NO: 579), that is predicted to encode a polypeptide containing an EMP24_GP25L domain. For example, a biomass-modulating polypeptide can comprise an EMP24_GP25L domain having 60 percent or greater (e.g., 65, 70, 75, 80, 85, 90, 95, 97, 98, 99, or 100%) sequence identity to residues 36 to 224 of SEQ ID NO: 580. In some embodiments, a biomass-modulating polypeptide can comprise an EMP24_GP25L domain having 60 percent or greater (e.g., 65, 70, 75, 80, 85, 90, 95, 97, 98, 99, or 100%) sequence identity to the EMP24_GP25L domain of one or more of the polypeptides set forth in SEQ ID NOs: 582, 584, 585, 587, 589, 591, 592, 594, 595, 596, 598, 600, 601, 603, 604, 606, 607, 608, 610, 611, 613, 615, 617, 619, 621, 623, 625, 626, 628, 629, 630, 631, or 632. The EMP24 GP25L domains of such sequences are set forth in the Sequence Listing. Members of the EMP24_GP25L family are implicated in bringing cargo forward from the ER and binding to coat proteins by their cytoplasmic domains. This domain corresponds closely to the beta-strand rich GOLD domain described in Anantharaman and Aravind, *Genome Biol.* 2002; 3(5):1-7; Epub 2002 Apr. 24. The GOLD domain is found combined with lipid- or membrane-association domains. Members of the p24 family are type I membrane proteins with a signal peptide at the amino terminus, a lumenal coiled-coil (extracytosolic) domain, a single transmembrane domain with conserved amino acids, and a short cytoplasmic tail.

A biomass-modulating polypeptide can contain a Methyltransf_3 domain, which is predicted to be characteristic of a biomass-modulating polypeptide. SEQ ID NO: 53 sets forth the amino acid sequence of a *Populus balsamifera* subsp. *trichocarpa* clone, identified herein as CeresAnnot: 1514289 (SEQ ID NO: 52), that is predicted to encode a polypeptide containing a Methyltransf_3 domain. For example, a biomass-modulating polypeptide can comprise a Methyltransf_3 domain having 60 percent or greater (e.g., 65, 70, 75, 80, 85, 90, 95, 97, 98, 99, or 100%) sequence identity to residues 34 to 246 of SEQ ID NO: 53. In some embodiments, a biomass-modulating polypeptide can comprise a Methyltransf_3 domain having 60 percent or greater (e.g., 65, 70, 75, 80, 85, 90, 95, 97, 98, 99, or 100%) sequence identity to the Methyltransf_3 domain of one or more of the polypeptides set forth in SEQ ID NOs: 54, 56-61, 63-67, 69, 70, 72-76, 78, 80-83, 85, 86, 88-91, 93-97, 99-103, 105, 107, 109, 110, 112, 113, 115, 117, or 119-152. The methyltransf 3 domain is characteristic of O-methyltransferases, which catalyze the transfer of a methyl group from S-adenosyl-L-methionine to either nitrogen, oxygen or carbon atoms of DNA, RNA, proteins, or small molecules.

A biomass-modulating polypeptide can contain a SRF-TF domain and a K-box domain, which are predicted to be characteristic of a biomass-modulating polypeptide. SEQ ID NO: 1112 sets forth the amino acid sequence of a *Zea mays* clone, identified herein as CeresClone:466497 (SEQ ID NO: 1111), that is predicted to encode a polypeptide containing a SRF-TF domain and a K-box domain. For example, a biomass-modulating polypeptide can comprise a SRF-TF domain having 60 percent or greater (e.g., 65, 70, 75, 80, 85, 90, 95, 97, 98, 99, or 100%) sequence identity to residues 11 to 61 of SEQ ID NO: 1112 and a K-box domain having 60 percent or greater (e.g., 65, 70, 75, 80, 85, 90, 95, 97, 98, 99, or 100%) sequence identity to residues 79 to 179 of SEQ ID NO:1112. In some embodiments, a biomass-modulating polypeptide can comprise a SRF-TF domain and a K-box domain having 60 percent or greater (e.g., 65, 70, 75, 80, 85, 90, 95, 97, 98, 99, or 100%) sequence identity to the SRF-TF domain and a K-box domain of one or more of the polypeptides set forth in SEQ ID NOs: 1112, 1114-1116, 1118, 1120-1123, 1125, 1127-1131, 1133, 1134, 1136, 1137, 1139-1145, 1147-1156, 1158-1161, 1163, 1165-1178, 1180-1188, 1190, 1191, 1193-1202, 1204, 1205-1207, or 1209-1213. A SRF-TF domain and a K-box domain are characteristic of serum response factor (SRF)-type transcription factors. A core domain of about 90 amino acids is sufficient for the activities of DNA-binding, dimerization, and interaction with accessory factors. The core DNA-binding region is designated the MADS box (Pellegrini et al., *Nature*, 376: 490-8 (1995)) and is highly similar to many eukaryotic regulatory proteins. MADS genes in plants encode developmental regulators of vegetative and reproductive development. The MADS-box domain is commonly found associated with a keratin-like (K-box) domain, which promotes protein dimerization.

A biomass-modulating polypeptide can contain a zinc finger (zf)-C3HC4 domain, which is predicted to be characteristic of a biomass-modulating polypeptide. SEQ ID NO: 634 sets forth the amino acid sequence of a *Gossypium hirsutum* clone, identified herein as CeresClone: 1841236_CW00741 (SEQ ID NO: 633), that is predicted to encode a polypeptide containing a zf-C3HC4 domain. For example, a biomass-modulating polypeptide can comprise a zf-C3HC4 domain having 60 percent or greater (e.g., 65, 70, 75, 80, 85, 90, 95, 97, 98, 99, or 100%) sequence identity to residues 95 to 136 of SEQ ID NO: 633. In some embodiments, a biomass-modulating polypeptide can comprise a zf-C3HC4 domain having 60 percent or greater (e.g., 65, 70, 75, 80, 85, 90, 95, 97, 98, 99, or 100%) sequence identity to the zf-C3HC4 domain of one or more of the polypeptides set forth in SEQ ID NOs: 636, 638, 640, 642, 643, 645, 647, 649, 651, 653, 655, 657, 659, or 661. The C3HC4 type zinc-finger (RING finger) is a cysteine-rich domain of 40 to 60 residues that coordinates two zinc ions, and has the consensus sequence: C-X2-C-X(9-39)-C-X(1-3)-H-X(2-3)-C-X2-C-X(4-48)-C-X2-C where X is any amino acid. See Borden and Freemont, *Curr Opin Struct Biol* 6:395-401 (1996). Many proteins containing a RING finger play a role in the ubiquitination pathway.

A biomass-modulating polypeptide can contain an epimerase domain, which is predicted to be characteristic of a biomass-modulating polypeptide. SEQ ID NO: 368 sets forth the amino acid sequence of a *Panicum virgatum* clone, identified herein as CeresClone:1790897_CW00776 (SEQ ID NO: 367), that is predicted to encode a polypeptide containing an epimerase domain. For example, a biomass-modulating polypeptide can comprise an epimerase domain having 60 percent or greater (e.g., 65, 70, 75, 80, 85, 90, 95, 97, 98, 99, or 100%) sequence identity to residues 5 to 244 of SEQ ID NO: 368. In some embodiments, a biomass-modulating polypeptide can comprise an epimerase domain having 60 percent or greater (e.g., 65, 70, 75, 80, 85, 90, 95, 97, 98, 99, or 100%) sequence identity to the epimerase domain of one or more of the polypeptides set forth in SEQ ID NOs: 370, 372, 373, 375-378, 380, 382-387, 389, 391, 393, 395, 396, 398-404, 406-414, 416, 418, 420, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, or 497-502. The epimerase domain is found in the NAD dependent epimerase/dehydratase family. Proteins in the family use NAD as a cofactor and nucleotide-sugar substrates for a variety of chemical reactions.

A biomass-modulating polypeptide can contain an UDPGP domain, which is predicted to be characteristic of a biomass-modulating polypeptide. SEQ ID NO: 1599 sets forth the amino acid sequence of a *Panicum virgatum* clone, identified herein as CeresClone:1780416_CW00778 (SEQ ID NO: 1598), that is predicted to encode a polypeptide containing an UDPGP domain. For example, a biomass-modulating polypeptide can comprise an UDPGP domain having 60 percent or greater (e.g., 65, 70, 75, 80, 85, 90, 95, 97, 98, 99, or 100%) sequence identity to residues 31 to 442 of SEQ ID NO: 1599. In some embodiments, a biomass-modulating polypeptide can comprise an UDPGP domain having 60 percent or greater (e.g., 65, 70, 75, 80, 85, 90, 95, 97, 98, 99, or 100%) sequence identity to the UDPGP domain of one or more of the polypeptides set forth in SEQ ID NOs: 1600, 1602-1606, 1608-1613, 1615, 1616, 1618- 1626, 1628, 1629, 1631, 1633, 1634, 1636, 1637, 1639-1643, 1645, or 1646-1739. UDPGP refers to the family of UTP-glucose-1-phosphate uridylyltransferases (EC:2.7.7.9) (also known as UDP-glucose pyrophosphorylase or Glucose-1-phosphate uridylyltransferase). UTP-glucose-1-phosphate uridylyltransferase catalyses the interconversion of MgUTP+glucose-1-phosphate and UDP-glucose+MgPPi.

A biomass-modulating polypeptide can contain a Myb_DNA-binding domain, which is predicted to be characteristic of a biomass-modulating polypeptide. SEQ ID NO: 741 sets forth the amino acid sequence of a *Zea mays* clone, identified herein as CeresClone:896483_CW00787 (SEQ ID NO: 740), that is predicted to encode a polypeptide containing a Myb_DNA-binding domain. For example, a biomass-modulating polypeptide can comprise a Myb_DNA-binding domain having 60 percent or greater (e.g., 65, 70, 75, 80, 85, 90, 95, 97, 98, 99, or 100%) sequence identity to residues 14 to 59 of SEQ ID NO: 741. In some embodiments, a biomass-modulating polypeptide can comprise a Myb_DNA-binding domain having 60 percent or greater (e.g., 65, 70, 75, 80, 85, 90, 95, 97, 98, 99, or 100%) sequence identity to the Myb_DNA-binding domain of one or more of the polypeptides set forth in SEQ ID NOs: 743, 745, 746, 748, 750, 752, 754, 756, 758, 760-764, 766, 768, 770, 772, 774, 776, 778, 780, 782, 784, 785, 787, 789, 791, 793-795, 797, 799, 801, 803, 805, 806, 808, 810, 812, 814, 816, 818-820, 822-824, 826, 828, 830, 832, 834, 836, 838-840, 842, 843, 845-847, or 849. The Myb_DNA-binding domain is found in the family of Myb proteins, as well as the SANT domain family. See, Aasland et al., *Trends Biochem Sci* 121:87-88 (1996). The SANT domain family specifically recognizes the sequence YAAC (G/T)G.

A biomass-modulating polypeptide can contain a zf-C3HC4 domain, which is predicted to be characteristic of a biomass-modulating polypeptide. SEQ ID NO: 187 sets forth the amino acid sequence of a *Zea mays* clone, identified herein as CeresClone:225681_CW00792 (SEQ ID NO: 186), that is predicted to encode a polypeptide containing a zf-C3HC4 domain. For example, a biomass-modulating polypeptide can comprise a zf-C3HC4 domain having 60 percent or greater (e.g., 65, 70, 75, 80, 85, 90, 95, 97, 98, 99, or 100%) sequence identity to residues 132 to 173 of SEQ ID NO: 186. In some embodiments, a biomass-modulating polypeptide can comprise a zf-C3HC4 domain having 60 percent or greater (e.g., 65, 70, 75, 80, 85, 90, 95, 97, 98, 99, or 100%) sequence identity to the zf-C3HC4 domain of one or more of the polypeptides set forth in SEQ ID NOs: 188, 190, 192, 193, 194, or 196.

A biomass-modulating polypeptide can contain an IQ domain, which is predicted to be characteristic of a biomass-modulating polypeptide. SEQ ID NO: 1065 sets forth the amino acid sequence of an *Arabidopsis thaliana* clone, identified herein as CeresClone:106263_CW00780 (SEQ ID NO: 1064), that is predicted to encode a polypeptide containing an IQ domain. For example, a biomass-modulating polypeptide can comprise an IQ domain having 60 percent or greater (e.g., 65, 70, 75, 80, 85, 90, 95, 97, 98, 99, or 100%) sequence identity to residues 115 to 135 of SEQ ID NO: 1065. In some embodiments, a biomass-modulating polypeptide can comprise an IQ domain having 60 percent or greater (e.g., 65, 70, 75, 80, 85, 90, 95, 97, 98, 99, or 100%) sequence identity to the IQ domain of one or more of the polypeptides set forth in SEQ ID NOs: 1067, 1069, 1070, 1072, 1073, 1075, 1076, 1078-1080, 1082, 1083, 1085, 1087, 1089, 1091, 1093, 1095, 1096, 1098, 1100, 1101, 1103, 1105, 1106, 1108, or 1110. The IQ domain is a consensus for calcium-independent binding of calmodulin, which is a calcium sensor and helps regulate events through its interaction with a diverse group of cellular proteins. See Rhoads and Friedberg, *FASEB J.,* 11(5):331-40 (1997).

A biomass-modulating polypeptide can contain an AUX_IAA domain, which is predicted to be characteristic of a biomass-modulating polypeptide. SEQ ID NO: 1592 sets forth the amino acid sequence of an *Arabidopsis thaliana* clone, identified herein as CeresAnnot:1310682 (SEQ ID NO: 1591), that is predicted to encode a polypeptide containing an AUX_IAA domain. For example, a biomass-modulating polypeptide can comprise an AUX_IAA domain having 60 percent or greater (e.g., 65, 70, 75, 80, 85, 90, 95, 97, 98, 99, or 100%) sequence identity to residues 32 to 190 of SEQ ID NO: 1592. In some embodiments, a biomass-modulating polypeptide can comprise an AUX_IAA domain having 60 percent or greater (e.g., 65, 70, 75, 80, 85, 90, 95, 97, 98, 99, or 100%) sequence identity to the AUX_IAA domain of one or more of the polypeptides set forth in SEQ ID NOs: 1580, 1582, 1583, 1585, 1587, 1589, 1590, 1593, 1595, 1597, 2604, 2605, 2606, 2607, 2608, 2609, 2610, 2611, 2613, 2615, 2617, 2619, 2620, 2621, 2622, or 2623. Transcription of genes in the Aux/IAA family is induced by auxin (indole-3-acetic acid, IAA), which regulates diverse cellular and developmental responses in plants, including cell division, expansion, differentiation and patterning of embryo responses. See, Kulaeva and Prokoptseva, *Biochemistry (Mosc).* 69(3):233-47 (2004). Aux/IAA proteins act as repressors of auxin-induced gene expression, possibly through modulating the activity of DNA-binding auxin response factors (ARFs).

A biomass-modulating polypeptide can contain a CRAL/TRIO and a CRAL/TRIO, N-terminus domain, which are predicted to be characteristic of a biomass-modulating polypeptide. SEQ ID NO: 851 sets forth the amino acid sequence of an *Arabidopsis thaliana* clone, identified herein as CeresAnnot:838049_CW00759 (SEQ ID NO: 850), that is predicted to encode a polypeptide containing CRAL/TRIO and CRAL/TRIO, N-terminus domains. For example, a biomass-modulating polypeptide can comprise a CRAL/TRIO domain having 60 percent or greater (e.g., 65, 70, 75, 80, 85, 90, 95, 97, 98, 99, or 100%) sequence identity to residues 212 to 391 of SEQ ID NO: 851 and a CRAL/TRIO, N-terminus domain having 60 percent or greater (e.g., 65, 70, 75, 80, 85, 90, 95, 97, 98, 99, or 100%) sequence identity to residues 114 to 200 of SEQ ID NO: 851. In some embodiments, a biomass-modulating polypeptide can comprise a CRAL/TRIO domain and a CRAL/TRIO, N-terminus domain having 60 percent or greater sequence identity to the CRAL/TRIO and CRAL/TRIO, N-terminus domains of one or more of the polypeptides set forth in SEQ ID NOs: 853, 854, 856-858, 860, 862, 863, 865, 866, 868, 870-873, 875-878, 880-882, 884-886, 888, 890, 892, 893, 895, 897, 899, 900, 902, 903, 905, 907, 909, 911, 912, 913, 915, 917, 919, 921, 923, 925, or 926. The CRAL/TRIO N-terminal domain is found in the N-terminal, and the CRAL/TRIO domain is found in the C-terminal of various retinaldehyde/retinal-binding proteins. Trio is a multidomain protein that binds to a transmembrane tyrosine phosphatase, contains a protein kinase domain, and has separate rac-specific and rho-specific guanine nucleotide exchange factor domains. See, DeBant et al., *Proc Natl Acad Sci USA.,* 93(11):5466-71 (1996). Trio is a multifunctional protein that integrates and amplifies signals involved in coordinating actin remodeling, which is necessary for cell migration and growth. Other members of the family are transfer proteins that include, guanine nucleotide exchange factor, phosphatidylinositol/phosphatidylcholine transfer protein that is required for the transport of secretory proteins from the golgi complex, and alpha-tocopherol transfer protein that enhances the transfer of the ligand between separate membranes.

A biomass-modulating polypeptide can contain a zinc-finger (zf) Dof domain, which is predicted to be characteristic of a biomass-modulating polypeptide. SEQ ID NO: 1955 sets forth the amino acid sequence of an *Arabidopsis thaliana* clone, identified herein as CeresAnnot:529860 (SEQ ID NO: 1954), that is predicted to encode a polypeptide containing a zf-D of domain. For example, a biomass-modulating polypeptide can comprise a zf-D of domain having 60 percent or greater (e.g., 65, 70, 75, 80, 85, 90, 95, 97, 98, 99, or 100%) sequence identity to residues 35 to 97 of SEQ ID NO: 1955. In some embodiments, a biomass-modulating polypeptide can comprise a zf-Dof domain having 60 percent or greater (e.g., 65, 70, 75, 80, 85, 90, 95, 97, 98, 99, or 100%) sequence identity to the zf-D of domain of one or more of the polypeptides set forth in SEQ ID NOs: 1956, 1957, 1958, 1960, 1962, 1964, 1966, 1967, 1968, 1970, 1972, 1973, 1974, 1975, 1976, or 1978. The D of domain is a zinc finger DNA-binding domain that shows resemblance to the Cys2 zinc finger although it has a longer putative loop where an extra Cys residue is conserved. See, Shimofurutani et al., *FEBS Lett* 430:251-256 (1998).

A biomass-modulating polypeptide can contain a bZIP transcription factor domain, which is predicted to be characteristic of a biomass-modulating polypeptide. SEQ ID NO: 2150 sets forth the amino acid sequence of an *Arabidopsis thaliana* clone, identified herein as CeresAnnot: 853198 (SEQ ID NO: 2149), that is predicted to encode a polypeptide containing a bZIP transcription factor domain. For example, a biomass-modulating polypeptide can comprise a bZIP transcription factor domain having 60 percent or greater (e.g., 65, 70, 75, 80, 85, 90, 95, 97, 98, 99, or 100%) sequence identity to residues 118 to 181 of SEQ ID NO: 2150. In some embodiments, a biomass-modulating polypeptide can comprise a bZIP transcription factor domain having 60 percent or greater (e.g., 65, 70, 75, 80, 85, 90, 95, 97, 98, 99, or 100%) sequence identity to the bZIP transcription factor domain of one or more of the polypeptides set forth in SEQ ID NOs: 2152, 2154, 2155, 2157, 2159-2161, 2163, 2165, 2166, 2168, 2170, 2172-2175, 2177, 2179, 2181, 2183, and 2184. The bZIP transcription factor domain is a basic region mediating sequence-specific DNA-binding followed by a leucine zipper region required for dimerization. See, Hurst., *Protein Profile.* 2(2):101-68 (1995).

A biomass-modulating polypeptide can contain an Ammonium_transp domain, which is predicted to be characteristic of a biomass-modulating polypeptide. SEQ ID NO: 2196 sets forth the amino acid sequence of an *Arabidopsis thaliana* clone, identified herein as CeresAnnot: 873343 (SEQ ID NO: 2195), that is predicted to encode a polypeptide containing an Ammonium_transp domain. For example, a biomass-modulating polypeptide can comprise an Ammonium_transp domain having 60 percent or greater (e.g., 65, 70, 75, 80, 85, 90, 95, 97, 98, 99, or 100%) sequence identity to residues 47 to 471 of SEQ ID NO: 2196. In some embodiments, a biomass-modulating polypeptide can comprise an Ammonium_transp domain having 60 percent or greater (e.g., 65, 70, 75, 80, 85, 90, 95, 97, 98, 99, or 100%) sequence identity to the Ammonium_transp domain of one or more of the polypeptides set forth in SEQ ID NOs: 2197, 2199-2202, 2204, 2206-2208, 2210-2212, 2214, 2215, 2217-2220, 2222, 2224-2226, 2228, 2230-2232, 2234-2242, 2244-2254, and 2256-2269. Members of the ammonium transporter family are ammonia or ammonium uptake transporters. Some, but not others, also transport methylammonium. See, for example, Marini et al., *Mol Cell Biol* 17:4282-4293 (1997); and Marini et al., *Trends Biochem Sci* 22:460-461 (1997).

A biomass-modulating polypeptide can contain a 2OG-FeII_Oxy domain, which is predicted to be characteristic of a biomass-modulating polypeptide. SEQ ID NO: 2493 sets forth the amino acid sequence of an *Arabidopsis thaliana* clone, identified herein as CeresAnnot:878887 (SEQ ID NO: 2492), that is predicted to encode a polypeptide containing a 2OG-FeII_Oxy domain. For example, a biomass-modulating polypeptide can comprise a 2OG-FeII_Oxy domain having 60 percent or greater (e.g., 65, 70, 75, 80, 85, 90, 95, 97, 98, 99, or 100%) sequence identity to residues 47 to 471 of SEQ ID NO: 2196. In some embodiments, a biomass-modulating polypeptide can comprise a 2OG-Fell Oxy domain having 60 percent or greater (e.g., 65, 70, 75, 80, 85, 90, 95, 97, 98, 99, or 100%) sequence identity to the 2OG-FeII_Oxy domain of one or more of the polypeptides set forth in SEQ ID NOs: 2494-2498, 2500-2510, 2512-2515, 2517-2531, 2533-2536, 2538-2542, 2544-2548, 2550, 2551, 2553, 2555-2558, 2560, 2562, and 2564. The 2OG-FeII_Oxy domain is found in the 2OG-Fe(II) oxygenase superfamily, which contains members of the 2-oxoglutarate (2OG) and Fe(II)-dependent oxygenase superfamily. This family includes the C-terminal of the prolyl 4-hydroxylase alpha subunit. The holoenzyme has the activity EC:1.14.11.2 and catalyzes the reaction: Procollagen L-proline+2-oxoglutarate+$O_2$<=>procollagen trans-4-hydroxy-L-proline+succinate+$CO_2$. The full enzyme consists of an $alpha_2$ $beta_2$ complex with the alpha subunit contributing most of the parts of the active site. The family also includes lysyl hydrolases, isopenicillin synthases and AlkB See, Aravind and Koonin, *Genome Biol.*, 2:RESEARCH0007 (2001); Annunen et al., *J Biol Chem* 272:17342-17348 (1997); Helaakoski et al., *Proc Natl Acad Sci USA* 92:4427-4431 (1995); and Roach et al., *Nature* 375:700-704 (1995).

A biomass-modulating polypeptide can contain a DUF640 domain, which is predicted to be characteristic of a biomass-modulating polypeptide. SEQ ID NO: 2271 sets forth the amino acid sequence of a *Populus balsamifera* subsp. *trichocarpa* clone, identified herein as CeresAnnot: 1440417 (SEQ ID NO: 2270), that is predicted to encode a polypeptide containing a DUF640 domain. For example, a biomass-modulating polypeptide can comprise a DUF640 domain having 60 percent or greater (e.g., 65, 70, 75, 80, 85, 90, 95, 97, 98, 99, or 100%) sequence identity to residues 30 to 162 of SEQ ID NO: 2271. In some embodiments, a biomass-modulating polypeptide can comprise a DUF640 domain having 60 percent or greater (e.g., 65, 70, 75, 80, 85, 90, 95, 97, 98, 99, or 100%) sequence identity to the DUF640 domain of one or more of the polypeptides set forth in SEQ ID NOs: 2273, 2274, 2276, 2278, 2280, 2281, 2283, 2285, 2286, 2288, 2290, 2292, 2294, 2296, 2297, 2299, 2301, 2303, 2305, 2307, 2309, 2311, 2313, 2314, 2316-2318, 2320, 2322, 2324, 2326, 2327, 2329, 2331, 2333, 2335, 2337, 2339, 2341, 2342, 2344, 2345, 2347-2349, 2351, 2353, 2355, 2357, 2359, 2361, 2363, 2365, 2367-2369, 2371, 2373, 2375, 2377, 2379, 2381, 2383, 2385, 2386, 2388, 2390, 2391, 2393, 2395, 2397, 2399, 2400, 2402, 2404, 2405, 2407, 2409, 2411, 2413, 2415, 2417, 2419, 2421, and 2423. The DUF640 domain is a conserved region found in plant proteins including Resistance protein-like protein.

A biomass-modulating polypeptide can contain a CCT and a zf-B_box domain, which are predicted to be characteristic of a biomass-modulating polypeptide. SEQ ID NO: 1741 sets forth the amino acid sequence of an *Arabidopsis thaliana* clone, identified herein as CeresClone:6639 (SEQ ID NO: 1740), that is predicted to encode a polypeptide containing a CCT and a zf-B_box domain. For example, a biomass-modulating polypeptide can comprise a CCT domain having 60 percent or greater (e.g., 65, 70, 75, 80, 85, 90, 95, 97, 98, 99, or 100%) sequence identity to residues 285 to 329 of SEQ ID NO: 1741 and a zf-B_box domain having 60 percent or greater (e.g., 65, 70, 75, 80, 85, 90, 95, 97, 98, 99, or 100%) sequence identity to residues 17 to 60 or 61-103 of SEQ ID NO: 1741. In some embodiments, a biomass-modulating polypeptide can comprise a CCT and a zf-B_box domain having 60 percent or greater (e.g., 65, 70, 75, 80, 85, 90, 95, 97, 98, 99, or 100%) sequence identity to the CCT and a zf-B_box domain of one or more of the polypeptides set forth in SEQ ID NOs: 1743, 1745, 1747-1756, 1758, 1760, 1762-1764, 1766, 1767, 1769, 1770, 1772-1774, 1776, 1778-1783, 1785-1792, 1794, 1796, 1798, 1799, 1801, 1802, 1804, 1806, and 1808-1810. The CCT (CONSTANS, CO-like, and TOC1) domain is a highly conserved basic module of approximately 43 amino acids, which is found near the C-terminus of plant proteins (e.g., proteins involved in light signal transduction). The CCT domain is found in association with other domains, such as the B-box-type zinc finger, the GATA-type zinc finger, the ZIM motif or the response regulatory domain. The CCT domain contains a putative nuclear localization signal within the second half of the CCT motif. See Strayer et al., *Science*, 289:768-771 (2000). B-box-type zinc finger domains are approximately 40 residues in length, and can be divided into two groups, type 1 and type 2, which differ in their consensus sequence and in the spacing of the 7-8 zinc-binding residues.

A biomass-modulating polypeptide can contain an X8 domain, which is predicted to be characteristic of a biomass-modulating polypeptide. SEQ ID NO: 1980 sets forth the amino acid sequence of an *Arabidopsis thaliana* clone, identified herein as CeresClone:11830 (SEQ ID NO: 1981), that is predicted to encode a polypeptide containing an X8 domain. For example, a biomass-modulating polypeptide can comprise an X8 domain having 60 percent or greater (e.g., 65, 70, 75, 80, 85, 90, 95, 97, 98, 99, or 100%) sequence identity to residues 29 to 115 of SEQ ID NO: 1980. In some embodiments, a biomass-modulating polypeptide can comprise an X8 domain having 60 percent or greater (e.g., 65, 70, 75, 80, 85, 90, 95, 97, 98, 99, or 100%) sequence identity to the X8 domain of one or more of the polypeptides set forth in SEQ ID NOs:1982, 1984-1986, 1988, 1990, 1991, 1993, 1995, 1997, 1999, 2001, 2003, 2005, 2007, 2009, 2011, 2013, 2015, 2017, 2019, 2021, 2023-2027, 2029, 2031, and 2033. The X8 domain contains 6 conserved cysteine residues that can form three disulphide bridges. The domain may be involved in carbohydrate binding. See, Barral et al., *J Immunol* 172:3644-3651 (2004); Henrissat and Davies, *Plant Physiol* 124:1515-1519 (2000); and Henrissat et al., *Plant Mol Biol* 47:55-72 (2001).

A biomass-modulating polypeptide can contain a Ribosomal_L18p domain, which is predicted to be characteristic of a biomass-modulating polypeptide. SEQ ID NO: 1812 sets forth the amino acid sequence of an *Arabidopsis thaliana* clone, identified herein as CeresClone:32753 (SEQ ID NO: 1811), that is predicted to encode a polypeptide containing a Ribosomal_L18p domain. For example, a biomass-modulating polypeptide can comprise a Ribosomal_L18p domain having 60 percent or greater (e.g., 65, 70, 75, 80, 85, 90, 95, 97, 98, 99, or 100%) sequence identity to residues 26 to 172 of SEQ ID NO: 1812. In some embodiments, a biomass-modulating polypeptide can comprise a Ribosomal_L18p domain having 60 percent or greater (e.g., 65, 70, 75, 80, 85, 90, 95, 97, 98, 99, or 100%) sequence identity to the Ribosomal_L18p domain of one or more of the polypeptides set forth in SEQ ID NOs: 1814, 1815, 1817, 1819, 1821, 1822, 1824, 1826-1830, 1832, 1834, 1835, 1837, 1839-1841, 1843, 1844, 1846, 1847, 1849, 1851, 1852, 1854, 1856, 1858, 1860-1863, and 1865-1953. The Ribosomal_L18p domain is found in ribosomal proteins from the large subunit. This family includes L18 from bacteria and L5 from eukaryotes.

A biomass-modulating polypeptide can contain a Ribosomal_S5 and a Ribosomal_S5_C domain, which are predicted to be characteristic of a biomass-modulating polypeptide. SEQ ID NO: 2035 sets forth the amino acid sequence of an *Arabidopsis thaliana* clone, identified herein as CeresClone:93867 (SEQ ID NO: 2034), that is predicted to encode a polypeptide containing a Ribosomal_S5 and a Ribosomal_S5_C domain. For example, a biomass-modulating polypeptide can comprise a Ribosomal_S5 domain having 60 percent or greater (e.g., 65, 70, 75, 80, 85, 90, 95, 97, 98, 99, or 100%) sequence identity to residues 94 to 160 of SEQ ID NO: 2035 and a Ribosomal_S5_C domain having 60 percent or greater (e.g., 65, 70, 75, 80, 85, 90, 95, 97, 98, 99, or 100%) sequence identity to residues 177 to 250 of SEQ ID NO: 2035. In some embodiments, a biomass-modulating polypeptide can comprise a Ribosomal_S5 and a Ribosomal_S5_C domain having 60 percent or greater (e.g., 65, 70, 75, 80, 85, 90, 95, 97, 98, 99, or 100%) sequence identity to the Ribosomal_S5 and Ribosomal_S5_C domains of one or more of the polypeptides set forth in SEQ ID NOs: 2037, 2039, 2041, 2043, 2045, 2047-2049, 2051-2057, 2059, 2061, 2063, 2065, 2067, 2069, 2071, 2073, 2075, 2077, 2079, 2080, 2082, 2084, 2086, 2088, 2090, 2092, 2093, 2095, 2097, 2098, and 2100-2122. The Ribosomal_S5 and Ribosomal_S5_C(C-terminal) domains are characteristics of a family of proteins related to the 30S ribosomal protein S5P from *Sulfolobus acidocaldarius*.

A biomass-modulating polypeptide can contain a PTR2 domain, which is predicted to be characteristic of a biomass-modulating polypeptide. SEQ ID NO: 2425 sets forth the amino acid sequence of an *Arabidopsis thaliana* clone, identified herein as CeresAnnot:837788 (SEQ ID NO: 2424), that is predicted to encode a polypeptide containing a PTR2 domain. For example, a biomass-modulating polypeptide can comprise a PTR2 domain having 60 percent or greater (e.g., 65, 70, 75, 80, 85, 90, 95, 97, 98, 99, or 100%) sequence identity to residues 90 to 486 of SEQ ID NO: 2425. In some embodiments, a biomass-modulating polypeptide can comprise a PTR2 domain having 60 percent or greater (e.g., 65, 70, 75, 80, 85, 90, 95, 97, 98, 99, or 100%) sequence identity to the PTR2 domain of one or more of the polypeptides set forth in SEQ ID NOs: 2426, 2428, 2430, 2431, 2433, 2435, 2437, 2438-2440, 2442, 2444, 2445, 2447, 2449, 2451, 2453, 2455, 2457, 2459, 2461, 2463-2468, 2470, 2472, 2474, 2476, 2478, 2479, 2481, 2482, 2484, 2485, and 2487-2491. The PTR2 (peptide transporter 2) domain is characteristic of the proton-dependent oligopeptide transport (POT) family. See, Paulsen and Skurray, *Trends Biochem Sci*, 19:404-404, (1994).

In some embodiments, a biomass-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the biomass-modulating activity of a truncated polypeptide. In some embodiments, a truncated polypeptide is a dominant negative polypeptide. Expression in a plant of such a truncated polypeptide confers a difference in the level of biomass of a plant as compared to the corresponding level of a control plant that does not comprise the truncation.

B. Functional Homologs Identified by Reciprocal Basic Local Alignment Search Tool (BLAST)®

In some embodiments, one or more functional homologs of a reference biomass-modulating polypeptide defined by one or more of the Pfam descriptions indicated above are suitable for use as biomass-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a biomass-modulating polypeptide, or by combining domains from the coding sequences for different naturally-occurring biomass-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of biomass-modulating polypeptides. Sequence analysis can involve Basic Local Alignment Search Tool (BLAST)®, Reciprocal BLAST®, or PSI-BLAST® analysis of nonredundant databases using a biomass-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a biomass-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in biomass-modulating polypeptides, e.g., conserved functional domains.

Conserved regions can be identified by locating a region within the primary amino acid sequence of a biomass-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Examples of amino acid sequences of functional homologs of the polypeptide set forth in SEQ ID NO: 2 (Ceres Clone. 1724838) are provided in the Sequence Listing. Such functional homologs include, for example, GI:297838817 (SEQ ID NO: 2589) and GI:297850868 (SEQ ID NO: 2590). In some cases, a functional homolog of SEQ ID NO: 2 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2. In some cases, a functional homolog of SEQ ID NO: 2 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO:2 described above or set forth in the Sequence Listing.

Figure 1B:
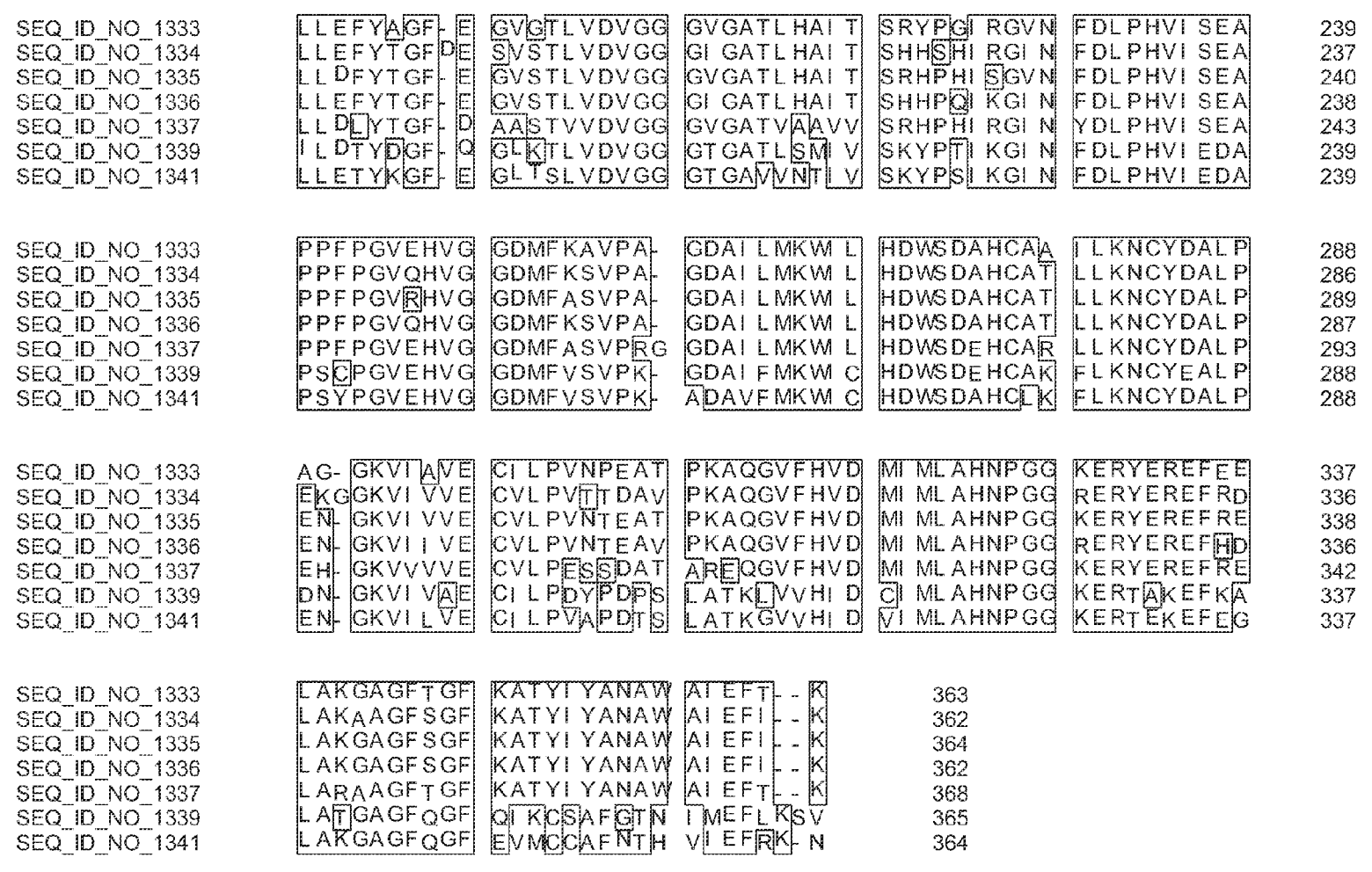

Examples of amino acid sequences of functional homologs of the polypeptide set forth in SEQ ID NO: 1333 are provided in FIG. 1 and in the Sequence Listing. Such functional homologs include, for example, GI:28569609 (SEQ ID NO: 1334), GI:729135 (SEQ ID NO: 1335), GI:29839259 (SEQ ID NO: 1336), GI:115474869 (SEQ ID NO: 1337), CeresClone:1838010 (SEQ ID NO: 1339), CeresAnnot:1521032 (SEQ ID NO: 1341), CeresClone:1769444 (SEQ ID NO: 1343), CeresClone:1869486 (SEQ ID NO: 1345), CeresAnnot:8704591 (SEQ ID NO: 1347), GI:18033964 (SEQ ID NO: 1348), GI:125602246 (SEQ ID NO: 1349), GI:125560205 (SEQ ID NO: 1350), CeresAnnot:1467665 (SEQ ID NO: 1352), CeresAnnot:1472909 (SEQ ID NO: 1354), CeresClone:253173 (SEQ ID NO: 1356), CeresClone:464420 (SEQ ID NO: 1358), CeresClone:1086143 (SEQ ID NO: 1360), CeresClone:1118817 (SEQ ID NO: 1362), or CeresClone:1128033 (SEQ ID NO: 1364). In some cases, a functional homolog of SEQ ID NO: 1333 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1333. In some cases, a functional homolog of SEQ ID NO: 1333 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO:1333 described above or set forth in the Sequence Listing.

Examples of amino acid sequences of functional homologs of the polypeptide set forth in SEQ ID NO: 1489 are provided in FIG. 2 and in the Sequence Listing. Such functional homologs include, for example, CeresAnnot:8642776 (SEQ ID NO:1491), GI:212276047 (SEQ ID NO:1492), GI:15217280 (SEQ ID NO:1493), CeresAnnot:1539881 (SEQ ID NO:1495), GI:225458601 (SEQ ID NO:1496), CeresAnnot:879992 (SEQ ID NO:1498), GI:116789722 (SEQ ID NO:1499), CeresClone:517025 (SEQ ID NO:1501), CeresClone:1948550 (SEQ ID NO:1503), GI:125542675 (SEQ ID NO:1504), CeresAnnot:1486466 (SEQ ID NO:1506), CeresClone:1794546 (SEQ ID NO:1508), CeresAnnot:8669878 (SEQ ID NO:1510), GI:115441423 (SEQ ID NO:1511), CeresAnnot:8679606 (SEQ ID NO:1513), GI:46391126 (SEQ ID NO:1514), CeresClone:1792549 (SEQ ID NO:1516), GI:186478283 (SEQ ID NO:1517), GI:157335049 (SEQ ID NO:1518), GI:46389857 (SEQ ID NO:1519), GI:15221943 (SEQ ID NO:1520), GI:60657590 (SEQ ID NO:1521), CeresAnnot:1505332 (SEQ ID NO:1523), GI:225450971 (SEQ ID NO:1524), CeresAnnot:1452239 (SEQ ID NO:1526), CeresAnnot:8462522 (SEQ ID NO:1528), GI:147866346 (SEQ ID NO:1529), GI:168006895 (SEQ ID NO:1530), GI:22330689 (SEQ ID NO:1531), GI:150036251 (SEQ ID NO:1532), CeresAnnot:542553 (SEQ ID NO:1534), CeresAnnot:1488968 (SEQ ID NO:1536), ACR36345 (SEQ ID NO:1537), Q10QT1_ORYSJ (SEQ ID NO:1538), or B9F5J9 ORYSJ (SEQ ID NO:1539). In some cases, a functional homolog of SEQ ID NO: 1489 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1489. In some cases, a functional homolog of SEQ ID NO: 1489 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1489 described above or set forth in the Sequence Listing.

Examples of amino acid sequences of functional homologs of the polypeptide set forth in SEQ ID NO: 504 are provided in FIG. 3 and in the Sequence Listing. Such functional homologs include, for example, CeresClone:457093 (SEQ ID NO: 506), CeresAnnot:8701524 (SEQ ID NO: 508), GI:90265053 (SEQ ID NO: 509), CeresAnnot:1473716 (SEQ ID NO: 511), GI:225456842 (SEQ ID NO: 512), GI:488787 (SEQ ID NO: 513), GI:91075914 (SEQ ID NO: 514), GI:15292677 (SEQ ID NO: 515), GI:167100 (SEQ ID NO: 516), GI:38345247 (SEQ ID NO: 517), CeresAnnot:1480323 (SEQ ID NO: 519), CeresClone:1807161 (SEQ ID NO: 521), GI:29838631 (SEQ ID NO: 522), CeresAnnot:875520 (SEQ ID NO: 524), GI:225441787 (SEQ ID NO: 525), GI:115471135 (SEQ ID NO: 526), GI:125546144 (SEQ ID NO: 527), CeresClone:1533376 (SEQ ID NO: 529), GI:125557655 (SEQ ID NO: 530), CeresAnnot:8632040 (SEQ ID NO: 532), GI:50540754 (SEQ ID NO: 533), CeresAnnot:8645125 (SEQ ID NO: 535), GI:29838629 (SEQ ID NO: 536), GI:87128422 (SEQ ID NO: 537), CeresClone:826233 (SEQ ID NO: 539), CeresAnnot:1474940 (SEQ ID NO: 541), CeresClone:927786 (SEQ ID NO: 543), CeresAnnot:1453705 (SEQ ID NO: 545), GI:148925503 (SEQ ID NO: 546), CeresAnnot:8714640 (SEQ ID NO: 548), CeresAnnot:1528375 (SEQ ID NO: 550), CeresClone:1768954 (SEQ ID NO: 552), GI:23452226 (SEQ ID NO: 553), GI:7242785 (SEQ ID NO: 554), GI:30694660 (SEQ ID NO: 555), CeresAnnot:1532021 (SEQ ID NO: 557), GI:168002098 (SEQ ID NO: 558), CeresClone:1806608 (SEQ ID NO: 560), CeresAnnot:8457131 (SEQ ID NO: 562), CeresAnnot:8735307 (SEQ ID NO: 564), CeresAnnot:1453769 (SEQ ID NO: 566), CeresAnnot:1478531 (SEQ ID NO: 568), CeresClone:1575663 (SEQ ID NO: 570), GI:42572711 (SEQ ID NO: 571), XP_002448054 (SEQ ID NO: 572), SEQ ID NO: 573, SEQ ID NO: 574, B9FFR9_ORYSJ (SEQ ID NO: 575), SEQ ID NO: 576, Q0JCB5_ORYSJ (SEQ ID NO: 577), or SEQ ID NO: 578. In some cases, a functional homolog of SEQ ID NO: 504 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 504. In some cases, a functional homolog of SEQ ID NO: 504 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 504 described above or set forth in the Sequence Listing.

Figure 4A:
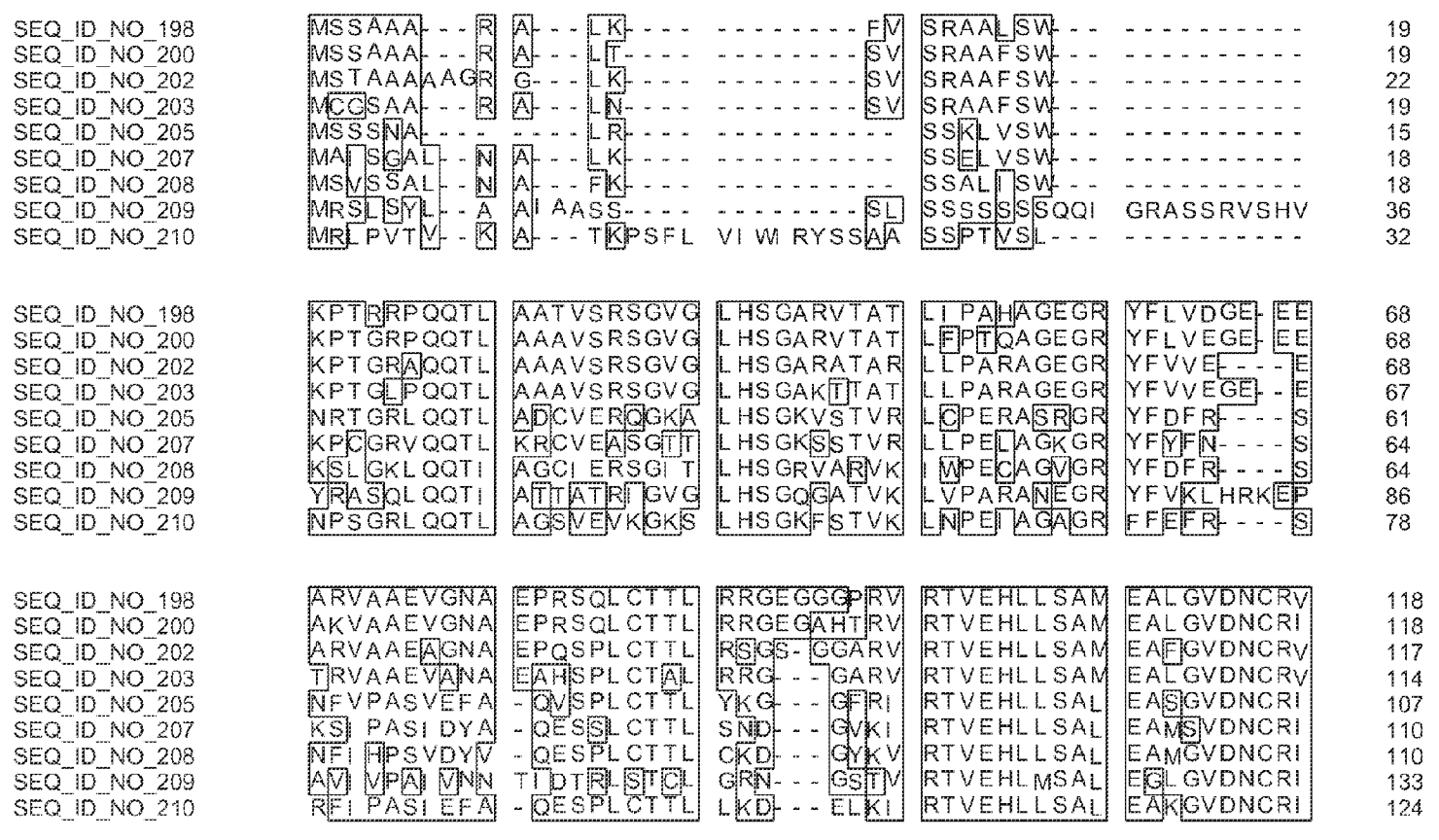
Figure 4B:
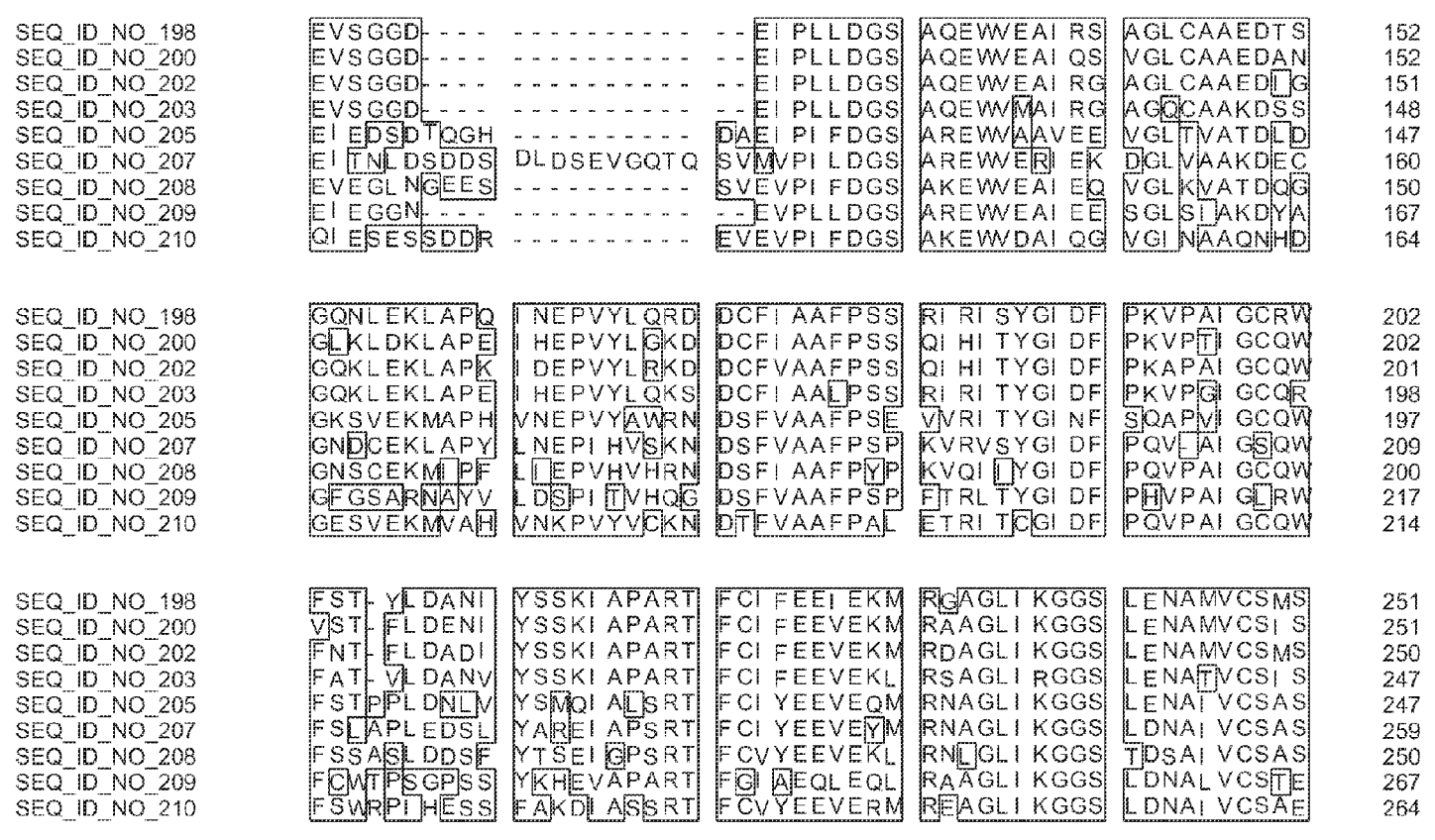
Figure 4C:
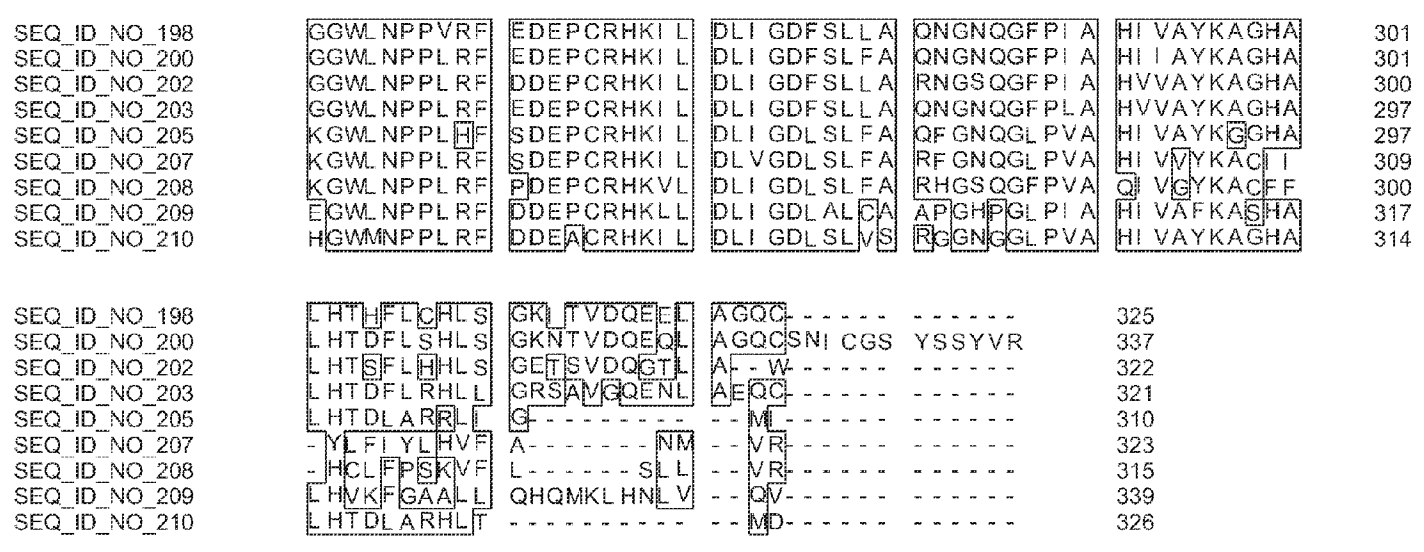

Examples of amino acid sequences of functional homologs of the polypeptide set forth in SEQ ID NO: 198 are provided in FIG. 4 and in the Sequence Listing. Such functional homologs include, for example, CeresAnnot: 8642356 (SEQ ID NO: 200), CeresClone:935672 (SEQ ID NO: 202), GI:115451651 (SEQ ID NO: 203), CeresClone: 553404 (SEQ ID NO: 205), CeresAnnot:1517043 (SEQ ID NO: 207), GI:157339009 (SEQ ID NO: 208), GI:167997651 (SEQ ID NO: 209), GI:186478838 (SEQ ID NO: 210), GI:24308613 (SEQ ID NO: 211), CeresAnnot:1463744 (SEQ ID NO: 213), GI:147769548 (SEQ ID NO: 214), GI:17229762 (SEQ ID NO: 215), GI:75906320 (SEQ ID NO: 216), GI:225148780 (SEQ ID NO: 217), GI:224402519 (SEQ ID NO: 218), GI:170076947 (SEQ ID NO: 219), GI:67924367 (SEQ ID NO: 220), GI:196258900 (SEQ ID NO: 221), GI:186683207 (SEQ ID NO: 222), GI:16329599 (SEQ ID NO: 223), GI:196244340 (SEQ ID NO: 224), GI:166366663 (SEQ ID NO: 225), GI:113476833 (SEQ ID NO: 226), GI:172037292 (SEQ ID NO: 227), GI:22299333 (SEQ ID NO: 228), GI:159027881 (SEQ ID NO: 229), GI:158333778 (SEQ ID NO: 230), GI:86610210 (SEQ ID NO: 231), GI:119491435 (SEQ ID NO: 232), GI:86606600 (SEQ ID NO: 233), GI:119511195 (SEQ ID NO: 234), GI:116073620 (SEQ ID NO: 235), GI:37521434 (SEQ ID NO: 236), GI:113954355 (SEQ ID NO: 237), GI:88807444 (SEQ ID NO: 238), GI:56750622 (SEQ ID NO: 239), GI:87123666 (SEQ ID NO: 240), GI:33865092 (SEQ ID NO: 241), GI:148240294 (SEQ ID NO: 242), GI:116071234 (SEQ ID NO: 243), GI:78213633 (SEQ ID NO: 244), GI:148242917 (SEQ ID NO: 245), GI:159903932 (SEQ ID NO: 246), GI:72382747 (SEQ ID NO: 247), GI:124026469 (SEQ ID NO: 248), GI:87301187 (SEQ ID NO: 249), GI:78184132 (SEQ ID NO: 250), or SEQ ID NO: 251. In some cases, a functional homolog of SEQ ID NO: 198 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 198. In some cases, a functional homolog of SEQ ID NO: 198 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 198 described above or set forth in the Sequence Listing.

Examples of amino acid sequences of functional homologs of the polypeptide set forth in SEQ ID NO: 253 are provided in FIG. 5 and in the Sequence Listing. Such functional homologs include, for example, CeresAnnot: 8680534 (SEQ ID NO: 255), CeresAnnot:1694297 (SEQ ID NO:257), GI:225459251 (SEQ ID NO:258), CeresAnnot: 1443484 (SEQ ID NO:260), GI:225462851 (SEQ ID NO:261), GI:62241065 (SEQ ID NO:262), CeresClone: 1925472 (SEQ ID NO:264), GI:15219870 (SEQ ID NO:265), CeresClone:514069 (SEQ ID NO:267), GI:37993655 (SEQ ID NO:268), GI:157734205 (SEQ ID NO:269), GI:159171968 (SEQ ID NO:270), GI:125541183 (SEQ ID NO:271), GI:115448767 (SEQ ID NO:272), CeresAnnot:8680541 (SEQ ID NO:274), GI:225465718 (SEQ ID NO:275), GI:225459253 (SEQ ID NO:276), GI:225459257 (SEQ ID NO:277), GI:225459268 (SEQ ID NO:278), GI:225459266 (SEQ ID NO:279), CeresAnnot: 1441002 (SEQ ID NO:281), GI:225468662 (SEQ ID NO:282), GI:225459270 (SEQ ID NO:283), CeresAnnot: 1476414 (SEQ ID NO:285), CeresAnnot:1529873 (SEQ ID NO:287), GI:62241067 (SEQ ID NO:288), GI:225468664 (SEQ ID NO:289), GI:225467440 (SEQ ID NO:290), GI:225468668 (SEQ ID NO:291), GI:17065006 (SEQ ID NO:292), CeresAnnot:865380 (SEQ ID NO:294), GI:225468660 (SEQ ID NO:295), GI:19911203 (SEQ ID NO:296), GI:42571589 (SEQ ID NO:297), CeresAnnot: 1503910 (SEQ ID NO:299), CeresClone:1747545 (SEQ ID NO:301), CeresAnnot:1476416 (SEQ ID NO:303), GI:54292902 (SEQ ID NO:304), GI:225465732 (SEQ ID NO:305), CeresAnnot:1456348 (SEQ ID NO:307), CeresClone:1768985 (SEQ ID NO:309), GI:79349376 (SEQ ID NO:310), CeresAnnot:1476405 (SEQ ID NO:312), CeresClone:1597737 (SEQ ID NO:314), CeresClone:1862526 (SEQ ID NO:316), GI:79318336 (SEQ ID NO:317), GI:125541186 (SEQ ID NO:318), CeresClone:624581 (SEQ ID NO:320), GI:15219867 (SEQ ID NO:321), CeresClone:1797125 (SEQ ID NO:323), CeresAnnot:8701197 (SEQ ID NO:325), CeresAnnot:1453378 (SEQ ID NO:327), GI:115457712 (SEQ ID NO:328), GI:125547765 (SEQ ID NO:329), CeresAnnot:1453373 (SEQ ID NO:331), GI:115446887 (SEQ ID NO:332), CeresClone:1492154 (SEQ ID NO:334), GI:125525771 (SEQ ID NO:335), CeresClone:1571410 (SEQ ID NO:337), GI:115334817 (SEQ ID NO:338), GI:133874192 (SEQ ID NO:339), CeresAnnot: 1453383 (SEQ ID NO:341), GI:152149367 (SEQ ID NO:342), CeresClone:791790 (SEQ ID NO:344), GI:125561485 (SEQ ID NO:345), CeresClone:474849 (SEQ ID NO:347), CeresAnnot:1474602 (SEQ ID NO:349), CeresAnnot:8713073 (SEQ ID NO:351), CeresClone: 795726 (SEQ ID NO:353), CeresAnnot:8656770 (SEQ ID NO:355), CeresAnnot:8679871 (SEQ ID NO:357), CeresAnnot:833488 (SEQ ID NO:359), CeresClone:1769061 (SEQ ID NO:361), SEQ ID NO:362, SEQ ID NO:363, SEQ ID NO:364, B8AIT5_ORYSI (SEQ ID NO:365), or SEQ ID NO:366. In some cases, a functional homolog of SEQ ID NO: 253 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 253. In some cases, a functional homolog of SEQ ID NO: 253 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 253 described above or set forth in the Sequence Listing.

Examples of amino acid sequences of functional homologs of the polypeptide set forth in SEQ ID NO: 1541 are provided in FIG. 6 and in the Sequence Listing. Such functional homologs include, for example, GI:194708348 (SEQ ID NO: 1542), CeresAnnot:8636073 (SEQ ID NO:1544), GI:115482024 (SEQ ID NO:1545), CeresClone: 703931 (SEQ ID NO:1547), GI:87240452 (SEQ ID NO:1548), CeresClone:529175 (SEQ ID NO:1550), CeresAnnot:1468685 (SEQ ID NO:1552), GI:116785783 (SEQ ID NO:1553), CeresClone:1832487 (SEQ ID NO:1555), GI:125531919 (SEQ ID NO:1556), GI:147820457 (SEQ ID NO:1557), GI:225435151 (SEQ ID NO:1558), GI:110556116 (SEQ ID NO:1559), CeresAnnot:8723603

(SEQ ID NO:1561), CeresClone:1674549 (SEQ ID NO:1563), GI:125531926 (SEQ ID NO:1564), GI:212721998 (SEQ ID NO:1565), CeresClone:1962414 (SEQ ID NO:1567), GI:115482030 (SEQ ID NO:1568), CeresAnnot:8684516 (SEQ ID NO:1570), GI:115482028 (SEQ ID NO:1571), CeresClone:633976 (SEQ ID NO:1573), CeresAnnot:1488712 (SEQ ID NO:1575), GI:147819531 (SEQ ID NO:1576), or CeresAnnot:8458360 (SEQ ID NO:1578). In some cases, a functional homolog of SEQ ID NO: 1541 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1541. In some cases, a functional homolog of SEQ ID NO: 1541 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1541 described above or set forth in the Sequence Listing.

Figure 7A:
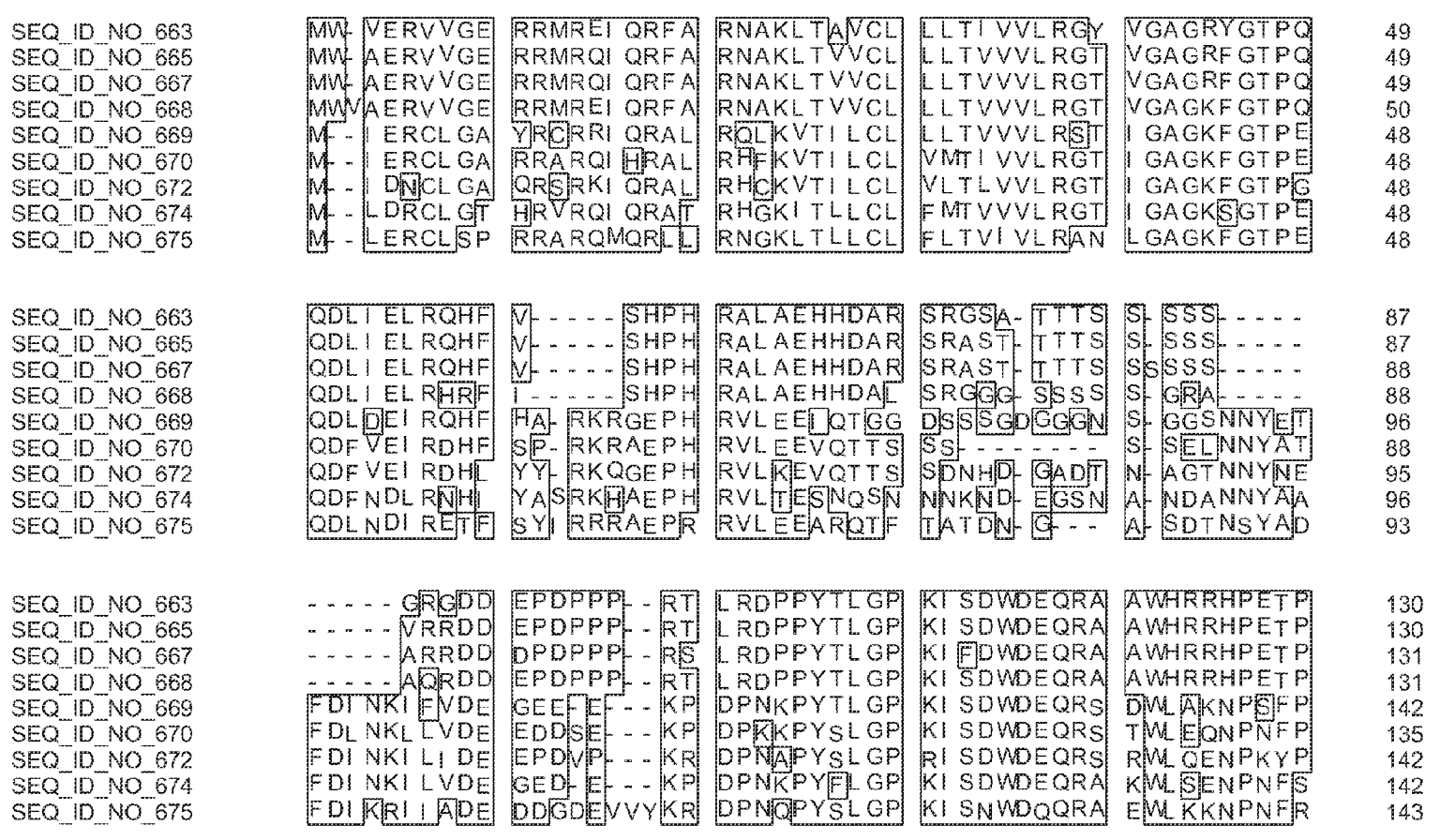

Examples of amino acid sequences of functional homologs of the polypeptide set forth in SEQ ID NO: 663 are provided in FIG. 7 and in the Sequence Listing. Such functional homologs include, for example, CeresAnnot: 8641619 (SEQ ID NO: 665), CeresClone:351171 (SEQ ID NO:667), GI:108707680 (SEQ ID NO:668), GI:18411962 (SEQ ID NO:669), GI:225437312 (SEQ ID NO:670), CeresClone:1928792 (SEQ ID NO:672), CeresAnnot:1481731 (SEQ ID NO:674), GI:190887122 (SEQ ID NO:675), CeresClone:1909588 (SEQ ID NO:677), CeresClone:287316 (SEQ ID NO:679), GI:125543514 (SEQ ID NO:680), GI:3892054 (SEQ ID NO:681), GI:147836354 (SEQ ID NO:682), CeresClone:1948406 (SEQ ID NO:684), GI:157350046 (SEQ ID NO:685), CeresClone:111543 (SEQ ID NO:687), CeresAnnot:1462791 (SEQ ID NO:689), GI:116786926 (SEQ ID NO:690), GI:55956972 (SEQ ID NO:691), GI:225457345 (SEQ ID NO:692), CeresClone: 1883805 (SEQ ID NO:694), GI:147855862 (SEQ ID NO:695), GI:55956986 (SEQ ID NO:696), GI:15221224 (SEQ ID NO:697), GI:55956984 (SEQ ID NO:698), CeresAnnot:881752 (SEQ ID NO:700), GI:55956988 (SEQ ID NO:701), GI:168048546 (SEQ ID NO:702), GI:84794310 (SEQ ID NO:703), GI:115446469 (SEQ ID NO:704), CeresAnnot:8679332 (SEQ ID NO:706), GI:162464392 (SEQ ID NO:707), CeresClone:1814558 (SEQ ID NO:709), GI:168049396 (SEQ ID NO:710), GI:186478616 (SEQ ID NO:711), GI:125535778 (SEQ ID NO:712), GI:168040071 (SEQ ID NO:713), GI:115487346 (SEQ ID NO:714), GI:168005537 (SEQ ID NO:715), GI:125543557 (SEQ ID NO:716), GI:115452571 (SEQ ID NO:717), GI:108707732 (SEQ ID NO:718), CeresAnnot:8715381 (SEQ ID NO:720), CeresAnnot:8658448 (SEQ ID NO:722), CeresAnnot: 8641531 (SEQ ID NO:724), CeresClone:793770 (SEQ ID NO:726), GI:168038797 (SEQ ID NO:727), GI:168034676 (SEQ ID NO:728), CeresAnnot:8641532 (SEQ ID NO:730), GI:168006484 (SEQ ID NO:731), CeresAnnot:8715380 (SEQ ID NO:733), SEQ ID NO:734, C0P7T0 MAIZE (SEQ ID NO:735), SEQ ID NO:736, A7NW49_VITVI (SEQ ID NO:737), Q5TIN5_VITVI (SEQ ID NO:738), or B9RT50_RICCO (SEQ ID NO:739). In some cases, a functional homolog of SEQ ID NO: 663 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 663. In some cases, a functional homolog of SEQ ID NO: 663 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 663 described above or set forth in the Sequence Listing.

Figure 8A:
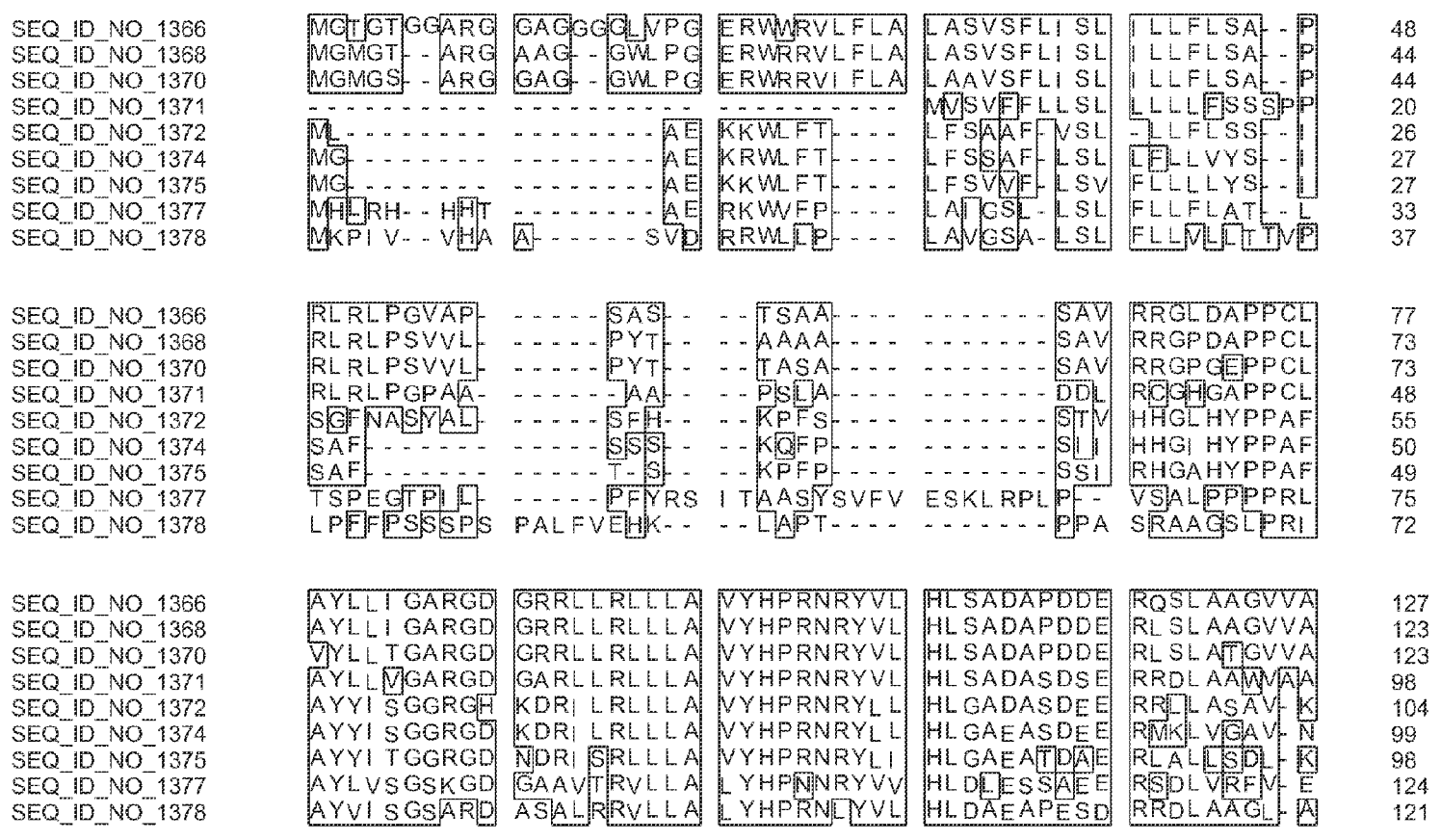
Figure 8B:
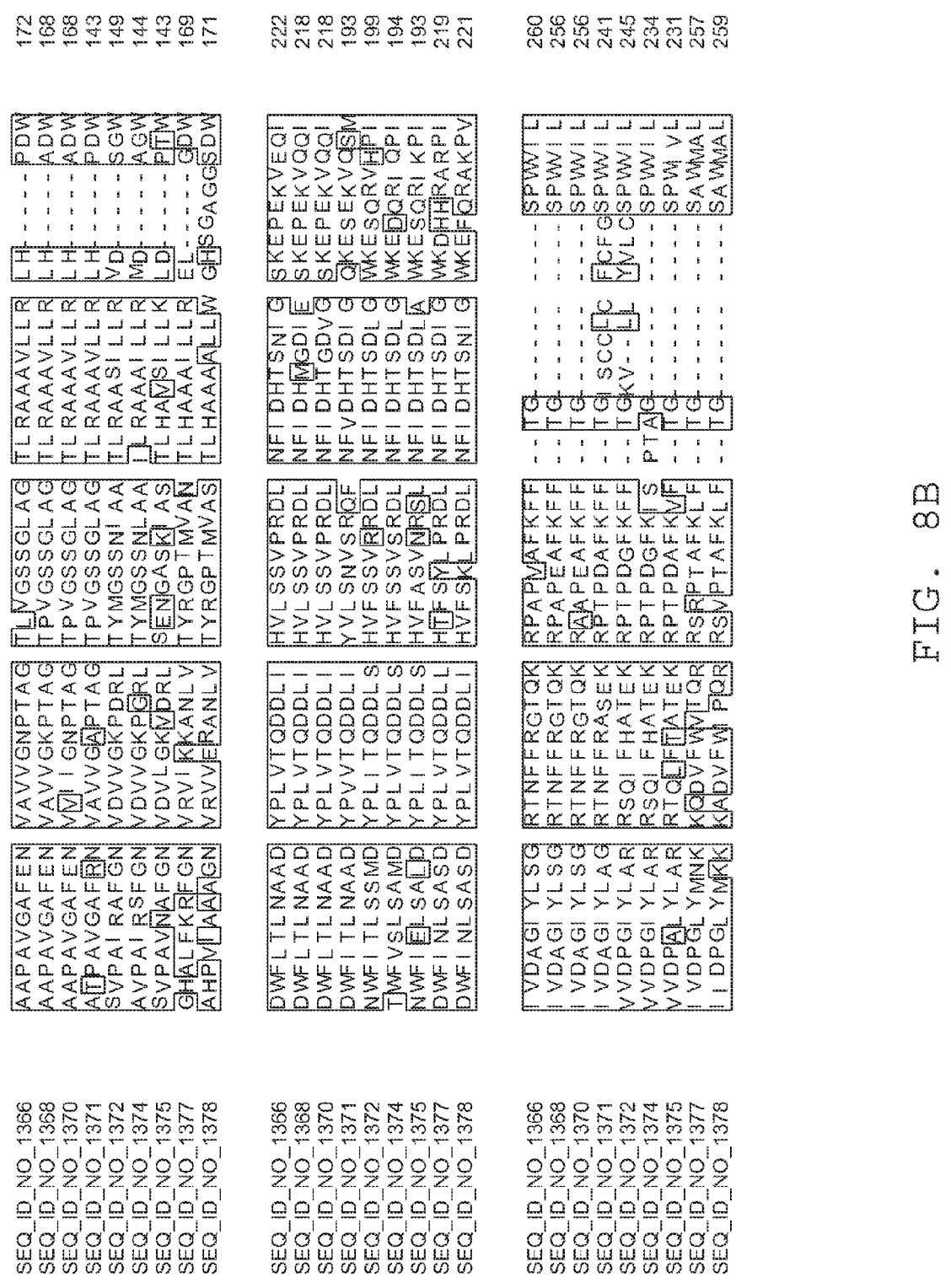

Examples of amino acid sequences of functional homologs of the polypeptide set forth in SEQ ID NO: 1366 are provided in FIG. 8 and in the Sequence Listing. Such functional homologs include, for example, CeresAnnot: 8724997 (SEQ ID NO: 1368), CeresClone:210401 (SEQ ID NO:1370), GI:52353585 (SEQ ID NO:1371), GI:157338893 (SEQ ID NO:1372), CeresAnnot:1517155 (SEQ ID NO:1374), GI:18409754 (SEQ ID NO:1375), CeresClone:479516 (SEQ ID NO:1377), GI:61656778 (SEQ ID NO:1378), GI:13486801 (SEQ ID NO:1379), CeresClone:494392 (SEQ ID NO:1381), CeresAnnot: 8659030 (SEQ ID NO:1383), GI:168060848 (SEQ ID NO:1384), CeresClone:794127 (SEQ ID NO:1386), CeresAnnot:8724191 (SEQ ID NO:1388), GI:15242532 (SEQ ID NO:1389), GI:225452656 (SEQ ID NO:1390), CeresClone:25053 (SEQ ID NO:1392), GI:115489808 (SEQ ID NO:1393), GI:46358506 (SEQ ID NO:1394), GI:55276719 (SEQ ID NO:1395), GI:61656789 (SEQ ID NO:1396), GI:61656799 (SEQ ID NO:1397), CeresClone:1857630 (SEQ ID NO:1399), GI:168052705 (SEQ ID NO:1400), CeresClone:105097 (SEQ ID NO:1402), GI:116786996 (SEQ ID NO:1403), CeresClone:532355 (SEQ ID NO:1405), CeresAnnot:1530144 (SEQ ID NO:1407), GI:225424849 (SEQ ID NO:1408), GI:147787134 (SEQ ID NO:1409), GI:116794047 (SEQ ID NO:1410), CeresClone: 1562166 (SEQ ID NO:1412), GI:168043094 (SEQ ID NO:1413), GI:116308950 (SEQ ID NO:1414), GI:116789207 (SEQ ID NO:1415), GI:115457614 (SEQ ID NO:1416), GI:60657606 (SEQ ID NO:1417), GI:125555973 (SEQ ID NO:1418), CeresClone:508189 (SEQ ID NO:1420), CeresAnnot:1502889 (SEQ ID NO:1422), CeresClone:1808311 (SEQ ID NO:1424), CeresClone:349234 (SEQ ID NO:1426), CeresAnnot:1457604 (SEQ ID NO:1428), CeresAnnot:8743317 (SEQ ID NO:1430), CeresAnnot:1523979 (SEQ ID NO:1432), GI:225433389 (SEQ ID NO:1433), GI:115454715 (SEQ ID NO:1434), GI:157344331 (SEQ ID NO:1435), GI:157342943 (SEQ ID NO:1436), CeresClone:1018703 (SEQ ID NO:1438), CeresAnnot:8643189 (SEQ ID NO:1440), CeresClone:1888533 (SEQ ID NO:1442), GI:118485429 (SEQ ID NO:1443), GI:102139993 (SEQ ID NO:1444), CeresAnnot:863010 (SEQ ID NO:1446), GI:115474761 (SEQ ID NO:1447), CeresAnnot:1438095 (SEQ ID NO:1449), GI:70663986 (SEQ ID NO:1450), CeresAnnot:8633314 (SEQ ID NO:1452), GI:15236287 (SEQ ID NO:1453), GI:108707468 (SEQ ID NO:1454), CeresClone:468692 (SEQ ID NO:1456), GI:225461471 (SEQ ID NO:1457), CeresAnnot:1462238 (SEQ ID NO:1459), GI:15229570 (SEQ ID NO:1460), CeresAnnot: 8641860 (SEQ ID NO:1462), GI:9454535 (SEQ ID NO:1463), CeresClone:1553206 (SEQ ID NO:1465), GI:42567183 (SEQ ID NO:1466), GI:60657604 (SEQ ID NO:1467), GI:157359338 (SEQ ID NO:1468), CeresAnnot: 1520081 (SEQ ID NO:1470), GI:18400725 (SEQ ID NO:1471), CeresAnnot:1523194 (SEQ ID NO:1473), CeresClone:1927095 (SEQ ID NO:1475), CeresClone: 1810164 (SEQ ID NO:1477), GI:115482162 (SEQ ID NO:1478), SEQ ID NO:1479, B8AY55_ORYSI (SEQ ID NO:1480), SEQ ID NO:1481, C7J2B6 ORYSJ (SEQ ID NO:1482), SEQ ID NO:1483, CeresAnnot:8704386 (SEQ ID NO:1485), or CeresAnnot:8657984 (SEQ ID NO:1487). In some cases, a functional homolog of SEQ ID NO: 1366 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1366. In some cases, a functional homolog of SEQ ID NO: 1366 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1366 described above or set forth in the Sequence Listing.

Examples of amino acid sequences of functional homologs of the polypeptide set forth in SEQ ID NO: 928 are provided in FIG. 9 and in the Sequence Listing. Such functional homologs include, for example, CeresAnnot:8640603 (SEQ ID NO: 930), CeresClone:285169 (SEQ ID NO: 932), GI:125586664 (SEQ ID NO: 933), CeresClone:829440 (SEQ ID NO: 935), GI:118488472 (SEQ ID NO: 936), GI:90657534 (SEQ ID NO: 937), GI:225456557 (SEQ ID NO: 938), CeresAnnot:1355066 (SEQ ID NO: 940), GI:38194917 (SEQ ID NO: 941), CeresClone:1237946 (SEQ ID NO: 943), GI:157341292 (SEQ ID NO: 944), GI:115453531 (SEQ ID NO: 945), CeresClone:1804732 (SEQ ID NO: 947), CeresAnnot:8656625 (SEQ ID NO: 949), GI:162462515 (SEQ ID NO: 950), CeresClone:570485 (SEQ ID NO: 952), GI:75133694 (SEQ ID NO: 953), GI:115473243 (SEQ ID NO: 954), GI:125559102 (SEQ ID NO: 955), CeresAnnot:1450186 (SEQ ID NO: 957), GI:125552171 (SEQ ID NO: 958), GI:115463639 (SEQ ID NO: 959), GI:116790012 (SEQ ID NO: 960), GI:38194916 (SEQ ID NO: 961), CeresClone:1806851 (SEQ ID NO: 963), CeresClone:236876 (SEQ ID NO: 965), GI:162459408 (SEQ ID NO: 966), GI:125545759 (SEQ ID NO: 967), GI:225456559 (SEQ ID NO: 968), GI:225451792 (SEQ ID NO: 969), CeresClone:17250 (SEQ ID NO: 971), GI:147780878 (SEQ ID NO: 972), CeresAnnot:1363625 (SEQ ID NO: 974), GI:30090032 (SEQ ID NO: 975), CeresClone:1848658 (SEQ ID NO: 977), GI:224124236 (SEQ ID NO: 978), CeresClone:1546455 (SEQ ID NO: 980), CeresClone:1788775 (SEQ ID NO: 982), CeresAnnot:1450185 (SEQ ID NO: 984), CeresClone:1883580 (SEQ ID NO: 986), CeresAnnot:1809854 (SEQ ID NO: 988), CeresAnnot:8640602 (SEQ ID NO: 990), CeresAnnot:1326475 (SEQ ID NO: 992), CeresClone:98007 (SEQ ID NO: 994), CeresAnnot:1481980 (SEQ ID NO: 996), CeresAnnot:8702104 (SEQ ID NO: 998), CeresAnnot:1297618 (SEQ ID NO: 1000), ACA04978 (SEQ ID NO: 1001), SEQ ID NO: 1002, SEQ ID NO: 1003, XP_002514628 (SEQ ID NO: 1004), XP_002330107 (SEQ ID NO: 1005), SEQ ID NO: 1006, XP_002277911 (SEQ ID NO: 1007), B6E8Y8_9MYRT (SEQ ID NO: 1008), XP_002265282 (SEQ ID NO: 1009), C6T7C7 SOYBN (SEQ ID NO: 1010), SEQ ID NO: 1011, C6T8T2 SOYBN (SEQ ID NO: 1012), XP_002330106 (SEQ ID NO: 1013), or SEQ ID NO: 1014. In some cases, a functional homolog of SEQ ID NO: 928 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 928. In some cases, a functional homolog of SEQ ID NO: 928 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 928 described above or set forth in the Sequence Listing.

Examples of amino acid sequences of functional homologs of the polypeptide set forth in SEQ ID NO: 1215 are provided in FIG. 10 and in the Sequence Listing. Such functional homologs include, for example, CeresAnnot:8679388 (SEQ ID NO: 1217), GI:162460472 (SEQ ID NO:1218), GI:82470028 (SEQ ID NO:1219), GI:158513202 (SEQ ID NO:1220), GI:71153895 (SEQ ID NO:1221), CeresClone:696222 (SEQ ID NO:1223), GI:26986190 (SEQ ID NO:1224), GI:27802647 (SEQ ID NO:1225), GI:18324 (SEQ ID NO:1226), GI:166079160 (SEQ ID NO:1227), GI:157346189 (SEQ ID NO:1228), CeresAnnot:1100195 (SEQ ID NO:1230), GI:551259 (SEQ ID NO:1231), CeresClone:1148635 (SEQ ID NO:1233), GI:115446509 (SEQ ID NO:1234), GI:20196210 (SEQ ID NO:1235), GI:125539762 (SEQ ID NO:1236), GI:82470026 (SEQ ID NO:1237), GI:158563895 (SEQ ID NO:1238), GI:115458296 (SEQ ID NO:1239), GI:33694260 (SEQ ID NO:1240), GI:38346326 (SEQ ID NO:1241), CeresAnnot:8752603 (SEQ ID NO:1243), CeresClone:483472 (SEQ ID NO:1245), CeresAnnot:8752602 (SEQ ID NO:1247), CeresAnnot:8752608 (SEQ ID NO:1249), GI:115458294 (SEQ ID NO:1250), GI:33694264 (SEQ ID NO:1251), GI:38346325 (SEQ ID NO:1252), CeresAnnot:8632838 (SEQ ID NO:1254), GI:162461901 (SEQ ID NO:1255), CeresAnnot:8752594 (SEQ ID NO:1257), GI:3342240 (SEQ ID NO:1258), GI:166079162 (SEQ ID NO:1259), CeresAnnot:1475229 (SEQ ID NO:1261), CeresAnnot:1528678 (SEQ ID NO:1263), GI:2500928 (SEQ ID NO:1264), CeresAnnot:1139380 (SEQ ID NO:1266), GI:2500929 (SEQ ID NO:1267), GI:719270 (SEQ ID NO:1268), GI:16225878 (SEQ ID NO:1269), GI:7162116 (SEQ ID NO:1270), GI:861155 (SEQ ID NO:1271), GI:87240831 (SEQ ID NO:1272), CeresAnnot:1475230 (SEQ ID NO:1274), GI:4886267 (SEQ ID NO:1275), GI:7414364 (SEQ ID NO:1276), CeresAnnot:861091 (SEQ ID NO:1278), CeresClone:118038 (SEQ ID NO:1280), CeresAnnot:8462885 (SEQ ID NO:1282), GI:79314823 (SEQ ID NO:1283), GI:33636090 (SEQ ID NO:1284), GI:3152880 (SEQ ID NO:1285), GI:4205115 (SEQ ID NO:1286), CeresClone:1789943 (SEQ ID NO:1288), GI:21322514 (SEQ ID NO:1289), CeresAnnot:867594 (SEQ ID NO:1291), GI:2500930 (SEQ ID NO:1292), GI:2597853 (SEQ ID NO:1293), GI:53127612 (SEQ ID NO:1294), GI:70780260 (SEQ ID NO:1295), GI:112383512 (SEQ ID NO:1296), GI:38141533 (SEQ ID NO:1297), GI:18072861 (SEQ ID NO:1298), GI:160625677 (SEQ ID NO:1299), GI:13940209 (SEQ ID NO:1300), GI:160625675 (SEQ ID NO:1301), GI:4127662 (SEQ ID NO:1302), GI:13940211 (SEQ ID NO:1303), GI:162793818 (SEQ ID NO:1304), SEQ ID NO:1305, SEQ ID NO:1306, SEQ ID NO:1307, SEQ ID NO:1308, B7ZZM5_MAIZE (SEQ ID NO:1309), SEQ ID NO:1310, SEQ ID NO:1311, SEQ ID NO:1312, SEQ ID NO:1313, -SEQ ID NO:1314, SEQ ID NO:1315, SEQ ID NO:1316, SEQ ID NO:1317, SEQ ID NO:1318, SEQ ID NO:1319, AAF06991 (SEQ ID NO:1320), SEQ ID NO:1321, SEQ ID NO:1322, SEQ ID NO:1323, AAF06992 (SEQ ID NO:1324), AAD02510 (SEQ ID NO:1325), B6U1H5_MAIZE (SEQ ID NO:1326), CAH67363 (SEQ ID NO:1327), SEQ ID NO:1328, SEQ ID NO:1329, C6JS51_SORBI (SEQ ID NO:1330), or SEQ ID NO:1331. In some cases, a functional homolog of SEQ ID NO: 1215 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1215. In some cases, a functional homolog of SEQ ID NO: 1215 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1215 described above or set forth in the Sequence Listing.

Examples of amino acid sequences of functional homologs of the polypeptide set forth in SEQ ID NO: 4 are provided in FIG. 11 and in the Sequence Listing. Such functional homologs include, for example, CeresAnnot: 8682811 (SEQ ID NO: 6), GI:115483997 (SEQ ID NO: 7), GI:119507455 (SEQ ID NO: 8), GI:33151175 (SEQ ID NO: 9), CeresAnnot:1506572 (SEQ ID NO: 11), CeresClone: 549408 (SEQ ID NO: 13), GI:157313302 (SEQ ID NO: 14), GI:157072586 (SEQ ID NO: 15), CeresClone:1786359 (SEQ ID NO: 17), GI:13398412 (SEQ ID NO: 18), Ceres-Clone:1789981 (SEQ ID NO: 20), GI:116310992 (SEQ ID NO: 21), GI:38347003 (SEQ ID NO: 22), GI:115484005 (SEQ ID NO: 23), GI:37777015 (SEQ ID NO: 24), GI:116739148 (SEQ ID NO: 25), GI:157072584 (SEQ ID NO: 26), GI:37777013 (SEQ ID NO: 27), CeresAnnot: 556941 (SEQ ID NO: 29), CeresAnnot:1453426 (SEQ ID NO: 31), GI:225440254 (SEQ ID NO: 32), GI:22327075 (SEQ ID NO: 33), CeresAnnot:1528070 (SEQ ID NO: 35), GI:22324432 (SEQ ID NO: 36), CeresAnnot:8657414 (SEQ ID NO: 38), GI:108707861 (SEQ ID NO: 39), GI:50507838 (SEQ ID NO: 40), GI:168060089 (SEQ ID NO: 41), ACN33779 (SEQ ID NO: 42), SEQ ID NO: 43, ACN34313 (SEQ ID NO: 44), SEQ ID NO: 45, NP_001066062 (SEQ ID NO: 46), SEQ ID NO: 47, SEQ ID NO: 48, B9SCF3_RICCO (SEQ ID NO: 49), C9EA44_CARPA (SEQ ID NO: 50), or B9IHH9_POPTR (SEQ ID NO: 51). In some cases, a functional homolog of SEQ ID NO: 4 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 4. In some cases, a functional homolog of SEQ ID NO: 4 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 4 described above or set forth in the Sequence Listing.

Examples of amino acid sequences of functional homologs of the polypeptide set forth in SEQ ID NO: 580 are provided in FIG. 12 and in the Sequence Listing. Such functional homologs include, for example, CeresClone: 100919106 (SEQ ID NO: 582), CeresAnnot:8656883 (SEQ ID NO:584), GI:115473539 (SEQ ID NO:585), CeresClone: 632946 (SEQ ID NO:587), CeresAnnot:1511794 (SEQ ID NO:589), CeresClone:661231 (SEQ ID NO:591), GI:225452883 (SEQ ID NO:592), CeresAnnot:865775 (SEQ ID NO:594), GI:116781949 (SEQ ID NO:595), GI:124360246 (SEQ ID NO:596), CeresClone:241236 (SEQ ID NO:598), CeresClone:100923096 (SEQ ID NO:600), GI:125601197 (SEQ ID NO:601), CeresAnnot: 8640957 (SEQ ID NO:603), GI:115453237 (SEQ ID NO:604), CeresClone:373329 (SEQ ID NO:606), GI:118489897 (SEQ ID NO:607), GI:224112183 (SEQ ID NO:608), CeresClone:117183 (SEQ ID NO:610), GI:147853846 (SEQ ID NO:611), CeresClone:646035 (SEQ ID NO:613), CeresAnnot:1476847 (SEQ ID NO:615), CeresAnnot:864422 (SEQ ID NO:617), CeresAnnot: 1517733 (SEQ ID NO:619), CeresClone:125621 (SEQ ID NO:621), CeresAnnot:868892 (SEQ ID NO:623), Ceres-Clone:1363654 (SEQ ID NO:625), GI:168026300 (SEQ ID NO:626), CeresAnnot:873900 (SEQ ID NO:628), GI:168059834 (SEQ ID NO:629), SEQ ID NO:630, SEQ ID NO:631, or SEQ ID NO:632. In some cases, a functional homolog of SEQ ID NO: 580 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 580. In some cases, a functional homolog of SEQ ID NO: 580 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 580 described above or set forth in the Sequence Listing.

Figure 13B:
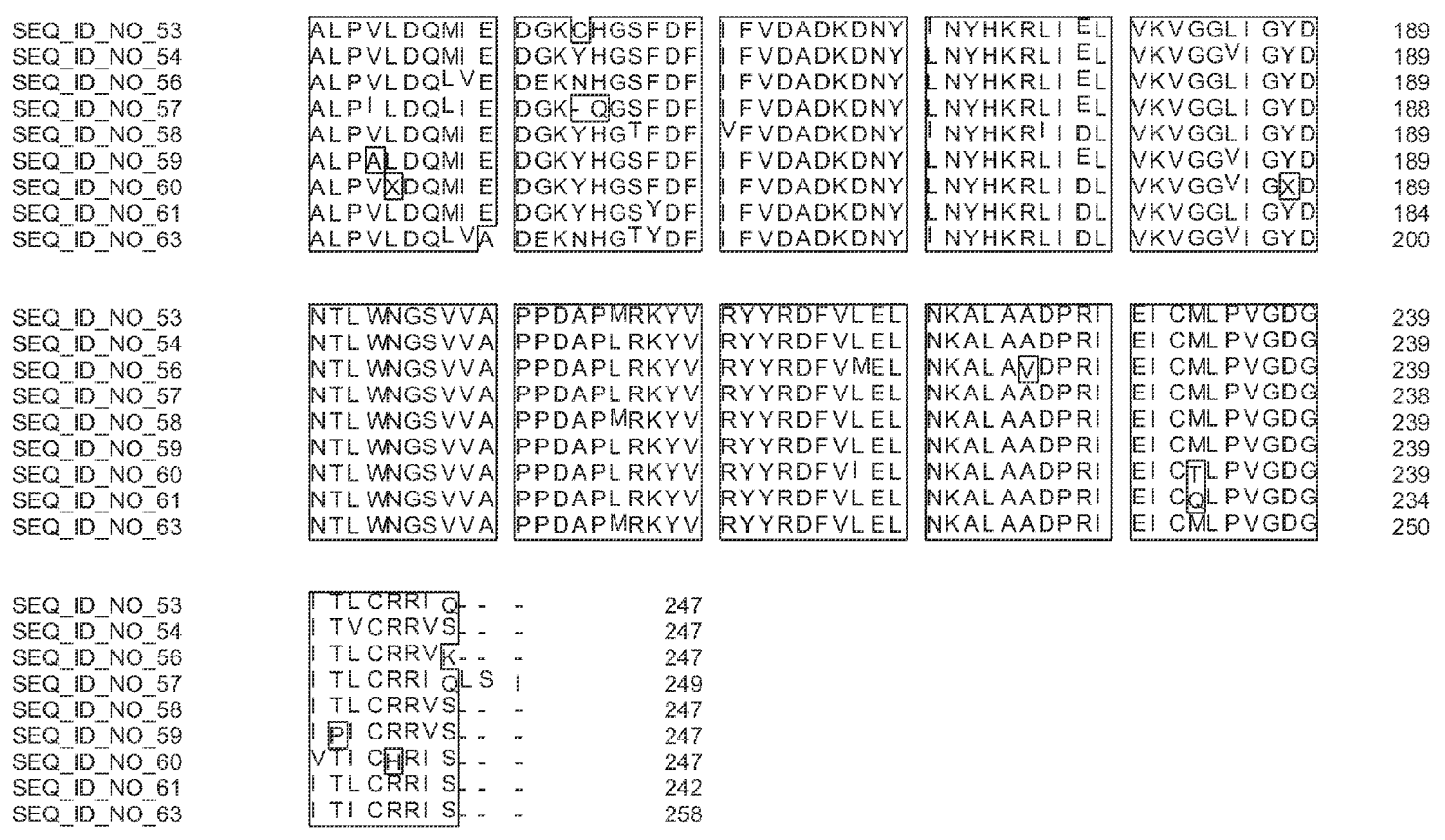

Examples of amino acid sequences of functional homologs of the polypeptide set forth in SEQ ID NO: 53 are provided in FIG. 13 and in the Sequence Listing. Such functional homologs include, for example, GI:47680455 (SEQ ID NO:54), CeresClone:1843515 (SEQ ID NO: 56), GI:3023419 (SEQ ID NO: 57), GI:82941443 (SEQ ID NO: 58), GI:55724835 (SEQ ID NO: 59), GI:167613943 (SEQ ID NO: 60), GI:30580349 (SEQ ID NO: 61), CeresClone: 1365873 (SEQ ID NO: 63), GI:3023436 (SEQ ID NO: 64), GI:190710715 (SEQ ID NO: 65), GI:13249171 (SEQ ID NO: 66), GI:119655556 (SEQ ID NO: 67), CeresAnnot: 1441117 (SEQ ID NO: 69), GI:3023437 (SEQ ID NO: 70), CeresClone:100036370 (SEQ ID NO: 72), GI:225428851 (SEQ ID NO: 73), GI:91771911 (SEQ ID NO: 74), GI:74053616 (SEQ ID NO: 75), GI:105671415 (SEQ ID NO: 76), CeresClone:8049 (SEQ ID NO: 78), CeresClone: 541352 (SEQ ID NO: 80), GI:40795556 (SEQ ID NO: 81), GI:30580341 (SEQ ID NO: 82), GI:193290676 (SEQ ID NO: 83), CeresAnnot:8454550 (SEQ ID NO: 85), GI:21595512 (SEQ ID NO: 86), CeresAnnot:8454548 (SEQ ID NO: 88), GI:30580343 (SEQ ID NO: 89), GI:30580381 (SEQ ID NO: 90), GI:30580324 (SEQ ID NO: 91), Ceres-Clone:1605906 (SEQ ID NO: 93), GI:30580325 (SEQ ID NO: 94), GI:115559 (SEQ ID NO: 95), GI:68271859 (SEQ ID NO: 96), GI:48093469 (SEQ ID NO: 97), CeresAnnot: 8454545 (SEQ ID NO: 99), GI:157863689 (SEQ ID NO: 100), GI:30580342 (SEQ ID NO: 101), GI:116780030 (SEQ ID NO: 102), GI:115466622 (SEQ ID NO: 103), CeresAnnot:8735228 (SEQ ID NO: 105), CeresClone:1281422 (SEQ ID NO: 107), CeresClone:239406 (SEQ ID NO: 109), GI:30580380 (SEQ ID NO: 110), CeresClone:100834883 (SEQ ID NO: 112), GI:32347427 (SEQ ID NO: 113), CeresClone:558470 (SEQ ID NO: 115), CeresClone:320643 (SEQ ID NO: 117), CeresClone:786185 (SEQ ID NO: 119), ABK94003 (SEQ ID NO: 120), SEQ ID NO: 121, SEQ ID NO: 122, SEQ ID NO: 123, SEQ ID NO: 124, ACJ38669 (SEQ ID NO: 125), SEQ ID NO: 126, CAN72492 (SEQ ID NO: 127), XP_002282867 (SEQ ID NO: 128), SEQ ID NO: 129, XP_002518739 (SEQ ID NO: 130), ACJ84500 (SEQ ID NO: 131), BAG71894 (SEQ ID NO: 132), SEQ ID NO: 133, ACY66929 (SEQ ID NO: 134), B5LZY1_LINUS (SEQ ID NO: 135), ACX37696 (SEQ ID NO: 136), BAG71889 (SEQ ID NO: 137), A9QWL5_9FABA (SEQ ID NO: 138), B6F0U5 CARTI (SEQ ID NO: 139), ABB89956 (SEQ ID NO: 140), BAG71891 (SEQ ID NO: 141), BAG71893 (SEQ ID NO: 142), A0S6W2_9CONI (SEQ ID NO: 143), BAG71892 (SEQ ID NO: 144), ABO26812 (SEQ ID NO: 145), ACY66930 (SEQ ID NO: 146), ACX37697 (SEQ ID NO: 147), SEQ ID NO: 148, A2Y9Q8_ORYSI (SEQ ID NO: 149), SEQ ID NO: 150, SEQ ID NO: 151, or SEQ ID NO: 152. In some cases, a functional homolog of SEQ ID NO: 53 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 53. In some cases, a functional homolog of SEQ ID NO: 53 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 53 described above or set forth in the Sequence Listing.

Examples of amino acid sequences of functional homologs of the polypeptide set forth in SEQ ID NO: 1112 are provided in FIG. 14 and in the Sequence Listing. Such functional homologs include, for example, CeresAnnot: 8721881 (SEQ ID NO: 1114), GI:115488672 (SEQ ID NO:1115), GI:62132631 (SEQ ID NO:1116), CeresClone: 1820645 (SEQ ID NO:1118), CeresClone:522963 (SEQ ID NO:1120), GI:11120557 (SEQ ID NO:1121), GI:33309870 (SEQ ID NO:1122), GI:154551049 (SEQ ID NO:1123), CeresAnnot:8656632 (SEQ ID NO:1125), CeresClone: 246416 (SEQ ID NO:1127), GI:115473253 (SEQ ID NO:1128), GI:115455399 (SEQ ID NO:1129), GI:6175371 (SEQ ID NO:1130), GI:158517760 (SEQ ID NO:1131), CeresClone:1815457 (SEQ ID NO:1133), GI:7592642 (SEQ ID NO:1134), CeresClone:100955082 (SEQ ID NO:1136), GI:6606070 (SEQ ID NO:1137), CeresClone: 1908817 (SEQ ID NO:1139), GI:33309864 (SEQ ID NO:1140), GI:158954871 (SEQ ID NO:1141), GI:30090030 (SEQ ID NO:1142), GI:58422998 (SEQ ID NO:1143), GI:224118942 (SEQ ID NO:1144), GI:58422996 (SEQ ID NO:1145), CeresClone:1757409 (SEQ ID NO:1147), GI:30721847 (SEQ ID NO:1148), GI:39843110 (SEQ ID NO:1149), GI:58866601 (SEQ ID NO:1150), GI:95981882 (SEQ ID NO:1151), GI:31712055 (SEQ ID NO:1152), GI:110164923 (SEQ ID NO:1153), GI:3688589 (SEQ ID NO:1154), GI:4204232 (SEQ ID NO:1155), GI:194500619 (SEQ ID NO:1156), CeresClone:1793949 (SEQ ID NO:1158), GI:28630953 (SEQ ID NO:1159), GI:162458731 (SEQ ID NO:1160), GI:39843112 (SEQ ID NO:1161), CeresClone:257029 (SEQ ID NO:1163), CeresClone: 100883955 (SEQ ID NO:1165), GI:9367313 (SEQ ID NO:1166), GI:95981890 (SEQ ID NO:1167), GI:148540534 (SEQ ID NO:1168), GI:78127315 (SEQ ID NO:1169), GI:3947985 (SEQ ID NO:1170), GI:28630955 (SEQ ID NO:1171), GI:4204234 (SEQ ID NO:1172), GI:157674589 (SEQ ID NO:1173), GI:63094571 (SEQ ID NO:1174), GI:33342030 (SEQ ID NO:1175), GI:225423412 (SEQ ID NO:1176), GI:110164939 (SEQ ID NO:1177), GI:78127313 (SEQ ID NO:1178), CeresAnnot:8643934 (SEQ ID NO:1180), GI:196166890 (SEQ ID NO:1181), GI:9367309 (SEQ ID NO:1182), GI:6467974 (SEQ ID NO:1183), GI:89152252 (SEQ ID NO:1184), GI:22091473 (SEQ ID NO:1185), GI:6634708 (SEQ ID NO:1186), GI:1483232 (SEQ ID NO:1187), GI:33391153 (SEQ ID NO:1188), CeresClone:467075 (SEQ ID NO:1190), GI:5070142 (SEQ ID NO:1191), CeresClone:480529 (SEQ ID NO:1193), GI:27373049 (SEQ ID NO:1194), GI:197244651 (SEQ ID NO:1195), GI:60100338 (SEQ ID NO:1196), GI:14518447 (SEQ ID NO:1197), GI:16052 (SEQ ID NO:1198), GI:4102111 (SEQ ID NO:1199), GI:3913001 (SEQ ID NO:1200), GI:82734203 (SEQ ID NO:1201), GI:106636058 (SEQ ID NO:1202), CeresAnnot:857111 (SEQ ID NO:1204), GI:16549085 (SEQ ID NO:1205), GI:602908 (SEQ ID NO:1206), GI:6606306 (SEQ ID NO:1207), CeresClone:25591 (SEQ ID NO:1209), GI:73537279 (SEQ ID NO:1210), SEQ ID NO:1211, SEQ ID NO:1212, or ACN33552 (SEQ ID NO:1213). In some cases, a functional homolog of SEQ ID NO: 1112 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1112. In some cases, a functional homolog of SEQ ID NO: 1112 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1112 described above or set forth in the Sequence Listing.

Figure 15:
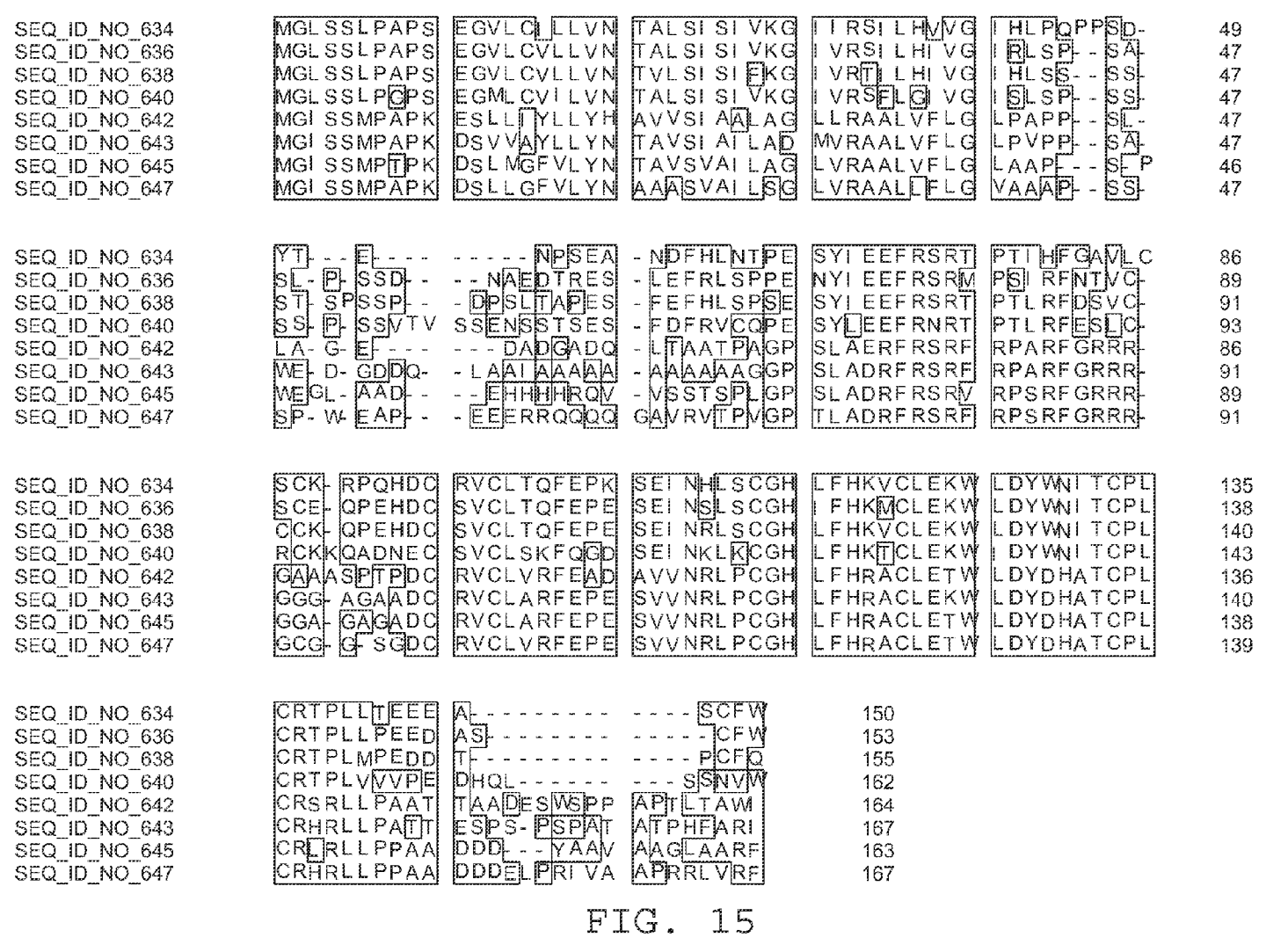

Examples of amino acid sequences of functional homologs of the polypeptide set forth in SEQ ID NO: 634 are provided in FIG. 15 and in the Sequence Listing. Such functional homologs include, for example, CeresAnnot: 1525600 (SEQ ID NO: 636), CeresClone:473509 (SEQ ID NO: 638), CeresAnnot:550729 (SEQ ID NO: 640), CeresClone:633470 (SEQ ID NO: 642), GI:115477050 (SEQ ID NO: 643), CeresClone:1790901 (SEQ ID NO: 645), CeresAnnot:8714668 (SEQ ID NO: 647), CeresClone:1808334 (SEQ ID NO: 649), CeresAnnot:1472192 (SEQ ID NO: 651), CeresClone:1662527 (SEQ ID NO: 653), CeresClone: 952050 (SEQ ID NO: 655), CeresClone:1460088 (SEQ ID NO: 657), CeresClone:1816723 (SEQ ID NO: 659), or CeresClone:374439 (SEQ ID NO: 661). In some cases, a functional homolog of SEQ ID NO: 634 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 634. In some cases, a functional homolog of SEQ ID NO: 634 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 634 described above or set forth in the Sequence Listing.

Figure 16C:
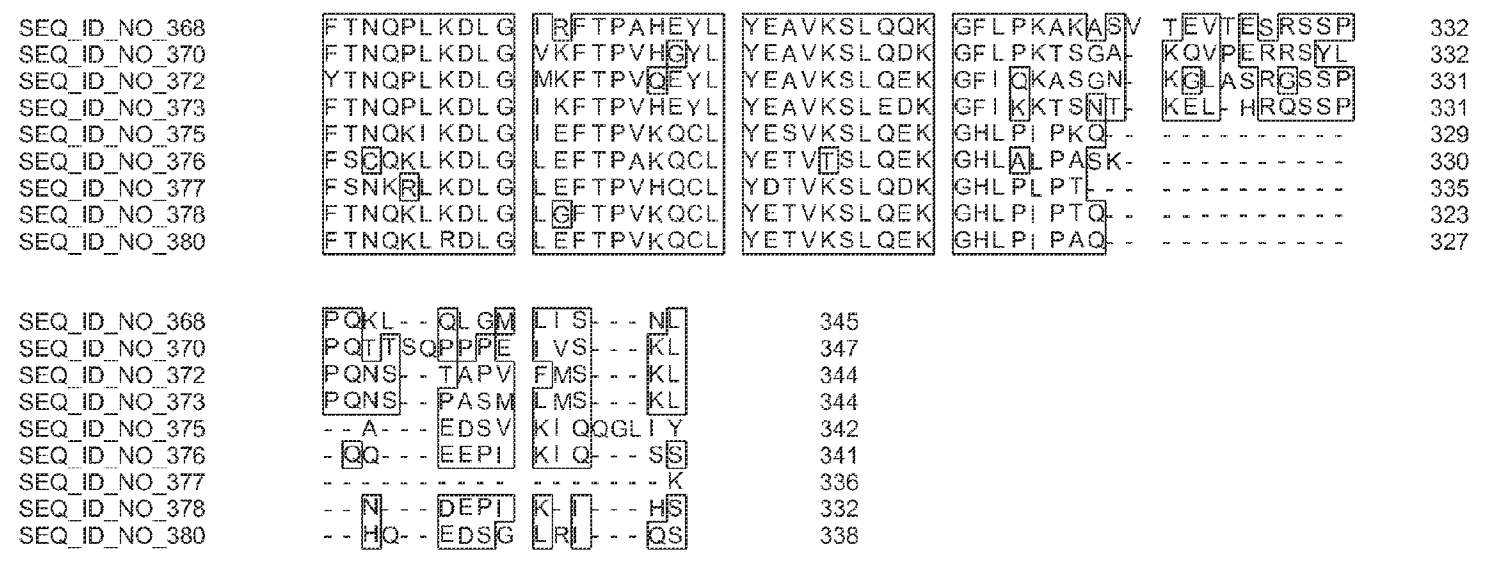

Examples of amino acid sequences of functional homologs of the polypeptide set forth in SEQ ID NO: 368 are provided in FIG. 16 and in the Sequence Listing. Such functional homologs include, for example, CeresClone: 1583304 (SEQ ID NO: 370), CeresClone:703342 (SEQ ID NO: 372), GI:115444625 (SEQ ID NO: 373), CeresAnnot: 1490808 (SEQ ID NO: 375), GI:57282092 (SEQ ID NO: 376), GI:115501961 (SEQ ID NO: 377), GI:25140434 (SEQ ID NO: 378), CeresClone:1895447 (SEQ ID NO: 380), CeresClone:2023103 (SEQ ID NO: 382), GI:28544965 (SEQ ID NO: 383), GI:59805044 (SEQ ID NO: 384), GI:28544959 (SEQ ID NO: 385), GI:125562805 (SEQ ID NO: 386), GI:115478030 (SEQ ID NO: 387), CeresClone: 1821848 (SEQ ID NO: 389), CeresAnnot:1483675 (SEQ ID NO: 391), CeresAnnot:1483663 (SEQ ID NO: 393), CeresAnnot:1448084 (SEQ ID NO: 395), GI:190710713 (SEQ ID NO: 396), CeresClone:1602920 (SEQ ID NO: 398), GI:40233135 (SEQ ID NO: 399), GI:2960364 (SEQ ID NO: 400), GI:25140432 (SEQ ID NO: 401), GI:65306614 (SEQ ID NO: 402), GI:9964087 (SEQ ID NO: 403), GI:2058311 (SEQ ID NO: 404), CeresClone:1243741 (SEQ ID NO: 406), GI:50345916 (SEQ ID NO: 407), GI:170285663 (SEQ ID NO: 408), GI:7239228 (SEQ ID NO: 409), GI:225465530 (SEQ ID NO: 410), GI:25989515 (SEQ ID NO: 411), GI:90902167 (SEQ ID NO: 412), GI:3341511 (SEQ ID NO: 413), GI:50345922 (SEQ ID NO: 414), CeresClone:475958 (SEQ ID NO: 416), CeresAnnot: 1437997 (SEQ ID NO: 418), CeresClone:1724312 (SEQ ID NO: 420), GI:10304406 (SEQ ID NO: 421), CeresClone: 1993306 (SEQ ID NO: 423), CeresAnnot:1255335 (SEQ ID NO: 425), CeresClone:1819180 (SEQ ID NO: 427), CeresClone:238838 (SEQ ID NO: 429), CeresClone:1039956 (SEQ ID NO: 431), CeresClone:705402 (SEQ ID NO: 433), CeresClone:1115220 (SEQ ID NO: 435), CeresAnnot: 8713261 (SEQ ID NO: 437), CeresClone:100960981 (SEQ ID NO: 439), CeresClone:1823576 (SEQ ID NO: 441), CeresClone:34141 (SEQ ID NO: 443), CeresClone:32255

(SEQ ID NO: 445), CeresClone:785059 (SEQ ID NO: 447), CeresClone:763048 (SEQ ID NO: 449), CeresAnnot: 8735461 (SEQ ID NO: 451), CeresAnnot:1483659 (SEQ ID NO: 453), CeresAnnot:8682158 (SEQ ID NO: 455), CeresClone:1996254 (SEQ ID NO: 457), CeresAnnot:8682157 (SEQ ID NO: 459), CeresAnnot:1224770 (SEQ ID NO: 461), CeresClone:100877847 (SEQ ID NO: 463), CeresClone:2023344 CeresAnnot:8659462 (SEQ ID NO: 465), CeresAnnot:8659462 (SEQ ID NO: 467), CeresClone: 1804701 (SEQ ID NO: 469), CeresClone:100056656 (SEQ ID NO: 471), CeresClone:1823484 (SEQ ID NO: 473), CeresAnnot:8659864 (SEQ ID NO: 475), CeresClone: 1780698 (SEQ ID NO: 477), CeresClone:218097 (SEQ ID NO: 479), CeresClone:6748 (SEQ ID NO: 481), CeresClone:703077 (SEQ ID NO: 483), CeresAnnot:1514866 (SEQ ID NO: 485), CeresClone:297597 (SEQ ID NO: 487), CeresAnnot:8673965 (SEQ ID NO: 489), CeresClone: 626124 (SEQ ID NO: 491), CeresClone:1724968 (SEQ ID NO: 493), CeresAnnot:8743556 (SEQ ID NO: 495), CeresClone:1850477 (SEQ ID NO: 497), ACZ74586 (SEQ ID NO: 498), ACZ74585 (SEQ ID NO: 499), ACZ74587 (SEQ ID NO: 500), C5XWV7 SORBI (SEQ ID NO: 501), or ACG45043 (SEQ ID NO: 502). In some cases, a functional homolog of SEQ ID NO: 368 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 368. In some cases, a functional homolog of SEQ ID NO: 368 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 368 described above or set forth in the Sequence Listing.

Examples of amino acid sequences of functional homologs of the polypeptide set forth in SEQ ID NO: 1599 are provided in FIG. 17 and in the Sequence Listing. Such functional homologs include, for example, GI:212275438 (SEQ ID NO: 1600), CeresAnnot:8655553 (SEQ ID NO: 1602), GI:37729658 (SEQ ID NO: 1603), GI:158705664 (SEQ ID NO: 1604), GI:115480571 (SEQ ID NO: 1605), GI:6136111 (SEQ ID NO: 1606), CeresClone:604729 (SEQ ID NO: 1608), GI:12585489 (SEQ ID NO: 1609), GI:82659609 (SEQ ID NO: 1610), GI:136739 (SEQ ID NO: 1611), GI:1388021 (SEQ ID NO: 1612), GI:192338746 (SEQ ID NO: 1613), CeresClone:1924295 (SEQ ID NO: 1615), GI:225431563 (SEQ ID NO: 1616), CeresClone: 220954 (SEQ ID NO: 1618), GI:88866516 (SEQ ID NO: 1619), GI:115443819 (SEQ ID NO: 1620), GI:7417426 (SEQ ID NO: 1621), GI:21599 (SEQ ID NO: 1622), GI:32527831 (SEQ ID NO: 1623), GI:28863909 (SEQ ID NO: 1624), GI:17026394 (SEQ ID NO: 1625), GI:90820120 (SEQ ID NO: 1626), CeresClone:577563 (SEQ ID NO: 1628), GI:6136112 (SEQ ID NO: 1629), CeresClone: 713920 (SEQ ID NO: 1631), CeresClone:1926174 (SEQ ID NO: 1633), GI:12585472 (SEQ ID NO: 1634), CeresAnnot: 1487348 (SEQ ID NO: 1636), GI:15228498 (SEQ ID NO: 1637), CeresClone:256780 (SEQ ID NO: 1639), GI:13605559 (SEQ ID NO: 1640), GI:76160958 (SEQ ID NO: 1641), GI:148887793 (SEQ ID NO: 1642), GI:116787113 (SEQ ID NO: 1643), CeresAnnot:8671040 (SEQ ID NO: 1645), GI:168057301 (SEQ ID NO: 1646), GI:19911799 (SEQ ID NO: 1647), GI:168014649 (SEQ ID NO: 1648), GI:19911797 (SEQ ID NO: 1649), GI:220682974 (SEQ ID NO: 1650), GI:224814363 (SEQ ID NO: 1651), GI:4140688 (SEQ ID NO: 1652), GI:71023003 (SEQ ID NO: 1653), GI:47086583 (SEQ ID NO: 1654), GI:58264886 (SEQ ID NO: 1655), GI:213513005 (SEQ ID NO: 1656), GI:148235435 (SEQ ID NO: 1657), GI:126304392 (SEQ ID NO: 1658), GI:19343890 (SEQ ID NO: 1659), GI:73969769 (SEQ ID NO: 1660), GI:53130600 (SEQ ID NO: 1661), GI:6136108 (SEQ ID NO: 1662), GI:109103119 (SEQ ID NO: 1663), GI:169846774 (SEQ ID NO: 1664), GI:67078526 (SEQ ID NO: 1665), GI:449441 (SEQ ID NO: 1666), GI:50292841 (SEQ ID NO: 1667), GI:149727538 (SEQ ID NO: 1668), GI:148234947 (SEQ ID NO: 1669), GI:41386780 (SEQ ID NO: 1670), GI:194374183 (SEQ ID NO: 1671), GI:6322815 (SEQ ID NO: 1672), GI:45383884 (SEQ ID NO: 1673), GI:7415873 (SEQ ID NO: 1674), GI:48255968 (SEQ ID NO: 1675), GI:156543768 (SEQ ID NO: 1676), GI:149238918 (SEQ ID NO: 1677), GI:197098334 (SEQ ID NO: 1678), GI:72006253 (SEQ ID NO: 1679), GI:47522786 (SEQ ID NO: 1680), GI:157775599 (SEQ ID NO: 1681), GI:68491920 (SEQ ID NO: 1682), GI:156848676 (SEQ ID NO: 1683), GI:73969767 (SEQ ID NO: 1684), GI:17554108 (SEQ ID NO: 1685), GI:189208247 (SEQ ID NO: 1686), GI:116181760 (SEQ ID NO: 1687), GI:196014839 (SEQ ID NO: 1688), GI:50312377 (SEQ ID NO: 1689), GI:46107282 (SEQ ID NO: 1690), GI:50427861 (SEQ ID NO: 1691), GI:19075632 (SEQ ID NO: 1692), GI:171696094 (SEQ ID NO: 1693), GI:150863853 (SEQ ID NO: 1694), GI:156405246 (SEQ ID NO: 1695), GI:157110519 (SEQ ID NO: 1696), GI:145613451 (SEQ ID NO: 1697), GI:170097792 (SEQ ID NO: 1698), GI:169613428 (SEQ ID NO: 1699), GI:154301169 (SEQ ID NO: 1700), GI:164427705 (SEQ ID NO: 1701), GI:66816096 (SEQ ID NO: 1702), GI:156057023 (SEQ ID NO: 1703), GI:66536233 (SEQ ID NO: 1704), GI:195442796 (SEQ ID NO: 1705), GI:119188835 (SEQ ID NO: 1706), GI:195377136 (SEQ ID NO: 1707), GI:118795048 (SEQ ID NO: 1708), GI:154279628 (SEQ ID NO: 1709), GI:194751331 (SEQ ID NO: 1710), GI:195126913 (SEQ ID NO: 1711), GI:62484278 (SEQ ID NO: 1712), GI:195490906 (SEQ ID NO: 1713), GI:50543038 (SEQ ID NO: 1714), GI:195015057 (SEQ ID NO: 1715), GI:195173943 (SEQ ID NO: 1716), GI:194867745 (SEQ ID NO: 1717), GI:170039309 (SEQ ID NO: 1718), GI:167536224 (SEQ ID NO: 1719), GI:111144847 (SEQ ID NO: 1720), GI:111144907 (SEQ ID NO: 1721), GI:111144899 (SEQ ID NO: 1722), GI:170589920 (SEQ ID NO: 1723), GI:109103123 (SEQ ID NO: 1724), GI:119489040 (SEQ ID NO: 1725), GI:169781996 (SEQ ID NO: 1726), GI:121709268 (SEQ ID NO: 1727), GI:70982442 (SEQ ID NO: 1728), GI:145245828 (SEQ ID NO: 1729), GI:193713936 (SEQ ID NO: 1730), GI:170098292 (SEQ ID NO: 1731), SEQ ID NO: 1732, SEQ ID NO: 1733, SEQ ID NO: 1734, SEQ ID NO: 1735, SEQ ID NO: 1736, SEQ ID NO: 1737, SEQ ID NO: 1738, or SEQ ID NO: 1739. In some cases, a functional homolog of SEQ ID NO: 1599 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1599. In some cases, a functional homolog of SEQ ID NO: 1599 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1599 described above or set forth in the Sequence Listing.

Examples of amino acid sequences of functional homologs of the polypeptide set forth in SEQ ID NO: 154 are provided in FIG. 18 and in the Sequence Listing. Such functional homologs include, for example, CeresAnnot: 8701724 (SEQ ID NO: 156), CeresClone:1531656 (SEQ ID NO: 158), GI:115456900 (SEQ ID NO: 159), CeresClone: 869980 (SEQ ID NO: 161), CeresClone:1739862 (SEQ ID NO: 163), CeresAnnot:1452831 (SEQ ID NO: 165), CeresClone:1123182 (SEQ ID NO: 167), GI:225427800 (SEQ ID NO: 168), CeresClone:1649408 (SEQ ID NO: 170), CeresAnnot:1442596 (SEQ ID NO: 172), CeresClone: 100011527 (SEQ ID NO: 174), CeresClone:1347664 (SEQ ID NO: 176), CeresClone:679875 (SEQ ID NO: 178), CeresClone:1606594 (SEQ ID NO: 180), SEQ ID NO: 181, ACG30817 (SEQ ID NO: 182), ACG26737 (SEQ ID NO: 183), ABK92849 (SEQ ID NO: 184), or XP_002305470 (SEQ ID NO: 185). In some cases, a functional homolog of SEQ ID NO: 154 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 154. In some cases, a functional homolog of SEQ ID NO: 154 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 154 described above or set forth in the Sequence Listing.

Figure 19:
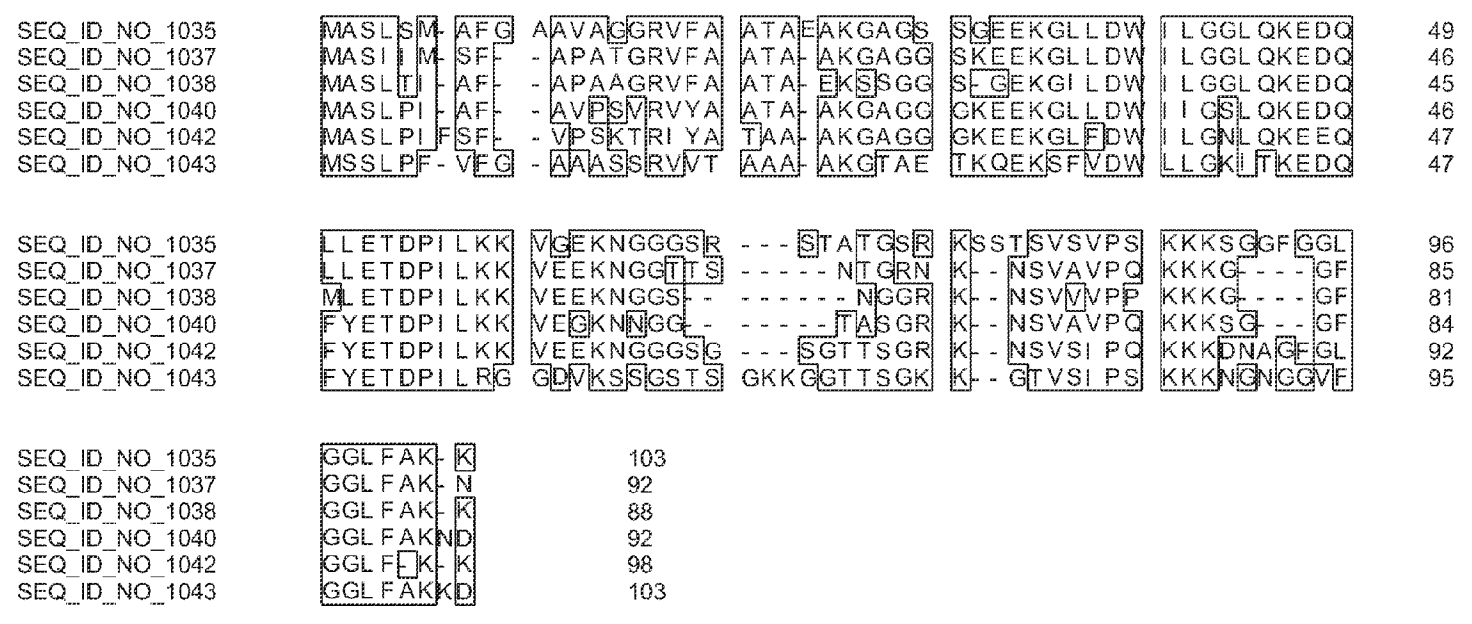

Examples of amino acid sequences of functional homologs of the polypeptide set forth in SEQ ID NO: 1035 are provided in FIG. 19 and in the Sequence Listing. Such functional homologs include, for example, CeresClone: 1660759 (SEQ ID NO: 1037), GI:225434658 (SEQ ID NO: 1038), CeresAnnot:1439822 (SEQ ID NO: 1040), CeresClone:1808650 (SEQ ID NO: 1042), GI:27529048 (SEQ ID NO: 1043), CeresClone:1743842 (SEQ ID NO: 1045), CeresClone:560309 (SEQ ID NO: 1047), CeresAnnot: 1461680 (SEQ ID NO: 1049), CeresClone:1853867 (SEQ ID NO: 1051), CeresClone:1087882 (SEQ ID NO: 1053), CeresClone:1108470 (SEQ ID NO: 1055), CeresClone: 1605553 (SEQ ID NO: 1057), CeresClone:25829 (SEQ ID NO: 1059), CeresClone:958635 (SEQ ID NO: 1061), SEQ ID NO: 1062, or B9SHY8_RICCO (SEQ ID NO: 1063). In some cases, a functional homolog of SEQ ID NO: 1035 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1035. In some cases, a functional homolog of SEQ ID NO: 1035 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1035 described above or set forth in the Sequence Listing.

Examples of amino acid sequences of functional homologs of the polypeptide set forth in SEQ ID NO: 741 are provided in FIG. 20 and in the Sequence Listing. Such functional homologs include, for example, CeresClone: 1515957 (SEQ ID NO: 743), CeresAnnot:8734086 (SEQ ID NO: 745), GI:125553354 (SEQ ID NO: 746), CeresClone: 1785379 (SEQ ID NO: 748), CeresAnnot:1460824 (SEQ ID NO: 750), CeresClone:638126 (SEQ ID NO: 752), CeresAnnot:850366 (SEQ ID NO: 754), CeresClone:2034321 (SEQ ID NO: 756), CeresAnnot:8667941 (SEQ ID NO: 758), CeresClone:100965215 (SEQ ID NO: 760), GI:125527154 (SEQ ID NO: 761), GI:115471859 (SEQ ID NO: 762), GI:125558161 (SEQ ID NO: 763), GI:55773837 (SEQ ID NO: 764), CeresClone:1722230 (SEQ ID NO: 766), CeresAnnot:1487827 (SEQ ID NO: 768), CeresClone: 1910072 (SEQ ID NO: 770), CeresClone:143475 (SEQ ID NO: 772), CeresAnnot:1514100 (SEQ ID NO: 774), CeresClone:1069222 (SEQ ID NO: 776), CeresAnnot:1510450 (SEQ ID NO: 778), CeresClone:100068619 (SEQ ID NO: 780), CeresAnnot:8734211 (SEQ ID NO: 782), CeresAnnot: 8456508 (SEQ ID NO: 784), GI:225428460 (SEQ ID NO: 785), CeresClone:100067803 (SEQ ID NO: 787), CeresAnnot:1450327 (SEQ ID NO: 789), CeresClone:1787372 (SEQ ID NO: 791), CeresAnnot:1457249 (SEQ ID NO: 793), GI:7981380 (SEQ ID NO: 794), GI:147767321 (SEQ ID NO: 795), CeresClone:1916884 (SEQ ID NO: 797), CeresClone:1775942 (SEQ ID NO: 799), CeresClone:1761808 (SEQ ID NO: 801), CeresClone:1914387 (SEQ ID NO: 803), CeresAnnot:8734209 (SEQ ID NO: 805), GI:225428458 (SEQ ID NO: 806), CeresClone:1847251 (SEQ ID NO: 808), CeresClone:477814 (SEQ ID NO: 810), CeresAnnot:543794 (SEQ ID NO: 812), CeresAnnot: 1679467 (SEQ ID NO: 814), CeresClone:1523182 (SEQ ID NO: 816), CeresAnnot:1495620 (SEQ ID NO: 818), GI:118137433 (SEQ ID NO: 819), GI:5091605 (SEQ ID NO: 820), CeresAnnot:838426 (SEQ ID NO: 822), GI:110931736 (SEQ ID NO: 823), GI:125553458 (SEQ ID NO: 824), CeresClone:1113584 (SEQ ID NO: 826), CeresClone:857342 (SEQ ID NO: 828), CeresAnnot:827713 (SEQ ID NO: 830), CeresClone:331755 (SEQ ID NO: 832), CeresClone:1723374 (SEQ ID NO: 834), CeresClone: 1785685 (SEQ ID NO: 836), CeresClone:1927753 (SEQ ID NO: 838), GI:112292438 (SEQ ID NO: 839), GI:116830269 (SEQ ID NO: 840), CeresClone:100002959 (SEQ ID NO: 842), GI:112292440 (SEQ ID NO: 843), CeresClone:41695 (SEQ ID NO: 845), GI:124264312 (SEQ ID NO: 846), GI:115438765 (SEQ ID NO: 847) or CeresAnnot:1445878 (SEQ ID NO: 849). In some cases, a functional homolog of SEQ ID NO: 741 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 741. In some cases, a functional homolog of SEQ ID NO: 741 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 741 described above or set forth in the Sequence Listing.

Examples of amino acid sequences of functional homologs of the polypeptide set forth in SEQ ID NO: 187 are provided in FIG. 21 and in the Sequence Listing. Such functional homologs include, for example, GI:115480375 (SEQ ID NO: 188), CeresClone:632248 (SEQ ID NO: 190), CeresAnnot:8657298 (SEQ ID NO: 192), GI:194703722 (SEQ ID NO: 193), GI:125564503 (SEQ ID NO: 194), or CeresClone:313499 (SEQ ID NO: 196). In some cases, a functional homolog of SEQ ID NO: 187 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 187. In some cases, a functional homolog of SEQ ID NO: 187 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 187 described above or set forth in the Sequence Listing.

Examples of amino acid sequences of functional homologs of the polypeptide set forth in SEQ ID NO: 1065 are provided in FIG. 22 and in the Sequence Listing. Such functional homologs include, for example, CeresClone: 467508 (SEQ ID NO: 1067), CeresClone:1942871 (SEQ ID NO: 1069), GI:157347478 (SEQ ID NO: 1070), CeresAnnot:1528800 (SEQ ID NO: 1072), GI:54306075 (SEQ ID NO: 1073), CeresAnnot:8724651 (SEQ ID NO: 1075), GI:194696788 (SEQ ID NO: 1076), CeresClone:1792902 (SEQ ID NO: 1078), GI:7413581 (SEQ ID NO: 1079), GI:15232741 (SEQ ID NO: 1080), CeresAnnot:1484880 (SEQ ID NO: 1082), GI:147809623 (SEQ ID NO: 1083), CeresAnnot:1475350 (SEQ ID NO: 1085), CeresClone:1886384 (SEQ ID NO: 1087), CeresAnnot:1465047 (SEQ ID NO: 1089), CeresClone:228069 (SEQ ID NO: 1091), CeresClone:1806867 (SEQ ID NO: 1093), CeresClone:1897134 (SEQ ID NO: 1095), GI:157344055 (SEQ ID NO: 1096), CeresClone:1727738 (SEQ ID NO: 1098), CeresClone:1919901 (SEQ ID NO: 1100), GI:15231175 (SEQ ID NO: 1101), CeresClone:1747444 (SEQ ID NO: 1103), CeresClone:2034697 (SEQ ID NO: 1105), GI:194702278 (SEQ ID NO: 1106), CeresAnnot:8669409 (SEQ ID NO: 1108), or CeresAnnot:1161946 (SEQ ID NO: 1110). In some cases, a functional homolog of SEQ ID NO: 1065 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1065. In some cases, a functional homolog of SEQ ID NO: 1065 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1065 described above or set forth in the Sequence Listing.

Examples of amino acid sequences of functional homologs of the polypeptide set forth in SEQ ID NO: 1592 are provided in FIG. 23 and in the Sequence Listing. Such functional homologs include, for example, Ceres Annot 1298824 (SEQ ID NO:1580), CeresAnnot:1463921 (SEQ ID NO: 1582), GI:157338847 (SEQ ID NO: 1583), CeresAnnot:8458737 (SEQ ID NO: 1585), CeresAnnot:8682232 (SEQ ID NO: 1587), CeresClone:846036 (SEQ ID NO: 1589), GI:6899651 (SEQ ID NO: 1590), GI:147787084 (SEQ ID NO: 1593), CeresClone:13741 (SEQ ID NO: 1595), CeresClone:147816 (SEQ ID NO: 1597), CeresAnnot:1463921 (SEQ ID NO:2604), GI:297737772 (SEQ ID NO:2605), GI:255570659 (SEQ ID NO:2606), GI:225424081 (SEQ ID NO:2607), GI:147787084 (SEQ ID NO:2608), GI:297814362 (SEQ ID NO: 2609), GI:115449665 (SEQ ID NO:2610), GI:226509392 (SEQ ID NO:2611), CeresClone:846036 (SEQ ID NO:2613), CeresClone:1791455 (SEQ ID NO:2615), CeresAnnot:8682232 (SEQ ID NO:2617), CeresClone:846036 (SEQ ID NO:2619), GI:238014206 (SEQ ID NO:2620), SoyY23_accession (SEQ ID N:2621), GI:297849932 (SEQ ID NO:2622), and GI:224108407 (SEQ ID NO:2623). In some cases, a functional homolog of SEQ ID NO: 1592 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1592. In some cases, a functional homolog of SEQ ID NO: 1592 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1592 described above or set forth in the Sequence Listing.

Figure 24A:
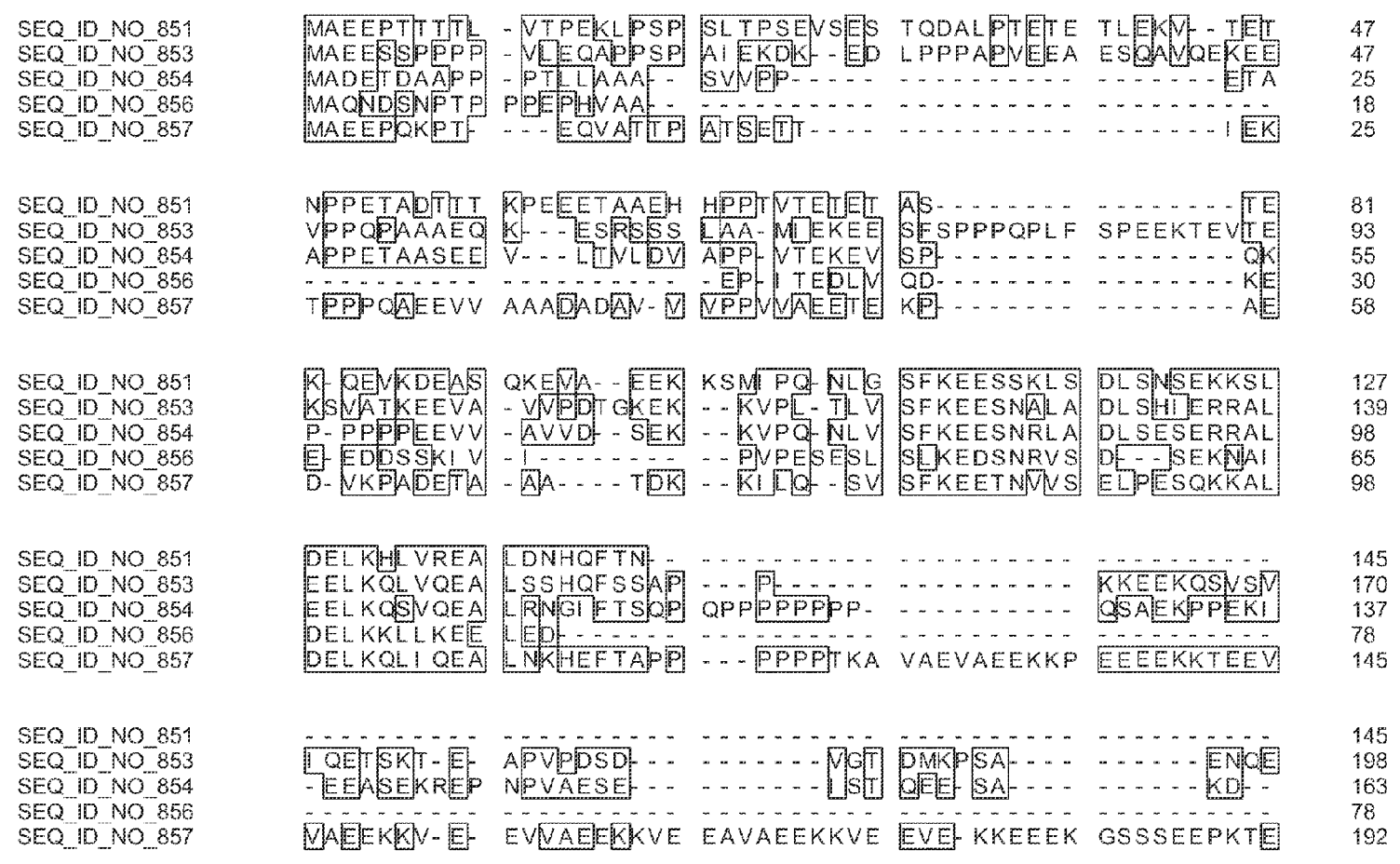

Examples of amino acid sequences of functional homologs of the polypeptide set forth in SEQ ID NO: 851 are provided in FIG. 24 and in the Sequence Listing. Such functional homologs include, for example, CeresAnnot: 1486825 (SEQ ID NO: 853), GI:147859031 (SEQ ID NO: 854), CeresClone:524404 (SEQ ID NO: 856), GI:84453208 (SEQ ID NO: 857), GI:30680992 (SEQ ID NO: 858), CeresClone:1152744 (SEQ ID NO: 860), CeresAnnot:1479687 (SEQ ID NO: 862), GI:7267559 (SEQ ID NO: 863), CeresAnnot:1532284 (SEQ ID NO: 865), GI:157357696 (SEQ ID NO: 866), CeresAnnot:1480239 (SEQ ID NO: 868), CeresAnnot:1486823 (SEQ ID NO: 870), GI:82469976 (SEQ ID NO: 871), GI:225460394 (SEQ ID NO: 872), GI:212275574 (SEQ ID NO: 873), CeresClone:846541 (SEQ ID NO: 875), GI:147859032 (SEQ ID NO: 876), GI:125528559 (SEQ ID NO: 877), GI:115441357 (SEQ ID NO: 878), CeresClone:325220 (SEQ ID NO: 880), GI:115464035 (SEQ ID NO: 881), GI:225444143 (SEQ ID NO: 882), CeresAnnot:544140 (SEQ ID NO: 884), GI:125572823 (SEQ ID NO: 885), GI:147864826 (SEQ ID NO: 886), CeresAnnot:8692801 (SEQ ID NO: 888), CeresAnnot:869188 (SEQ ID NO: 890), CeresAnnot:8456541 (SEQ ID NO: 892), GI:147801354 (SEQ ID NO: 893), CeresAnnot:1442146 (SEQ ID NO: 895), CeresClone:1838310 (SEQ ID NO: 897), CeresAnnot:866220 (SEQ ID NO: 899), GI:225439560 (SEQ ID NO: 900), CeresClone:1209913 (SEQ ID NO: 902), GI:115469468 (SEQ ID NO: 903), CeresClone:1727755 (SEQ ID NO: 905), CeresClone:240809 (SEQ ID NO: 907), CeresClone:1769321 (SEQ ID NO: 909), CeresClone:704211 (SEQ ID NO: 911), GI:115463311 (SEQ ID NO: 912), GI:125551906 (SEQ ID NO: 913), CeresClone:1868378 (SEQ ID NO: 915), CeresClone:1812513 (SEQ ID NO: 917), CeresClone:209421 (SEQ ID NO: 919), CeresAnnot:8730934 (SEQ ID NO: 921), CeresAnnot:1452687 (SEQ ID NO: 923), CeresClone:351936 (SEQ ID NO: 925), or SEQ ID NO: 926. In some cases, a functional homolog of SEQ ID NO: 851 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 851. In some cases, a functional homolog of SEQ ID NO: 851 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 851 described above or set forth in the Sequence Listing.

Figure 25A:
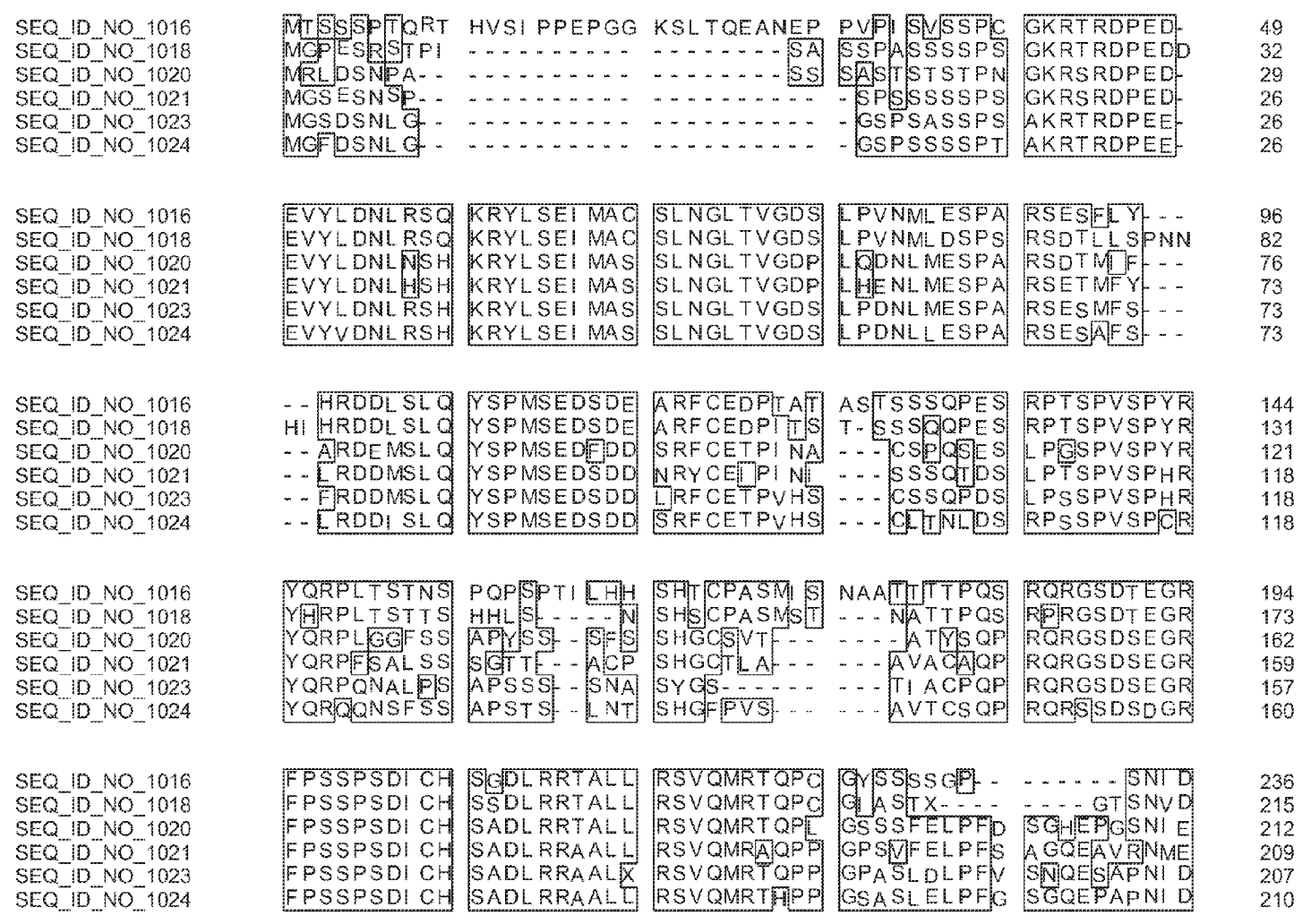

Examples of amino acid sequences of functional homologs of the polypeptide set forth in SEQ ID NO: 1016 are provided in FIG. 25 and in the Sequence Listing. Such functional homologs include, for example, CeresClone:949027 (SEQ ID NO: 1018), CeresAnnot:1471603 (SEQ ID NO: 1020), GI:225437511 (SEQ ID NO: 1021), CeresClone:527044 (SEQ ID NO: 1023), GI:61611694 (SEQ ID NO: 1024), CeresClone:1343264 (SEQ ID NO: 1026), GI:118482768 (SEQ ID NO: 1027), CeresAnnot:1497745 (SEQ ID NO: 1029), GI:147783944 (SEQ ID NO: 1030), CeresAnnot:1444766 (SEQ ID NO: 1032), GI:118485088 (SEQ ID NO: 1033), GI:29782568 (SEQ ID NO:2578), GI:255548507 (SEQ ID NO:2579), CeresClone:226231 (SEQ ID NO:2581), CeresAnnot:8725117 (SEQ ID NO:2583), GI:115462191 (SEQ ID NO:2584), GI:218196129 (SEQ ID NO:2585), CeresClone:779610 (SEQ ID NO:2587), and GI:294463836 (SEQ ID NO:2588). In some cases, a functional homolog of SEQ ID NO: 1016 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1016. In some cases, a functional homolog of SEQ ID NO: 1016 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1016 described above or set forth in the Sequence Listing.

Figure 26:
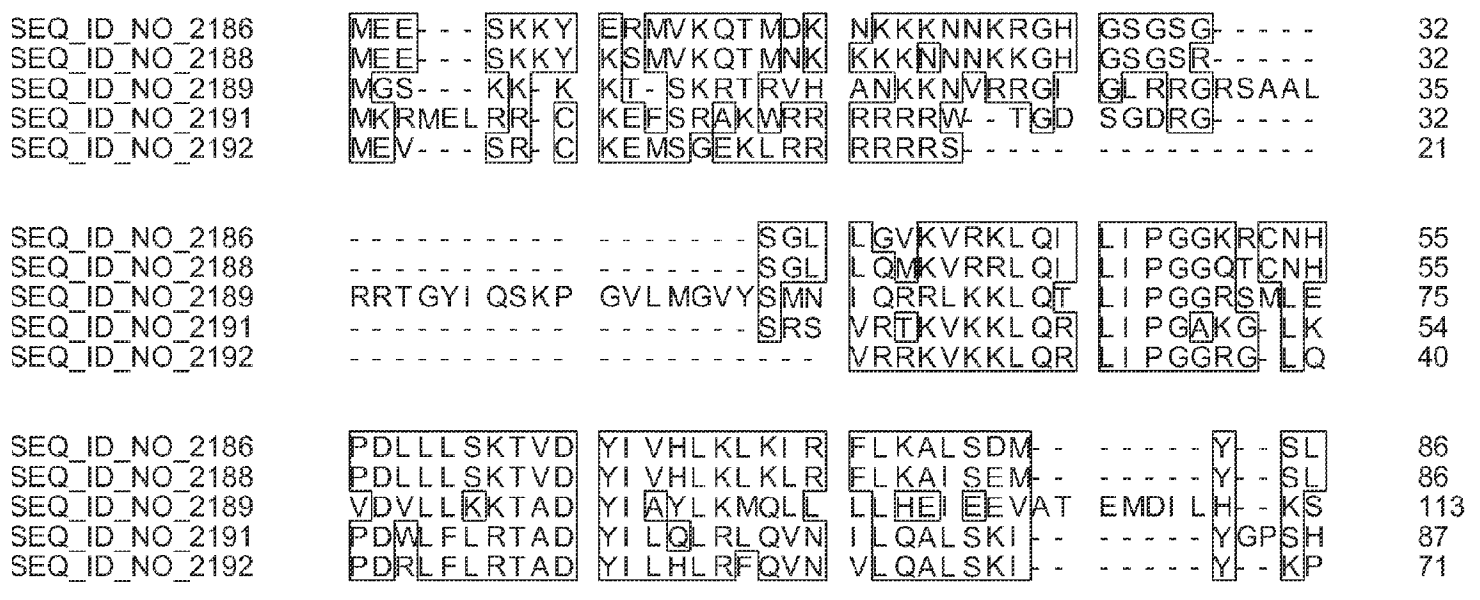

Examples of amino acid sequences of functional homologs of the polypeptide set forth in SEQ ID NO: 2186 are provided in FIG. 26 and in the Sequence Listing. Such functional homologs include, for example, CeresClone: 260808 (SEQ ID NO: 2188), CeresAnnot:1471 GI:116786056 (SEQ ID NO: 2189), CeresClone:1916112 (SEQ ID NO:2191), GI:225424709 (SEQ ID NO: 2192), GI:238478596 (SEQ ID NO: 2193), and GI:255560021 (SEQ ID NO: 2194). In some cases, a functional homolog of SEQ ID NO: 2186 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2186. In some cases, a functional homolog of SEQ ID NO: 2186 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 2186 described above or set forth in the Sequence Listing.

Examples of amino acid sequences of functional homologs of the polypeptide set forth in SEQ ID NO: 1955 are provided in FIG. 27 and in the Sequence Listing. Such functional homologs include, for example, GI:147810484 (SEQ ID NO: 1956), GI:37051125 (SEQ ID NO: 1957), GI:112363376 (SEQ ID NO: 1958), CeresAnnot:1702519 (SEQ ID NO: 1960), CeresClone:286416 (SEQ ID NO: 1962), CeresAnnot:8702387 (SEQ ID NO: 1964), CeresClone:1951902 (SEQ ID NO: 1966), GI:113205234 (SEQ ID NO: 1967), GI:5689615 (SEQ ID NO: 1968), CeresClone:1107598 (SEQ ID NO: 1970), CeresClone:543840 (SEQ ID NO: 1972), GI:6092016 (SEQ ID NO: 1973), GI:20372847 (SEQ ID NO: 1974), GI:20372895 (SEQ ID NO: 1975), GI:38344272 (SEQ ID NO: 1976), and CeresClone:738478 (SEQ ID NO: 1978). In some cases, a functional homolog of SEQ ID NO: 1955 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1955. In some cases, a functional homolog of SEQ ID NO: 1955 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1955 described above or set forth in the Sequence Listing.

Figure 28:
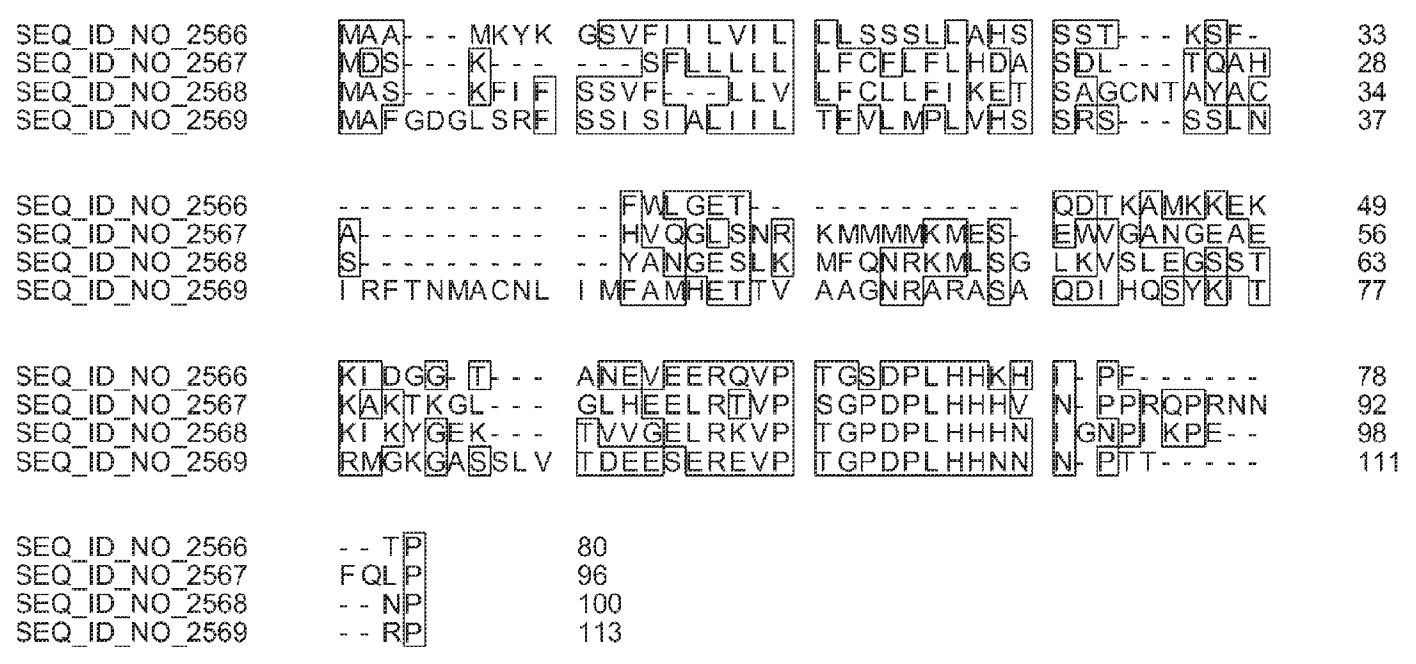

Examples of amino acid sequences of functional homologs of the polypeptide set forth in SEQ ID NO: 2566 are provided in FIG. 28 and in the Sequence Listing. Such functional homologs include, for example, GI:84028190 (SEQ ID NO:2567), GI:124359888 (SEQ ID NO:2568), GI:224057515 (SEQ ID NO:2569), GI:255544778 (SEQ ID NO:2570), GI:4680323 (SEQ ID NO:2571), GI:5306272 (SEQ ID NO:2572), GI:42570935 (SEQ ID NO:2573), CeresAnnot:860028 (SEQ ID NO:2575), EE521385_Brassica (SEQ ID NO:2576), DY002473_Brassica (SEQ ID NO:2577), and GI:297811417 (SEQ ID NO:2591). In some cases, a functional homolog of SEQ ID NO: 2566 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2566. In some cases, a functional homolog of SEQ ID NO: 2566 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 2566 described above or set forth in the Sequence Listing.

Examples of amino acid sequences of functional homologs of the polypeptide set forth in SEQ ID NO: 2150 are provided in FIG. 29 and in the Sequence Listing. Such functional homologs include, for example, CeresAnnot: 1534418 (SEQ ID NO:2152), CeresClone:1045493 (SEQ ID NO:2154), GI:193237559 (SEQ ID NO:2155), CeresClone: 1811618 (SEQ ID NO:2157), CeresAnnot:8671739 (SEQ ID NO:2159), GI:212723754 (SEQ ID NO:2160), GI:115445455 (SEQ ID NO:2161), CeresClone:616810 (SEQ ID NO:2163), CeresAnnot:1480933 (SEQ ID NO:2165), GI:113367184 (SEQ ID NO:2166), CeresClone: 657501 (SEQ ID NO:2168), CeresClone:1902421 (SEQ ID NO:2170), CeresClone:1812854 (SEQ ID NO:2172), GI:13365772 (SEQ ID NO:2173), GI:49388982 (SEQ ID NO:2174), GI:113367144 (SEQ ID NO:2175), CeresAnnot: 8743947 (SEQ ID NO:2177), CeresClone:1810791 (SEQ ID NO:2179), CeresClone:297691 (SEQ ID NO:2181), CeresClone:775677 (SEQ ID NO:2183), and GI:115469364 (SEQ ID NO:2184). In some cases, a functional homolog of SEQ ID NO: 2150 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2150. In some cases, a functional homolog of SEQ ID NO: 2150 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 2150 described above or set forth in the Sequence Listing.

Examples of amino acid sequences of functional homologs of the polypeptide set forth in SEQ ID NO: 2196 are provided in FIG. 30 and in the Sequence Listing. Such functional homologs include, for example, GI:11066960 (SEQ ID NO:2197), CeresAnnot:1462983 (SEQ ID NO:2199), GI:10637893 (SEQ ID NO:2200), GI:121485994 (SEQ ID NO:2201), GI:147805516 (SEQ ID NO:2202), CeresAnnot:8463421 (SEQ ID NO:2204), CeresClone:1854329 (SEQ ID NO:2206), GI:50428339 (SEQ ID NO:2207), GI:226508974 (SEQ ID NO:2208), CeresAnnot:8701853 (SEQ ID NO:2210), GI:15705368 (SEQ ID NO:2211), GI:38684027 (SEQ ID NO:2212), CeresClone:1789833 (SEQ ID NO:2214), GI:15230090 (SEQ ID NO:2215), CeresAnnot:877376 (SEQ ID NO:2217), GI:10952510 (SEQ ID NO:2218), GI:225433318 (SEQ ID NO:2219), GI:57283313 (SEQ ID NO:2220), CeresAnnot:1478997 (SEQ ID NO:2222), CeresAnnot:1445817 (SEQ ID NO:2224), GI:31322044 (SEQ ID NO:2225), GI:15235398 (SEQ ID NO:2226), CeresAnnot:8462622 (SEQ ID NO:2228), CeresAnnot:1445818 (SEQ ID NO:2230), GI:22001520 (SEQ ID NO:2231), GI:46409004 (SEQ ID NO:2232), CeresAnnot:868358 (SEQ ID NO:2234), GI:51371875 (SEQ ID NO:2235), GI:5880357 (SEQ ID NO:2236), GI:226508974 (SEQ ID NO:2237), GI:116311063 (SEQ ID NO:2238), GI:52550773 (SEQ ID NO:2239), GI:188506975 (SEQ ID NO:2240), GI:226500244 (SEQ ID NO:2241), GI:115447353 (SEQ ID NO:2242), CeresAnnot:8680294 (SEQ ID NO:2244), GI:212276282 (SEQ ID NO:2245), GI:168011841 (SEQ ID NO:2246), GI:115447351 (SEQ ID NO:2247), GI:168067175 (SEQ ID NO:2248), GI:168068394 (SEQ ID NO:2249), GI:15705372 (SEQ ID NO:2250), GI:168011817 (SEQ ID NO:2251), GI:168011819 (SEQ ID NO:2252), GI:15705370 (SEQ ID NO:2253), GI:225434604 (SEQ ID NO:2254), CeresAnnot:1514946 (SEQ ID NO:2256), GI:22001522 (SEQ ID NO:2257), GI:145356298 (SEQ ID NO:2258), GI:159478831 (SEQ ID NO:2259), GI:14028761 (SEQ ID NO:2260), GI:66816227 (SEQ ID NO:2261), GI:156361112 (SEQ ID NO:2262), GI:72171193 (SEQ ID NO:2263), GI:159900308 (SEQ ID NO:2264), GI:156741881 (SEQ ID NO:2265), GI:146297474 (SEQ ID NO:2266), GI:167038063 (SEQ ID NO:2267), GI:163846579 (SEQ ID NO:2268), and GI:148657093 (SEQ ID NO:2269). In some cases, a functional homolog of SEQ ID NO: 2196 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2196. In some cases, a functional homolog of SEQ ID NO: 2196 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 2196 described above or set forth in the Sequence Listing.

Figure 31A:
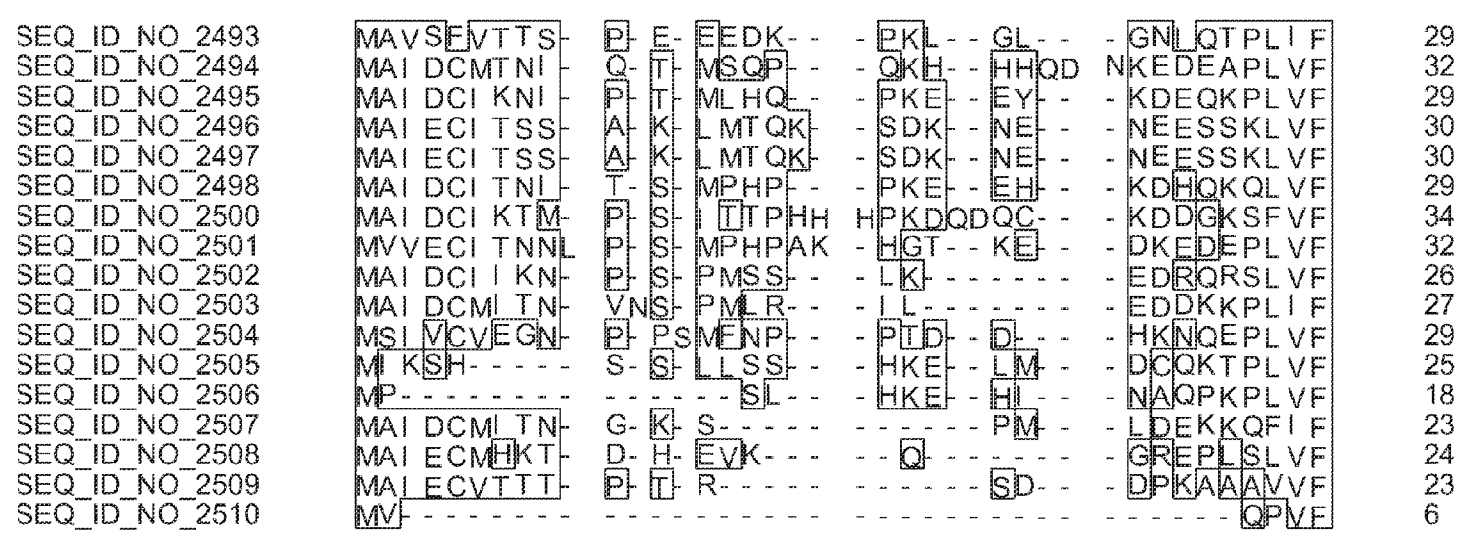
Figure 31K:
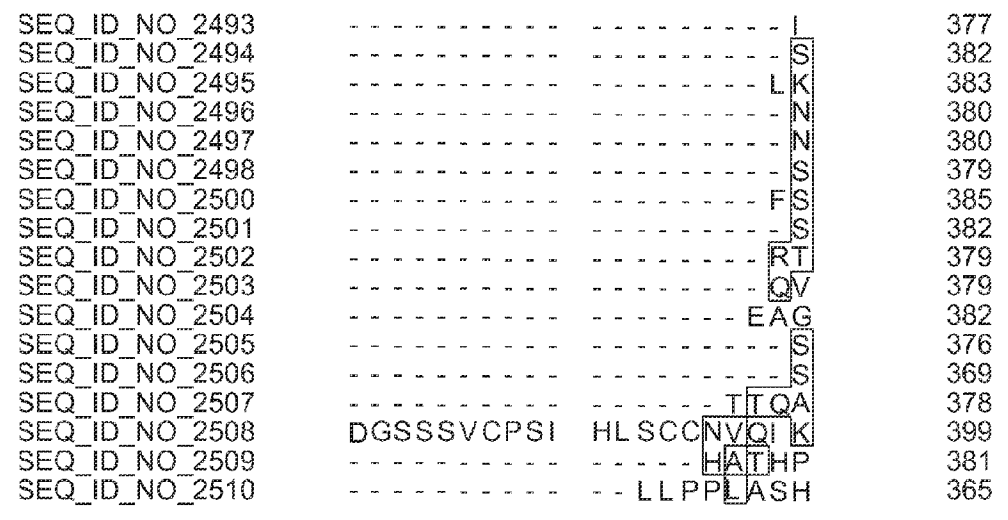

Examples of amino acid sequences of functional homologs of the polypeptide set forth in SEQ ID NO: 2493 are provided in FIG. 31 and in the Sequence Listing. Such functional homologs include, for example, GI:2262201 (SEQ ID NO:2494), GI:8919865 (SEQ ID NO:2495), GI:2108428 (SEQ ID NO:2496), GI:1848146 (SEQ ID NO:2497), GI:18496057 (SEQ ID NO:2498), CeresAnnot: 1474270 (SEQ ID NO:2500), GI:160623443 (SEQ ID NO:2501), GI:187455574 (SEQ ID NO:2502), GI:30519873 (SEQ ID NO:2503), GI:99032729 (SEQ ID NO:2504), GI:190192210 (SEQ ID NO:2505), GI:4164143 (SEQ ID NO:2506), GI:4321496 (SEQ ID NO:2507), GI:109729787 (SEQ ID NO:2508), GI:60498576 (SEQ ID NO:2509), GI:75276875 (SEQ ID NO:2510), CeresClone: 156575 (SEQ ID NO:2512), GI:9791186 (SEQ ID NO:2513), GI:9791187 (SEQ ID NO:2514), GI:15242189 (SEQ ID NO:2515), CeresClone:1101515 (SEQ ID NO:2517), GI:28316358 (SEQ ID NO:2518), GI:9650811 (SEQ ID NO:2519), GI:53139594 (SEQ ID NO:2520), GI:40233167 (SEQ ID NO:2521), GI:53139616 (SEQ ID NO:2522), GI:53139588 (SEQ ID NO:2523), GI:53139592 (SEQ ID NO:2524), GI:77632796 (SEQ ID NO:2525), GI:34013374 (SEQ ID NO:2526), GI:53139654 (SEQ ID NO:2527), GI:2108432 (SEQ ID NO:2528), GI:53139590 (SEQ ID NO:2529), GI:160623445 (SEQ ID NO:2530), GI:53139610 (SEQ ID NO:2531), CeresClone:1842451 (SEQ ID NO:2533), GI:53139612 (SEQ ID NO:2534), GI:4164141 (SEQ ID NO:2535), GI:3327245 (SEQ ID NO:2536), CeresClone:624633 (SEQ ID NO:2538), GI:158392463 (SEQ ID NO:2539), GI:3402332 (SEQ ID NO:2540), GI:169403818 (SEQ ID NO:2541), GI:27124556 (SEQ ID NO:2542), CeresAnnot:1497117 (SEQ ID NO:2544), GI:190192208 (SEQ ID NO:2545), GI:12231168 (SEQ ID NO:2546), GI:21322508 (SEQ ID NO:2547), GI:51011360 (SEQ ID NO:2548), CeresAnnot: 8461546 (SEQ ID NO:2550), GI:10800976 (SEQ ID NO:2551), CeresAnnot:1524411 (SEQ ID NO:2553), CeresAnnot:881675 (SEQ ID NO:2555), GI:1144390 (SEQ ID NO:2556), GI:9971219 (SEQ ID NO:2557), GI:3327247 (SEQ ID NO:2558), CeresClone:818172 (SEQ ID NO:2560), CeresClone:329121 (SEQ ID NO:2562), and CeresAnnot:8631464 (SEQ ID NO:2564). In some cases, a functional homolog of SEQ ID NO: 2493 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2493. In some cases, a functional homolog of SEQ ID NO: 2493 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 2493 described above or set forth in the Sequence Listing.

Figure 32C:
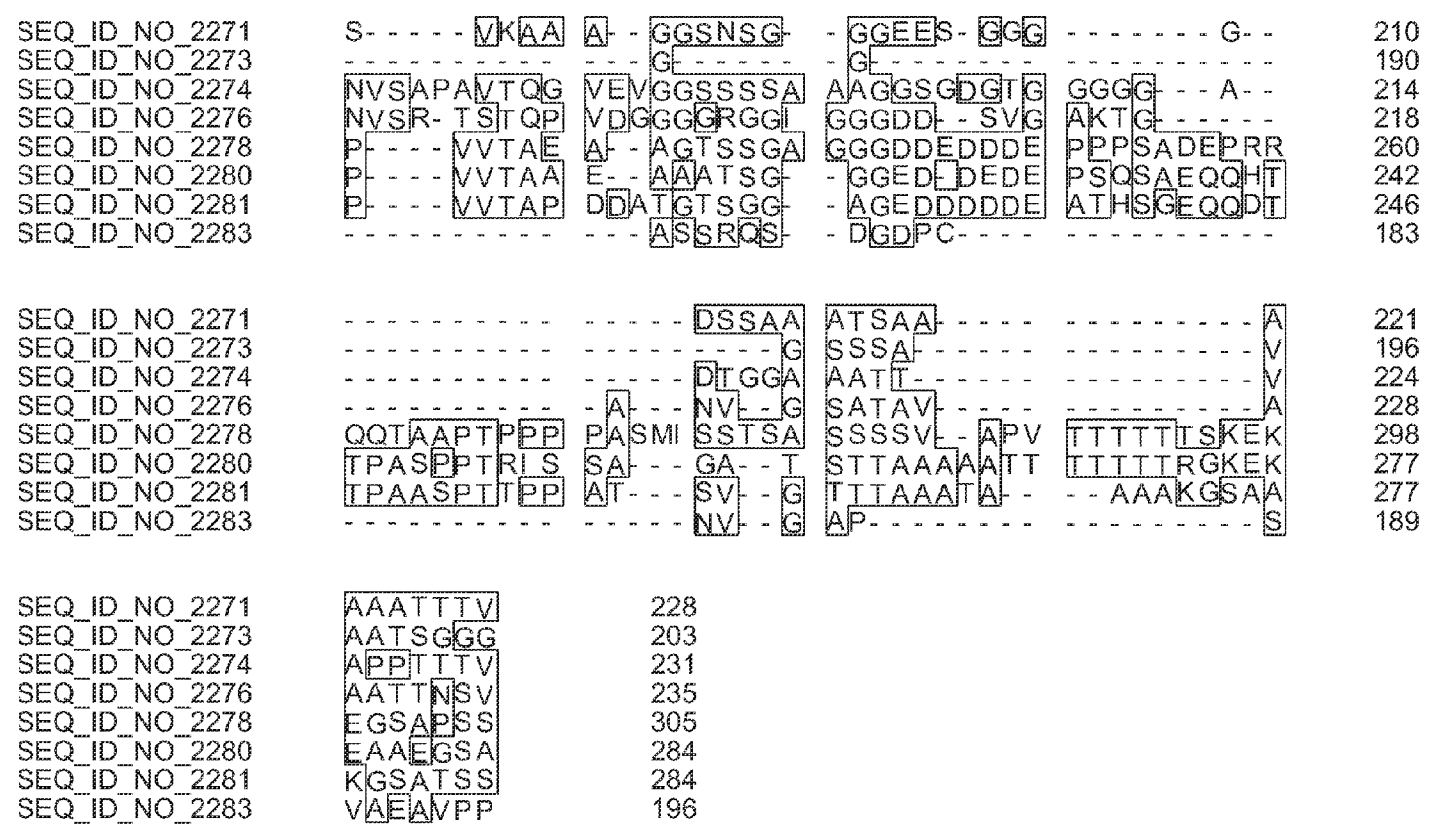

Examples of amino acid sequences of functional homologs of the polypeptide set forth in SEQ ID NO: 2271 are provided in FIG. 32 and in the Sequence Listing. Such functional homologs include, for example, CeresClone: 1245717 (SEQ ID NO:2273), GI:147768778 (SEQ ID NO:2274), CeresClone:1855399 (SEQ ID NO:2276), CeresClone:281322 (SEQ ID NO:2278), CeresClone:1048839 (SEQ ID NO:2280), GI:115463333 (SEQ ID NO:2281), CeresClone:28780 (SEQ ID NO:2283), CeresAnnot: 1461298 (SEQ ID NO:2285), GI:225434496 (SEQ ID NO:2286), CeresClone:1942084 (SEQ ID NO:2288), CeresClone:662149 (SEQ ID NO:2290), CeresClone:100901314 (SEQ ID NO:2292), CeresAnnot:1373087 (SEQ ID NO:2294), CeresClone:1118987 (SEQ ID NO:2296), GI:125543059 (SEQ ID NO:2297), CeresClone:1073674 (SEQ ID NO:2299), CeresClone:100846865 (SEQ ID NO:2301), CeresClone:240797 (SEQ ID NO:2303), CeresClone:1797203 (SEQ ID NO:2305), CeresAnnot:8733177 (SEQ ID NO:2307), CeresAnnot:8669372 (SEQ ID NO:2309), CeresClone:100867501 (SEQ ID NO:2311), CeresClone:2012696 (SEQ ID NO:2313), GI:51038155 (SEQ ID NO:2314), CeresClone:2004419 (SEQ ID NO:2316), GI:125552681 (SEQ ID NO:2317), GI:115449465 (SEQ ID NO:2318), CeresClone:773100 (SEQ ID NO:2320), CeresAnnot:8670506 (SEQ ID NO:2322), CeresClone:298827 (SEQ ID NO:2324), CeresAnnot:1442133 (SEQ ID NO:2326), GI:225444171 (SEQ ID NO:2327), CeresClone:1386592 (SEQ ID NO:2329), CeresAnnot:1467194 (SEQ ID NO:2331), CeresAnnot: 8680326 (SEQ ID NO:2333), CeresAnnot:1469591 (SEQ ID NO:2335), CeresClone:1790902 (SEQ ID NO:2337), CeresAnnot:1484626 (SEQ ID NO:2339), CeresAnnot: 8635017 (SEQ ID NO:2341), GI:115459426 (SEQ ID NO:2342), CeresClone:660540 (SEQ ID NO:2344), GI:125590992 (SEQ ID NO:2345), CeresClone:100873191 (SEQ ID NO:2347), GI:47847657 (SEQ ID NO:2348), GI:259490587 (SEQ ID NO:2349), CeresClone:1464359 (SEQ ID NO:2351), CeresClone:1988960 (SEQ ID NO:2353), CeresClone:100871850 (SEQ ID NO:2355), CeresClone:34761 (SEQ ID NO:2357), CeresClone:964932 (SEQ ID NO:2359), CeresClone:1288341 (SEQ ID NO:2361), CeresClone:916104 (SEQ ID NO:2363), CeresAnnot:8701919 (SEQ ID NO:2365), CeresAnnot:828846 (SEQ ID NO:2367), GI:116780542 (SEQ ID NO:2368), GI:212723306 (SEQ ID NO:2369), CeresAnnot:856813 (SEQ ID NO:2371), CeresClone:2010260 (SEQ ID NO:2373), CeresClone:662956 (SEQ ID NO:2375), CeresAnnot:1459517 (SEQ ID NO:2377), CeresClone:1994588 (SEQ ID NO:2379), CeresClone:571893 (SEQ ID NO:2381), CeresClone:572195 (SEQ ID NO:2383), CeresClone:1990206 (SEQ ID NO:2385), GI:115444445 (SEQ ID NO:2386), CeresClone:1461999 (SEQ ID NO:2388), CeresClone:1884986 (SEQ ID NO:2390), GI:125580940 (SEQ ID NO:2391), CeresClone:625781 (SEQ ID NO:2393), CeresAnnot:8454580 (SEQ ID NO:2395), CeresClone:1457623 (SEQ ID NO:2397), CeresAnnot: 853637 (SEQ ID NO:2399), GI:147795605 (SEQ ID NO:2400), CeresAnnot:1482911 (SEQ ID NO:2402), CeresAnnot:861920 (SEQ ID NO:2404), GI:147776506 (SEQ ID NO:2405), CeresAnnot:839537 (SEQ ID NO:2407), CeresAnnot:8453882 (SEQ ID NO:2409), CeresClone: 1987520 (SEQ ID NO:2411), CeresAnnot:1466494 (SEQ ID NO:2413), CeresAnnot:870022 (SEQ ID NO:2415), CeresAnnot:8744064 (SEQ ID NO:2417), CeresClone: 1848017 (SEQ ID NO:2419), CeresClone:1650005 (SEQ ID NO:2421), and CeresAnnot:1449022 (SEQ ID NO:2423). In some cases, a functional homolog of SEQ ID NO: 2271 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2271. In some cases, a functional homolog of SEQ ID NO: 2271 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 2271 described above or set forth in the Sequence Listing.

Examples of amino acid sequences of functional homologs of the polypeptide set forth in SEQ ID NO: 1741 are provided in FIG. 33 and in the Sequence Listing. Such functional homologs include, for example, CeresAnnot: 1482536 (SEQ ID NO:1743), CeresClone:1842825 (SEQ ID NO:1745), CeresClone:463157 (SEQ ID NO:1747), GI:186915025 (SEQ ID NO:1748), GI:197726026 (SEQ ID NO:1749), GI:4091806 (SEQ ID NO:1750), GI:111378451 (SEQ ID NO:1751), GI:150014754 (SEQ ID NO:1752), GI:170779036 (SEQ ID NO:1753), GI:61611682 (SEQ ID NO:1754), GI:18424009 (SEQ ID NO:1755), GI:9759262 (SEQ ID NO:1756), CeresClone:1834027 (SEQ ID NO:1758), CeresAnnot:8457547 (SEQ ID NO:1760), CeresAnnot:1455741 (SEQ ID NO:1762), GI:52840166 (SEQ ID NO:1763), GI:118489345 (SEQ ID NO:1764), CeresClone:1937613 (SEQ ID NO:1766), GI:189014382 (SEQ ID NO:1767), CeresAnnot:1477832 (SEQ ID NO:1769), GI:4091804 (SEQ ID NO:1770), CeresClone:530984 (SEQ ID NO:1772), GI:116787635 (SEQ ID NO:1773), GI:3341723 (SEQ ID NO:1774), CeresClone:949 (SEQ ID NO:1776), CeresClone:17434 (SEQ ID NO:1778), GI:186911828 (SEQ ID NO:1779), GI:170779038 (SEQ ID NO:1780), GI:60459257 (SEQ ID NO:1781), GI:110277457 (SEQ ID NO:1782), GI:41323976 (SEQ ID NO:1783), CeresClone:1755065 (SEQ ID NO:1785), GI:21667485 (SEQ ID NO:1786), GI:90657642 (SEQ ID NO:1787), GI:41323978 (SEQ ID NO:1788), GI:168063317 (SEQ ID NO:1789), GI:115447239 (SEQ ID NO:1790), GI:168030717 (SEQ ID NO:1791), GI:125540249 (SEQ ID NO:1792), CeresClone:7088 (SEQ ID NO:1794), CeresClone:1996408 (SEQ ID NO:1796), CeresAnnot:8701721 (SEQ ID NO:1798), GI:66841020 (SEQ ID NO:1799), CeresAnnot:882715 (SEQ ID NO:1801), GI:21655154 (SEQ ID NO:1802), CeresClone: 1770031 (SEQ ID NO:1804), CeresClone:1559496 (SEQ ID NO:1806), CeresAnnot:8680182 (SEQ ID NO:1808), GI:15242402 (SEQ ID NO:1809), and GI:108859363 (SEQ ID NO:1810). In some cases, a functional homolog of SEQ ID NO: 1741 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1741. In some cases, a functional homolog of SEQ ID NO: 1741 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1741 described above or set forth in the Sequence Listing.

Examples of amino acid sequences of functional homologs of the polypeptide set forth in SEQ ID NO: 1980 are provided in FIG. 34 and in the Sequence Listing. Such functional homologs include, for example, CeresAnnot: 1472114 (SEQ ID NO:1982), CeresClone:1058242 (SEQ ID NO:1984), GI:147772269 (SEQ ID NO:1985), GI:116784922 (SEQ ID NO:1986), CeresAnnot:1525524 (SEQ ID NO:1988), CeresAnnot:1453309 (SEQ ID NO:1990), GI:118481810 (SEQ ID NO:1991), CeresAnnot: 826234 (SEQ ID NO:1993), CeresAnnot:1466045 (SEQ ID NO:1995), CeresClone:1248956 (SEQ ID NO:1997), CeresClone:1650911 (SEQ ID NO:1999), CeresAnnot:1495956 (SEQ ID NO:2001), CeresClone:2008765 (SEQ ID NO:2003), CeresClone:100817949 (SEQ ID NO:2005), CeresClone:100821842 (SEQ ID NO:2007), CeresClone: 2001181 (SEQ ID NO:2009), CeresClone:2030722 (SEQ ID NO:2011), CeresClone:343585 (SEQ ID NO:2013), CeresClone:1869093 (SEQ ID NO:2015), CeresClone:1790958 (SEQ ID NO:2017), CeresAnnot:1489440 (SEQ ID NO:2019), CeresClone:1657593 (SEQ ID NO:2021), CeresAnnot:887360 (SEQ ID NO:2023), GI:225446539 (SEQ ID NO:2024), GI:225446539 (SEQ ID NO:2025), GI:116793199 (SEQ ID NO:2026), GI:125557245 (SEQ ID NO:2027), CeresClone:603590 (SEQ ID NO:2029), CeresClone:981503 (SEQ ID NO:2031), and CeresClone: 1919739 (SEQ ID NO:2033). In some cases, a functional homolog of SEQ ID NO: 1980 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1980. In some cases, a functional homolog of SEQ ID NO: 1980 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1980 described above or set forth in the Sequence Listing.

Examples of amino acid sequences of functional homologs of the polypeptide set forth in SEQ ID NO: 1812 are provided in FIG. 35 and in the Sequence Listing. Such functional homologs include, for example, CeresClone: 1073884 (SEQ ID NO:1814), GI:224127226 (SEQ ID NO:1815), CeresClone:544072 (SEQ ID NO:1817), CeresClone:1974604 (SEQ ID NO:1819), CeresClone:339870 (SEQ ID NO:1821), GI:55976189 (SEQ ID NO:1822), CeresClone:1724322 (SEQ ID NO:1824), CeresClone: 1072407 (SEQ ID NO:1826), GI:77999273 (SEQ ID NO:1827), GI:158513203 (SEQ ID NO:1828), GI:116778980 (SEQ ID NO:1829), GI:18404552 (SEQ ID NO:1830), CeresClone:21756 (SEQ ID NO:1832), CeresClone:1894842 (SEQ ID NO:1834), GI:118483391 (SEQ ID NO:1835), CeresAnnot:8460689 (SEQ ID NO:1837), CeresClone:278897 (SEQ ID NO:1839), GI:224121940 (SEQ ID NO:1840), GI:118484032 (SEQ ID NO:1841), CeresClone:1726573 (SEQ ID NO:1843), GI:115441607 (SEQ ID NO:1844), CeresClone:1833880 (SEQ ID NO:1846), GI:21952858 (SEQ ID NO:1847), CeresAnnot: 1480607 (SEQ ID NO:1849), CeresClone:1614435 (SEQ ID NO:1851), GI:168062894 (SEQ ID NO:1852), CeresClone: 1729334 (SEQ ID NO:1854), CeresClone:1921953 (SEQ ID NO:1856), CeresClone:1849983 (SEQ ID NO:1858), CeresAnnot:1534090 (SEQ ID NO:1860), GI:159463258 (SEQ ID NO:1861), GI:6094086 (SEQ ID NO:1862), GI:6094085 (SEQ ID NO:1863), CeresClone:2023733 (SEQ ID NO:1865), GI:145354281 (SEQ ID NO:1866), GI:116055139 (SEQ ID NO:1867), GI:2500286 (SEQ ID NO:1868), GI:122050162 (SEQ ID NO:1869), GI:155966157 (SEQ ID NO:1870), GI:156388083 (SEQ ID NO:1871), GI:198420685 (SEQ ID NO:1872), GI:15293871 (SEQ ID NO:1873), GI:195999960 (SEQ ID NO:1874), GI:116007382 (SEQ ID NO:1875), GI:74829222 (SEQ ID NO:1876), GI:50344868 (SEQ ID NO:1877), GI:194769639 (SEQ ID NO:1878), GI:195355748 (SEQ ID NO:1879), GI:195437688 (SEQ ID NO:1880), GI:148230833 (SEQ ID NO:1881), GI:195164533 (SEQ ID NO:1882), GI:40642990 (SEQ ID NO:1883), GI:268530064 (SEQ ID NO:1884), GI:47215976 (SEQ ID NO:1885), GI:112983276 (SEQ ID NO:1886), GI:164690935 (SEQ ID NO:1887), GI:17534333 (SEQ ID NO:1888), GI:45360909 (SEQ ID NO:1889), GI:197632317 (SEQ ID NO:1890), GI:115723047 (SEQ ID NO:1891), GI:14591909 (SEQ ID NO:1892), GI:112907480 (SEQ ID NO:1893), GI:170049217 (SEQ ID NO:1894), GI:157105498 (SEQ ID NO:1895), GI:166796061 (SEQ ID NO:1896), GI:108862056 (SEQ ID NO:1897), GI:114557920 (SEQ ID NO:1898), GI:75076080 (SEQ ID NO:1899), GI:45383023 (SEQ ID NO:1900), GI:187609312 (SEQ ID NO:1901), GI:149626807 (SEQ ID NO:1902), GI:22758888 (SEQ ID NO:1903), GI:126305867 (SEQ ID NO:1904), GI:13592051 (SEQ ID NO:1905), GI:74845700 (SEQ ID NO:1906), GI:90991371 (SEQ ID NO:1907), GI:193627230 (SEQ ID NO:1908), GI:23956082 (SEQ ID NO:1909), GI:121701409 (SEQ ID NO:1910), GI:197128747 (SEQ ID NO:1911), GI:159145700 (SEQ ID NO:1912), GI:167206806 (SEQ ID NO:1913), GI:119495376 (SEQ ID NO:1914), GI:45185790 (SEQ ID NO:1915), GI:156089549 (SEQ ID NO:1916), GI:74848092 (SEQ ID NO:1917), GI:71030018 (SEQ ID NO:1918), GI:152031669 (SEQ ID NO:1919), GI:170783723 (SEQ ID NO:1920), GI:19577350 (SEQ ID NO:1921), GI:5007074 (SEQ ID NO:1922), GI:145240087 (SEQ ID NO:1923), GI:50294105 (SEQ ID NO:1924), GI:84995804 (SEQ ID NO:1925), GI:50306789 (SEQ ID NO:1926), GI:169861151 (SEQ ID NO:1927), GI:169763400 (SEQ ID NO:1928), GI:46136989 (SEQ ID NO:1929), GI:67517624 (SEQ ID NO:1930), GI:154294907 (SEQ ID NO:1931), GI:156044424 (SEQ ID NO:1932), GI:85098188 (SEQ ID NO:1933), GI:170586178 (SEQ ID NO:1934), GI:171694355 (SEQ ID NO:1935), GI:71021101 (SEQ ID NO:1936), GI:188572500 (SEQ ID NO:1937), GI:133003 (SEQ ID NO:1938), GI:39971465 (SEQ ID NO:1939), GI:154271618 (SEQ ID NO:1940), GI:115491879 (SEQ ID NO:1941), GI:189207733 (SEQ ID NO:1942), GI:116197729 (SEQ ID NO:1943), GI:149235570 (SEQ ID NO:1944), GI:66816906 (SEQ ID NO:1945), GI:126133112 (SEQ ID NO:1946), GI:156843920 (SEQ ID NO:1947), GI:170091820 (SEQ ID NO:1948), GI:167519038 (SEQ ID NO:1949), GI:70995808 (SEQ ID NO:1950), GI:154344695 (SEQ ID NO:1951), GI:119181612 (SEQ ID NO:1952), and GI:72547732 (SEQ ID NO:1953). In some cases, a functional homolog of SEQ ID NO: 1812 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1812. In some cases, a functional homolog of SEQ ID NO: 1812 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 1812 described above or set forth in the Sequence Listing.

Figure 36A:
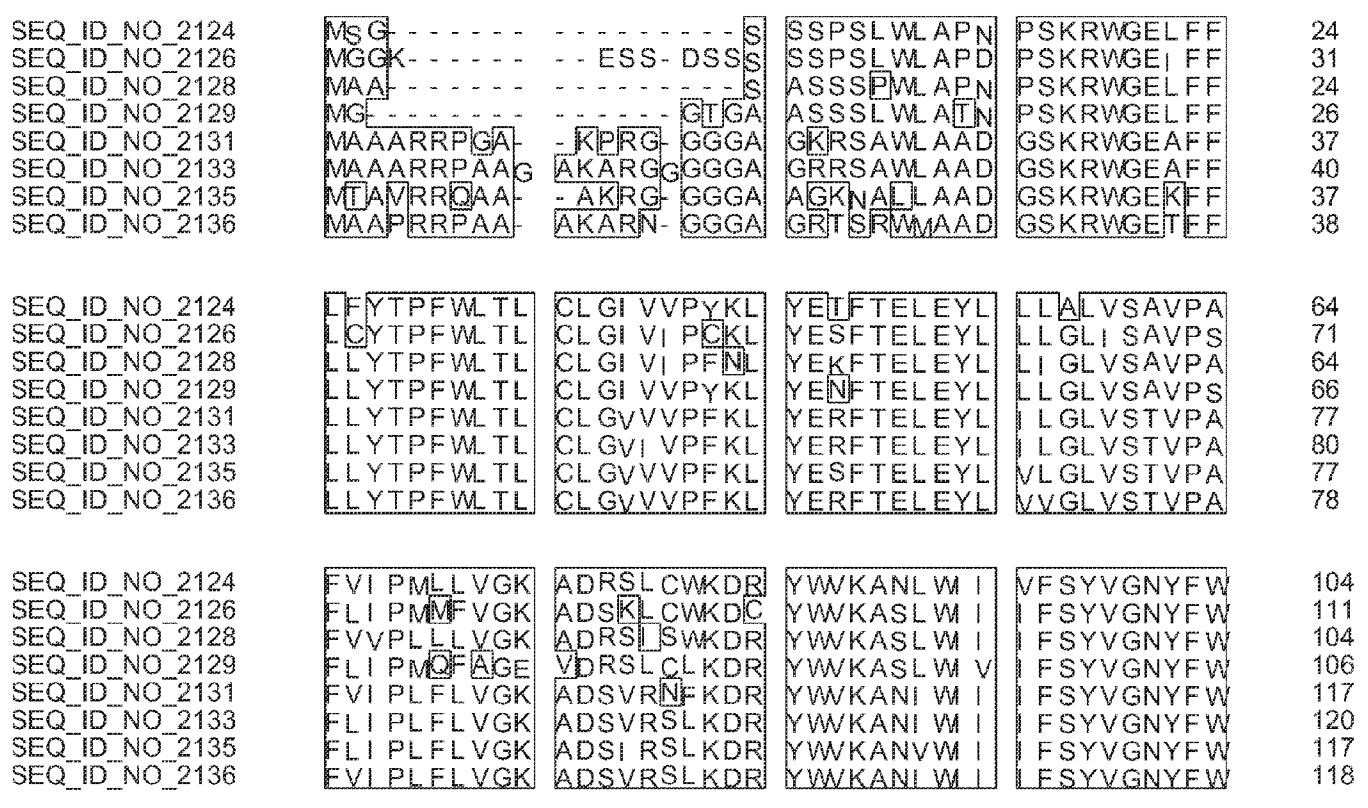
Figure 36B:
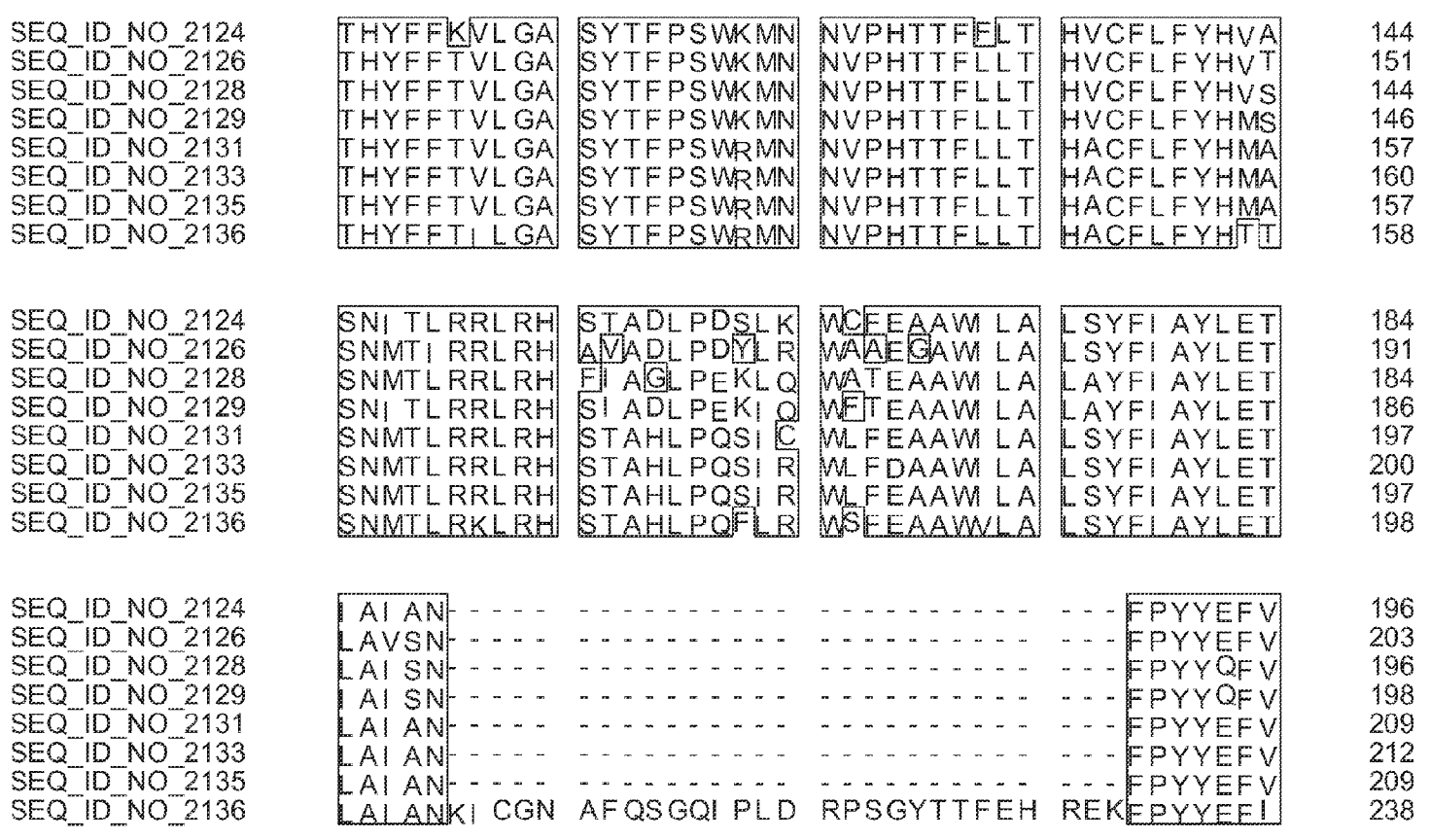

Examples of amino acid sequences of functional homologs of the polypeptide set forth in SEQ ID NO: 2124 are provided in FIG. 36 and in the Sequence Listing. Such functional homologs include, for example, CeresAnnot: 1527229 (SEQ ID NO:2126), CeresClone:716942 (SEQ ID NO:2128), GI:225456280 (SEQ ID NO:2129), CeresClone: 285554 (SEQ ID NO:2131), CeresClone:1818640 (SEQ ID NO:2133), CeresClone:904080 (SEQ ID NO:2135), GI:125534155 (SEQ ID NO:2136), GI:62320905 (SEQ ID NO:2137), CeresAnnot:8724644 (SEQ ID NO:2139), CeresAnnot:8724715 (SEQ ID NO:2141), GI:62732798 (SEQ ID NO:2142), CeresAnnot:1473809 (SEQ ID NO:2144), GI:168012270 (SEQ ID NO:2145), GI:159479658 (SEQ ID NO:2146), GI:116057462 (SEQ ID NO:2147), GI:66827159 (SEQ ID NO:2148), GI:297792349 (SEQ ID NO:2592), GI:209976078 (SEQ ID NO:2593), GI:242086735 (SEQ ID NO:2594), GI:255647881 (SEQ ID NO:2595), GI:217073736 (SEQ ID NO:2596), GI:302846059 (SEQ ID NO:2597), GI:302763909 (SEQ ID NO:2598), GI:323454458 (SEQ ID NO:2599), GI:298707227 (SEQ ID NO:2600), GI:303282359 (SEQ ID NO:2601), and GI:219128011 (SEQ ID NO:2602). In some cases, a functional homolog of SEQ ID NO: 2124 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2124. In some cases, a functional homolog of SEQ ID NO: 2124 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 2124 described above or set forth in the Sequence Listing.

Figure 37A:
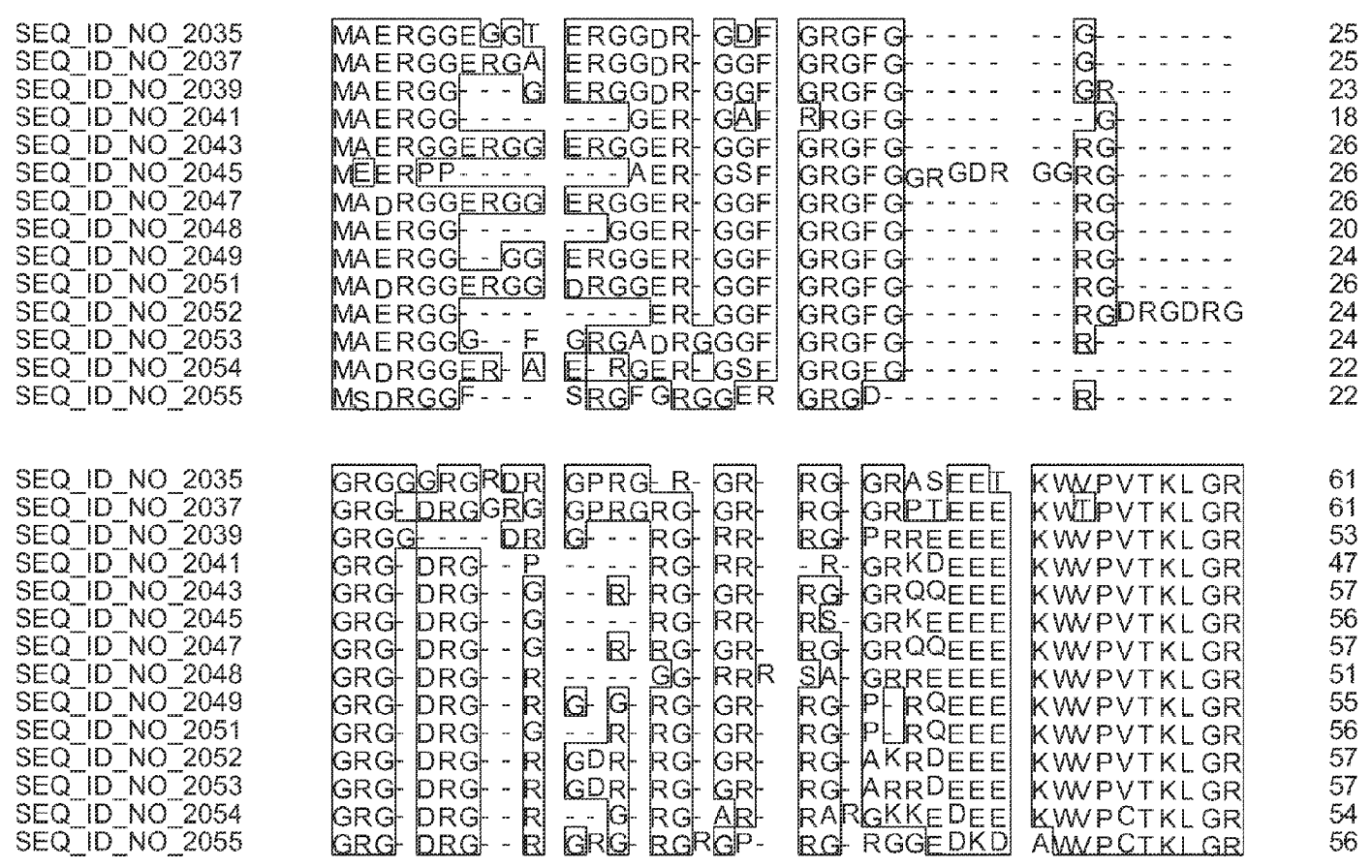

Examples of amino acid sequences of functional homologs of the polypeptide set forth in SEQ ID NO: 2035 are provided in FIG. 37 and in the Sequence Listing. Such functional homologs include, for example, CeresClone: 1070374 (SEQ ID NO:2037), CeresClone:1619978 (SEQ ID NO:2039), CeresClone:1869432 (SEQ ID NO:2041), CeresClone:295792 (SEQ ID NO:2043), CeresAnnot:1474944 (SEQ ID NO:2045), CeresClone:1819159 (SEQ ID NO:2047), GI:225441799 (SEQ ID NO:2048), GI:34393314 (SEQ ID NO:2049), CeresClone:1320533 (SEQ ID NO:2051), GI:168002136 (SEQ ID NO:2052), GI:116791016 (SEQ ID NO:2053), GI:159462880 (SEQ ID NO:2054), GI:116055788 (SEQ ID NO:2055), GI:15217951 (SEQ ID NO:2056), GI:21539457 (SEQ ID NO:2057), CeresClone:17415 (SEQ ID NO:2059), CeresClone:101250 (SEQ ID NO:2061), CeresClone:1243814 (SEQ ID NO:2063), CeresClone:1840067 (SEQ ID NO:2065), CeresClone:1853717 (SEQ ID NO:2067), CeresAnnot:1506849 (SEQ ID NO:2069), CeresClone:1895361 (SEQ ID NO:2071), CeresClone:1793726 (SEQ ID NO:2073), CeresClone:1448380 (SEQ ID NO:2075), CeresAnnot:1453696 (SEQ ID NO:2077), CeresClone:1725377 (SEQ ID NO:2079), GI:115456089 (SEQ ID NO:2080), CeresAnnot:8632056 (SEQ ID NO:2082), CeresClone: 100058895 (SEQ ID NO:2084), CeresClone:100925979 (SEQ ID NO:2086), CeresClone:841942 (SEQ ID NO:2088), CeresClone:1776801 (SEQ ID NO:2090), CeresClone:1732292 (SEQ ID NO:2092), GI:116780779 (SEQ ID NO:2093), CeresAnnot:1492957 (SEQ ID NO:2095), CeresClone:1073758 (SEQ ID NO:2097), GI:145355259 (SEQ ID NO:2098), CeresClone:2004511 (SEQ ID NO:2100), GI:126335470 (SEQ ID NO:2101), GI:148232341 (SEQ ID NO:2102), GI:213512306 (SEQ ID NO:2103), GI:74151470 (SEQ ID NO:2104), GI:124221922 (SEQ ID NO:2105), GI:56118428 (SEQ ID NO:2106), GI:47086117 (SEQ ID NO:2107), GI:114647215 (SEQ ID NO:2108), GI:91081061 (SEQ ID NO:2109), GI:47218049 (SEQ ID NO:2110), GI:90991375 (SEQ ID NO:2111), GI:72010709 (SEQ ID NO: 2112), GI:37577051 (SEQ ID NO:2113), GI:157125338 (SEQ ID NO:2114), GI:62083451 (SEQ ID NO:2115), GI:156404514 (SEQ ID NO:2116), GI:159145750 (SEQ ID NO:2117), GI:196000424 (SEQ ID NO:2118), GI:1350976 (SEQ ID NO:2119), GI:48103127 (SEQ ID NO:2120), GI:156550181 (SEQ ID NO:2121), and GI:56417564 (SEQ ID NO:2122). In some cases, a functional homolog of SEQ ID NO: 2035 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2035. In some cases, a functional homolog of SEQ ID NO: 2035 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 2035 described above or set forth in the Sequence Listing.

Examples of amino acid sequences of functional homologs of the polypeptide set forth in SEQ ID NO: 2425 are provided in FIG. 38 and in the Sequence Listing. Such functional homologs include, for example, GI:225424885 (SEQ ID NO:2426), CeresAnnot:1513435 (SEQ ID NO:2428), CeresAnnot:8458807 (SEQ ID NO:2430), GI:115489782 (SEQ ID NO:2431), CeresAnnot:8633356 (SEQ ID NO:2433), CeresAnnot:868948 (SEQ ID NO:2435), CeresClone:1381517 (SEQ ID NO:2437), GI:12325237 (SEQ ID NO:2438), GI:186478915 (SEQ ID NO:2439), GI:125537558 (SEQ ID NO:2440), CeresClone:1863500 (SEQ ID NO:2442), CeresAnnot:1468256 (SEQ ID NO:2444), GI:225456647 (SEQ ID NO:2445), CeresClone:792606 (SEQ ID NO:2447), CeresClone:1576419 (SEQ ID NO:2449), CeresAnnot:8723986 (SEQ ID NO:2451), CeresAnnot:1521620 (SEQ ID NO:2453), CeresClone:1570203 (SEQ ID NO:2455), CeresAnnot:1440475 (SEQ ID NO:2457), CeresAnnot:8644892 (SEQ ID NO:2459), CeresClone:1529998 (SEQ ID NO:2461), CeresClone:1823719 (SEQ ID NO:2463), GI:115489780 (SEQ ID NO:2464), GI:11933400 (SEQ ID NO:2465), GI:115454673 (SEQ ID NO:2466), GI:11933397 (SEQ ID NO:2467), GI:15221883 (SEQ ID NO:2468), CeresAnnot:1493344 (SEQ ID NO:2470), CeresAnnot:874402 (SEQ ID NO:2472), CeresAnnot:1475704 (SEQ ID NO:2474), CeresAnnot:8703346 (SEQ ID NO:2476), CeresAnnot:1455393 (SEQ ID NO:2478), GI:145358511 (SEQ ID NO:2479), CeresAnnot:1492266 (SEQ ID NO:2481), GI:225429973 (SEQ ID NO:2482), CeresClone:1944137 (SEQ ID NO:2484), GI:115440087 (SEQ ID NO:2485), CeresAnnot:875119 (SEQ ID NO:2487), GI:125527793 (SEQ ID NO:2488), GI:116788004 (SEQ ID NO:2489), GI:15391731 (SEQ ID NO:2490), and GI:168064734 (SEQ ID NO:2491). In some cases, a functional homolog of SEQ ID NO: 2425 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2425. In some cases, a functional homolog of SEQ ID NO: 2425 has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one or more functional homologs of SEQ ID NO: 2425 described above or set forth in the Sequence Listing.

The identification of conserved regions in a biomass-modulating polypeptide facilitates production of variants of biomass-modulating polypeptides. Variants of biomass-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIG. 1, FIG. 2, FIG. 3, FIG. 4, FIG. 5, FIG. 6, FIG. 7, FIG. 8, FIG. 9, FIG. 10, FIG. 11, FIG. 12, FIG. 13, FIG. 14, FIG. 15, FIG. 16, FIG. 17, FIG. 18, FIG. 19, FIG. 20, FIG. 21, FIG. 22, FIG. 23, FIG. 24, FIG. 25, FIG. 26, FIG. 27, FIG. 28, FIG. 29, FIG. 30, FIG. 31, FIG. 32, FIG. 33, FIG. 34, FIG. 35, FIG. 36, FIG. 37, or FIG. 38 and/or homologs identified in the Sequence Listing. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at a position marked by dashes, such a polypeptide has a length that is the sum of the amino acid residues in all conserved regions and all dashes.

C. Functional Homologs Identified by HMMER

In some embodiments, useful biomass-modulating polypeptides include those that fit a Hidden Markov Model based on the polypeptides set forth in any one of FIGS. 1-25. A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, -consistency REPS of 2; -ir, -iterative-refinement REPS of 100; -pre, -pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as hmmer.janelia.org; hmmer.wustl.edu; and fr.com/hmmer232/. Hmmbuild outputs the model as a text file.

The HMM for a group of functional homologs can be used to determine the likelihood that a candidate biomass-modulating polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the Prob-Cons program. Nevertheless, such HMM bit score variation is minor.

The biomass-modulating polypeptides discussed below fit the indicated HMM with an HMM bit score greater than to 65 (e.g., greater than 70, 80, 90, 100, 120, 140, 200, 300, 500, 1000, 1500, or 2000). In some embodiments, the HMM bit score of a biomass-modulating polypeptide discussed below is about 50%, 60%, 70%, 80%, 90%, or 95% of the HMM bit score of a functional homolog provided in the Sequence Listing of this application. In some embodiments, a biomass-modulating polypeptide discussed below fits the indicated HMM with an HMM bit score greater than 210, and has a domain indicative of a biomass-modulating polypeptide. In some embodiments, a biomass-modulating polypeptide discussed below fits the indicated HMM with an HMM bit score greater than 210, and has 65% or greater sequence identity (e.g., 75%, 80%, 85%, 90%, 95%, or 100% sequence identity) to an amino acid sequence shown in any one of FIGS. 1-38.

Examples of polypeptides are shown in the sequence listing that have HMM bit scores greater than 700 (e.g., greater than 800) when fitted to an HMM generated from the amino acid sequences set forth in FIG. 1 are identified in the Sequence Listing of this application. Such polypeptides include, for example, SEQ ID NOs: 1333, 1334, 1335, 1336, 1337, 1339, 1341, 1343, 1345, 1347, 1348, 1349, 1350, 1352, 1354, 1356, 1358, 1360, 1362, and 1364.

Examples of polypeptides are shown in the sequence listing that have HMM bit scores greater than 450 (e.g., greater than 500, 600, 700, 800, 900, 1000, 1100, 1200, 1300, or 1400) when fitted to an HMM generated from the amino acid sequences set forth in FIG. 2 are identified in the Sequence Listing of this application. Such polypeptides include, for example, SEQ ID NOs: 1489, 1491, 1492, 1493, 1495, 1496, 1498, 1499, 1501, 1503, 1504, 1506, 1508, 1510, 1511, 1513, 1514, 1516, 1517, 1518, 1519, 1520, 1521, 1523, 1524, 1526, 1528, 1529, 1530, 1531, 1532, 1534, 1536, 1537, 1538, and 1539.

Examples of polypeptides are shown in the sequence listing that have HMM bit scores greater than 1200 (e.g., greater than 1300, 1400, 1500, 1600, 1700, 1800, or 1900) when fitted to an HMM generated from the amino acid sequences set forth in FIG. 3 are identified in the Sequence Listing of this application. Such polypeptides include, for example, SEQ ID NOs: 504, 506, 508, 509, 511, 512, 513, 514, 515, 516, 517, 519, 521, 522, 524, 525, 526, 527, 529, 530, 532, 533, 535, 536, 537, 539, 541, 543, 545, 546, 548, 550, 552, 553, 554, 555, 557, 558, 560, 562, 564, 566, 568, 570, 571, 572, 573, 574, 575, 576, 577, or 578.

Examples of polypeptides are shown in the sequence listing that have HMM bit scores greater than 229 (e.g., greater than 300, 400, 500, 600, or 700) when fitted to an HMM generated from the amino acid sequences set forth in FIG. 4 are identified in the Sequence Listing of this application. Such polypeptides include, for example, SEQ ID NOs: 198, 200, 202, 203, 205, 207, 208, 209, 210, 211, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, or 251.

Examples of polypeptides are shown in the sequence listing that have HMM bit scores greater than 748 (e.g., greater than 800, 900, 1000, 1100, or 1200) when fitted to an HMM generated from the amino acid sequences set forth in FIG. 5 are identified in the Sequence Listing of this application. Such polypeptides include, for example, SEQ ID NOs: 253, 255, 257, 258, 260, 261, 262, 264, 265, 267, 268, 269, 270, 271, 272, 274, 275, 276, 277, 278, 279, 281, 282, 283, 285, 287, 288, 289, 290, 291, 292, 294, 295, 296, 297, 299, 301, 303, 304, 305, 307, 309, 310, 312, 314, 316, 317, 318, 320, 321, 323, 325, 327, 328, 329, 331, 332, 334, 335, 337, 338, 339, 341, 342, 344, 345, 347, 349, 351, 353, 355, 357, 359, 361, 362, 363, 364, 365, or 366.

Examples of polypeptides are shown in the sequence listing that have HMM bit scores greater than 250 (e.g., greater than 300, 400, 500, 600, or 700) when fitted to an HMM generated from the amino acid sequences set forth in FIG. 6 are identified in the Sequence Listing of this application. Such polypeptides include, for example, SEQ ID NOs: 1541, 1542, 1544, 1545, 1547, 1548, 1550, 1552, 1553, 1555, 1556, 1557, 1558, 1559, 1561, 1563, 1564, 1565, 1567, 1568, 1570, 1571, 1573, 1575, 1576, or 1578.

Examples of polypeptides are shown in the sequence listing that have HMM bit scores greater than 490 (e.g., greater than 600, 700, 800, 900, 1000, 1100, or 1200), when fitted to an HMM generated from the amino acid sequences set forth in FIG. 7 are identified in the Sequence Listing of this application. Such polypeptides include, for example, SEQ ID NOs: 663, 665, 667, 668, 669, 670, 672, 674, 675, 677, 679, 680, 681, 682, 684, 685, 687, 689, 690, 691, 692, 694, 695, 696, 697, 698, 700, 701, 702, 703, 704, 706, 707, 709, 710, 711, 712, 713, 714, 715, 716, 717, 718, 720, 722, 724, 726, 727, 728, 730, 731, 733, 734, 735, 736, 737, 738, or 739.

Examples of polypeptides are shown in the sequence listing that have HMM bit scores greater than 534 (e.g., greater than 600, 700, 800, 900, or 1000) when fitted to an HMM generated from the amino acid sequences set forth in FIG. 8 are identified in the Sequence Listing of this application. Such polypeptides include, for example, SEQ ID NOs: 1366, 1368, 1370, 1371, 1372, 1374, 1375, 1377, 1378, 1379, 1381, 1383, 1384, 1386, 1388-1390, 1392, 1393, 1394, 1395, 1396, 1397, 1399, 1400, 1402, 1403, 1405, 1407, 1408, 1409, 1410, 1412, 1413, 1414, 1415, 1416, 1417, 1418, 1420, 1422, 1424, 1426, 1428, 1430, 1432, 1433, 1434, 1435, 1436, 1438, 1440, 1442, 1443, 1444, 1446, 1447, 1449, 1450, 1452, 1453, 1454, 1456, 1457, 1459, 1460, 1462, 1463, 1465, 1466, 1467, 1468, 1470, 1471, 1473, 1475, 1477, 1478, 1479, 1480, 1481, 1482, 1483, 1485, or 1487.

Examples of polypeptides are shown in the sequence listing that have HMM bit scores greater than 570 (e.g., greater than 600, 700, 800, 900, 1000, or 1100) when fitted to an HMM generated from the amino acid sequences set forth in FIG. 9 are identified in the Sequence Listing of this application. Such polypeptides include, for example, SEQ ID NOs: 928, 930, 932, 933, 935, 936, 937, 938, 940, 941, 943, 944, 945, 947, 949, 950, 952, 953, 954, 955, 957, 958, 959, 960, 961, 963, 965, 966, 967, 968, 969, 971, 972, 974, 975, 977, 978, 980, 982, 984, 986, 988, 990, 992, 994, 996, 998, 1000, 1001, 1002, 1003, 1004, 1005, 1006, 1007, 1008, 1009, 1010, 1011, 1012, 1013, or 1014.

Examples of polypeptides are shown in the sequence listing that have HMM bit scores greater than 830 (e.g., greater than 900, 1000, 1100, or 1200), when fitted to an HMM generated from the amino acid sequences set forth in FIG. 10 are identified in the Sequence Listing of this application. Such polypeptides include, for example, SEQ ID NOs: 1215, 217, 1218, 1219, 1220, 1221, 1223, 1224, 1225, 1226, 1227, 1228, 1230, 1231, 1233, 1234, 1235, 1236, 1237, 1238, 1239, 1240, 1241, 1243, 1245, 1247, 1249, 1250, 1251, 1252, 1254, 1255, 1257, 1258, 1259, 1261, 1263, 1264, 1266, 1267, 1268, 1269, 1270, 1271, 1272, 1274, 1275, 1276, 1278, 1280, 1282, 1283, 1284, 1285, 1286, 1288, 1289, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, or 1331.

Examples of polypeptides are shown in the sequence listing that have HMM bit scores greater than 1100 (e.g., greater than 1200, 1300, 1400, 1500, 1600, or 1700) when fitted to an HMM generated from the amino acid sequences set forth in FIG. 11 are identified in the Sequence Listing of this application. Such polypeptides include, for example, SEQ ID NOs: 4, 6, 7, 8, 9, 11, 13, 14, 15, 17, 18, 20, 21, 22, 23, 24, 25, 26, 27, 29, 31, 32, 33, 35, 36, 38, 39, 40, 41, 42, 43, 44, 45, 46, 47, 48, 49, 50, or 51.

Examples of polypeptides are shown in the sequence listing that have HMM bit scores greater than 364 (e.g., greater than 400 or 500) when fitted to an HMM generated from the amino acid sequences set forth in FIG. 12 are identified in the Sequence Listing of this application. Such polypeptides include, for example, SEQ ID NOs: 582, 584, 585, 587, 589, 591, 592, 594, 595, 596, 598, 600, 601, 603, 604, 606, 607, 608, 610, 611, 613, 615, 617, 619, 621, 623, 625, 626, 628, 629, 630, 631, or 632.

Examples of polypeptides are shown in the sequence listing that have HMM bit scores greater than 540 (e.g., greater than 600 or 700) when fitted to an HMM generated from the amino acid sequences set forth in FIG. 13 are identified in the Sequence Listing of this application. Such polypeptides include, for example, SEQ ID NOs: 53, 54, 56-61, 63-67, 69, 70, 72-76, 78, 80-83, 85, 86, 88-91, 93-97, 99-103, 105, 107, 109, 110, 112, 113, 115, 117, and 119-152.

Examples of polypeptides are shown in the sequence listing that have HMM bit scores greater than 451 (e.g., greater than 500 or 600) when fitted to an HMM generated from the amino acid sequences set forth in FIG. 14 are identified in the Sequence Listing of this application. Such polypeptides include, for example, SEQ ID NOs: 1112, 1114-1116, 1118, 1120-1123, 1125, 1127-1131, 1133, 1134, 1136, 1137, 1139-1145, 1147-1156, 1158-1161, 1163, 1165-1178, 1180-1188, 1190, 1191, 1193-1202, 1204, 1205-1207, 1209-1213.

Examples of polypeptides are shown in the sequence listing that have HMM bit scores greater than 283 when fitted to an HMM generated from the amino acid sequences set forth in FIG. 15 are identified in the Sequence Listing of this application. Such polypeptides include, for example, SEQ ID NOs: 634, 636, 638, 640, 642, 643, 645, 647, 649, 651, 653, 655, 657, 659, or 661.

Examples of polypeptides are shown in the sequence listing that have HMM bit scores greater than 225 (e.g., greater than 300, 400, 500, 600, 700, or 800) when fitted to an HMM generated from the amino acid sequences set forth in FIG. 16 are identified in the Sequence Listing of this application. Such polypeptides include, for example, SEQ ID NOs: 368, 370, 372, 373, 375-378, 380, 382-387, 389, 391, 393, 395, 396, 398-404, 406-414, 416, 418, 420, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497, 498, 499, 500, 501, or 502.

Examples of polypeptides are shown in the sequence listing that have HMM bit scores greater than 584 (e.g., greater than 600, 700, 800, 900, 1000, 1100, 1200, or 1300) when fitted to an HMM generated from the amino acid sequences set forth in FIG. 17 are identified in the Sequence Listing of this application. Such polypeptides include, for example, SEQ ID NOs: 1599, 1600, 1602-1606, 1608-1613, 1615, 1616, 1618-1626, 1628, 1629, 1631, 1633, 1634, 1636, 1637, 1639-1643, 1645, or 1646-1739.

Examples of polypeptides are shown in the sequence listing that have HMM bit scores greater than 100 when fitted to an HMM generated from the amino acid sequences set forth in FIG. 18 are identified in the Sequence Listing of this application. Such polypeptides include, for example, SEQ ID NOs: 154, 156, 158, 159, 161, 163, 165, 167, 168, 170, 172, 174, 176, 178, 180, 181, 182, 183, 184, or 185.

Examples of polypeptides are shown in the sequence listing that have HMM bit scores greater than 101 (e.g., greater than 200) when fitted to an HMM generated from the amino acid sequences set forth in FIG. 19 are identified in the Sequence Listing of this application. Such polypeptides include, for example, SEQ ID NOs: 1035, 1037, 1038, 1040, 1042, 1043, 1045, 1047, 1049, 1051, 1053, 1055, 1057, 1059, 1061, 1062, or 1063.

Examples of polypeptides are shown in the sequence listing that have HMM bit scores greater than 111 (e.g., greater than 200) when fitted to an HMM generated from the amino acid sequences set forth in FIG. 20 are identified in the Sequence Listing of this application. Such polypeptides include, for example, SEQ ID NOs: 741, 743, 745, 746, 748, 750, 752, 754, 756, 758, 760-764, 766, 768, 770, 772, 774, 776, 778, 780, 782, 784, 785, 787, 789, 791, 793-795, 797, 799, 801, 803, 805, 806, 808, 810, 812, 814, 816, 818-820, 822-824, 826, 828, 830, 832, 834, 836, 838-840, 842, 843, 845-847, or 849.

Examples of polypeptides are shown in the sequence listing that have HMM bit scores greater than 108 (e.g., greater than 200, 300, 400, 500, 600, or 700) when fitted to an HMM generated from the amino acid sequences set forth in FIG. 21 are identified in the Sequence Listing of this application. Such polypeptides include, for example, SEQ ID NOs: 187, 188, 190, 192-194, or 196.

Examples of polypeptides are shown in the sequence listing that have HMM bit scores greater than 534 (e.g., greater than 600, 700, 800, 900, 1000, or 1100) when fitted to an HMM generated from the amino acid sequences set forth in FIG. 22 are identified in the Sequence Listing of this application. Such polypeptides include, for example, SEQ ID NOs: 1065, 1067, 1069, 1070, 1072, 1073, 1075, 1076, 1078-1080, 1082, 1083, 1085, 1087, 1089, 1091, 1093, 1095, 1096, 1098, 1100, 1101, 1103, 1105, 1106, 1108, or 1110.

Examples of polypeptides are shown in the sequence listing that have HMM bit scores greater than 30 (e.g., greater than 40, 50, 60, 70, 80, 90, 100, 125, 150, 175, 200, 225, 250, 275, 300, 350, 400, 450, or 460) when fitted to an HMM generated from the amino acid sequences set forth in FIG. 23 are identified in the Sequence Listing of this application. Such polypeptides include, for example, SEQ ID NOs: 1580, 1582, 1583, 1585, 1587, 1589, 1590, 1592, 1593, 1595, 1597, 2604-2611, 2613, 2615, 2617, or 2619-2623.

Examples of polypeptides are shown in the sequence listing that have HMM bit scores greater than 359 (e.g., greater than 500, 600, 700, 800, 900, or 1000) when fitted to an HMM generated from the amino acid sequences set forth in FIG. 24 are identified in the Sequence Listing of this application. Such polypeptides include, for example, SEQ ID NOs: 851, 853, 854, 856-858, 860, 862, 863, 865, 866, 868, 870-873, 875-878, 880-882, 884-886, 888, 890, 892, 893, 895, 897, 899, 900, 902, 903, 905, 907, 909, 911, 912, 913, 915, 917, 919, 921, 923, 925, or 926.

Examples of polypeptides are shown in the sequence listing that have HMM bit scores greater than 324 (e.g., greater than 400 or 500) when fitted to an HMM generated from the amino acid sequences set forth in FIG. 25 are identified in the Sequence Listing of this application. Such polypeptides include, for example, SEQ ID NOs: 1016, 1018, 1020, 1021, 1023, 1024, 1026, 1027, 1029, 1030, 1032, 1033, 2578, 2579, 2581, 2583, 2584, 2585, 2587, or 2588.

Examples of polypeptides are shown in the sequence listing that have HMM bit scores greater than 105 (e.g., greater than 170, 183, or 260) when fitted to an HMM generated from the amino acid sequences set forth in FIG. 26 are identified in the Sequence Listing of this application. Such polypeptides include, for example, SEQ ID NOs: 2186, 2188, 2189, 2191, 2192, 2193, or 2194.

Examples of polypeptides are shown in the sequence listing that have HMM bit scores greater than 105 (e.g., greater than 170, 183, or 260) when fitted to an HMM generated from the amino acid sequences set forth in FIG. 27 are identified in the Sequence Listing of this application. Such polypeptides include, for example, SEQ ID NOs: 1955, 1956, 1957, 1958, 1960, 1962, 1964, 1966, 1967, 1968, 1970, 1972, 1973, 1974, 1975, 1976, or 1978.

Examples of polypeptides are shown in the sequence listing that have HMM bit scores greater than 10 (e.g., greater than 88, 106, 153, 190, 212, 230, or 260) when fitted to an HMM generated from the amino acid sequences set forth in FIG. 28 are identified in the Sequence Listing of this application. Such polypeptides include, for example, SEQ ID NOs: 2566, 2567, 2568, 2569, 2570, 2571, 2572, 2573, 2575, 2576, 2577, or 2591.

Examples of polypeptides are shown in the sequence listing that have HMM bit scores greater than 191 (e.g., greater than 200, 250, 320, 450, 550, 650, 700, or 730) when fitted to an HMM generated from the amino acid sequences set forth in FIG. 29 are identified in the Sequence Listing of this application. Such polypeptides include, for example, SEQ ID NOs: 2150, 2152, 2154, 2155, 2157, 2159-2161, 2163, 2165, 2166, 2168, 2170, 2172-2175, 2177, 2179, 2181, 2183, or 2184.

Examples of polypeptides are shown in the sequence listing that have HMM bit scores greater than 281 (e.g., greater than 320, 450, 500, 600, 700, 800, 900, 1000, 1050, 1100, 1150, or 1200) when fitted to an HMM generated from the amino acid sequences set forth in FIG. 30 are identified in the Sequence Listing of this application. Such polypeptides include, for example, SEQ ID NOs: 2196, 2197, 2199-2202, 2204, 2206-2208, 2210-2212, 2214, 2215, 2217-2220, 2222, 2224-2226, 2228, 2230-2232, 2234-2242, 2244-2254, or 2256-2269.

Examples of polypeptides are shown in the sequence listing that have HMM bit scores greater than 676 (e.g., greater than 728, 800, 850, or 900) when fitted to an HMM generated from the amino acid sequences set forth in FIG. 31 are identified in the Sequence Listing of this application. Such polypeptides include, for example, SEQ ID NOs: 2493-2498, 2500-2510, 2512-2515, 2517-2531, 2533-2536, 2538-2542, 2544-2548, 2550, 2551, 2553, 2555-2558, 2560, 2562, or 2564.

Examples of polypeptides are shown in the sequence listing that have HMM bit scores greater than 273 (e.g., greater than 300, 310, 320, 330, 340, 350, 375, 400, 425, 450, or 475) when fitted to an HMM generated from the amino acid sequences set forth in FIG. 32 are identified in the Sequence Listing of this application. Such polypeptides include, for example, SEQ ID NOs: 2271, 2273, 2274, 2276, 2278, 2280, 2281, 2283, 2285, 2286, 2288, 2290, 2292, 2294, 2296, 2297, 2299, 2301, 2303, 2305, 2307, 2309, 2311, 2313, 2314, 2316-2318, 2320, 2322, 2324, 2326, 2327, 2329, 2331, 2333, 2335, 2337, 2339, 2341, 2342, 2344, 2345, 2347-2349, 2351, 2353, 2355, 2357, 2359, 2361, 2363, 2365, 2367-2369, 2371, 2373, 2375, 2377, 2379, 2381, 2383, 2385, 2386, 2388, 2390, 2391, 2393, 2395, 2397, 2399, 2400, 2402, 2404, 2405, 2407, 2409, 2411, 2413, 2415, 2417, 2419, 2421, or 2423.

Examples of polypeptides are shown in the sequence listing that have HMM bit scores greater than 320 (e.g., greater than 350, 400, 450, 500, 600, 700, 800, or 900) when fitted to an HMM generated from the amino acid sequences set forth in FIG. 33 are identified in the Sequence Listing of this application. Such polypeptides include, for example, SEQ ID NOs: 1741, 1743, 1745, 1747-1756, 1758, 1760, 1762-1764, 1766, 1767, 1769, 1770, 1772-1774, 1776, 1778-1783, 1785-1792, 1794, 1796, 1798, 1799, 1801, 1802, 1804, 1806, or 1808-1810.

Examples of polypeptides are shown in the sequence listing that have HMM bit scores greater than 90 (e.g., greater than 95, 100, 125, 150, 175, 200, 250, 300, or 325) when fitted to an HMM generated from the amino acid sequences set forth in FIG. 34 are identified in the Sequence Listing of this application. Such polypeptides include, for example, SEQ ID NOs: 1980, 1982, 1984-1986, 1988, 1990, 1991, 1993, 1995, 1997, 1999, 2001, 2003, 2005, 2007, 2009, 2011, 2013, 2015, 2017, 2019, 2021, 2023-2027, 2029, 2031, or 2033.

Examples of polypeptides are shown in the sequence listing that have HMM bit scores greater than 399 (e.g., greater than 410, 425, 450, 475, 500, 550, 600, 650, 700, 750, or 800) when fitted to an HMM generated from the amino acid sequences set forth in FIG. 35 are identified in the Sequence Listing of this application. Such polypeptides include, for example, SEQ ID NOs: 1812, 1814, 1815, 1817, 1819, 1821, 1822, 1824, 1826-1830, 1832, 1834, 1835, 1837, 1839-1841, 1843, 1844, 1846, 1847, 1849, 1851, 1852, 1854, 1856, 1858, 1860-1863, or 1865-1953.

Examples of polypeptides are shown in the sequence listing that have HMM bit scores greater than 222 (e.g., greater than 225, 250, 300, 325, 350, 400, 450, 500, 600, 700, or 750) when fitted to an HMM generated from the amino acid sequences set forth in FIG. 36 are identified in the Sequence Listing of this application. Such polypeptides include, for example, SEQ ID NOs: 2124, 2126, 2128, 2129, 2131, 2133, 2135-2137, 2139, 2141, 2142, 2144-2148, or 2592-2602.

Examples of polypeptides are shown in the sequence listing that have HMM bit scores greater than 450 (e.g., greater than 475, 500, 525, 550, 575, 600, 625, 650, or 675) when fitted to an HMM generated from the amino acid sequences set forth in FIG. 37 are identified in the Sequence Listing of this application. Such polypeptides include, for example, SEQ ID NOs: 2035, 2037, 2039, 2041, 2043, 2045, 2047-2049, 2051-2057, 2059, 2061, 2063, 2065, 2067, 2069, 2071, 2073, 2075, 2077, 2079, 2080, 2082, 2084, 2086, 2088, 2090, 2092, 2093, 2095, 2097, 2098, or 2100-2122.

Examples of polypeptides are shown in the sequence listing that have HMM bit scores greater than 493 (e.g., greater than 500, 600, 700, 800, 900, 1000, 1100, 1200, 1300, 1400, 1500, 1600, 1700, 1750, or 1775) when fitted to an HMM generated from the amino acid sequences set forth in FIG. 38 are identified in the Sequence Listing of this application. Such polypeptides include, for example, SEQ ID NOs: 2425, 2426, 2428, 2430, 2431, 2433, 2435, 2437, 2438-2440, 2442, 2444, 2445, 2447, 2449, 2451, 2453, 2455, 2457, 2459, 2461, 2463-2468, 2470, 2472, 2474, 2476, 2478, 2479, 2481, 2482, 2484, 2485, or 2487-2491.

D. Percent Identity

In some embodiments, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one of the amino acid sequences set forth in SEQ ID NOs: 2, 4, 6-9, 11, 13-15, 17, 18, 20-27, 29, 31-33, 35, 36, 38-51, 53, 54, 56-61, 63-67, 69, 70, 72-76, 78, 80-83, 85, 86, 88-91, 93-97, 99-103, 105, 107, 109, 110, 112, 113, 115, 117, 119-152, 154, 156, 158, 159, 161, 163, 165, 167, 168, 170, 172, 174, 176, 178, 180-185, 187, 188, 190, 192-194, 196, 198, 200, 202, 203, 205, 207-211, 213-251, 253, 255, 257, 258, 260-262, 264, 265, 267-272, 274-279, 281-283, 285, 287-292, 294, 295-297, 299, 301, 303-305, 307, 309, 310, 312, 314, 316-318, 320, 321, 323, 325, 327-329, 331, 332, 334, 335, 337-339, 341, 342, 344, 345, 347, 349, 351, 353, 355, 357, 359, 361-366, 368, 370, 372, 373, 375-378, 380, 382-387, 389, 391, 393, 395, 396, 398-404, 406-414, 416, 418, 420, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497-502, 504, 506, 508, 509, 511-517, 519, 521, 522, 524-527, 529, 530, 532, 533, 535, 536, 537, 539, 541, 543, 545, 546, 548, 550, 552-555, 557, 558, 560, 562, 564, 566, 568, 570-578, 580, 582, 584, 585, 587, 589, 591, 592, 594-596, 598, 600, 601, 603, 604, 606-608, 610, 611, 613, 615, 617, 619, 621, 623, 625, 626, 628-632, 634, 636, 638, 640, 642, 643, 645, 647, 649, 651, 653, 655, 657, 659, 661, 663, 665, 667-670, 672, 674, 675, 677, 679-682, 684, 685, 687, 689-692, 694-698, 700-704, 706, 707, 709-718, 720, 722, 724, 726-728, 730, 731, 733-739, 741, 743, 745, 746, 748, 750, 752, 754, 756, 758, 760-764, 766, 768, 770, 772, 774, 776, 778, 780, 782, 784, 785, 787, 789, 791, 793-795, 797, 799, 801, 803, 805, 806, 808, 810, 812, 814, 816, 818-820, 822-824, 826, 828, 830, 832, 834, 836, 838-840, 842, 843, 845-847, 849, 851, 853, 854, 856-858, 860, 862, 863, 865, 866, 868, 870-873, 875-878, 880-882, 884-886, 888, 890, 892, 893, 895, 897, 899, 900, 902, 903, 905, 907, 909, 911, 912, 913, 915, 917, 919, 921, 923, 925, 926, 928, 930, 932, 933, 935, 936-938, 940, 941, 943-945, 947, 949, 950, 952-955, 957-961, 963, 965-969, 971, 972, 974, 975, 977, 978, 980, 982, 984, 986, 988, 990, 992, 994, 996, 998, 1000-1014, 1016, 1018, 1020, 1021, 1023, 1024, 1026, 1027, 1029, 1030, 1032, 1033, 1035, 1037, 1038, 1040, 1042, 1043, 1045, 1047, 1049, 1051, 1053, 1055, 1057, 1059, 1061-1063, 1065, 1067, 1069, 1070, 1072, 1073, 1075, 1076, 1078-1080, 1082, 1083, 1085, 1087, 1089, 1091, 1093, 1095, 1096, 1098, 1100, 1101, 1103, 1105, 1106, 1108, 1110, 1112, 1114-1116, 1118, 1120-1123, 1125, 1127-1131, 1133, 1134, 1136, 1137, 1139-1145, 1147-1156, 1158-1161, 1163, 1165-1178, 1180-1188, 1190, 1191, 1193-1202, 1204, 1205-1207, 1209-1213, 1215, 1217-1221, 1223-1228, 1230, 1231, 1233-1241, 1243, 1245, 1247, 1249-1252, 1254, 1255, 1257-1259, 1261, 1263, 1264, 1266-1272, 1274-1276, 1278, 1280, 1282-1286, 1288, 1289, 1291-1331, 1333-1337, 1339, 1341, 1343, 1345, 1347-1350, 1352, 1354, 1356, 1358, 1360, 1362, 1364, 1366, 1368, 1370-1372, 1374, 1375, 1377-1379, 1381, 1383, 1384, 1386, 1388-1390, 1392-1397, 1399, 1400, 1402, 1403, 1405, 1407-1410, 1412-1418, 1420, 1422, 1424, 1426, 1428, 1430, 1432-1436, 1438, 1440, 1442-1444, 1446, 1447, 1449, 1450, 1452-1454, 1456, 1457, 1459, 1460, 1462, 1463, 1465-1468, 1470, 1471, 1473, 1475, 1477-1483, 1485, 1487, 1489, 1491-1493, 1495, 1496, 1498, 1499, 1501, 1503, 1504, 1506, 1508, 1510, 1511, 1513, 1514, 1516-1521, 1523, 1524, 1526, 1528-1532, 1534, 1536-1539, 1541, 1542, 1544, 1545, 1547, 1548, 1550, 1552, 1553, 1555-1559, 1561, 1563-1565, 1567, 1568, 1570, 1571, 1573, 1575, 1576, 1578, 1580, 1582, 1583, 1585, 1587, 1589, 1590, 1592, 1593, 1595, 1597, 1599, 1600, 1602-1606, 1608-1613, 1615, 1616, 1618-1626, 1628, 1629, 1631, 1633, 1634, 1636, 1637, 1639-1643, 1645, or 1646-1739, 1741, 1743, 1745, 1747-1756, 1758, 1760, 1762-1764, 1766, 1767, 1769, 1770, 1772-1774, 1776, 1778-1783, 1785-1792, 1794, 1796, 1798, 1799, 1801, 1802, 1804, 1806, 1808-1810, 1812, 1814, 1815, 1817, 1819, 1821, 1822, 1824, 1826-1830, 1832, 1834, 1835, 1837, 1839-1841, 1843, 1844, 1846, 1847, 1849, 1851, 1852, 1854, 1856, 1858, 1860-1863, 1865-1953, 1955-1958, 1960, 1962, 1964, 1966-1968, 1970, 1972-1976, 1978, 1980, 1982, 1984-1986, 1988, 1990, 1991, 1993, 1995, 1997, 1999, 2001, 2003, 2005, 2007, 2009, 2011, 2013, 2015, 2017, 2019, 2021, 2023-2027, 2029, 2031, 2033, 2035, 2037, 2039, 2041, 2043, 2045, 2047-2049, 2051-2057, 2059, 2061, 2063, 2065, 2067, 2069, 2071, 2073, 2075, 2077, 2079, 2080, 2082, 2084, 2086, 2088, 2090, 2092, 2093, 2095, 2097, 2098, 2100-2122, 2124, 2126, 2128, 2129, 2131, 2133, 2135-2137, 2139, 2141, 2142, 2144-2148, 2150, 2152, 2154, 2155, 2157, 2159-2161, 2163, 2165, 2166, 2168, 2170, 2172-2175, 2177, 2179, 2181, 2183, 2184, 2186, 2188, 2189, 2191-2194, 2196, 2197, 2199-2202, 2204, 2206-2208, 2210-2212, 2214, 2215, 2217-2220, 2222, 2224-2226, 2228, 2230-2232, 2234-2242, 2244-2254, 2256-2269, 2271, 2273, 2274, 2276, 2278, 2280, 2281, 2283, 2285, 2286, 2288, 2290, 2292, 2294, 2296, 2297, 2299, 2301, 2303, 2305, 2307, 2309, 2311, 2313, 2314, 2316-2318, 2320, 2322, 2324, 2326, 2327, 2329, 2331, 2333, 2335, 2337, 2339, 2341, 2342, 2344, 2345, 2347-2349, 2351, 2353, 2355, 2357, 2359, 2361, 2363, 2365, 2367-2369, 2371, 2373, 2375, 2377, 2379, 2381, 2383, 2385, 2386, 2388, 2390, 2391, 2393, 2395, 2397, 2399, 2400, 2402, 2404, 2405, 2407, 2409, 2411, 2413, 2415, 2417, 2419, 2421, 2423, 2425, 2426, 2428, 2430, 2431, 2433, 2435, 2437, 2438-2440, 2442, 2444, 2445, 2447, 2449, 2451, 2453, 2455, 2457, 2459, 2461, 2463-2468, 2470, 2472, 2474, 2476, 2478, 2479, 2481, 2482, 2484, 2485, 2487-2491, 2493-2498, 2500-2510, 2512-2515, 2517-2531, 2533-2536, 2538-2542, 2544-2548, 2550, 2551, 2553, 2555-2558, 2560, 2562, 2564, 2566-2573, 2575-2579, 2581, 2583-2585, 2587-2602, 2604-2611, 2613, 2615, 2617, or 2619-2623. Polypeptides having such a percent sequence identity often have a domain indicative of a biomass-modulating polypeptide and/or have an HMM bit score that is greater than 65, as discussed above. Amino acid sequences of biomass-modulating polypeptides having at least 80% sequence identity to one of the amino acid sequences set forth in SEQ ID NOs: 2, 4, 6-9, 11, 13-15, 17, 18, 20-27, 29, 31-33, 35, 36, 38-51, 53, 54, 56-61, 63-67, 69, 70, 72-76, 78, 80-83, 85, 86, 88-91, 93-97, 99-103, 105, 107, 109, 110, 112, 113, 115, 117, 119-152, 154, 156, 158, 159, 161, 163, 165, 167, 168, 170, 172, 174, 176, 178, 180-185, 187, 188, 190, 192-194, 196, 198, 200, 202, 203, 205, 207-211, 213-251, 253, 255, 257, 258, 260-262, 264, 265, 267-272, 274-279, 281-283, 285, 287-292, 294, 295-297, 299, 301, 303-305, 307, 309, 310, 312, 314, 316-318, 320, 321, 323, 325, 327-329, 331, 332, 334, 335, 337-339, 341, 342, 344, 345, 347, 349, 351, 353, 355, 357, 359, 361-366, 368, 370, 372, 373, 375-378, 380, 382-387, 389, 391, 393, 395, 396, 398-404, 406-414, 416, 418, 420, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497-502, 504, 506, 508, 509, 511-517, 519, 521, 522, 524-527, 529, 530, 532, 533, 535, 536, 537, 539, 541, 543, 545, 546, 548, 550, 552-555, 557, 558, 560, 562, 564, 566, 568, 570-578, 580, 582, 584, 585, 587, 589, 591, 592, 594-596, 598, 600, 601, 603, 604, 606-608, 610, 611, 613, 615, 617, 619, 621, 623, 625, 626, 628-632, 634, 636, 638, 640, 642, 643, 645, 647, 649, 651, 653, 655, 657, 659, 661, 663, 665, 667-670, 672, 674, 675, 677, 679-682, 684, 685, 687, 689-692, 694-698, 700-704, 706, 707, 709-718, 720, 722, 724, 726-728, 730, 731, 733-739, 741, 743, 745, 746, 748, 750, 752, 754, 756, 758, 760-764, 766, 768, 770, 772, 774, 776, 778, 780, 782, 784, 785, 787, 789, 791, 793-795, 797, 799, 801, 803, 805, 806, 808, 810, 812, 814, 816, 818-820, 822-824, 826, 828, 830, 832, 834, 836, 838-840, 842, 843, 845-847, 849, 851, 853, 854, 856-858, 860, 862, 863, 865, 866, 868, 870-873, 875-878, 880-882, 884-886, 888, 890, 892, 893, 895, 897, 899, 900, 902, 903, 905, 907, 909, 911, 912, 913, 915, 917, 919, 921, 923, 925, 926, 928, 930, 932, 933, 935, 936-938, 940, 941, 943-945, 947, 949, 950, 952-955, 957-961, 963, 965-969, 971, 972, 974, 975, 977, 978, 980, 982, 984, 986, 988, 990, 992, 994, 996, 998, 1000-1014, 1016, 1018, 1020, 1021, 1023, 1024, 1026, 1027, 1029, 1030, 1032, 1033, 1035, 1037, 1038, 1040, 1042, 1043, 1045, 1047, 1049, 1051, 1053, 1055, 1057, 1059, 1061-1063, 1065, 1067, 1069, 1070, 1072, 1073, 1075, 1076, 1078-1080, 1082, 1083, 1085, 1087, 1089, 1091, 1093, 1095, 1096, 1098, 1100, 1101, 1103, 1105, 1106, 1108, 1110, 1112, 1114-1116, 1118, 1120-1123, 1125, 1127-1131, 1133, 1134, 1136, 1137, 1139-1145, 1147-1156, 1158-1161, 1163, 1165-1178, 1180-1188, 1190, 1191, 1193-1202, 1204, 1205-1207, 1209-1213, 1215, 1217-1221, 1223-1228, 1230, 1231, 1233-1241, 1243, 1245, 1247, 1249-1252, 1254, 1255, 1257-1259, 1261, 1263, 1264, 1266-1272, 1274-1276, 1278, 1280, 1282-1286, 1288, 1289, 1291-1331, 1333-1337, 1339, 1341, 1343, 1345, 1347-1350, 1352, 1354, 1356, 1358, 1360, 1362, 1364, 1366, 1368, 1370-1372, 1374, 1375, 1377-1379, 1381, 1383, 1384, 1386, 1388-1390, 1392-1397, 1399, 1400, 1402, 1403, 1405, 1407-1410, 1412-1418, 1420, 1422, 1424, 1426, 1428, 1430, 1432-1436, 1438, 1440, 1442-1444, 1446, 1447, 1449, 1450, 1452-1454, 1456, 1457, 1459, 1460, 1462, 1463, 1465-1468, 1470, 1471, 1473, 1475, 1477-1483, 1485, 1487, 1489, 1491-1493, 1495, 1496, 1498, 1499, 1501, 1503, 1504, 1506, 1508, 1510, 1511, 1513, 1514, 1516-1521, 1523, 1524, 1526, 1528-1532, 1534, 1536-1539, 1541, 1542, 1544, 1545, 1547, 1548, 1550, 1552, 1553, 1555-1559, 1561, 1563-1565, 1567, 1568, 1570, 1571, 1573, 1575, 1576, 1578, 1580, 1582, 1583, 1585, 1587, 1589, 1590, 1592, 1593, 1595, 1597, 1599, 1600, 1602-1606, 1608-1613, 1615, 1616, 1618-1626, 1628, 1629, 1631, 1633, 1634, 1636, 1637, 1639-1643, 1645, 1646-1739, 1741, 1743, 1745, 1747-1756, 1758, 1760, 1762-1764, 1766, 1767, 1769, 1770, 1772-1774, 1776, 1778-1783, 1785-1792, 1794, 1796, 1798, 1799, 1801, 1802, 1804, 1806, 1808-1810, 1812, 1814, 1815, 1817, 1819, 1821, 1822, 1824, 1826-1830, 1832, 1834, 1835, 1837, 1839-1841, 1843, 1844, 1846, 1847, 1849, 1851, 1852, 1854, 1856, 1858, 1860-1863, 1865-1953, 1955-1958, 1960, 1962, 1964, 1966-1968, 1970, 1972-1976, 1978, 1980, 1982, 1984-1986, 1988, 1990, 1991, 1993, 1995, 1997, 1999, 2001, 2003, 2005, 2007, 2009, 2011, 2013, 2015, 2017, 2019, 2021, 2023-2027, 2029, 2031, 2033, 2035, 2037, 2039, 2041, 2043, 2045, 2047-2049, 2051-2057, 2059, 2061, 2063, 2065, 2067, 2069, 2071, 2073, 2075, 2077, 2079, 2080, 2082, 2084, 2086, 2088, 2090, 2092, 2093, 2095, 2097, 2098, 2100-2122, 2124, 2126, 2128, 2129, 2131, 2133, 2135-2137, 2139, 2141, 2142, 2144-2148, 2150, 2152, 2154, 2155, 2157, 2159-2161, 2163, 2165, 2166, 2168, 2170, 2172-2175, 2177, 2179, 2181, 2183, 2184, 2186, 2188, 2189, 2191-2194, 2196, 2197, 2199-2202, 2204, 2206-2208, 2210-2212, 2214, 2215, 2217-2220, 2222, 2224-2226, 2228, 2230-2232, 2234-2242, 2244-2254, 2256-2269, 2271, 2273, 2274, 2276, 2278, 2280, 2281, 2283, 2285, 2286, 2288, 2290, 2292, 2294, 2296, 2297, 2299, 2301, 2303, 2305, 2307, 2309, 2311, 2313, 2314, 2316-2318, 2320, 2322, 2324, 2326, 2327, 2329, 2331, 2333, 2335, 2337, 2339, 2341, 2342, 2344, 2345, 2347-2349, 2351, 2353, 2355, 2357, 2359, 2361, 2363, 2365, 2367-2369, 2371, 2373, 2375, 2377, 2379, 2381, 2383, 2385, 2386, 2388, 2390, 2391, 2393, 2395, 2397, 2399, 2400, 2402, 2404, 2405, 2407, 2409, 2411, 2413, 2415, 2417, 2419, 2421, 2423, 2425, 2426, 2428, 2430, 2431, 2433, 2435, 2437, 2438-2440, 2442, 2444, 2445, 2447, 2449, 2451, 2453, 2455, 2457, 2459, 2461, 2463-2468, 2470, 2472, 2474, 2476, 2478, 2479, 2481, 2482, 2484, 2485, 2487-2491, 2493-2498, 2500-2510, 2512-2515, 2517-2531, 2533-2536, 2538-2542, 2544-2548, 2550, 2551, 2553, 2555-2558, 2560, 2562, 2564, 2566-2573, 2575-2579, 2581, 2583-2585, 2587-2602, 2604-2611, 2613, 2615, 2617, or 2619-2623 are provided in FIGS. 1-38 and in the Sequence Listing.

"Percent sequence identity" refers to the degree of sequence identity between any given reference sequence, e.g., SEQ ID NO: 1, and a candidate biomass-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., *Nucleic Acids Res.*, 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1333. Amino acid sequences of polypeptides having greater than 45% sequence identity to the polypeptide set forth in SEQ ID NO: 1333 are provided in FIG. 1 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1489. Amino acid sequences of polypeptides having greater than 45% sequence identity to the polypeptide set forth in SEQ ID NO: 1489 are provided in FIG. 2 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 504. Amino acid sequences of polypeptides having greater than 45% sequence identity to the polypeptide set forth in SEQ ID NO: 504 are provided in FIG. 3 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 198. Amino acid sequences of polypeptides having greater than 45% sequence identity to the polypeptide set forth in SEQ ID NO: 198 are provided in FIG. 4 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 253. Amino acid sequences of polypeptides having greater than 45% sequence identity to the polypeptide set forth in SEQ ID NO: 253 are provided in FIG. 5 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1541. Amino acid sequences of polypeptides having greater than 45% sequence identity to the polypeptide set forth in SEQ ID NO: 1541 are provided in FIG. 6 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 663. Amino acid sequences of polypeptides having greater than 45% sequence identity to the polypeptide set forth in SEQ ID NO: 663 are provided in FIG. 7 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1366. Amino acid sequences of polypeptides having greater than 45% sequence identity to the polypeptide set forth in SEQ ID NO: 1366 are provided in FIG. 8 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 928. Amino acid sequences of polypeptides having greater than 45% sequence identity to the polypeptide set forth in SEQ ID NO: 928 are provided in FIG. 9 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1215. Amino acid sequences of polypeptides having greater than 45% sequence identity to the polypeptide set forth in SEQ ID NO: 1215 are provided in FIG. 10 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 4. Amino acid sequences of polypeptides having greater than 45% sequence identity to the polypeptide set forth in SEQ ID NO: 4 are provided in FIG. 11 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 580. Amino acid sequences of polypeptides having greater than 45% sequence identity to the polypeptide set forth in SEQ ID NO: 580 are provided in FIG. 12 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 53. Amino acid sequences of polypeptides having greater than 45% sequence identity to the polypeptide set forth in SEQ ID NO: 53 are provided in FIG. 13 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1112. Amino acid sequences of polypeptides having greater than 45% sequence identity to the polypeptide set forth in SEQ ID NO: 1112 are provided in FIG. 14 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 634. Amino acid sequences of polypeptides having greater than 45% sequence identity to the polypeptide set forth in SEQ ID NO: 634 are provided in FIG. 15 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 368. Amino acid sequences of polypeptides having greater than 45% sequence identity to the polypeptide set forth in SEQ ID NO: 368 are provided in FIG. 16 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1599. Amino acid sequences of polypeptides having greater than 45% sequence identity to the polypeptide set forth in SEQ ID NO: 1599 are provided in FIG. 17 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 154. Amino acid sequences of polypeptides having greater than 45% sequence identity to the polypeptide set forth in SEQ ID NO: 154 are provided in FIG. 18 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1035. Amino acid sequences of polypeptides having greater than 45% sequence identity to the polypeptide set forth in SEQ ID NO: 1035 are provided in FIG. 19 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 741. Amino acid sequences of polypeptides having greater than 45% sequence identity to the polypeptide set forth in SEQ ID NO: 741 are provided in FIG. 20 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 187. Amino acid sequences of polypeptides having greater than 45% sequence identity to the polypeptide set forth in SEQ ID NO: 187 are provided in FIG. 21 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1065. Amino acid sequences of polypeptides having greater than 45% sequence identity to the polypeptide set forth in SEQ ID NO: 1065 are provided in FIG. 22 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1592. Amino acid sequences of polypeptides having greater than 45% sequence identity to the polypeptide set forth in SEQ ID NO: 1592 are provided in FIG. 23 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 851. Amino acid sequences of polypeptides having greater than 45% sequence identity to the polypeptide set forth in SEQ ID NO: 851 are provided in FIG. 24 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1016. Amino acid sequences of polypeptides having greater than 45% sequence identity to the polypeptide set forth in SEQ ID NO: 1016 are provided in FIG. 25 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2186. Amino acid sequences of polypeptides having greater than 45% sequence identity to the polypeptide set forth in SEQ ID NO: 2186 are provided in FIG. 26 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1955. Amino acid sequences of polypeptides having greater than 45% sequence identity to the polypeptide set forth in SEQ ID NO: 1955 are provided in FIG. 27 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2566. Amino acid sequences of polypeptides having greater than 45% sequence identity to the polypeptide set forth in SEQ ID NO: 2566 are provided in FIG. 28 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2150. Amino acid sequences of polypeptides having greater than 45% sequence identity to the polypeptide set forth in SEQ ID NO: 2150 are provided in FIG. 29 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2196. Amino acid sequences of polypeptides having greater than 45% sequence identity to the polypeptide set forth in SEQ ID NO: 2196 are provided in FIG. 30 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2493. Amino acid sequences of polypeptides having greater than 45% sequence identity to the polypeptide set forth in SEQ ID NO: 2493 are provided in FIG. 31 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2271. Amino acid sequences of polypeptides having greater than 45% sequence identity to the polypeptide set forth in SEQ ID NO: 2271 are provided in FIG. 32 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1741. Amino acid sequences of polypeptides having greater than 45% sequence identity to the polypeptide set forth in SEQ ID NO: 1741 are provided in FIG. 33 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1980. Amino acid sequences of polypeptides having greater than 45% sequence identity to the polypeptide set forth in SEQ ID NO: 1980 are provided in FIG. 34 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 1812. Amino acid sequences of polypeptides having greater than 45% sequence identity to the polypeptide set forth in SEQ ID NO: 1812 are provided in FIG. 35 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2124. Amino acid sequences of polypeptides having greater than 45% sequence identity to the polypeptide set forth in SEQ ID NO: 2124 are provided in FIG. 36 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2935. Amino acid sequences of polypeptides having greater than 45% sequence identity to the polypeptide set forth in SEQ ID NO: 2035 are provided in FIG. 37 and in the Sequence Listing.

In some cases, a biomass-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2425. Amino acid sequences of polypeptides having greater than 45% sequence identity to the polypeptide set forth in SEQ ID NO: 2425 are provided in FIG. 38 and in the Sequence Listing.

E. Other Sequences

It should be appreciated that a biomass-modulating polypeptide can include additional amino acids that are not involved in biomass modulation, and thus such a polypeptide can be longer than would otherwise be the case. For example, a biomass-modulating polypeptide can include a purification tag, a chloroplast transit peptide, a mitochondrial transit peptide, an amyloplast peptide, or a leader sequence added to the amino or carboxy terminus. In some embodiments, a biomass-modulating polypeptide includes an amino acid sequence that functions as a reporter, e.g., a green fluorescent protein or yellow fluorescent protein.

III. Nucleic Acids

Nucleic acids described herein include nucleic acids that are effective to modulate biomass levels when transcribed in a plant or plant cell. Such nucleic acids include, without limitation, those that encode a biomass-modulating polypeptide and those that can be used to inhibit expression of a biomass-modulating polypeptide via a nucleic acid based method.

A. Nucleic Acids Encoding Biomass-Modulating Polypeptides

Nucleic acids encoding biomass-modulating polypeptides are described herein. Examples of such nucleic acids include SEQ ID NOs: 1, 3, 5, 10, 12, 16, 19, 28, 30, 34, 37, 52, 55, 62, 68, 71, 77, 79, 84, 87, 92, 98, 104, 106, 108, 111, 114, 116, 118, 153, 155, 157, 160, 162, 164, 166, 169, 171, 173, 175, 177, 179, 186, 189, 191, 195, 197, 199, 201, 204, 206, 212, 252, 254, 256, 259, 263, 266, 273, 280, 284, 286, 293, 298, 300, 302, 306, 308, 311, 313, 315, 319, 322, 324, 326, 330, 333, 336, 340, 343, 346, 348, 350, 352, 354, 356, 358, 360, 367, 369, 371, 374, 379, 381, 388, 390, 392, 394, 397, 405, 415, 417, 419, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 503, 505, 507, 510, 518, 520, 523, 528, 531, 534, 538, 540, 542, 544, 547, 549, 551, 556, 559, 561, 563, 565, 567, 569, 579, 581, 583, 586, 588, 590, 593, 597, 599, 602, 605, 609, 612, 614, 616, 618, 620, 622, 624, 627, 633, 635, 637, 639, 641, 644, 646, 648, 650, 652, 654, 656, 658, 660, 662, 664, 666, 671, 673, 676, 678, 683, 686, 688, 693, 699, 705, 708, 719, 721, 723, 725, 729, 732, 740, 742, 744, 747, 749, 751, 753, 755, 757, 759, 765, 767, 769, 771, 773, 775, 777, 779, 781, 783, 786, 788, 790, 792, 796, 798, 800, 802, 804, 807, 809, 811, 813, 815, 817, 821, 825, 827, 829, 831, 833, 835, 837, 841, 844, 848, 850, 852, 855, 859, 861, 864, 867, 869, 874, 879, 883, 887, 889, 891, 894, 896, 898, 901, 904, 906, 908, 910, 914, 916, 918, 920, 922, 924, 927, 929, 931, 934, 939, 942, 946, 948, 951, 956, 962, 964, 970, 973, 976, 979, 981, 983, 985, 987, 989, 991, 993, 995, 997, 999, 1015, 1017, 1019, 1022, 1025, 1028, 1031, 1034, 1036, 1039, 1041, 1044, 1046, 1048, 1050, 1052, 1054, 1056, 1058, 1060, 1064, 1066, 1068, 1071, 1074, 1077, 1081, 1084, 1086, 1088, 1090, 1092, 1094, 1097, 1099, 1102, 1104, 1107, 1109, 1111, 1113, 1117, 1119, 1124, 1126, 1132, 1135, 1138, 1146, 1157, 1162, 1164, 1179, 1189, 1192, 1203, 1208, 1214, 1216, 1222, 1229, 1232, 1242, 1244, 1246, 1248, 1253, 1256, 1260, 1262, 1265, 1273, 1277, 1279, 1281, 1287, 1290, 1332, 1338, 1340, 1342, 1344, 1346, 1351, 1353, 1355, 1357, 1359, 1361, 1363, 1365, 1367, 1369, 1373, 1376, 1380, 1382, 1385, 1387, 1391, 1398, 1401, 1404, 1406, 1411, 1419, 1421, 1423, 1425, 1427, 1429, 1431, 1437, 1439, 1441, 1445, 1448, 1451, 1455, 1458, 1461, 1464, 1469, 1472, 1474, 1476, 1484, 1486, 1488, 1490, 1494, 1497, 1500, 1502, 1505, 1507, 1509, 1512, 1515, 1522, 1525, 1527, 1533, 1535, 1540, 1543, 1546, 1549, 1551, 1554, 1560, 1562, 1566, 1569, 1572, 1574, 1577, 1579, 1581, 1584, 1586, 1588, 1591, 1594, 1596, 1598, 1601, 1607, 1614, 1617, 1627, 1630, 1632, 1635, 1638, 1644, 1740, 1742, 1744, 1746, 1757, 1759, 1761, 1765, 1768, 1771, 1775, 1777, 1784, 1793, 1795, 1797, 1800, 1803, 1805, 1807, 1811, 1813, 1816, 1818, 1820, 1823, 1825, 1831, 1833, 1836, 1838, 1842, 1845, 1848, 1850, 1853, 1855, 1857, 1859, 1864, 1954, 1959, 1961, 1963, 1965, 1969, 1971, 1977, 1979, 1981, 1983, 1987, 1989, 1992, 1994, 1996, 1998, 2000, 2002, 2004, 2006, 2008, 2010, 2012, 2014, 2016, 2018, 2020, 2022, 2028, 2030, 2032, 2034, 2036, 2038, 2040, 2042, 2044, 2046, 2050, 2058, 2060, 2062, 2064, 2066, 2068, 2070, 2072, 2074, 2076, 2078, 2081, 2083, 2085, 2087, 2089, 2091, 2094, 2096, 2099, 2123, 2125, 2127, 2130, 2132, 2134, 2138, 2140, 2143, 2149, 2151, 2153, 2156, 2158, 2162, 2164, 2167, 2169, 2171, 2176, 2178, 2180, 2182, 2185, 2187, 2190, 2195, 2198, 2203, 2205, 2209, 2213, 2216, 2221, 2223, 2227, 2229, 2233, 2243, 2255, 2270, 2272, 2275, 2277, 2279, 2282, 2284, 2287, 2289, 2291, 2293, 2295, 2298, 2300, 2302, 2304, 2306, 2308, 2310, 2312, 2315, 2319, 2321, 2323, 2325, 2328, 2330, 2332, 2334, 2336, 2338, 2340, 2343, 2346, 2350, 2352, 2354, 2356, 2358, 2360, 2362, 2364, 2366, 2370, 2372, 2374, 2376, 2378, 2380, 2382, 2384, 2387, 2389, 2392, 2394, 2396, 2398, 2401, 2403, 2406, 2408, 2410, 2412, 2414, 2416, 2418, 2420, 2422, 2424, 2427, 2429, 2432, 2434, 2436, 2441, 2443, 2446, 2448, 2450, 2452, 2454, 2456, 2458, 2460, 2462, 2469, 2471, 2473, 2475, 2477, 2480, 2483, 2486, 2492, 2499, 2511, 2516, 2532, 2537, 2543, 2549, 2552, 2554, 2559, 2561, 2563, 2565, 2574, 2580, 2582, 2586, 2603, 2612, 2614, 2616, and 2618 as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NOs: 1, 3, 5, 10, 12, 16, 19, 28, 30, 34, 37, 52, 55, 62, 68, 71, 77, 79, 84, 87, 92, 98, 104, 106, 108, 111, 114, 116, 118, 153, 155, 157, 160, 162, 164, 166, 169, 171, 173, 175, 177, 179, 186, 189, 191, 195, 197, 199, 201, 204, 206, 212, 252, 254, 256, 259, 263, 266, 273, 280, 284, 286, 293, 298, 300, 302, 306, 308, 311, 313, 315, 319, 322, 324, 326, 330, 333, 336, 340, 343, 346, 348, 350, 352, 354, 356, 358, 360, 367, 369, 371, 374, 379, 381, 388, 390, 392, 394, 397, 405, 415, 417, 419, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 503, 505, 507, 510, 518, 520, 523, 528, 531, 534, 538, 540, 542, 544, 547, 549, 551, 556, 559, 561, 563, 565, 567, 569, 579, 581, 583, 586, 588, 590, 593, 597, 599, 602, 605, 609, 612, 614, 616, 618, 620, 622, 624, 627, 633, 635, 637, 639, 641, 644, 646, 648, 650, 652, 654, 656, 658, 660, 662, 664, 666, 671, 673, 676, 678, 683, 686, 688, 693, 699, 705, 708, 719, 721, 723, 725, 729, 732, 740, 742, 744, 747, 749, 751, 753, 755, 757, 759, 765, 767, 769, 771, 773, 775, 777, 779, 781, 783, 786, 788, 790, 792, 796, 798, 800, 802, 804, 807, 809, 811, 813, 815, 817, 821, 825, 827, 829, 831, 833, 835, 837, 841, 844, 848, 850, 852, 855, 859, 861, 864, 867, 869, 874, 879, 883, 887, 889, 891, 894, 896, 898, 901, 904, 906, 908, 910, 914, 916, 918, 920, 922, 924, 927, 929, 931, 934, 939, 942, 946, 948, 951, 956, 962, 964, 970, 973, 976, 979, 981, 983, 985, 987, 989, 991, 993, 995, 997, 999, 1015, 1017, 1019, 1022, 1025, 1028, 1031, 1034, 1036, 1039, 1041, 1044, 1046, 1048, 1050, 1052, 1054, 1056, 1058, 1060, 1064, 1066, 1068, 1071, 1074, 1077, 1081, 1084, 1086, 1088, 1090, 1092, 1094, 1097, 1099, 1102, 1104, 1107, 1109, 1111, 1113, 1117, 1119, 1124, 1126, 1132, 1135, 1138, 1146, 1157, 1162, 1164, 1179, 1189, 1192, 1203, 1208, 1214, 1216, 1222, 1229, 1232, 1242, 1244, 1246, 1248, 1253, 1256, 1260, 1262, 1265, 1273, 1277, 1279, 1281, 1287, 1290, 1332, 1338, 1340, 1342, 1344, 1346, 1351, 1353, 1355, 1357, 1359, 1361, 1363, 1365, 1367, 1369, 1373, 1376, 1380, 1382, 1385, 1387, 1391, 1398, 1401, 1404, 1406, 1411, 1419, 1421, 1423, 1425, 1427, 1429, 1431, 1437, 1439, 1441, 1445, 1448, 1451, 1455, 1458, 1461, 1464, 1469, 1472, 1474, 1476, 1484, 1486, 1488, 1490, 1494, 1497, 1500, 1502, 1505, 1507, 1509, 1512, 1515, 1522, 1525, 1527, 1533, 1535, 1540, 1543, 1546, 1549, 1551, 1554, 1560, 1562, 1566, 1569, 1572, 1574, 1577, 1579, 1581, 1584, 1586, 1588, 1591, 1594, 1596, 1598, 1601, 1607, 1614, 1617, 1627, 1630, 1632, 1635, 1638, 1644, 1740, 1742, 1744, 1746, 1757, 1759, 1761, 1765, 1768, 1771, 1775, 1777, 1784, 1793, 1795, 1797, 1800, 1803, 1805, 1807, 1811, 1813, 1816, 1818, 1820, 1823, 1825, 1831, 1833, 1836, 1838, 1842, 1845, 1848, 1850, 1853, 1855, 1857, 1859, 1864, 1954, 1959, 1961, 1963, 1965, 1969, 1971, 1977, 1979, 1981, 1983, 1987, 1989, 1992, 1994, 1996, 1998, 2000, 2002, 2004, 2006, 2008, 2010, 2012, 2014, 2016, 2018, 2020, 2022, 2028, 2030, 2032, 2034, 2036, 2038, 2040, 2042, 2044, 2046, 2050, 2058, 2060, 2062, 2064, 2066, 2068, 2070, 2072, 2074, 2076, 2078, 2081, 2083, 2085, 2087, 2089, 2091, 2094, 2096, 2099, 2123, 2125, 2127, 2130, 2132, 2134, 2138, 2140, 2143, 2149, 2151, 2153, 2156, 2158, 2162, 2164, 2167, 2169, 2171, 2176, 2178, 2180, 2182, 2185, 2187, 2190, 2195, 2198, 2203, 2205, 2209, 2213, 2216, 2221, 2223, 2227, 2229, 2233, 2243, 2255, 2270, 2272, 2275, 2277, 2279, 2282, 2284, 2287, 2289, 2291, 2293, 2295, 2298, 2300, 2302, 2304, 2306, 2308, 2310, 2312, 2315, 2319, 2321, 2323, 2325, 2328, 2330, 2332, 2334, 2336, 2338, 2340, 2343, 2346, 2350, 2352, 2354, 2356, 2358, 2360, 2362, 2364, 2366, 2370, 2372, 2374, 2376, 2378, 2380, 2382, 2384, 2387, 2389, 2392, 2394, 2396, 2398, 2401, 2403, 2406, 2408, 2410, 2412, 2414, 2416, 2418, 2420, 2422, 2424, 2427, 2429, 2432, 2434, 2436, 2441, 2443, 2446, 2448, 2450, 2452, 2454, 2456, 2458, 2460, 2462, 2469, 2471, 2473, 2475, 2477, 2480, 2483, 2486, 2492, 2499, 2511, 2516, 2532, 2537, 2543, 2549, 2552, 2554, 2559, 2561, 2563, 2565, 2574, 2580, 2582, 2586, 2603, 2612, 2614, 2616, and 2618.

A biomass-modulating nucleic acid can comprise the nucleotide sequence set forth in SEQ ID NO: 1. Alternatively, a biomass-modulating nucleic acid can be a variant of the nucleic acid having the nucleotide sequence set forth in SEQ ID NO: 1. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1.

A biomass-modulating nucleic acid can comprise the nucleotide sequence set forth in SEQ ID NO: 1332. Alternatively, a biomass-modulating nucleic acid can be a variant of the nucleic acid having the nucleotide sequence set forth in SEQ ID NO: 1332. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1332.

A biomass-modulating nucleic acid can comprise the nucleotide sequence set forth in SEQ ID NO: 1488. Alternatively, a biomass-modulating nucleic acid can be a variant of the nucleic acid having the nucleotide sequence set forth in SEQ ID NO: 1488. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1488.

A biomass-modulating nucleic acid can comprise the nucleotide sequence set forth in SEQ ID NO: 503. Alternatively, a biomass-modulating nucleic acid can be a variant of the nucleic acid having the nucleotide sequence set forth in SEQ ID NO: 503. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 503.

A biomass-modulating nucleic acid can comprise the nucleotide sequence set forth in SEQ ID NO: 197. Alternatively, a biomass-modulating nucleic acid can be a variant of the nucleic acid having the nucleotide sequence set forth in SEQ ID NO: 197. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 197.

A biomass-modulating nucleic acid can comprise the nucleotide sequence set forth in SEQ ID NO: 252. Alternatively, a biomass-modulating nucleic acid can be a variant of the nucleic acid having the nucleotide sequence set forth in SEQ ID NO: 252. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 252.

A biomass-modulating nucleic acid can comprise the nucleotide sequence set forth in SEQ ID NO: 1540. Alternatively, a biomass-modulating nucleic acid can be a variant of the nucleic acid having the nucleotide sequence set forth in SEQ ID NO: 1540. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1540.

A biomass-modulating nucleic acid can comprise the nucleotide sequence set forth in SEQ ID NO: 662. Alternatively, a biomass-modulating nucleic acid can be a variant of the nucleic acid having the nucleotide sequence set forth in SEQ ID NO: 662. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 662.

A biomass-modulating nucleic acid can comprise the nucleotide sequence set forth in SEQ ID NO: 1365. Alternatively, a biomass-modulating nucleic acid can be a variant of the nucleic acid having the nucleotide sequence set forth in SEQ ID NO: 1365. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1365.

A biomass-modulating nucleic acid can comprise the nucleotide sequence set forth in SEQ ID NO: 927. Alternatively, a biomass-modulating nucleic acid can be a variant of the nucleic acid having the nucleotide sequence set forth in SEQ ID NO: 927. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 927.

A biomass-modulating nucleic acid can comprise the nucleotide sequence set forth in SEQ ID NO: 1214. Alternatively, a biomass-modulating nucleic acid can be a variant of the nucleic acid having the nucleotide sequence set forth in SEQ ID NO: 1214. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1214.

A biomass-modulating nucleic acid can comprise the nucleotide sequence set forth in SEQ ID NO: 3. Alternatively, a biomass-modulating nucleic acid can be a variant of the nucleic acid having the nucleotide sequence set forth in SEQ ID NO: 3. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 3.

A biomass-modulating nucleic acid can comprise the nucleotide sequence set forth in SEQ ID NO: 579. Alternatively, a biomass-modulating nucleic acid can be a variant of the nucleic acid having the nucleotide sequence set forth in SEQ ID NO: 579. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 579.

A biomass-modulating nucleic acid can comprise the nucleotide sequence set forth in SEQ ID NO: 52. Alternatively, a biomass-modulating nucleic acid can be a variant of the nucleic acid having the nucleotide sequence set forth in SEQ ID NO: 52. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 52.

A biomass-modulating nucleic acid can comprise the nucleotide sequence set forth in SEQ ID NO: 1111. Alternatively, a biomass-modulating nucleic acid can be a variant of the nucleic acid having the nucleotide sequence set forth in SEQ ID NO: 1111. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1111.

A biomass-modulating nucleic acid can comprise the nucleotide sequence set forth in SEQ ID NO: 633. Alternatively, a biomass-modulating nucleic acid can be a variant of the nucleic acid having the nucleotide sequence set forth in SEQ ID NO: 633. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 633.

A biomass-modulating nucleic acid can comprise the nucleotide sequence set forth in SEQ ID NO: 367. Alternatively, a biomass-modulating nucleic acid can be a variant of the nucleic acid having the nucleotide sequence set forth in SEQ ID NO: 367. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 367.

A biomass-modulating nucleic acid can comprise the nucleotide sequence set forth in SEQ ID NO: 1598. Alternatively, a biomass-modulating nucleic acid can be a variant of the nucleic acid having the nucleotide sequence set forth in SEQ ID NO: 1598. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1598.

A biomass-modulating nucleic acid can comprise the nucleotide sequence set forth in SEQ ID NO: 153. Alternatively, a biomass-modulating nucleic acid can be a variant of the nucleic acid having the nucleotide sequence set forth in SEQ ID NO: 153. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 153.

A biomass-modulating nucleic acid can comprise the nucleotide sequence set forth in SEQ ID NO: 1034. Alternatively, a biomass-modulating nucleic acid can be a variant of the nucleic acid having the nucleotide sequence set forth in SEQ ID NO: 1034. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1034.

A biomass-modulating nucleic acid can comprise the nucleotide sequence set forth in SEQ ID NO: 740. Alternatively, a biomass-modulating nucleic acid can be a variant of the nucleic acid having the nucleotide sequence set forth in SEQ ID NO: 740. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 740.

A biomass-modulating nucleic acid can comprise the nucleotide sequence set forth in SEQ ID NO: 186. Alternatively, a biomass-modulating nucleic acid can be a variant of the nucleic acid having the nucleotide sequence set forth in SEQ ID NO: 186. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 186.

A biomass-modulating nucleic acid can comprise the nucleotide sequence set forth in SEQ ID NO: 1064. Alternatively, a biomass-modulating nucleic acid can be a variant of the nucleic acid having the nucleotide sequence set forth in SEQ ID NO: 1064. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1064.

A biomass-modulating nucleic acid can comprise the nucleotide sequence set forth in SEQ ID NO: 1591. Alternatively, a biomass-modulating nucleic acid can be a variant of the nucleic acid having the nucleotide sequence set forth in SEQ ID NO: 1591. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1591.

A biomass-modulating nucleic acid can comprise the nucleotide sequence set forth in SEQ ID NO: 850. Alternatively, a biomass-modulating nucleic acid can be a variant of the nucleic acid having the nucleotide sequence set forth in SEQ ID NO: 850. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 850.

A biomass-modulating nucleic acid can comprise the nucleotide sequence set forth in SEQ ID NO: 1015. Alternatively, a biomass-modulating nucleic acid can be a variant of the nucleic acid having the nucleotide sequence set forth in SEQ ID NO: 1015. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1015.

A biomass-modulating nucleic acid can comprise the nucleotide sequence set forth in SEQ ID NO: 2185. Alternatively, a biomass-modulating nucleic acid can be a variant of the nucleic acid having the nucleotide sequence set forth in SEQ ID NO: 2185. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 2185.

A biomass-modulating nucleic acid can comprise the nucleotide sequence set forth in SEQ ID NO: 1954. Alternatively, a biomass-modulating nucleic acid can be a variant of the nucleic acid having the nucleotide sequence set forth in SEQ ID NO: 1954. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1954.

A biomass-modulating nucleic acid can comprise the nucleotide sequence set forth in SEQ ID NO: 2565. Alternatively, a biomass-modulating nucleic acid can be a variant of the nucleic acid having the nucleotide sequence set forth in SEQ ID NO: 2565. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 2565.

A biomass-modulating nucleic acid can comprise the nucleotide sequence set forth in SEQ ID NO: 2149. Alternatively, a biomass-modulating nucleic acid can be a variant of the nucleic acid having the nucleotide sequence set forth in SEQ ID NO: 2149. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 2149.

A biomass-modulating nucleic acid can comprise the nucleotide sequence set forth in SEQ ID NO: 2195. Alternatively, a biomass-modulating nucleic acid can be a variant of the nucleic acid having the nucleotide sequence set forth in SEQ ID NO: 2195. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 2195.

A biomass-modulating nucleic acid can comprise the nucleotide sequence set forth in SEQ ID NO: 2492. Alternatively, a biomass-modulating nucleic acid can be a variant of the nucleic acid having the nucleotide sequence set forth in SEQ ID NO: 2492. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 2492.

A biomass-modulating nucleic acid can comprise the nucleotide sequence set forth in SEQ ID NO: 2270. Alternatively, a biomass-modulating nucleic acid can be a variant of the nucleic acid having the nucleotide sequence set forth in SEQ ID NO: 2270. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 2270.

A biomass-modulating nucleic acid can comprise the nucleotide sequence set forth in SEQ ID NO: 1740. Alternatively, a biomass-modulating nucleic acid can be a variant of the nucleic acid having the nucleotide sequence set forth in SEQ ID NO: 1740. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1740.

A biomass-modulating nucleic acid can comprise the nucleotide sequence set forth in SEQ ID NO: 1979. Alternatively, a biomass-modulating nucleic acid can be a variant of the nucleic acid having the nucleotide sequence set forth in SEQ ID NO: 1979. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1979.

A biomass-modulating nucleic acid can comprise the nucleotide sequence set forth in SEQ ID NO: 1811. Alternatively, a biomass-modulating nucleic acid can be a variant of the nucleic acid having the nucleotide sequence set forth in SEQ ID NO: 1811. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1811.

A biomass-modulating nucleic acid can comprise the nucleotide sequence set forth in SEQ ID NO: 2123. Alternatively, a biomass-modulating nucleic acid can be a variant of the nucleic acid having the nucleotide sequence set forth in SEQ ID NO: 2123. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 2123.

A biomass-modulating nucleic acid can comprise the nucleotide sequence set forth in SEQ ID NO: 2034. Alternatively, a biomass-modulating nucleic acid can be a variant of the nucleic acid having the nucleotide sequence set forth in SEQ ID NO: 2034. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 2034.

A biomass-modulating nucleic acid can comprise the nucleotide sequence set forth in SEQ ID NO: 2424. Alternatively, a biomass-modulating nucleic acid can be a variant of the nucleic acid having the nucleotide sequence set forth in SEQ ID NO: 2424. For example, a biomass-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 2424.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Biomass-Modulating Polypeptide A nucleic acid encoding one of the biomass-modulating polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular biomass-modulating polypeptide; i.e., for many amino acids, there is more than one nucleotide triplet that serves as the codon for the amino acid. Thus, codons in the coding sequence for a given biomass-modulating polypeptide can be modified such that optimal expression in a particular plant species is obtained, using appropriate codon bias tables for that species.

In some cases, expression of a biomass-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of a Biomass-Modulating Polypeptide

Polynucleotides and recombinant constructs described herein can be used to inhibit expression of a biomass-modulating polypeptide in a plant species of interest. See, e.g., Matzke and Birchler, *Nature Reviews Genetics* 6:24-35 (2005); Akashi et al., *Nature Reviews Mol. Cell. Biology* 6:413-422 (2005); Mittal, *Nature Reviews Genetics* 5:355-365 (2004); and *Nature Reviews RNA interference collection*, October 2005 on the World Wide Web at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding biomass-modulating polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in *Tetrahymena thermophile*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a biomass-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the biomass-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a biomass-modulating polypeptide, and the other strand of the stem portion of the double stranded RNA comprises a sequence that is similar or identical to the sequence that is complementary to the 3' or 5' untranslated region, respectively, or a fragment thereof, of the mRNA encoding the biomass-modulating polypeptide. In other embodiments, one strand of the stem portion of a double stranded RNA comprises a sequence that is similar or identical to the sequence of an intron, or a fragment thereof, in the pre-mRNA encoding a biomass-modulating polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence, or a fragment thereof, of a biomass-modulating polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary.

The sense or antisense sequence can be a sequence that is identical or complementary to the sequence of an mRNA, the 3' or 5' untranslated region of an mRNA, or an intron in a pre-mRNA encoding a biomass-modulating polypeptide, or a fragment of such sequences. In some embodiments, the sense or antisense sequence is identical or complementary to a sequence of the regulatory region that drives transcription of the gene encoding a biomass-modulating polypeptide. In each case, the sense sequence is the sequence that is complementary to the antisense sequence.

The sense and antisense sequences can be a length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a biomass-modulating polypeptide described herein. The sense sequence complementary to the antisense sequence can be a sequence present within the mRNA of the biomass-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have a suitable arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences or the left and right border-like sequences of the P-DNA flank, or are on either side of, the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, *Antisense Nucleic Acid Drug Dev.*, 7:187-195 (1997); Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate biomass levels. A recombinant nucleic acid construct can comprise a nucleic acid encoding a biomass-modulating polypeptide as described herein, operably linked to a regulatory region suitable for expressing the biomass-modulating polypeptide in the plant or cell. Thus, a nucleic acid can comprise a coding sequence that encodes a biomass-modulating polypeptides as set forth in SEQ ID NOs: 2, 4, 6-9, 11, 13-15, 17, 18, 20-27, 29, 31-33, 35, 36, 38-51, 53, 54, 56-61, 63-67, 69, 70, 72-76, 78, 80-83, 85, 86, 88-91, 93-97, 99-103, 105, 107, 109, 110, 112, 113, 115, 117, 119-152, 154, 156, 158, 159, 161, 163, 165, 167, 168, 170, 172, 174, 176, 178, 180-185, 187, 188, 190, 192-194, 196, 198, 200, 202, 203, 205, 207-211, 213-251, 253, 255, 257, 258, 260-262, 264, 265, 267-272, 274-279, 281-283, 285, 287-292, 294, 295-297, 299, 301, 303-305, 307, 309, 310, 312, 314, 316-318, 320, 321, 323, 325, 327-329, 331, 332, 334, 335, 337-339, 341, 342, 344, 345, 347, 349, 351, 353, 355, 357, 359, 361-366, 368, 370, 372, 373, 375-378, 380, 382-387, 389, 391, 393, 395, 396, 398-404, 406-414, 416, 418, 420, 421, 423, 425, 427, 429, 431, 433, 435, 437, 439, 441, 443, 445, 447, 449, 451, 453, 455, 457, 459, 461, 463, 465, 467, 469, 471, 473, 475, 477, 479, 481, 483, 485, 487, 489, 491, 493, 495, 497-502, 504, 506, 508, 509, 511-517, 519, 521, 522, 524-527, 529, 530, 532, 533, 535, 536, 537, 539, 541, 543, 545, 546, 548, 550, 552-555, 557, 558, 560, 562, 564, 566, 568, 570-578, 580, 582, 584, 585, 587, 589, 591, 592, 594-596, 598, 600, 601, 603, 604, 606-608, 610, 611, 613, 615, 617, 619, 621, 623, 625, 626, 628-632, 634, 636, 638, 640, 642, 643, 645, 647, 649, 651, 653, 655, 657, 659, 661, 663, 665, 667-670, 672, 674, 675, 677, 679-682, 684, 685, 687, 689-692, 694-698, 700-704, 706, 707, 709-718, 720, 722, 724, 726-728, 730, 731, 733-739, 741, 743, 745, 746, 748, 750, 752, 754, 756, 758, 760-764, 766, 768, 770, 772, 774, 776, 778, 780, 782, 784, 785, 787, 789, 791, 793-795, 797, 799, 801, 803, 805, 806, 808, 810, 812, 814, 816, 818-820, 822-824, 826, 828, 830, 832, 834, 836, 838-840, 842, 843, 845-847, 849, 851, 853, 854, 856-858, 860, 862, 863, 865, 866, 868, 870-873, 875-878, 880-882, 884-886, 888, 890, 892, 893, 895, 897, 899, 900, 902, 903, 905, 907, 909, 911, 912, 913, 915, 917, 919, 921, 923, 925, 926, 928, 930, 932, 933, 935, 936-938, 940, 941, 943-945, 947, 949, 950, 952-955, 957-961, 963, 965-969, 971, 972, 974, 975, 977, 978, 980, 982, 984, 986, 988, 990, 992, 994, 996, 998, 1000-1014, 1016, 1018, 1020, 1021, 1023, 1024, 1026, 1027, 1029, 1030, 1032, 1033, 1035, 1037, 1038, 1040, 1042, 1043, 1045, 1047, 1049, 1051, 1053, 1055, 1057, 1059, 1061-1063, 1065, 1067, 1069, 1070, 1072, 1073, 1075, 1076, 1078-1080, 1082, 1083, 1085, 1087, 1089, 1091, 1093, 1095, 1096, 1098, 1100, 1101, 1103, 1105, 1106, 1108, 1110, 1112, 1114-1116, 1118, 1120-1123, 1125, 1127-1131, 1133, 1134, 1136, 1137, 1139-1145, 1147-1156, 1158-1161, 1163, 1165-1178, 1180-1188, 1190, 1191, 1193-1202, 1204, 1205-1207, 1209-1213, 1215, 1217-1221, 1223-1228, 1230, 1231, 1233-1241, 1243, 1245, 1247, 1249-1252, 1254, 1255, 1257-1259, 1261, 1263, 1264, 1266-1272, 1274-1276, 1278, 1280, 1282-1286, 1288, 1289, 1291-1331, 1333-1337, 1339, 1341, 1343, 1345, 1347-1350, 1352, 1354, 1356, 1358, 1360, 1362, 1364, 1366, 1368, 1370-1372, 1374, 1375, 1377-1379, 1381, 1383, 1384, 1386, 1388-1390, 1392-1397, 1399, 1400, 1402, 1403, 1405, 1407-1410, 1412-1418, 1420, 1422, 1424, 1426, 1428, 1430, 1432-1436, 1438, 1440, 1442-1444, 1446, 1447, 1449, 1450, 1452-1454, 1456, 1457, 1459, 1460, 1462, 1463, 1465-1468, 1470, 1471, 1473, 1475, 1477-1483, 1485, 1487, 1489, 1491-1493, 1495, 1496, 1498, 1499, 1501, 1503, 1504, 1506, 1508, 1510, 1511, 1513, 1514, 1516-1521, 1523, 1524, 1526, 1528-1532, 1534, 1536-1539, 1541, 1542, 1544, 1545, 1547, 1548, 1550, 1552, 1553, 1555-1559, 1561, 1563-1565, 1567, 1568, 1570, 1571, 1573, 1575, 1576, 1578, 1580, 1582, 1583, 1585, 1587, 1589, 1590, 1592, 1593, 1595, 1597, 1599, 1600, 1602-1606, 1608-1613, 1615, 1616, 1618-1626, 1628, 1629, 1631, 1633, 1634, 1636, 1637, 1639-1643, 1645, or 1646-1739, 1741, 1743, 1745, 1747-1756, 1758, 1760, 1762-1764, 1766, 1767, 1769, 1770, 1772-1774, 1776, 1778-1783, 1785-1792, 1794, 1796, 1798, 1799, 1801, 1802, 1804, 1806, 1808-1810, 1812, 1814, 1815, 1817, 1819, 1821, 1822, 1824, 1826-1830, 1832, 1834, 1835, 1837, 1839-1841, 1843, 1844, 1846, 1847, 1849, 1851, 1852, 1854, 1856, 1858, 1860-1863, 1865-1953, 1955-1958, 1960, 1962, 1964, 1966-1968, 1970, 1972-1976, 1978, 1980, 1982, 1984-1986, 1988, 1990, 1991, 1993, 1995, 1997, 1999, 2001, 2003, 2005, 2007, 2009, 2011, 2013, 2015, 2017, 2019, 2021, 2023-2027, 2029, 2031, 2033, 2035, 2037, 2039, 2041, 2043, 2045, 2047-2049, 2051-2057, 2059, 2061, 2063, 2065, 2067, 2069, 2071, 2073, 2075, 2077, 2079, 2080, 2082, 2084, 2086, 2088, 2090, 2092, 2093, 2095, 2097, 2098, 2100-2122, 2124, 2126, 2128, 2129, 2131, 2133, 2135-2137, 2139, 2141, 2142, 2144-2148, 2150, 2152, 2154, 2155, 2157, 2159-2161, 2163, 2165, 2166, 2168, 2170, 2172-2175, 2177, 2179, 2181, 2183, 2184, 2186, 2188, 2189, 2191-2194, 2196, 2197, 2199-2202, 2204, 2206-2208, 2210-2212, 2214, 2215, 2217-2220, 2222, 2224-2226, 2228, 2230-2232, 2234-2242, 2244-2254, 2256-2269, 2271, 2273, 2274, 2276, 2278, 2280, 2281, 2283, 2285, 2286, 2288, 2290, 2292, 2294, 2296, 2297, 2299, 2301, 2303, 2305, 2307, 2309, 2311, 2313, 2314, 2316-2318, 2320, 2322, 2324, 2326, 2327, 2329, 2331, 2333, 2335, 2337, 2339, 2341, 2342, 2344, 2345, 2347-2349, 2351, 2353, 2355, 2357, 2359, 2361, 2363, 2365, 2367-2369, 2371, 2373, 2375, 2377, 2379, 2381, 2383, 2385, 2386, 2388, 2390, 2391, 2393, 2395, 2397, 2399, 2400, 2402, 2404, 2405, 2407, 2409, 2411, 2413, 2415, 2417, 2419, 2421, 2423, 2425, 2426, 2428, 2430, 2431, 2433, 2435, 2437, 2438-2440, 2442, 2444, 2445, 2447, 2449, 2451, 2453, 2455, 2457, 2459, 2461, 2463-2468, 2470, 2472, 2474, 2476, 2478, 2479, 2481, 2482, 2484, 2485, 2487-2491, 2493-2498, 2500-2510, 2512-2515, 2517-2531, 2533-2536, 2538-2542, 2544-2548, 2550, 2551, 2553, 2555-2558, 2560, 2562, 2564, 2566-2573, 2575-2579, 2581, 2583-2585, 2587-2602, 2604-2611, 2613, 2615, 2617, or 2619-2623. Examples of nucleic acids encoding biomass-modulating polypeptides are set forth in SEQ ID NOs: 1, 3, 5, 10, 12, 16, 19, 28, 30, 34, 37, 52, 55, 62, 68, 71, 77, 79, 84, 87, 92, 98, 104, 106, 108, 111, 114, 116, 118, 153, 155, 157, 160, 162, 164, 166, 169, 171, 173, 175, 177, 179, 186, 189, 191, 195, 197, 199, 201, 204, 206, 212, 252, 254, 256, 259, 263, 266, 273, 280, 284, 286, 293, 298, 300, 302, 306, 308, 311, 313, 315, 319, 322, 324, 326, 330, 333, 336, 340, 343, 346, 348, 350, 352, 354, 356, 358, 360, 367, 369, 371, 374, 379, 381, 388, 390, 392, 394, 397, 405, 415, 417, 419, 422, 424, 426, 428, 430, 432, 434, 436, 438, 440, 442, 444, 446, 448, 450, 452, 454, 456, 458, 460, 462, 464, 466, 468, 470, 472, 474, 476, 478, 480, 482, 484, 486, 488, 490, 492, 494, 496, 503, 505, 507, 510, 518, 520, 523, 528, 531, 534, 538, 540, 542, 544, 547, 549, 551, 556, 559, 561, 563, 565, 567, 569, 579, 581, 583, 586, 588, 590, 593, 597, 599, 602, 605, 609, 612, 614, 616, 618, 620, 622, 624, 627, 633, 635, 637, 639, 641, 644, 646, 648, 650, 652, 654, 656, 658, 660, 662, 664, 666, 671, 673, 676, 678, 683, 686, 688, 693, 699, 705, 708, 719, 721, 723, 725, 729, 732, 740, 742, 744, 747, 749, 751, 753, 755, 757, 759, 765, 767, 769, 771, 773, 775, 777, 779, 781, 783, 786, 788, 790, 792, 796, 798, 800, 802, 804, 807, 809, 811, 813, 815, 817, 821, 825, 827, 829, 831, 833, 835, 837, 841, 844, 848, 850, 852, 855, 859, 861, 864, 867, 869, 874, 879, 883, 887, 889, 891, 894, 896, 898, 901, 904, 906, 908, 910, 914, 916, 918, 920, 922, 924, 927, 929, 931, 934, 939, 942, 946, 948, 951, 956, 962, 964, 970, 973, 976, 979, 981, 983, 985, 987, 989, 991, 993, 995, 997, 999, 1015, 1017, 1019, 1022, 1025, 1028, 1031, 1034, 1036, 1039, 1041, 1044, 1046, 1048, 1050, 1052, 1054, 1056, 1058, 1060, 1064, 1066, 1068, 1071, 1074, 1077, 1081, 1084, 1086, 1088, 1090, 1092, 1094, 1097, 1099, 1102, 1104, 1107, 1109, 1111, 1113, 1117, 1119, 1124, 1126, 1132, 1135, 1138, 1146, 1157, 1162, 1164, 1179, 1189, 1192, 1203, 1208, 1214, 1216, 1222, 1229, 1232, 1242, 1244, 1246, 1248, 1253, 1256, 1260, 1262, 1265, 1273, 1277, 1279, 1281, 1287, 1290, 1332, 1338, 1340, 1342, 1344, 1346, 1351, 1353, 1355, 1357, 1359, 1361, 1363, 1365, 1367, 1369, 1373, 1376, 1380, 1382, 1385, 1387, 1391, 1398, 1401, 1404, 1406, 1411, 1419, 1421, 1423, 1425, 1427, 1429, 1431, 1437, 1439, 1441, 1445, 1448, 1451, 1455, 1458, 1461, 1464, 1469, 1472, 1474, 1476, 1484, 1486, 1488, 1490, 1494, 1497, 1500, 1502, 1505, 1507, 1509, 1512, 1515, 1522, 1525, 1527, 1533, 1535, 1540, 1543, 1546, 1549, 1551, 1554, 1560, 1562, 1566, 1569, 1572, 1574, 1577, 1579, 1581, 1584, 1586, 1588, 1591, 1594, 1596, 1598, 1601, 1607, 1614, 1617, 1627, 1630, 1632, 1635, 1638, 1644, 1740, 1742, 1744, 1746, 1757, 1759, 1761, 1765, 1768, 1771, 1775, 1777, 1784, 1793, 1795, 1797, 1800, 1803, 1805, 1807, 1811, 1813, 1816, 1818, 1820, 1823, 1825, 1831, 1833, 1836, 1838, 1842, 1845, 1848, 1850, 1853, 1855, 1857, 1859, 1864, 1954, 1959, 1961, 1963, 1965, 1969, 1971, 1977, 1979, 1981, 1983, 1987, 1989, 1992, 1994, 1996, 1998, 2000, 2002, 2004, 2006, 2008, 2010, 2012, 2014, 2016, 2018, 2020, 2022, 2028, 2030, 2032, 2034, 2036, 2038, 2040, 2042, 2044, 2046, 2050, 2058, 2060, 2062, 2064, 2066, 2068, 2070, 2072, 2074, 2076, 2078, 2081, 2083, 2085, 2087, 2089, 2091, 2094, 2096, 2099, 2123, 2125, 2127, 2130, 2132, 2134, 2138, 2140, 2143, 2149, 2151, 2153, 2156, 2158, 2162, 2164, 2167, 2169, 2171, 2176, 2178, 2180, 2182, 2185, 2187, 2190, 2195, 2198, 2203, 2205, 2209, 2213, 2216, 2221, 2223, 2227, 2229, 2233, 2243, 2255, 2270, 2272, 2275, 2277, 2279, 2282, 2284, 2287, 2289, 2291, 2293, 2295, 2298, 2300, 2302, 2304, 2306, 2308, 2310, 2312, 2315, 2319, 2321, 2323, 2325, 2328, 2330, 2332, 2334, 2336, 2338, 2340, 2343, 2346, 2350, 2352, 2354, 2356, 2358, 2360, 2362, 2364, 2366, 2370, 2372, 2374, 2376, 2378, 2380, 2382, 2384, 2387, 2389, 2392, 2394, 2396, 2398, 2401, 2403, 2406, 2408, 2410, 2412, 2414, 2416, 2418, 2420, 2422, 2424, 2427, 2429, 2432, 2434, 2436, 2441, 2443, 2446, 2448, 2450, 2452, 2454, 2456, 2458, 2460, 2462, 2469, 2471, 2473, 2475, 2477, 2480, 2483, 2486, 2492, 2499, 2511, 2516, 2532, 2537, 2543, 2549, 2552, 2554, 2559, 2561, 2563, 2565, 2574, 2580, 2582, 2586, 2603, 2612, 2614, 2616, and 2618, or in the Sequence Listing. The biomass-modulating polypeptide encoded by a recombinant nucleic acid can be a native biomass-modulating polypeptide, or can be heterologous to the cell. In some cases, the recombinant construct contains a nucleic acid that inhibits expression of a biomass-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen® (Madison, Wis.), Clontech® (Palo Alto, Calif.), Stratagene® (La Jolla, Calif.), and Invitrogen/Life Technologies® (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al., *Plant Cell*, 1:855-866 (1989); Bustos et al., *Plant Cell*, 1:839-854 (1989); Green et al., *EMBO J.*, 7:4035-4044 (1988); Meier et al., *Plant Cell*, 3:309-316 (1991); and Zhang et al., *Plant Physiology*, 110:1069-1079 (1996).

Examples of various classes of regulatory regions are described below. Some of the regulatory regions indicated below as well as additional regulatory regions are described in more detail in U.S. Patent Application Ser. Nos. 60/505,689; 60/518,075; 60/544,771; 60/558,869; 60/583,691; 60/619,181; 60/637,140; 60/757,544; 60/776,307; 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA,* 86:7890-7894 (1989)), root cell specific promoters reported by Conkling et al., *Plant Physiol.,* 93:1203-1211 (1990), and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., *Plant Cell,* 1(9):839-853 (1989)), the soybean trypsin inhibitor promoter (Riggs et al., *Plant Cell,* 1(6):609-621 (1989)), the ACP promoter (Baerson et al., *Plant Mol. Biol.,* 22(2):255-267 (1993)), the stearoyl-ACP desaturase promoter (Slocombe et al., *Plant Physiol.,* 104(4):167-176 (1994)), the soybean α' subunit of β-conglycinin promoter (Chen et al., *Proc. Natl. Acad. Sci. USA,* 83:8560-8564 (1986)), the oleosin promoter (Hong et al., *Plant Mol. Biol.,* 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell. Biol.,* 13:5829-5842 (1993)), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see, Urao, *Plant Mol. Biol.,* 32:571-57 (1996); Conceicao, *Plant,* 5:493-505 (1994)); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan, *Genetics,* 142:1009-1020 (1996)); maize Cat3 (see, GenBank No. L05934; Abler, *Plant Mol. Biol.,* 22:10131-1038 (1993)). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* 20:647-654 (2001)), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.,* 35:773-778 (1994)), the Cab-1 promoter from wheat (Fejes et al., *Plant Mol. Biol.,* 15:921-932 (1990)), the CAB-1 promoter from spinach (Lubberstedt et al., *Plant Physiol.,* 104:997-1006 (1994)), the cab1R promoter from rice (Luan et al., *Plant Cell,* 4:971-981 (1992)), the pyruvate orthophosphate dikinase (PPDK) promoter from corn (Matsuoka et al., *Proc. Natl. Acad. Sci. USA,* 90:9586-9590 (1993)), the tobacco Lhcb1*2 promoter (Cerdan et al., *Plant Mol. Biol.,* 33:245-255 (1997)), the *Arabidopsis thaliana* SUC2 sucrose-H+ symporter promoter (Truernit et al., *Planta,* 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, *Plant Cell*, 3(10):1051-1061 (1991)), the Commelina yellow mottle virus (CoYMV) promoter (Medberry et al., *Plant Cell*, 4(2):185-192 (1992)), and the rice tungro bacilliform virus (RTBV) promoter (Dai et al., *Proc. Natl. Acad. Sci. USA*, 101(2):687-692 (2004)).

ix. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) Nature Biotech 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Stem Promoters

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and CryIA (b) and CryIA(c) (Braga et al. 2003, Journal of New Seeds 5:209-221).

xii. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a biomass-modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

IV. Transgenic Plants and Plant Cells

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous biomass-modulating polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of a biomass-modulating polypeptide or nucleic acid. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of biomass. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a biomass level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea*.

Suitable species include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Medicago sativa* (alfalfa), *Arundo donax* (giant reed), *Secale cereale* (rye), *Salix* spp. (willow), *Eucalyptus* spp. (eucalyptus), *Triticosecale* (triticum—wheat X rye) and bamboo.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea*.

Suitable species also include *Beta vulgaris* (sugarbeet), and *Manihot esculenta* (cassaya)

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii,* and *Tanacetum parthenium*.

Suitable species also include *Parthenium argentatum* (guayule), *Hevea* spp. (rubber), *Mentha spicata* (mint), *Mentha piperita* (mint), *Bixa orellana*, and *Alstroemeria* spp.

Suitable species also include *Rosa* spp. (rose), *Dianthus caryophyllus* (carnation), *Petunia* spp. (petunia) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy).

In some embodiments, a suitable species can be a wild, weedy, or cultivated *Pennisetum* species such as, but not limited to, *Pennisetum alopecuroides, Pennisetum arnhemicum, Pennisetum caffrum, Pennisetum clandestinum, Pennisetum divisum, Pennisetum glaucum, Pennisetum latifolium, Pennisetum macrostachyum, Pennisetum macrourum, Pennisetum orientale, Pennisetum pedicellatum, Pennisetum polystachion, Pennisetum polystachion* ssp. *Setosum, Pennisetum purpureum, Pennisetum setaceum, Pennisetum subangustum, Pennisetum typhoides, Pennisetum villosum*, or hybrids thereof (e.g., *Pennisetum purpureum×Pennisetum typhoidum*).

In some embodiments, a suitable species can be a wild, weedy, or cultivated *Miscanthus* species and/or variety such as, but not limited to, *Miscanthus×giganteus, Miscanthus sinensis, Miscanthus×ogiformis, Miscanthus floridulus, Miscanthus transmorrisonensis, Miscanthus oligostachyus, Miscanthus nepalensis, Miscanthus sacchariflorus, Miscanthus×giganteus* 'Amuri', *Miscanthus×giganteus* 'Nagara', *Miscanthus×giganteus* 'Illinois', *Miscanthus sinensis* var. 'Goliath', *Miscanthus sinensis* var. 'Roland', *Miscanthus sinensis* var. 'Africa', *Miscanthus sinensis* var. 'Fern Osten', *Miscanthus sinensis* var. gracillimus, *Miscanthus sinensis* var. variegates, *Miscanthus sinensis* var. purpurascens, *Miscanthus sinensis* var. 'Malepartus', *Miscanthus sacchariflorus* var. 'Robusta', *Miscanthus sinensis* var. 'Silberfedher' (aka. Silver Feather), *Miscanthus transmorrisonensis, Miscanthus condensatus, Miscanthus yakushimanum, Miscanthus* var. 'Alexander', *Miscanthus* var. 'Adagio', *Miscanthus* var. 'Autumn Light', *Miscanthus* var. 'Cabaret', *Miscanthus* var. 'Condensatus', *Miscanthus* var. 'Cosmopolitan', *Miscanthus* var. 'Dixieland', *Miscanthus* var. 'Gilded Tower' (U.S. Pat. No. PP14,743), *Miscanthus* var. 'Gold Bar' (U.S. Pat. No. PP15,193), *Miscanthus* var. 'Gracillimus', *Miscanthus* var. 'Graziella', *Miscanthus* var. 'Grosse Fontaine', *Miscanthus* var. 'Hinjo aka Little Nicky'™, *Miscanthus* var. 'Juli', *Miscanthus* var. 'Kaskade', *Miscanthus* var. 'Kirk Alexander', *Miscanthus* var. 'Kleine Fontaine', *Miscanthus* var. 'Kleine Silberspinne' (aka. 'Little Silver Spider'), *Miscanthus* var. 'Little Kitten', *Miscanthus* var. 'Little Zebra' (U.S. Pat. No. PP13,008), *Miscanthus* var. 'Lottum', *Miscanthus* var. 'Malepartus', *Miscanthus* var. 'Morning Light', *Miscanthus* var. 'Mysterious Maiden' (U.S. Pat. No. PP16,176), *Miscanthus* var. 'Nippon', *Miscanthus* var. 'November Sunset', *Miscanthus* var. 'Parachute', *Miscanthus* var. 'Positano', *Miscanthus* var. 'Puenktchen' (aka 'Little Dot'), *Miscanthus* var. 'Rigoletto', *Miscanthus* var. 'Sarabande', *Miscanthus* var. 'Silberpfeil' (aka. Silver Arrow), *Miscanthus* var. 'Silverstripe', *Miscanthus* var. 'Super Stripe' (U.S. Pat. No. PP18,161), *Miscanthus* var. 'Strictus', or *Miscanthus* var. 'Zebrinus'.

In some embodiments, a suitable species can be a wild, weedy, or cultivated sorghum species and/or variety such as, but not limited to, *Sorghum almum, Sorghum amplum, Sorghum angustum, Sorghum arundinaceum, Sorghum bicolor* (such as bicolor, guinea, caudatum, kafir, and durra), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare*, or hybrids such as *Sorghum× almum, Sorghum×sudangrass* or *Sorghum×drummondii*.

Thus, the methods and compositions can be used over a broad range of plant species, including species from the dicot genera *Brassica, Carthamus, Glycine, Gossypium, Helianthus, Jatropha, Parthenium, Populus*, and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum*, and *Zea*. In some embodiments, a plant is a member of the species *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledonous plants and plant cell systems, wherein such plants are hybrids of different species or varieties of a specific species (e.g., *Saccharum* sp.× *Miscanthus* sp., *Sorghum* sp.×*Miscanthus* sp., e.g., *Panicum virgatum×Panicum amarum, Panicum virgatum×Panicum amarulum*, and *Pennisetum purpureum×Pennisetum typhoidum*).

D. Transgenic Plant Phenotypes

In some embodiments, a plant in which expression of a biomass-modulating polypeptide is modulated can have increased levels of biomass in plants. For example, a biomass-modulating polypeptide described herein can be expressed in a transgenic plant, resulting in increased levels of vegetative tissue. The biomass level can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the biomass level in a corresponding control plant that does not express the transgene. In some embodiments, a plant in which expression of a biomass-modulating polypeptide is modulated can have decreased levels of seed production. The level can be decreased by at least 2 percent, e.g., 2, 3, 4, 5, 10, 15, 20, 25, 30, 35, or more than 35 percent, as compared to the seed production level in a corresponding control plant that does not express the transgene.

Increases in seed production in such plants can provide improved nutritional availability in geographic locales where intake of plant foods is often insufficient, or for biofuel production. In some embodiments, decreases in biomass in such plants can be useful in situations where vegetative tissues are not the primary plant part that is harvested for human or animal consumption (i.e., seeds are harvested).

In some embodiments, a plant in which expression of a biomass-modulating polypeptide is modulated can have increased or decreased levels of biomass in one or more plant tissues, e.g., vegetative tissues, reproductive tissues, or root tissues. For example, the biomass level can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the biomass level in a corresponding control plant that does not express the transgene. In some embodiments, a plant in which expression of a biomass-modulating polypeptide is modulated can have decreased levels of biomass in one or more plant tissues. The biomass level can be decreased by at least 2 percent, e.g., 2, 3, 4, 5, 10, 15, 20, 25, 30, 35, or more than 35 percent, as compared to the biomass level in a corresponding control plant that does not express the transgene.

Increases in biomass in such plants can provide improved food quantity, or improved energy production. Decreases in biomass can provide more efficient partitioning of nutrients to plant part(s) that are harvested for human or animal consumption.

Typically, a difference in the amount of biomass in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the amount of biomass is statistically significant at $p<0.01$, $p<0.005$, or $p<0.001$. A statistically significant difference in, for example, the amount of biomass in a transgenic plant compared to the amount of a control plant indicates that the recombinant nucleic acid present in the transgenic plant results in altered biomass levels.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

Biomass can include harvestable plant tissues such as leaves, stems, and reproductive structures, or all plant tissues such as leaves, stems, roots, and reproductive structures. In some embodiments, biomass encompasses only above ground plant parts. In some embodiments, biomass encompasses only stem plant parts. In some embodiments, biomass encompasses only above ground plant parts except inflorescence and seed parts of a plant. Biomass can be measured as described in the examples section. Biomass can be quantified as dry matter yield, which is the mass of biomass produced (usually reported in T/acre) if the contribution of water is subtracted from the fresh mater weight. Dry matter yield (DMY) yield is calculated using the fresh matter weight (FMW) and a measurement of weight percent moisture (M) in the following equation. DMY=((100−M)/100)*FMW. Biomass can be quantified as fresh matter yield, which is the mass of biomass produced (usually reported in T/acre) on an as-received basis, which includes the weight of moisture.

V. Modifying Endogenous Nucleic Acids Encoding Biomass-Modulating Polypeptides This document also features plant cells and plants in which an endogenous biomass-modulating nucleic acid described herein has been modified (e.g., a regulatory region, intron, or coding region of the biomass-modulating nucleic acid has been modified). The biomass of such plants is altered relative to the corresponding level of a control plant in which the endogenous nucleic acid is not modified. Such plants are referred to herein as modified plants and may be used to produce, for example, increased amounts of biomass.

Endogenous nucleic acid can be modified by homologous recombination techniques. For example, sequence specific endonucleases (e.g., zinc finger nucleases (ZFNs)) and meganucleases can be used to stimulate homologous recombination at endogenous plant genes. See, e.g., Townsend et al., Nature 459:442-445 (2009); Tovkach et al., Plant J., 57:747-757 (2009); and Lloyd et al., Proc. Natl. Acad. Sci. USA, 102:2232-2237 (2005). In particular, ZFNs engineered to create DNA double strand breaks at specific loci can be used to make targeted sequence changes in endogenous plant genes. For example, an endogenous plant gene can be replaced with a variant containing one or more mutations (e.g., produced using site-directed mutagenesis or directed evolution).

In some embodiments, endogenous nucleic acids can be modified by methylation or demethylation such that the expression of the modified endogenous nucleic acid is altered. For example, a double stranded RNA can be used to activate gene expression by targeting noncoding regulatory regions in gene promoters. See Shibuya et al., Proc Natl Acad Sci USA, 106(5): 1660-1665 (2009); and Li et al., Proc Natl Acad Sci USA, 103(46):17337-42 (2006).

In some embodiments, endogenous nucleic acids can be modified using activation tagging. For example, a vector containing multiple copies of an enhancer element from the constitutively active promoter of the cauliflower mosaic virus (CaMV) 35S gene can be used to activate an endogenous gene. See, Weigel et al., Plant Physiology, 122:1003-1013 (2000).

In some embodiments, endogenous nucleic acids can be modified by introducing an engineered transcription activation/repression factor (e.g., zinc finger protein transcription factor, or ZFP TF. See, for example, the world wide web at sangamo.com/tech/tech_plat_over.html#whatarezfp). An engineered transcription activation/repression factor (such as ZFP TF) can activate, repress, or switch the target endogenous biomass gene expression by binding specifically to the promoter region or coding region of the endogenous gene.

In some embodiments, endogenous nucleic acids can be modified by mutagenesis. Genetic mutations can be introduced within regenerable plant tissue using one or more mutagenic agents. Suitable mutagenic agents include, for example, ethyl methane sulfonate (EMS), N-nitroso-N-ethylurea (ENU), methyl N-nitrosoguanidine (MNNG), ethidium bromide, diepoxybutane, ionizing radiation, x-rays, UV rays and other mutagens known in the art. Suitable types of mutations include, for example, insertions or deletions of nucleotides, and transitions or transversions in the endogenous nucleic acid sequence. In one embodiment, TILLING (Targeted Induced Local Lesions In Genomes) can be used to produce plants having a modified endogenous nucleic acid. TILLING combines high-density mutagenesis with high-throughput screening methods. See, for example, McCallum et al., *Nat Biotechnol* 18: 455-457 (2000); reviewed by Stemple, *Nat Rev Genet.* 5(2):145-50 (2004).

In some embodiments, an endogenous nucleic acid can be modified via a gene silencing technique. See, for example, the section herein regarding "Inhibition of Expression of a Biomass-Modulating Polypeptide."

A population of plants can be screened and/or selected for those members of the population that have a modified nucleic acid. A population of plants also can be screened and/or selected for those members of the population that have a trait or phenotype conferred by expression of the modified nucleic acid. As an alternative, a population of plants can be screened for those plants having a desired trait, such as a modulated level of biomass. For example, a population of progeny can be screened for those plants having a desired level of expression of a biomass-modulating polypeptide or nucleic acid. Physical and biochemical methods can be used to identify modified nucleic acids and/or expression levels as described with transgenic plants. Selection and/or screening can be carried out over one or more generations, and/or in more than one geographic location. In some cases, plants can be grown and selected under conditions which induce a desired phenotype or are otherwise necessary to produce a desired phenotype in a modified plant. In addition, selection and/or screening can be applied during a particular developmental stage in which the phenotype is expected to be exhibited by the plant. Selection and/or screening can be carried out to choose those modified plants having a statistically significant difference in a biomass level relative to a control plant in which the nucleic acid has not been modified. Selected or screened modified plants have an altered phenotype as compared to a corresponding control plant, as described in the "Transgenic Plant Phenotypes" section herein.

Although a plant or plant cell in which an endogenous biomass-modulating nucleic acid has been modified is not transgenic for that particular nucleic acid, it will be appreciated that such a plant or cell may contain transgenes. For example, a modified plant can contain a transgene for other traits, such as herbicide tolerance or insect resistance. As another example, a modified plant can contain one or more transgenes that, in conjuction with modifications of one or more endogenous nucleic acids, exhibits an increase in biomass.

As with transgenic plant cells, modified plant cells can constitute part or all of a whole plant. Such plants can be grown in the same manner as described for transgenic plants and can be bred or propagated in the same manner as described for transgenic plants.

VI. Plant Breeding

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. For example, PCR techniques can be used to enzymatically amplify a genetic marker associated with a nucleotide sequence conferring a specific trait (e.g., nucleotide sequences described herein). PCR can be used to amplify specific sequences from DNA as well as RNA, including sequences from total genomic DNA or total cellular RNA. When using RNA as a source of template, reverse transcriptase can be used to synthesize complementary DNA (cDNA) strands. Various PCR methods are described, for example, in *PCR Primer: A Laboratory Manual*, Dieffenbach and Dveksler, eds., Cold Spring Harbor Laboratory Press, 1995.

Generally, sequence information from polynucleotides flanking the region of interest or beyond is employed to design oligonucleotide primers that are identical or similar in sequence to opposite strands of the template to be amplified. Primers are typically 14 to 40 nucleotides in length, but can range from 10 nucleotides to hundreds of nucleotides in length. Template and amplified DNA is repeatedly denatured at a high temperature to separate the double strand, then cooled to allow annealing of primers and the extension of nucleotide sequences through the microsatellite, resulting in sufficient DNA for detection of PCR products. If the probes flank an SSR in the population, PCR products of different sizes will be produced. See, e.g., U.S. Pat. No. 5,766,847.

PCR products can be qualitative or quantitatively analyzed using several techniques. For example, PCR products can be stained with a fluorescent molecule (e.g., PicoGreen® or OliGreen®) and detected in solution using spectrophotometry or capillary electrophoresis. In some cases, PCR products can be separated in a gel matrix (e.g., agarose or polyacrylamide) by electrophoresis, and size-fractionated bands comprising PCR products can be visualized using nucleic acid stains. Suitable stains can fluoresce under UV light (e.g., Ethidium bromide, GR Safe, SYBR® Green, or SYBR® Gold). The results can be visualized via transillumination or epi-illumination, and an image of the fluorescent pattern can be acquired using a camera or scanner, for example. The image can be processed and analyzed using specialized software (e.g., ImageJ) to measure and compare the intensity of a band of interest against a standard loaded on the same gel.

Alternatively, SSR polymorphisms can be identified by using PCR product(s) as a probe against Southern blots from different individuals in the population. See, U. H. Refseth et al., (1997) *Electrophoresis* 18: 1519. Briefly, PCR products are separated by length through gel electrophoresis and transferred to a membrane. SSR-specific DNA probes, such as oligonucleotides labeled with radioactive, fluorescent, or chromogenic molecules, are applied to the membrane and hybridize to bound PCR products with a complementary nucleotide sequence. The pattern of hybridization can be visualized by autoradiography or by development of color on the membrane, for example.

In some cases, PCR products can be quantified using a real-time thermocycler detection system. For example, Quantitative real-time PCR can use a fluorescent dye that forms a DNA-dye-complex (e.g., SYBR® Green), or a fluorophore-containing DNA probe, such as single-stranded oligonucleotides covalently bound to a fluorescent reporter or fluorophore (e.g. 6-carboxyfluorescein or tetrachlorofluorescin) and quencher (e.g., tetramethylrhodamine or dihydrocyclopyrroloindole tripeptide minor groove binder). The fluorescent signal allows detection of the amplified product in real time, thereby indicating the presence of a sequence of interest, and allowing quantification of the copy number of a sequence of interest in cellular DNA or expression level of a sequence of interest from cellular mRNA.

The identification of RFLPs is discussed, for example, in Alonso-Blanco et al. (*Methods in Molecular Biology*, vol. 82, "Arabidopsis Protocols", pp. 137-146, J. M. Martinez-Zapater and J. Salinas, eds., c. 1998 by Humana Press, Totowa, N.J.); Burr ("Mapping Genes with Recombinant Inbreds", pp. 249-254, in Freeling, M. and V. Walbot (Ed.), *The Maize Handbook*, c. 1994 by Springer-Verlag New York, Inc.: New York, N.Y., USA; Berlin Germany; Burr et al. *Genetics* (1998) 118: 519; and Gardiner, J. et al., (1993) *Genetics* 134: 917). For example, to produce a RFLP library enriched with single- or low-copy expressed sequences, total DNA can be digested with a methylation-sensitive enzyme (e.g., PstI). The digested DNA can be separated by size on a preparative gel. Polynucleotide fragments (500 to 2000 bp) can be excised, eluted and cloned into a plasmid vector (e.g., pUC18). Southern blots of plasmid digests can be probed with total sheared DNA to select clones that hybridize to single- and low-copy sequences. Additional restriction endonucleases can be tested to increase the number of polymorphisms detected.

The identification of AFLPs is discussed, for example, in EP 0 534 858 and U.S. Pat. No. 5,878,215. In general, total cellular DNA is digested with one or more restriction enzymes. Restriction halfsite-specific adapters are ligated to all restriction fragments and the fragments are selectively amplified with two PCR primers that have corresponding adaptor and restriction site specific sequences. The PCR products can be visualized after size-fractionation, as described above.

In some embodiments, the methods are directed to breeding a plant line. Such methods use genetic polymorphisms identified as described above in a marker assisted breeding program to facilitate the development of lines that have a desired alteration in the biomass trait. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VII. Articles of Manufacture

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein often produce higher yields of grain and/or biomass per hectare, relative to control plants that lack the exogenous nucleic acid or lack the modified endogenous nucleic acid. For example, transgenic plants described herein can have a grain yield that is increased about 5% to about 20% (e.g., increased 5% to 10%, 5% to 15%, 10% to 15%, 10% to 20%, or 15% to 20%) relative to that of control plants lacking the exogenous nucleic acid or lacking the modified endogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought. In some embodiments, plants described herein have a composition that permits more efficient processing into free sugars, and subsequently ethanol, for energy production. In some embodiments, such plants provide higher yields of ethanol, butanol, dimethyl ether, other biofuel molecules, and/or sugar-derived co-products per kilogram of plant material, relative to control plants. Such processing efficiencies are believed to be derived from the composition of the plant material, including, but not limited to, content of glucan, cellulose, hemicellulose, and lignin. By providing higher biomass yields at an equivalent or even decreased cost of production, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

The invention will be further described in the following examples, which do not limit the scope of the invention described in the claims.

VIII. Examples

Example 1

Transgenic Rice Plants

The following symbols are used in with respect to rice transformation: $T_0$: plant regenerated from transformed tissue culture; $T_1$: first generation progeny of self-pollinated $T_0$ plants; $T_2$: second generation progeny of self-pollinated $T_1$ plants; $T_3$: third generation progeny of self-pollinated $T_2$ plants.

The following is a list of nucleic acids that were isolated from *Arabidopsis thaliana* plants: CeresAnnot: 553111_CW00758 (SEQ ID NO:1015), CeresAnnot: 838049_CW00759 (SEQ ID NO:850), CeresClone: 106263_CW00780 (SEQ ID NO:1064), CeresAnnot: 1298824_CW00817 (SEQ ID NO:1579), CeresClone:32753 (SEQ ID NO:1811), CeresClone:6639 (SEQ ID NO:1740), CeresAnnot:851842 (SEQ ID NO:2565), CeresClone:39378 (SEQ ID NO:2123), CeresAnnot:529860 (SEQ ID NO:1954), CeresAnnot:873343 (SEQ ID NO:2195), CeresAnnot:837788 (SEQ ID NO:2424), CeresAnnot:853198 (SEQ ID NO:2149), CeresClone:93867 (SEQ ID NO:2034), CeresAnnot:878887 (SEQ ID NO:2492), CeresClone:11830

(SEQ ID NO:1979), and CeresAnnot:1310682 (SEQ ID NO:1592). The following nucleic acids were isolated from *Zea mays* plants: CeresClone:896483_CW00787 (SEQ ID NO:740) and CeresClone:225681_CW00792 (SEQ ID NO:187). CeresClone:1773290_CW00761 (SEQ ID NO:153), CeresClone:1790897_CW00776 (SEQ ID NO:367), and CeresClone:1780416_CW00778 (SEQ ID NO:1598) were isolated from *Panicum virgatum* plants. CeresClone:1841236_CW00741 (SEQ ID NO:633) was isolated from *Gossypium hirsutum* plants. CeresClone:1744499_CW00813 (SEQ ID NO:1034) was isolated from *Musa acuminate* plants. CeresClone:1238706 (SEQ ID NO:2185) was isolated from *Glycine max* plants. CeresAnnot:1440417 (SEQ ID NO:2270) was isolated from *Populus balsamifera* subsp. *trichocarpa* plants.

Each isolated nucleic acid described above was cloned into a Ti plasmid vector containing a phosphinothricin acetyltransferase gene which confers Finale™ resistance to transformed plants. Constructs were made using the above mentioned nucleic acids that contained each operably linked to a 326F promoter construct was introduced into callus cells of the rice cultivar Kitaake by an *Agrobacterium*-mediated transformation protocol. Approximately 20-30 independent $T_0$ transgenic plants were generated from each transformation, as well as for the control plasmid (empty vector). Preliminary phenotypic analysis indicated that $T_0$ transformants did not show any significant phenotypic anomalies in vegetative organs, with a few exceptions where some plants appeared small with reduced fertility, most likely due to tissue culture effects.

$T_0$ plants were grown in a greenhouse, allowed to self-pollinate, and $T_1$ seeds collected. $T_1$ and $T_2$ plants were grown in a field. The presence of each construct was confirmed by PCR.

Rice seeds were soaked for 3-4 days before spring germination and transplanted to the field about one month later in Langfang, China. The distance between rows was 25 cm and the distance between plants was 15 cm. The combined fertilizer (16N-16P-16K) was applied at 25 kg/mu (666.7 m$^2$) just before transplanting. 12.5 kg/mu of urea was applied at two times during the growing season prior to panicle development.

Ten plants were grown per transgenic event within one row. Only those rows that were visibly different from control plants were measured. Plant height was measured at maturity.

Biomass (Dry weight) measurements were collected from $T_1$ plants. The stems with leaves and leaf sheaths but without panicles were dried in a greenhouse for at least a month, and then weighed for each plant (all tillers weighed together for each plant). Tiller number was counted after 4 months of growth.

Example 2

Results for Rice Events CW741-15, CeresClone:1841236_CW00741, (SEQ ID NO:633)

$T_1$ seed from one event of CW741-15 containing CeresClone:1841236_CW00741 was analyzed as described in Example 1. Table 1 contains the plant height, dry-weight biomass, panicle weight, and number of tillers that had inflorescence of transgenic $T_1$ plants in comparison to plants not containing the transgene grown at the same location. The table data row corresponds to a field row. The data points represent an average of 10 transgenic plants (1 row of same event) and an average of 40 control plants (4 rows). An increase in biomass was observed as indicated by the increased dry-weight biomass and plant height in the transgenic plants in comparison to plants not containing the transgene. The transgenic plants also had increased panicle weight in comparison to plants not containing the transgene.

TABLE 1

| Plant Height (cm) | | Dry-Weight Biomass (g) | | Panicle weight (g) | | No. of tillers | |
|---|---|---|---|---|---|---|---|
| CW741-15 | WT | CW741-15 | WT | CW741-15 | WT | CW741-15 | WT |
| 84.3 | 76.43 | 23.5 | 19.25 | 35.3 | 33.65 | 21.6 | 22.08 |

Example 3

Results for Rice Events CW00758, CeresAnnot:553111_CW00758 (SEQ ID NO:1015)

$T_1$ seed from one event of CW758-23 containing CeresAnnot:553111_CW00758 was analyzed as described in Example 1. Table 2 contains the plant height, biomass, panicle weight, and number of tillers that had inflorescence of transgenic $T_1$ plants in comparison to plants not containing the transgene grown at the same location. The table data row corresponds to a field row. The data points represent an average of 10 transgenic plants (1 row of same event) and an average of 40 control plants (4 rows). An increase in biomass was observed as indicated by the increased dry-weight biomass, plant height, and number of tillers in transgenic plants in comparison to plants not containing the transgene. The transgenic plants also had increased panicle weight in comparison to plants not containing the transgene.

TABLE 2

| Plant Height (cm) | | Dry-weight Biomass (g) | | Panicle weight (g) | | No. of tillers | |
|---|---|---|---|---|---|---|---|
| CW758-23 | WT | CW758-23 | WT | CW758-23 | WT | CW758-23 | WT |
| 81.8 | 76.6 | 23.8 | 20.13 | 40.1 | 33.08 | 26.4 | 23.50 |

Example 4

Results for Rice Events CW00759, CeresAnnot:838049_CW00759 (SEQ ID NO:850)

$T_1$ seed from one event of CW00759-01 containing CeresAnnot:838049 was analyzed as described in Example 1.

The plant height, dry-weight biomass, panicle weight, and number of tillers that had inflorescence of transgenic $T_1$ plants in comparison to plants not containing the transgene grown at the same location is shown in Table 3. The table data row corresponds to a field row. The data points represent an average of 10 transgenic plants (1 row of same event) and an average of 40 control plants (4 rows). An increase in biomass was observed as indicated by the increased plant height in the transgenic plants in comparison to plants not containing the transgene. The transgenic plants also had increased panicle weight in comparison to plants not containing the transgene.

TABLE 3

| Plant Height (cm) | | Dry-weight Biomass (g) | | Panicle weight (g) | | No. of tillers | |
|---|---|---|---|---|---|---|---|
| CW759-01 | WT | CW759-01 | WT | CW759-01 | WT | CW759-01 | WT |
| 81.9 | 76.73 | 18.3 | 20.13 | 38.4 | 33.9 | 24.2 | 23.93 |

Example 5

Results for Rice Events
CeresClone:1773290_CW00761 (SEQ ID NO:153)

$T_1$ seed from one event of CW00761-09 containing CeresClone:1773290 was analyzed as described in Example 1. The plant height, biomass, panicle weight, and number of tillers that had inflorescence of transgenic $T_1$ plants in comparison to plants not containing the transgene grown at the same location is shown in Table 4. The table data row corresponds to a field row. The data points represent an average of 10 transgenic plants (1 row of same event) and an average of 40 control plants (4 rows). An increase in biomass was observed as indicated by the increased dry-weight biomass and plant height in the transgenic plants in comparison to plants not containing the transgene. The transgenic plants also had increased panicle weight in comparison to plants not containing the transgene.

Example 6

Results for Rice Events CW00776-21,
CeresClone:1790897_CW00776 (SEQ ID NO:367)

$T_1$ seed from one event of CW00776-21 containing CeresClone:1790897 was analyzed as described in Example 1. The plant height, dry-weight biomass, panicle weight, and number of tillers that had inflorescence of transgenic $T_1$ plants in comparison to plants not containing the transgene grown at the same location is shown in Table 5. The table data row corresponds to a field row. The data points represent an average of 10 transgenic plants (1 row of same event) and an average of 40 control plants (4 rows). An increase in biomass was observed as indicated by the increased dry-weight biomass, plant height, and number of tillers in the transgenic plants in comparison to plants not containing the transgene. The transgenic plants also had increased panicle weight in comparison to plants not containing the transgene.

TABLE 5

| Plant Height (cm) | | Dry-weight Biomass (g) | | Panicle weight (g) | | No. of tillers | |
|---|---|---|---|---|---|---|---|
| CW776-21 | WT | CW776-21 | WT | CW776-21 | WT | CW776-21 | WT |
| 84.6 | 75.7 | 27.0 | 21.33 | 39.9 | 33.13 | 33.5 | 26.85 |

Example 7

Results for Rice Events CW00778,
CeresClone:1780416_CW00778 (SEQ ID NO:1598)

$T_1$ seed from one event of CW00778-08 containing CeresClone:1780416 was analyzed as described in Example 1. The plant height, dry-weight biomass, panicle weight, and number of tillers that had inflorescence of transgenic $T_1$ plants in comparison to plants not containing the transgene grown at the same location are shown in Table 6. Each table

TABLE 4

| Plant Height (cm) | | Dry-weight Biomass (g) | | Panicle weight (g) | | No. of tillers | |
|---|---|---|---|---|---|---|---|
| CW761-09 | WT | CW761-09 | WT | CW761-09 | WT | CW761-09 | WT |
| 86.2 | 77.03 | 25.2 | 18.053 | 36.4 | 29.35 | 25.8 | 24.0 | data row corresponds to a field row. The data points represent an average of 10 transgenic plants (1 row of same event) and an average of 40 control plants (4 rows). An increase in biomass was observed as indicated by the increased dry-weight biomass and plant height in the transgenic plants in comparison to plants not containing the transgene. The transgenic plants also had increased panicle weight in comparison to plants not containing the transgene.

TABLE 6

| Plant Height (cm) | | Dry-weight Biomass (g) | | Panicle weight (g) | | No. of tillers | |
| --- | --- | --- | --- | --- | --- | --- | --- |
| CW778-08 | WT | CW778-08 | WT | CW778-08 | WT | CW778-08 | WT |
| 82.5 | 75.11 | 26.5 | 20.74 | 31.9 | 31.77 | 24.5 | 24.74 |

Example 8

Results for Rice Events CW00780, CeresClone:106263_CW00780 (SEQ ID NO:1064)

$T_1$ seed from one event of CW00780-16 containing Ceres Clone: 638126 was analyzed as described in Example 1. The plant height, dry-weight biomass, panicle weight, and number of tillers of transgenic $T_1$ plants in comparison to plants not containing the transgene grown at the same location are shown in Table 7. The table data row corresponds to a field row. The data points represent an average of 10 transgenic plants (1 row of same event) and an average of 40 control plants (4 rows). An increase in biomass was observed as indicated by the increased dry-weight biomass and plant height in the transgenic plants in comparison to plants not containing the transgene.

TABLE 7

| Plant Height (cm) | | Dry-weight Biomass (g) | | Panicle weight (g) | | No. of tillers | |
| --- | --- | --- | --- | --- | --- | --- | --- |
| CW780-16 | WT | CW780-16 | WT | CW780-16 | WT | CW780-16 | WT |
| 88.8 | 76.30 | 34.5 | 24.54 | 33.8 | 36.60 | 21.0 | 28.18 |

Example 9

Results for Rice Events CW00787, CeresClone:896483_CW00787 (SEQ ID NO: 740)

$T_1$ seed from three events of CW00787-02 containing Ceres Clone: 896483 was analyzed as described in Example 1. The plant height, biomass, panicle weight, and number of tillers of transgenic T1 plants in comparison to plants not containing the transgene grown at the same location are shown in Table 8. The data points represent an average of 10 transgenic plants (1 row of same event) and an average of 40 control plants (4 rows). An increase in biomass was observed as indicated by the increased plant height in the transgenic plants in comparison to plants not containing the transgene.

TABLE 8

| Plant Height (cm) | | Dry-weight Biomass (g) | | Panicle weight (g) | | No. of tillers | |
| --- | --- | --- | --- | --- | --- | --- | --- |
| CW787-02 | WT | CW787-02 | WT | CW787-02 | WT | CW787-02 | WT |
| 83.3 | 78.11 | 23.5 | 24.58 | 33.0 | 34.75 | 25.2 | 28.77 |

Example 10

Results for Rice Events CW00813, CeresClone:1744499_CW00813 (SEQ ID NO:1034)

$T_1$ seed from one event of CW00813-09 containing Ceres Clone: 1744499 was analyzed as described in Example 1. The plant height, dry-weight biomass, panicle weight, and number of tillers that had inflorescence of transgenic $T_1$ plants in comparison to plants not containing the transgene grown at the same location is shown in Table 9. The table data row corresponds to a field row. The data points represent an average of 10 transgenic plants (1 row of same event) and an average of 40 control plants (4 rows). An increase in biomass was observed as indicated by the increased dry-weight biomass in the transgenic plants in comparison to plants not containing the transgene. The transgenic plants also had increased panicle weight in comparison to plants not containing the transgene.

TABLE 9

| Plant Height (cm) | | Dry-weight Biomass (g) | | Panicle weight (g) | | No. of tillers | |
|---|---|---|---|---|---|---|---|
| CW813-09 | WT | CW813-09 | WT | CW813-09 | WT | CW813-09 | WT |
| 83.3 | 74.64 | 19.8 | 22.06 | 37.2 | 36.17 | 20.0 | 24.47 |

Example 11

Results for Rice Events CW792, CeresClone:225681_CW00792 (SEQ ID NO:187)

T1 seed from one event of CW00792-10 containing Ceres Clone 225681 was analyzed as described in Example 1. The plant height, dry-weight biomass, panicle weight, and number of tillers that had inflorescence of transgenic T1 plants in comparison to plants not containing the transgene grown at the same location are shown in Table 10. The table data row corresponds to a field row. The data points represent an average of 10 transgenic plants (1 row of same event) and an average of 40 control plants (4 rows). An increase in biomass was observed as indicated by the increased plant height and dry-weight biomass in comparison to plants not containing the transgene.

TABLE 10

| Plant Height (cm) | | Dry-weight Biomass (g) | | Panicle weight (g) | | No. of tillers | |
|---|---|---|---|---|---|---|---|
| CW792-10 | WT | CW792-10 | WT | CW792-10 | WT | CW792-10 | WT |
| 82.6 | 74.97 | 26.7 | 20.82 | 33.2 | 35.19 | 25.2 | 26.69 |

Example 12

Results for Rice Events CW817, CeresAnnot:1298824_CW00817 (SEQ ID NO:1579)

$T_1$ seed from one event of CW00817-13 containing CeresAnnot:1298824 was analyzed as described in Example 1. This event was chosen to be quantitatively phenotyped from a number of events transformed with the same sequence that on visual inspection showed similar phenotypes compared to the wild type. Table 11 provides the plant height, dry-weight biomass, panicle weight, and number of tillers that had inflorescence of transgenic $T_1$ plants in comparison to plants not containing the transgene grown at the same location (WT). The table data row corresponds to a field row. The data points represent an average of 10 transgenic plants (1 row of same event) and an average of 40 control plants (4 rows). An increase in biomass was observed as indicated by the increased plant height and dry-weight biomass in the transgenic plants in comparison to plants not containing the transgene. The transgenic plants also had increased panicle weight in comparison to plants not containing the transgene.

The plant height, number of tillers that had inflorescence, panicle weight, and seed size of transgenic $T_2$ plants in comparison to plants not containing the transgene grown at the same location are shown in Table 12.

TABLE 11

| Plant Height (cm) | | Dry-weight Biomass (g) | | Panicle weight (g) | | No. of tillers | |
|---|---|---|---|---|---|---|---|
| CW817-13 | WT | CW817-13 | WT | CW817-13 | WT | CW817-13 | WT |
| 84.9 | 74.84 | 21.2 | 20.03 | 37.4 | 33.92 | 25.5 | 25.63 |

TABLE 12

| | | Rep I | Rep II | Rep III | Average |
|---|---|---|---|---|---|
| Panicle Wt (g) | WT | 23.6 | 21.4 | 24.5 | 23.2 |
| | CW00817 | 27.5 | 29.4 | 26.7 | 27.9 |
| No. of tillers | WT | 22.5 | 26.2 | 26.4 | 25.0 |
| | CW00817 | 24.3 | 28.42 | 24.9 | 25.9 |
| Plant Height (cm) | WT | 67.3 | 67.7 | 68.5 | 67.8 |
| | CW00817 | 76.5 | 76.1 | 76.7 | 76.4 |

TABLE 12-continued

| | | Rep I | Rep II | Rep III | Average |
|---|---|---|---|---|---|
| Seed size (wt/200 seeds) | WT | 4.8 | 4.7 | 4.7 | 4.7 |
| | CW00817 | 4.3 | 4.3 | 4.4 | 4.3 |

Example 13

Results for Rice Events CW00219, CW00676, and CW00691

Seeds from CW00219 plants containing CeresClone: 32753 (SEQ ID NO:1811), CW00676 plants containing CeresClone: 6639 (SEQ ID NO:1740), and CW00691 plants containing CeresAnnot:851842 (SEQ ID NO:2565) were analyzed as described in Example 1. The plant height, dry-weight biomass, and panicle weight of transgenic $T_2$ plants in comparison to plants not containing the transgene grown at the same location are shown in Table 13. The data points for each replicate represent an average of 10 transgenic plants (1 row of same event) and an average of 40 control plants (4 rows). For CW00219, an increase in biomass was observed as indicated by the increased plant height and dry-weight biomass in the transgenic plants in comparison to plants not containing the transgene. For CW00676, an increase in biomass was observed as indicated by the increased plant height in the transgenic plants in comparison to plants not containing the transgene. The CW00676 transgenic plants also had increased panicle weight in comparison to plants not containing the transgene. For CW00691, an increase in biomass was observed as indicated by the increased plant height and dry-weight biomass in the transgenic plants in comparison to plants not containing the transgene.

TABLE 13

|  |  | Rep I | Rep II | Rep III | Average |
|---|---|---|---|---|---|
| Panicle Wt (g) | WT | 356.9 | 343.2 | 366.7 | 355.6 |
|  | CW0219 | 339.0 | 348.8 | 347.7 | 345.2 |
| Dry-weight | WT | 17.1 | 15.1 | 14.6 | 15.6 |
| Biomass (g) | CW0219 | 19.0 | 20.6 | 21.1 | 20.2 |
| Plant Height | WT | 77.3 | 76.9 | 77.4 | 77.2 |
| (cm) | CW0219 | 82.2 | 83.0 | 80.6 | 81.9 |
| Panicle Wt (g) | WT | 395.4 | 385.0 | 361.6 | 380.7 |
|  | CW0676 | 412.4 | 374.8 | 410.4 | 399.2 |
| Dry-weight | WT | 16.6 | 20.0 | 16.6 | 17.7 |
| Biomass (g) | CW0676 | 18.0 | 15.9 | 18.4 | 17.4 |
| Plant Height | WT | 80.3 | 73.3 | 77.2 | 76.9 |
| (cm) | CW0676 | 99.5 | 96.5 | 98.1 | 98.0 |
| Panicle Wt (g) | WT | 395.4 | 385.0 | 361.6 | 380.7 |
|  | CW0691 | 343.2 | 322.1 | 316.2 | 327.2 |
| Dry-weight | WT | 16.6 | 20.0 | 16.6 | 17.7 |
| Biomass (g) | CW0691 | 26.8 | 23.2 | 24.8 | 24.9 |
| Plant Height | WT | 80.3 | 73.3 | 77.2 | 76.9 |
| (cm) | CW0691 | 82.8 | 76.6 | 83.2 | 80.9 |

Example 14

Results for Rice Events CW00018, CW00318, and CW00506-20

Seeds from two events of CW00018 containing Ceres-Clone:39378 (SEQ ID NO:2123), two events of CW00318 containing CeresAnnot:529860 (SEQ ID NO:1954), and one event of CW00506-20 containing CeresAnnot:873343 (SEQ ID NO:2195 were planted and grown under either low nitrogen (5.3 kg/mu; 34.2% of regular nitrogen supply) or regular nitrogen (15.5 kg/mu; 666.7 square meters) conditions. The plant height, dry-weight biomass, and panicle weight of transgenic CW00018 and CW00318 transgenic $T_3$ plants, and CW00506 $T_2$ plants in comparison to plants not containing the transgene grown at the same location are shown in Tables 14-16, respectively. The data points represent an average for three replicates of 40 transgenic plants each and an average of 40 control plants (4 rows). For CW00018 and CW00318, a statistically significant decrease in plant height was observed under both low and regular nitrogen conditions. For CW00506-20, a statistically significant decrease in plant height was observed under low nitrogen conditions. Dry weight biomass and panicle weight of CW00018, CW00318, and CW00506-20 plants were not significantly different from the control plants.

TABLE 14

|  | WT | | CW0018-1 | | CW0018-4 | |
|---|---|---|---|---|---|---|
| Genotype | Low N | Regular N | Low N | Regular N | Low N | Regular N |
| Plant Height (cm) | 83.68 | 80.93 | 75.55** | 72.28** | 64.18** | 66.14** |
| Dry weight biomass (g) | 16.01 | 14.6 | 18 | 13.59 | 14.05 | 12.47 |
| Panicle Wt/plant (g) | 29.98 | 31.51 | 32.7 | 28.1 | 28.64 | 25.47 |

**statistically significant at 1%

TABLE 15

|  | WT | | CW00318-2 | | CW0031894 | |
|---|---|---|---|---|---|---|
| Genotype | Low N | Regular N | Low N | Regular N | Low N | Regular N |
| Plant Height (cm) | 83.68 | 80.93 | 83.97 | 79.62 | 73.78** | 66.95** |
| Dry weight biomass (g) | 16.01 | 14.6 | 16.2 | 13.48 | 18.2 | — |
| Panicle Wt/plant(g) | 29.98 | 31.51 | 32.38 | 31.96 | 25.15 | 23.43 |

**statistically significant at 1%

TABLE 16

|  | WT | | CW00506-20 | |
|---|---|---|---|---|
| Genotype | Low N | Regular N | Low N | Regular N |
| Plant Height (cm) | 83.68 | 80.93 | 73.37* | 67.83 |
| Dry weight biomass (g) | 16.01 | 14.6 | 15.57 | 11.52 |
| Panicle Wt/plant (g) | 29.98 | 31.51 | 29.37 | 27.04 |

*statistically significant at 5%

Example 15

Results for Rice Events CW00232

Seeds from CW00232 plants containing CeresAnnot: 837788 (SEQ ID NO:2424) were analyzed as described in Example 1. The plant height, dry-weight biomass, and panicle weight of transgenic $T_2$ plants in comparison to plants not containing the transgene grown at the same location are shown in Table 17. The data points for each replicate represent an average of 40 transgenic plants and an average of 40 control plants (4 rows). For CW00232, a decrease in biomass was observed as indicated by the decreased dry-weight biomass in the transgenic plants in comparison to plants not containing the transgene.

TABLE 17

|  | Panicle Wt/Plot (g) | | Plant Height (cm) | | Dry-Weight Biomass (g) | |
|---|---|---|---|---|---|---|
|  | WT | CW0232 | WT | CW0232 | WT | CW0232 |
| Rep I | 395.4 | 361.9 | 80.3 | 76.3 | 16.6 | 15.8 |
| Rep II | 385.0 | 369.3 | 73.3 | 75.1 | 20.0 | 14.6 |

TABLE 17-continued

|  | Panicle Wt/Plot (g) | | Plant Height (cm) | | Dry-Weight Biomass (g) | |
|---|---|---|---|---|---|---|
|  | WT | CW0232 | WT | CW0232 | WT | CW0232 |
| Rep III | 361.8 | 364.7 | 77.2 | 74.9 | 16.6 | 15.1 |
| Average | 380.7 | 365.3 | 76.9 | 75.4 | 17.7 | 15.2* |

*statistically significant at 5%

Example 16

Results for Rice Events CW0703, CW0398, CW00551, CW00569, and CW00584

Seeds from CW00703 plants containing CeresAnnot: 853198, CW00398 plants containing CeresClone93867, CW00551 plants containing CeresClone:878887 (SEQ ID NO:2492), CW00569 plants containing CeresClone: 1238706 (SEQ ID NO:2185), and CW00584 plants containing CeresAnnot:1440417 (SEQ ID NO:2270) were analyzed as described in Example 1. The plant height, dry-weight biomass, and panicle weight of transgenic $T_2$ plants in comparison to plants not containing the transgene grown at the same location are shown in Tables 18 and 19. The data points for each replicate represent an average of 40 transgenic plants and an average of 40 control plants (4 rows). For CW00703 and CW00398, an increase in biomass was observed as indicated by the increased plant height in the transgenic plants in comparison to plants not containing the transgene. An increased panicle weight also was observed. For CW00676, an increase in biomass was observed as indicated by the increased plant height in the transgenic plants in comparison to plants not containing the transgene. The CW00676 transgenic plants also had increased panicle weight in comparison to plants not containing the transgene. For CW00551, an increase in biomass was observed as indicated by the increased plant height and dry-weight biomass in the transgenic plants in comparison to plants not containing the transgene. For CW00569 and CW0584, an increase in biomass was observed as indicated by the increased plant height and dry-weight biomass in the transgenic plants in comparison to plants not containing the transgene. The CW00569 transgenic plants also had increased panicle weight in comparison to plants not containing the transgene.

TABLE 18

| Trait | Replicate | WT | CW00703 | CW00398 |
|---|---|---|---|---|
| Panicle Wt (g) | I | 395.4 | 393.5 | 388.9 |
|  | II | 385.0 | 421.2 | 398.4 |
|  | III | 361.6 | — | 433.1 |
|  | Average | 380.7 | 407.4 | 406.8 |
| Dry-weight biomass (g) | I | 16.63 | 16.04 | 15.79 |
|  | II | 19.96 | 17.09 | 14.83 |
|  | III | 16.57 | 17.12 | 17.70 |
|  | Average | 17.72 | 16.75 | 16.11 |
| Plant Height (cm) | I | 80.25 | 83.17 | 85.50 |
|  | II | 73.25 | 81.17 | 79.60 |
|  | III | 77.17 | 79.10 | 82.83 |
|  | Average | 76.89 | 81.14 | 82.64 |

TABLE 19

| Trait | Replicate | WT | CW00551 | CW00569 | CW00584 |
|---|---|---|---|---|---|
| Panicle Wt (g) | I | 356.9 | 343.2 | 424.6 | 349.3 |
|  | II | 343.2 | 379.1 | 381.6 | 368.4 |
|  | III | 366.7 | 347.1 | 373.2 | 356.1 |
|  | Average | 355.6 | 356.5 | 393.1 | 357.9 |
| Dry-weight Biomass (g) | I | 17.1 | 18.4 | 26.4 | 23.3 |
|  | II | 15.1 | 16.8 | 23.7 | 24.5 |
|  | III | 14.6 | 18.4 | 25.4 | 24.0 |
|  | Average | 15.6 | 17.9 | 25.2 | 23.9 |
| Plant Height (cm) | I | 77.3 | 87.7 | 98.6 | 93.1 |
|  | II | 76.9 | 90.9 | 99.0 | 93.9 |
|  | III | 77.4 | 85.0 | 99.0 | 90.4 |
|  | Average | 77.2 | 87.9 | 98.9 | 92.5 |

Example 17

Transgenic *Arabidopsis* Plants

The following is a list of nucleic acids that were isolated from *Panicum virgatum* plants: CeresClone:1786268 (SEQ ID NO:1365), CeresClone:1769374 (SEQ ID NO:1214), CeresClone:1909354 (SEQ ID NO:1488), CeresClone: 1815762 (SEQ ID NO:252), CeresClone:1819917 (SEQ ID NO:197), CeresClone:1724480 (SEQ ID NO:579), CeresClone:1882035 (SEQ ID NO:503), CeresClone:1753603 (SEQ ID NO:927), CeresClone:1781794, CeresClone: 1791384 (SEQ ID NO:662), CeresClone:1724838 (SEQ ID NO:1), CeresClone:1871521 (SEQ ID NO:1332), and CeresClone:1792015 (SEQ ID NO:1540). CeresClone: 466497 (SEQ ID NO:1111) was isolated from *Zea mays* plants. CeresAnnot:1514289 (SEQ ID NO:52) was isolated from *Populus balsamifera* subsp. *trichocarpa* plants.

Each isolated nucleic acid described above was cloned into a binary or cointegration Ti plasmid vector containing a selectable marker conferring resistance to Finale®. The nucleic acid was operably linked to a 35S promoter. Each vector was introduced into *Arabidopsis* ecotype Wassilewskija (WS) via *Agrobacterium*-mediated transformation using the floral dip method essentially as described in Bechtold, N. et al., *C.R. Acad. Sci. Paris,* 316:1194-1199 (1993). The presence of each construct was verified by PCR. At least two independent events from each transformation were selected for further study. $T_0$ plants are plants from transformed tissue culture. $T_1$ plants are first generation progeny of self-pollinated $T_0$ plants. $T_2$ plants are second generation progeny of self-pollinated $T_1$ plants.

Biomass samples were collected and processed to determine the dry matter yield of transgenic plants. $T_2$ seeds from several transformation events of *Arabidopsis* were sown in a soil mixture composed of 60% Sunshine Mix and 40% medium-size vermiculite. Two lines were used as controls: (1) untransformed wild-type *Arabidopsis* and (2) wild-type transformed with construct Bin4-Ec6-Luc::NMCH-Luc, which contains a sequence conferring Finale® resistance, a Ec6 promoter to drive expression of a luciferase polypeptide, and a NMCH promoter to drive expression of a second luciferase polypeptide.

The sown seeds were vernalized for at least 3 days at 4° C. then transferred to either a greenhouse or a walk-in growth chamber for germination and growth. About one week post-germination, the experimental plants and the transgenic control were sprayed with Finale® to select for herbicide-resistant transgenic plants. Each pot was thinned-out by randomly removing seedlings to reduce the density of seedlings per pot to at least 10. Plants were allowed to grow until senescence.

Vegetative tissue (stems and undropped leaves) from ten senesced plants of each event were collected in a pre-labeled envelope and dried in a 42° C. oven overnight. Reproductive structures (siliques and seeds) from senesced plants of each event were collected separately. After cooling, each sample of vegetative tissue was milled, processed for composition analysis, and weighed to obtain the dry matter yield for each event. The dry matter yield for plants of each transgenic event was compared to the corresponding value for control lines. Table 20 provides the number of positive events containing a dry biomass ratio of 1.2 or greater relative to control.

TABLE 20

| Clone ID | Number of positive events containing a dry biomass ratio of 1.2 or greater |
|---|---|
| 1786268 | 4 out of 6 |
| 1769374 | 5 out of 6 |
| 1909354 | 3 out of 6 |
| 466497 | 3 out of 4 |
| 1815762 | 3 out of 3 |
| 1819917 | 2 out of 5 |
| 1724480 | 3 out of 6 |
| 1882035 | 4 out of 5 |

TABLE 20-continued

| Clone ID | Number of positive events containing a dry biomass ratio of 1.2 or greater |
|---|---|
| 1753603 | 2 out of 6 |
| 1781794 | 5 out of 6 |
| 1791384 | 4 out of 6 |
| 1724838 | 5 out of 6 |
| 1871521 | 1 out of 3 |
| 1792015 | 2 out of 6 |
| Annot.1514289 | 3 out of 6 |

These results indicate that the dry matter yield of a transgenic plant can be modulated relative to a control plant.

Example 18

Field Trial Data for CW00264 Rice Events

Table 21 summarizes field trial data for $T_2$ CW00264 plants containing CeresClone:11830 (SEQ ID NO:1979). In Table 21, well-watered indicates regular irrigation while rain-fed indicates rain was the only source of water as there was no irrigation after transplanting in field.

TABLE 21

| Line ID | Well-watered | | | | | Rain-fed | | | | | Difference well-water vs rain-fed (%) |
|---|---|---|---|---|---|---|---|---|---|---|---|
| | I | II | III | AVE | p-Value | I | II | III | AVE | p-Value | |
| Panicle Wt/plant (g) | | | | | | | | | | | |
| CW6-27A | 35.5 | 27.7 | 34.5 | 32.6 | 0.71 | 29.4 | 26.2 | 21.5 | 25.7 | 0.36 | 21.1 |
| CW264-13 | 32.5 | 32.8 | 31.0 | 32.1 | 0.66 | 20.6 | 26.4 | 20.9 | 22.6 | 0.87 | 29.5 |
| CW264-14 | 28.4 | 26.3 | 28.7 | 27.8 | 0.08 | 20.0 | 20.4 | 24.5 | 21.6 | 0.46 | 22.2 |
| CW264-16 | 29.2 | 31.1 | 27.6 | 29.3 | 0.26 | 26.2 | 22.2 | 23.1 | 23.8 | 0.63 | 18.8 |
| CW264-17 | 34.0 | 34.0 | 28.9 | 32.3 | 0.71 | 24.2 | 25.0 | 24.9 | 24.7 | 0.16 | 23.6 |
| Kitaake (wild-type) | 34.0 | 30.2 | 30.2 | 31.4 | | 24.6 | 22.6 | 22.0 | 23.0 | | 26.8 |
| Stem biomass/plant (g) | | | | | | | | | | | |
| CW6-27A | 18.1 | 15.2 | 16.0 | 16.4 | 0.91 | 14.3 | 11.3 | 10.7 | 12.1 | 0.52 | 26.1 |
| CW264-13 | 18.0 | 16.2 | 15.3 | 16.5 | 0.94 | 9.8 | 12.2 | 9.5 | 10.5 | 0.70 | 36.2 |
| CW264-14 | 13.6 | 13.2 | 13.1 | 13.3 | 0.06 | 8.6 | 8.6 | 11.1 | 9.4 | 0.28 | 29.1 |
| CW264-16 | 16.8 | 16.5 | 14.0 | 15.8 | 0.56 | 11.4 | 9.1 | 11.6 | 10.7 | 0.78 | 32.3 |
| CW264-17 | 15.8 | 16.3 | 13.4 | 15.2 | 0.33 | 10.0 | 10.0 | 10.1 | 10.0 | 0.42 | 33.8 |
| Kitaake (wild-type) | 17.7 | 14.8 | 17.2 | 16.6 | | 13.1 | 10.4 | 9.7 | 11.1 | | 33.2 |
| Total Dry Weight Biomass | | | | | | | | | | | |
| CW6-27A | 53.6 | 42.9 | 50.5 | 49.0 | 0.81 | 43.7 | 37.6 | 32.2 | 37.8 | 0.39 | 22.8 |
| CW264-13 | 50.5 | 49.0 | 46.3 | 48.6 | 0.82 | 30.4 | 38.7 | 30.4 | 33.2 | 0.79 | 31.8 |
| CW264-14 | 42.0 | 39.5 | 41.7 | 41.1 | 0.06 | 28.6 | 29.0 | 35.6 | 31.1 | 0.36 | 24.4 |
| CW264-16 | 46.0 | 47.6 | 41.6 | 45.1 | 0.34 | 37.5 | 31.2 | 34.7 | 34.5 | 0.89 | 23.5 |
| CW264-17 | 49.8 | 50.3 | 42.3 | 47.5 | 0.88 | 34.2 | 35.0 | 35.0 | 34.7 | 0.76 | 26.9 |
| Kitaake (wild type) | 51.7 | 45.0 | 47.4 | 48.0 | | 37.6 | 33.0 | 31.7 | 34.1 | | 29.0 |
| Plant Height (cm) | | | | | | | | | | | |
| CW6-27A | 76.5 | 76.2 | 76.0 | 76.2 | 0.38 | 69.2 | 66.4 | 64.2 | 66.6 | 0.35 | 12.6 |
| CW264-13 | 71.9 | 75.4 | 74.5 | 73.9 | 0.24 | 59.5 | 64.7 | 59.5 | 61.2 | 0.16 | 17.2 |
| CW264-14 | 69.3 | 70.6 | 72.0 | 70.6 | 0.01 | 59.8 | 64.3 | 63.7 | 62.6 | 0.25 | 11.4 |
| CW264-16 | 76.7 | 76.3 | 75.9 | 76.3 | 0.34 | 68.9 | 67.6 | 67.8 | 68.1 | 0.02 | 10.8 |
| CW264-17 | 74.6 | 76.8 | 76.0 | 75.8 | 0.90 | 67.7 | 66.6 | 64.7 | 66.3 | 0.24 | 12.5 |
| Kitaake (wild type) | 75.6 | 76.6 | 74.8 | 75.7 | | 66.1 | 64.2 | 64.2 | 64.8 | | 14.3 |

Example 19

Results for Rice Events CW00716

T₁ seeds from CW00716 events containing CeresAnnot: 1310682 (SEQ ID NO:1592) were analyzed as described in Example 1. A number of independent transgenic events were recovered from the transformation with CeresAnnot: 1310682 (SEQ ID NO:1592). Visual inspection of $T_1$ progeny from different transgenic events indicated that many of the $T_1$ progeny appeared to have a similar amount of biomass as plants not containing the transgene. Progeny from one CW00716 event were chosen to be quantitatively phenotyped and the dry-weight biomass of individual transgenic $T_1$ plants of the same self-pollinated $T_0$ plant are shown in Table 22 in comparison to plants not containing the transgene and grown in the same location (WT). Table 23 provides the grain yield (g), plant height (cm), and stem weight (g) of transgenic $T_2$ plants (from same event as Table 22) in comparison to plants not containing the transgene grown at the same location (WT). An increase in grain yield and an increase in plant height were observed in the transgenic plants in comparison to plants not containing the transgene.

TABLE 22

Dry-weight Biomass (g) of Individual Plants

| | Individual T₁ plants | | | | | | | | | | Avg. |
|---|---|---|---|---|---|---|---|---|---|---|---|
| CW00716 | 20.29 | 24.25 | 14.84 | / | 19.11 | 28.81 | 19.93 | 12.55 | 15.48 | 38.41 | 21.52 |
| WT | 23.16 | 13.71 | 16.27 | 8.39 | 12.62 | 14.86 | 24.93 | 10.86 | 17.19 | 26.18 | 16.11 |
| WT | 13.22 | 14.75 | 18.63 | 14.26 | 19.61 | 12.14 | 19.75 | 14.75 | 16.82 | 25.46 | 17.35 |
| WT | 16.39 | 23.31 | 18.95 | 16.46 | 18.28 | 12.8 | 15.77 | 19.52 | 12.27 | 30.33 | 18.63 |
| WT | 18.05 | 17.06 | 16.65 | 11.87 | 11.96 | 21.72 | 23.86 | 14.25 | 15.02 | 15.07 | 16.38 |

TABLE 23

| | | Rep I | Rep II | Rep III | Average |
|---|---|---|---|---|---|
| Grain yield (g) | WT | 395.4 | 385 | 361.6 | 380.7 |
| | CW00716 | 397 | 391.2 | 429.6 | 405.9 |
| Plant Height (cm) | WT | 80.3 | 73.3 | 77.2 | 76.9 |
| | CW00716 | 86.9 | 82.5 | 88.3 | 85.9 |
| Stem weight (g) | WT | 16.6 | 20.0 | 16.6 | 17.7 |
| | CW00716 | 17.4 | 17.1 | 16.1 | 16.9 |

Example 20

Determination of Functional Homologs by Reciprocal BLAST®

A candidate sequence was considered a functional homolog of a reference sequence if the candidate and reference sequences encoded proteins having a similar function and/or activity. A process known as Reciprocal BLAST® (Rivera et al., *Proc. Natl. Acad. Sci. USA*, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST® process, a specific reference polypeptide was searched against all peptides from its source species using BLAST® in order to identify polypeptides having BLAST® sequence identity of 80% or greater to the reference polypeptide and an alignment length of 85% or greater along the shorter sequence in the alignment. The reference polypeptide and any of the aforementioned identified polypeptides were designated as a cluster.

The BLASTP® version 2.0 program from Washington University at Saint Louis, Mo., USA was used to determine BLAST® sequence identity and E-value. The BLASTP® version 2.0 program includes the following parameters: 1) an E-value cutoff of 1.0e-5; 2) a word size of 5; and 3) the -postsw option. The BLAST® sequence identity was calculated based on the alignment of the first BLAST® HSP (High-scoring Segment Pairs) of the identified potential functional homolog sequence with a specific reference polypeptide. The number of identically matched residues in the BLAST® HSP alignment was divided by the HSP length, and then multiplied by 100 to get the BLAST® sequence identity. The HSP length typically included gaps in the alignment, but in some cases gaps were excluded.

The main Reciprocal BLAST® process consists of two rounds of BLAST® searches; forward search and reverse search. In the forward search step, a reference polypeptide sequence, "polypeptide A," from source species SA was BLASTed® against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed® against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NOs: 1333, 1489, 504, 198, 253, 1541, 663, 1366, 928, 1215, 4, 580, 53, 1112, 634, 368, 1599, 154, 1035, 741, 187, 1065, 1592, 851, 1016, 2186, 1955, 2566, 2150, 2196, 2493, 2271, 1741, 1980, 1812, 2124, 2035, and 2425 are shown in FIGS. 1-38, respectively. Additional exemplary homologs are correlated to certain Figures in the Sequence Listing.

Example 21

Determination of Functional Homologs by Hidden Markov Models

Hidden Markov Models (HMMs) were generated by the program HMMER 2.3.2. To generate each HMM, the default HMMER 2.3.2 program parameters, configured for global alignments, were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO: 1333.

The procedure above was repeated and an HMM was generated for each group of sequences shown in FIGS. 2-38, using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09441233B2). An electronic copy of the "Sequence Listing" will also be available from the USPTO upon request and payment of the fee set forth in 37 CFR 1.19(b)(3).

What is claimed is:

1. A method of producing a plant, said method comprising:
    growing a plant cell comprising an exogenous nucleic acid, said exogenous nucleic acid comprising a regulatory region operably linked to a nucleotide sequence encoding a polypeptide having 95 percent or greater sequence identity to SEQ ID NO:1592, and
    producing a plant from said plant cell, wherein said plant has at least a 5% increase in grain yield as compared to the corresponding level of a control plant that does not comprise said nucleic acid,
    wherein said plant is a monocot plant selected from the genera *Elaeis, Festuca, Hordeum, Lolium, Orvza, Panicum, Pennisetum, Phleum, Poa, Saccharum, Secale, Sorghum, Triticosecale, Triticum*, or *Zea*.

2. A method of increasing the grain yield in a plant, said method comprising:
    growing a plant cell comprising an exogenous nucleic acid, said exogenous nucleic acid comprising a regulatory region operably linked to a nucleotide sequence encoding a polypeptide having 95 percent or greater sequence identity to SEQ ID NO:1592, and
    producing a plant from said plant cell, wherein said plant has at least a 5% increase in grain yield as compared to the corresponding level of a control plant that does not comprise said nucleic acid,
    wherein said plant is a monocot plant selected from the genera *Elaeis, Festuca, Hordeum, Lolium, Oryza, Panicum, Pennisetum, Phleum, Poa, Saccharum, Secale, Sorghum, Triticosecale, Triticum*, or *Zea*.

3. The method of claim 2, wherein said polypeptide comprises SEQ ID NO: 1592.

4. A method of producing a plant, said method comprising:
    growing a plant cell comprising an exogenous nucleic acid, said exogenous nucleic acid comprising a regulatory region operably linked to a nucleotide sequence encoding a polypeptide having 95 percent or greater sequence identity to SEQ ID NO:1592, and
    producing a plant from said plant cell, wherein said plant has an increase in plant height as compared to a corresponding level of a control plant that does not comprise said nucleic acid,
    wherein said plant is a monocot plant selected from the genera *Elaeis, Festuca, Hordeum, Lolium, Orvza, Panicum, Pennisetum, Phleum, Poa, Saccharum, Secale, Sorghum, Triticosecale, Triticum*, or *Zea*.

5. A method of producing a plant, said method comprising:
    growing a plant cell comprising an exogenous nucleic acid, said exogenous nucleic acid comprising a regulatory region operably linked to a nucleotide sequence having 95 percent or greater sequence identity to SEQ ID NO:1591, and
    producing a plant from said plant cell, wherein said plant has at least a 5% increase in grain yield as compared to the corresponding level of a control plant that does not comprise said nucleic acid,
    wherein said plant is a monocot plant selected from the genera *Elaeis, Festuca, Hordeum, Lolium, Orvza, Panicum, Pennisetum, Phleum, Poa, Saccharum, Secale, Sorghum, Triticosecale, Triticum*, or *Zea*.

6. The method of claim 1, wherein said polypeptide comprises residues 32 to 190 of SEQ ID NO: 1592.

7. The method of claim 6, wherein said polypeptide comprises SEQ ID NO: 1592.

8. The method of claim 4, wherein said polypeptide comprises residues 32 to 190 of SEQ ID NO: 1592.

9. The method of claim 8, wherein said polypeptide comprises SEQ ID NO: 1592.

* * * * *